United States Patent
Sabatini et al.

(10) Patent No.: US 10,123,985 B2
(45) Date of Patent: Nov. 13, 2018

(54) THERAPEUTIC STRATEGIES FOR TREATING MITOCHONDRIAL DISORDERS

(71) Applicants: Whitehead Institute for Biomedical Research, Cambridge, MA (US); Massachusetts Institute of Technology, Cambridge, MA (US)

(72) Inventors: David M. Sabatini, Cambridge, MA (US); Kivanc Birsoy, Cambridge, MA (US); Matthew George Vander Heiden, Belmont, MA (US); Lucas Bryan Sullivan, Boston, MA (US); Dan Yi Gui, Cambridge, MA (US)

(73) Assignees: Whitehead Institute for Biomedical Research, Cambridge, MA (US); Massachusetts Institute of Technology, Cambridge, MA (US); Howard Hughes Medical Institute, Chevy Chase, MD (US)

( * ) Notice: Subject to any disclaimer, the term of this patent is extended or adjusted under 35 U.S.C. 154(b) by 0 days.

(21) Appl. No.: 15/177,243

(22) Filed: Jun. 8, 2016

(65) Prior Publication Data
US 2016/0354332 A1  Dec. 8, 2016

Related U.S. Application Data

(60) Provisional application No. 62/198,653, filed on Jul. 29, 2015, provisional application No. 62/172,637, filed on Jun. 8, 2015.

(51) Int. Cl.
| | |
|---|---|
| *A61K 31/198* | (2006.01) |
| *A61K 31/194* | (2006.01) |
| *A61K 31/52* | (2006.01) |
| *A61K 38/00* | (2006.01) |
| *A61K 31/19* | (2006.01) |
| *A61K 31/505* | (2006.01) |
| *A61K 45/06* | (2006.01) |

(52) U.S. Cl.
CPC ............ *A61K 31/198* (2013.01); *A61K 31/19* (2013.01); *A61K 31/194* (2013.01); *A61K 31/505* (2013.01); *A61K 31/52* (2013.01); *A61K 38/00* (2013.01); *A61K 45/06* (2013.01)

(58) Field of Classification Search
CPC .... A61K 31/19; A61K 31/194; A61K 31/198; A61K 31/505; A61K 31/52; A61K 38/00; A61K 45/06
See application file for complete search history.

(56) References Cited

U.S. PATENT DOCUMENTS

| | | |
|---|---|---|
| 4,612,302 A | 9/1986 | Szabo et al. |
| 4,684,620 A | 8/1987 | Hruby et al. |
| 4,853,371 A | 8/1989 | Coy et al. |
| 9,000,147 B2 | 4/2015 | Sauve |
| 2003/0165457 A1* | 9/2003 | Martin ................. A61K 31/315 424/85.1 |
| 2006/0229265 A1 | 10/2006 | Milburn et al. |
| 2009/0263843 A1 | 10/2009 | Anderson et al. |
| 2014/0348749 A1 | 11/2014 | Birsoy et al. |
| 2017/0128395 A1* | 5/2017 | Huang ................... A61K 31/19 |

FOREIGN PATENT DOCUMENTS

WO   WO 2013/177426 A2   11/2013

OTHER PUBLICATIONS

Mechanisms of Carcinogenesis, 2010, International Agency for Research on Cancer, Section 3, p. 190, col. 1.*
Bell et al., The Qo site of the mitochondrial complex III is required for the transduction of hypoxic signaling via reactive oxygen species production. J Cell Biol. Jun. 18, 2007;177(6):1029-36.
Bender et al., High levels of mitochondrial DNA deletions in substantia nigra neurons in aging and Parkinson disease. Nat Genet. May 2006;38(5):515-7.
Berge et al., Pharmaceutical salts. J Pharm Sci. Jan. 1977;66(1):1-19.
Chen et al., Inhibition of ATPIF1 ameliorates severe mitochondrial respiratory chain dysfunction in mammalian cells. Cell Rep. Apr. 10, 2014;7(1):27-34. doi:10.1016/j.celrep.2014.02.046.
De Coo et al., A 4-base pair deletion in the mitochondrial cytochrome b gene associated with parkinsonism/MELAS overlap syndrome. Ann Neurol. Jan. 1999;45(1):130-3.
Di Lisa et al., Pathophysiological relevance of mitochondria in NAD(+).
Dimauro et al., Mitochondrial respiratory-chain diseases. N Engl J Med. Jun. 26, 2003;348(26):2656-68.
Dimauro, Pathogenesis and treatment of mitochondrial myopathies: recent advances. Acta Myol. Oct. 2010;29(2):333-8.
(Continued)

*Primary Examiner* — Rachael E Bredefeld
*Assistant Examiner* — Erinne R Dabkowski
(74) *Attorney, Agent, or Firm* — Wolf, Greenfield & Sacks, P.C.

(57) ABSTRACT

Provided herein are methods, compositions, and systems for treating mitochondrial disorders (e.g., MERRF, MELAS, Kearns-Sayre syndrome, chronic progressive external ophthalmoplegia, diabetes mellitus and deafness, lactic acidosis, Leber's hereditary optic neuropathy, Wolff-Parkinson-White syndrome, Leigh syndrome, NARP, myoneurogenic gastrointestinal encephalopathy, mitochondrial DNA depletion syndrome) or neurodegenerative diseases (e.g., Alzheimer's disease, Parkinson's disease) by administering aspartate, or an analog or prodrug thereof, or an agent that increases intracellular levels of aspartate. Pharmaceutical compositions and kits for use in treating mitochondrial disorders and neurodegenerative diseases are also described herein. Also provided are methods for treating disease by modulating the redox state of a cell, and methods of treating a proliferative disease by administering a cytosolic aspartate aminotransferase (GOT1) inhibitor.

13 Claims, 41 Drawing Sheets

Specification includes a Sequence Listing.

(56) References Cited

OTHER PUBLICATIONS

Fendt et al., Metformin decreases glucose oxidation and increases the dependency of prostate cancer cells on reductive glutamine metabolism. Cancer Res. Jul. 15, 2013;73(14):4429-38. doi: 10.1158/0008-5472.CAN-13/0080.
Fendt et al., Reductive glutamine metabolism is a function of the α-ketoglutarate to citrate ratio in cells. Nat Commun. 2013;4:2236. doi: 10.1038/ncomms3236.
Fujii et al., Efficacy of pyruvate therapy in patients with mitochondrial disease: a semi-quantitative clinical evaluation study. Mol Genet Metab. Jun. 2014;112(2):133-8. doi: 10.1016/j.ymgme.2014.04.008.
Geissler et al., Membrane potential-driven protein import into mitochondria. The sorting sequence of cytochrome b(2) modulates the deltapsi-dependence of translocation of the matrix-targeting sequence. Mol Biol Cell. Nov. 2000;11(11):3977-91.
Green et al., Mitochondria and apoptosis. Science. Aug. 28, 1998;281(5381):1309-12.
Han et al., Antimycin A as a mitochondrial electron transport inhibitor prevents the growth of human lung cancer A549 cells. Oncol Rep. Sep. 2008;20(3):689-93.
Harris, Pyruvate blocks expression of sensitivity to antimycin A and chloramphenicol. Somatic Cell Genet. Nov. 1980;6(6):699-708.
Hayashi et al., Recovery of the missing tumorigenicity in mitochondrial DNA-less HeLa cells by introduction of mitochondrial DNA from normal human cells. Somat Cell Mol Genet. Mar. 1992;18(2):123-9.
Kokotas et al., Mitochondrial deafness. Clin Genet. May 2007;71(5):379-91.
Koopman et al., Monogenic mitochondrial disorders. N Engl J Med. Mar. 22, 2012;366(12):1132-41. doi: 10.1056/NEJMra1012478.
Kwong et al., The mitochondrial respiratory chain is a modulator of apoptosis. J Cell Biol. Dec. 17, 2007;179(6):1163-77.
Mayers et al., Famine versus feast: understanding the metabolism of tumors in vivo. Trends Biochem Sci. Mar. 2015;40(3):130-40. doi:10.1016/j.tibs.2015.01.004.
Mullen et al., Reductive carboxylation supports growth in tumour cells with defective mitochondria. Nature. Nov. 20, 2011;481(7381):385-8. doi: 10.1038/nature10642.
Newmeyer et al., Mitochondria: releasing power for life and unleashing the machineries of death. Cell. Feb. 21, 2003;112(4):481-90. Review. Erratum in: Cell. Mar. 21, 2003;(112)6:873.
Nicholls et al., Mitochondria and neuronal survival. Physiol Rev. Jan. 2000;80(1):315-60.
Nunnari et al., Mitochondria: in sickness and in health. Cell. Mar. 16, 2012;148(6):1145-59. doi: 10.1016/j.cell.2012.02.035.
Owen et al., Evidence that metformin exerts its anti-diabetic effects through inhibition of complex 1 of the mitochondrial respiratory chain. Biochem J. Jun. 15, 2000;348 Pt 3:607-14.
Pagliarini et al., Hallmarks of a new era in mitochondrial biochemistry. Genes Dev. Dec. 15, 2013;27(24):2615-27. doi: 10.1101/gad.229724.113.
Park et al., A heteroplasmic, not homoplasmic, mitochondrial DNA mutation promotes tumorigenesis via alteration in reactive oxygen species generation and apoptosis. Hum Mol Genet. 1;18(9):1578-89. doi:10.1093/hmg/ddp069.
Pfeffer et al., Treatment for mitochondrial disorders. Cochrane Database Syst Rev. Apr. 2012 doi: 10.1002/14651858.CD004426.pub3.
Raimundo et al., Mitochondrial stress engages E2F1 apoptotic signaling to cause deafness. Cell. Feb. 17, 2012;148(4):716-26. doi:10.1016/j.cell.2011.12.027.
Saito et al., Pyruvate therapy for mitochondrial DNA depletion syndrome. Biochim Biophys Acta. May 2012;1820(5):632-6. doi: 10.1016/j.bbagen.2011.08.006.
Santidrian et al., Mitochondrial complex I activity and NAD+/NADH balance regulate breast cancer progression. J Clin Invest. Mar. 2013;123(3):1068-81. doi: 10.1172/JCI64264.
Schapira, Mitochondrial diseases. Lancet. May 12, 2012;379(9828):1825-34. doi: 10.1016/S0140-6736(11)61305-6.
Schon et al., Human mitochondrial DNA: roles of inherited and somatic mutations. Nat Rev Genet. Dec. 2012;13(12):878-90. doi: 10.1038/nrg3275.
Shoffner et al., Myoclonic epilepsy and ragged-red fiber disease (MERRF) is associated with a mitochondrial DNA tRNA(Lys) mutation. Cell. Jun. 15, 1990;61(6):931-7.
Stein et al., The dynamic regulation of NAD metabolism in mitochondria. Trends Endocrinol Metab. Sep. 2012;23(9):420-8. doi: 10.1016/j.tem.2012.06.005.
Tan et al., Mitochondrial genome acquisition restores respiratory function and tumorigenic potential of cancer cells without mitochondrial DNA. Cell Metab. Jan. 6, 2015;21(1):81-94. doi: 10.1016/j.cmet.2014.12.003.
Toney, Aspartate aminotransferase: an old dog teaches new tricks. Arch Biochem Biophys. Feb. 15, 2014;544:119-27. doi: 10.1016/j.abb.2013.10.002.
Wallace et al., Familial mitochondrial encephalomyopathy (MERRF): genetic, pathophysiological, and biochemical characterization of a mitochondrial DNA disease. Cell. Nov. 18, 1988;55(4):601-10.
Wallace, A mitochondrial bioenergetic etiology of disease. J Clin Invest. Apr. 2013;123(4):1405-12. doi: 10.1172/JCI61398.
Wallace, Mitochondrial diseases in man and mouse. Science. Mar. 5, 1999;283(5407):1482-8.
Weinberg et al., Mitochondrial metabolism and ROS generation are essential for Kras-mediated tumorigenicity. Proc Natl Acad Sci U S A. May 11, 2010;107(19):8788-93. doi: 10.1073/pnas.1003428107.
Wheaton et al., Metformin inhibits mitochondrial complex I of cancer cells to reduce tumorigenesis. Elife. May 13, 2014;3:e02242. doi: 10.7554/eLife.02242.
Wilkins et al., Cytoplasmic hybrid (cybrid) cell lines as a practical model for mitochondriopathies. Redox Biol. 2014;2:619-31. doi:10.1016/j.redox.2014.03.006.
Sgarbi et al., Human NARP mitochondrial mutation metabolism corrected with alpha-ketoglutarate/aspartate: a potential new therapy. Arch Neurol. Aug. 2009;66(8):951-7. doi: 10.1001/archneurol.2009.134.

* cited by examiner

A

B

A

B

A

B

C

SEQUENCE LISTING

<160> NUMBER OF SEQ ID NOS: 15

<210> SEQ ID NO 1
<211> LENGTH: 413
<212> TYPE: PRT
<213> ORGANISM: Homo sapiens

<400> SEQUENCE: 1

```
Met Ala Pro Pro Ser Val Phe Ala Glu Val Pro Gln Ala Gln Pro Val
1               5                   10                  15

Leu Val Phe Lys Leu Thr Ala Asp Phe Arg Glu Asp Pro Asp Pro Arg
            20                  25                  30

Lys Val Asn Leu Gly Val Gly Ala Tyr Arg Thr Asp Asp Cys His Pro
        35                  40                  45

Trp Val Leu Pro Val Val Lys Lys Val Glu Gln Lys Ile Ala Asn Asp
    50                  55                  60

Asn Ser Leu Asn His Glu Tyr Leu Pro Ile Leu Gly Leu Ala Glu Phe
65                  70                  75                  80

Arg Ser Cys Ala Ser Arg Leu Ala Leu Gly Asp Asp Ser Pro Ala Leu
                85                  90                  95

Lys Glu Lys Arg Val Gly Gly Val Gln Ser Leu Gly Gly Thr Gly Ala
            100                 105                 110

Leu Arg Ile Gly Ala Asp Phe Leu Ala Arg Trp Tyr Asn Gly Thr Asn
        115                 120                 125

Asn Lys Asn Thr Pro Val Tyr Val Ser Ser Pro Thr Trp Glu Asn His
    130                 135                 140

Asn Ala Val Phe Ser Ala Ala Gly Phe Lys Asp Ile Arg Ser Tyr Arg
145                 150                 155                 160

Tyr Trp Asp Ala Glu Lys Arg Gly Leu Asp Leu Gln Gly Phe Leu Asn
                165                 170                 175

Asp Leu Glu Asn Ala Pro Glu Phe Ser Ile Val Val Leu His Ala Cys
            180                 185                 190

Ala His Asn Pro Thr Gly Ile Asp Pro Thr Pro Glu Gln Trp Lys Gln
        195                 200                 205

Ile Ala Ser Val Met Lys His Arg Phe Leu Phe Pro Phe Phe Asp Ser
    210                 215                 220

Ala Tyr Gln Gly Phe Ala Ser Gly Asn Leu Glu Arg Asp Ala Trp Ala
225                 230                 235                 240

Ile Arg Tyr Phe Val Ser Glu Gly Phe Glu Phe Cys Ala Gln Ser
                245                 250                 255
```

-continued

```
Phe Ser Lys Asn Phe Gly Leu Tyr Asn Glu Arg Val Gly Asn Leu Thr
            260                 265                 270
Val Val Gly Lys Glu Pro Glu Ser Ile Leu Gln Val Leu Ser Gln Met
        275                 280                 285
Glu Lys Ile Val Arg Ile Thr Trp Ser Asn Pro Pro Ala Gln Gly Ala
    290                 295                 300
Arg Ile Val Ala Ser Thr Leu Ser Asn Pro Glu Leu Phe Glu Glu Trp
305                 310                 315                 320
Thr Gly Asn Val Lys Thr Met Ala Asp Arg Ile Leu Thr Met Arg Ser
                325                 330                 335
Glu Leu Arg Ala Arg Leu Glu Ala Leu Lys Thr Pro Gly Thr Trp Asn
            340                 345                 350
His Ile Thr Asp Gln Ile Gly Met Phe Ser Phe Thr Gly Leu Asn Pro
        355                 360                 365
Lys Gln Val Glu Tyr Leu Val Asn Glu Lys His Ile Tyr Leu Leu Pro
    370                 375                 380
Ser Gly Arg Ile Asn Val Ser Gly Leu Thr Thr Lys Asn Leu Asp Tyr
385                 390                 395                 400
Val Ala Thr Ser Ile His Glu Ala Val Thr Lys Ile Gln
                405                 410
```

```
<210> SEQ ID NO 2
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 2
caccggatag gctgagtcaa agaag                                          25

<210> SEQ ID NO 3
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 3
aaaccttctt tgactcagcc tatcc                                          25

<210> SEQ ID NO 4
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 4
caccggacat ctggatactg agtcg                                          25

<210> SEQ ID NO 5
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 5
aaaccgactc agtatccaga tgtcc                                          25
```

-continued

```
<210> SEQ ID NO 6
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 6
caccgcaggc ccggaacaca cgga                                          24

<210> SEQ ID NO 7
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 7
aaactccgtg tgttccgggc ctgc                                          24

<210> SEQ ID NO 8
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 8
gccggatcta gctagttaat taagccacca tgactaaaag caatggagaa gagccc       56

<210> SEQ ID NO 9
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 9
gggcggaatt tacgtagcct acatcttggt ttcactgtcg atggg                   45

<210> SEQ ID NO 10
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 10
ggctttatat atcttgtgga aaggacgaaa caccg                              35

<210> SEQ ID NO 11
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 11
ctagccttat tttaacttgc tatttctagc tctaaaac                           38

<210> SEQ ID NO 12
<211> LENGTH: 48
<212> TYPE: DNA
<213> ORGANISM: Artificial Sequence
<220> FEATURE:
<223> OTHER INFORMATION: Synthetic Polynucleotide
```

```
<400> SEQUENCE: 12
aatgatacgg cgaccaccga gatctagaat actgccattt gtctcaag            48

<210> SEQ ID NO 13
<211> LENGTH: 54
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (26)..(31)
<223> OTHER INFORMATION: n is a, c, g, or t

<400> SEQUENCE: 13
caagcagaag acggcatacg agatcnnnnn ntttcttggg tagtttgcag tttt     54

<210> SEQ ID NO 14
<211> LENGTH: 67
<212> TYPE: DNA
<213> ORGANISM: Artificial Sequence
<220> FEATURE:
<223> OTHER INFORMATION: Synthetic Polynucleotide

<400> SEQUENCE: 14
cggtgccact ttttcaagtt gataacggac tagccttatt ttaacttgct atttctagct  60
ctaaaac                                                            67

<210> SEQ ID NO 15
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 15
tttcaagtta cggtaagcat atgatagtcc attttaaaac ataattttaa aactgcaaac  60
tacccaagaa a                                                      71
```

THERAPEUTIC STRATEGIES FOR TREATING MITOCHONDRIAL DISORDERS

RELATED APPLICATIONS

The present application claims priority under 35 U.S.C. § 119(e) to U.S. provisional applications, U.S. Ser. No. 62/172,637, filed Jun. 8, 2015, and U.S. Ser. No. 62/198,653, filed Jul. 29, 2015, each of which is incorporated herein by reference.

GOVERNMENT SUPPORT

This invention was made with government support under grant numbers CA103866, CA168653, GG006413, and T32 GM007753 awarded by the National Institutes of Health. The government has certain rights in the invention.

BACKGROUND

Defects in many mitochondrial pathways, including the mitochondrial respiratory chain, can cause disease. Many such defects affect central nervous system cells or muscle cells and lead to mitochondrial encephalopathies, cardiopathies, and myopathies. See, e.g., DeMauro et al., *N. England. J. Med.* (2003), 348, 2656-2668. For some disorders, afflicted patients suffer from severe disabilities and impaired function of several major body systems, and may have limited life expectancy. There are few approved pharmaceutical treatments for the majority of mitochondrial disorders, and most therapeutic approaches focus on management of diet and exercise, and the use of various vitamins or supplements, many of which are recommended based on limited or anecdotal evidence of efficacy. See, e.g., Schapira et al., *Lancet* (2012) 379, 1825-1834.

There is a need for agents and therapeutic methods for treating mitochondrial disorders and neurodegenerative diseases.

SUMMARY

The importance of mitochondrial respiration in supporting cell proliferation is known, but the specific metabolic requirements provided by mitochondrial respiration have not been defined. It is widely assumed that ATP synthesis via oxidative phosphorylation is the critical output of respiration. The mitochondrial electron transport chain (ETC) consists of four enzyme complexes that transfer electrons from donors like NADH to oxygen, the ultimate electron acceptor. During electron transfer, the ETC pumps protons into the intermembrane space, generating a gradient across the inner mitochondrial membrane that drives ATP synthesis. See, e.g., Nicholls et al., *Physiol. Rev.* (2000) 80, 315-360. Many metabolic pathways, including glycolysis, the tricarboxylic acid (TCA) cycle, and beta-oxidation, produce the electron donors that fuel the ETC. Even though changes in ATP or reactive oxygen species (ROS) levels have been suggested to underlie the anti-proliferative effects of ETC inhibition (See, e.g., Wallace, *Science* (1999) 283, 1482-1488), the exact reason why proliferation requires the ETC is not understood. Interestingly, it has long been known that human cells lacking a functional ETC can proliferate if cultured in supra-physiological concentrations of pyruvate. See, e.g., King et al. *Science* (1989) 246, 500-503. While pyruvate can serve as a biosynthetic substrate or affect the redox state of the cell by promoting the regeneration of $NAD^+$ (See, e.g., Harris, *Somatic cell gen.* (1980) 6, 699-708; Howell et al., *Somatic cell gen.* (1979) 5, 833-845), why it reverses the suppressive effects of ETC inhibition on cell proliferation was unknown.

As elucidated by experiments described herein, the essential role of the electron transport chain (ETC) in cell proliferation is to enable the biosynthesis of aspartate. Even though ETC inhibition impacts many processes, the supplementation of media with just aspartate or the expression in cells of an aspartate transporter is sufficient to allow ETC-defective cells to proliferate in culture. The administration of aspartate and related analogs may be useful in the treatment of mitochondrial and neurodegenerative diseases, such as those associated with ETC defects. Additionally, agents that positively modulate aspartate biosynthesis or otherwise increase intracellular levels of aspartate may be useful in treating these conditions. α-Ketobutyrate and other electron acceptor agents, which can take the place of the electron transport chain (and $O_2$) in some biosynthetic pathways, are one class of agents that promote aspartate synthesis, by normalizing redox levels (e.g., the $NAD^+$/NADH ratio). Other useful agents include modulators of enzymes and transport proteins that contribute to aspartate biosynthesis, aspartate uptake, and/or the biosynthesis and uptake of electron acceptor agents.

Provided herein are methods, compositions, and systems for treating mitochondrial disorders or neurodegenerative diseases by administering aspartate, or an aspartate analog, to a subject in need thereof. Administration of an aspartate precursor, aspartate prodrug, or aspartate-rich polypeptide or protein are also contemplated. In another aspect, provided herein are methods of treating a mitochondrial disorder or neurodegenerative disease by administering an agent that increases the intracellular levels of aspartate. Such agents include activators and up-regulators of enzymes involved in aspartate biosynthesis, for example, cytosolic aspartate aminotransferase, an enzyme encoded by GOT1. Other useful agents include activators and up-regulators of enzymes that provide cofactors (e.g., $NAD^+$, FAD) necessary for the biosynthesis of aspartate. Also contemplated are agents that increase the activity or up-regulate the expression of transport proteins capable of enhancing the uptake of aspartate by cells, for example, a glutamate/aspartate transporter (e.g., solute carrier family 1, member 3 (SLC1A3)). Methods provided herein may include administering a combination of agents to increase both the supply and enhance the uptake of aspartate.

In another aspect, provided herein are methods, compositions, and systems for treating mitochondrial disorders or neurodegenerative diseases by administering an electron acceptor agent to a subject in need thereof. The electron acceptor agent may act as an electron acceptor in place of impaired mitochondrial respiration (e.g., a defective electron transport chain). The electron acceptor may increase intracellular aspartate levels by increasing levels of $NAD^+$, necessary for aspartate biosynthesis via the tricarboxylic acid cycle. In certain embodiments, the electron acceptor agent is a compound capable of oxidizing NADH. Electron acceptor agents contemplated herein include pyruvate, α-ketobutyrate, analogs of pyruvate and α-ketobutyrate, and other substrates of dehydrogenases (e.g., lactate dehydrogenase).

In another aspect, provided herein are methods, compositions, and systems for treating mitochondrial disorders or neurodegenerative diseases by administering an agent that increases the ratio of $NAD^+$ to NADH. Such agents include electron acceptors (e.g., pyruvate, α-ketobutyrate). Also contemplated are agents that increase intracellular levels of an electron acceptor agent, such as pyruvate. Agents that decrease consumption or uptake of pyruvate by the liver, allowing delivery at higher concentrations to non-liver cells, are described herein, and include inhibitors of pyruvate dehydrogenase complex and antagonists of monocarboxylate transporters, such as pyruvate translocase. In certain embodiments, the agent is an activator of NAD(P)H (quinone) dehydrogenase 1 or 2 (NQO1 or NQO2). In certain embodiments, the agent is nicotinamide, niacin, nicotinamide mononucleotide, or nicotinamide ribo side, or an analog thereof. The agent may be a substrate of NQO1 or NQO2, such as, benzoquinone, juglone, duroquinone, a Vitamin K, a Vitamin E, or analogs thereof.

An agent described herein may directly or indirectly cause more than one of the desired changes in cellular metabolism described herein. In another aspect, provided herein are methods, compositions, and systems for treating mitochondrial disorders or neurodegenerative diseases by administering an electron acceptor agent or an agent that increases the ratio of NAD$^+$ to NADH, and increases the intracellular levels of aspartate. For example, and electron acceptor agent (e.g., α-ketobutyrate) may increase the NAD$^+$/NADH ratio, and the increased ratio may promote aspartate biosynthesis leading to increased intracellular aspartate levels. In certain embodiments, the agent is an electron acceptor agent and is an agent that increases intracellular levels of aspartate in cells or tissue in need thereof. In certain embodiments, the agent is pyruvate or α-ketobutyrate, or an analog thereof, and is an agent that increases intracellular levels of aspartate in cells or tissue in need thereof.

The methods, compositions, and systems described herein may be useful in the treatment of any mitochondrial disorder or a disease associated with mitochondrial dysfunction. In certain embodiments, the mitochondrial disorder is associated with impairment of mitochondrial respiration and/or a defective electron transport chain. In certain embodiments, the mitochondrial disorder is a myopathy, encephalopathy, or cardiopathy, or a combination thereof. In certain embodiments, the mitochondrial disorder is a neurodegenerative disease. In certain embodiments, the mitochondrial disorder is an inherited disease (e.g., genetic disease). In certain embodiments, the mitochondrial disorder is myoclonic epilepsy with red ragged fibers (MERRF); mitochondrial encephalomyopathy, lactic acidosis, and stroke like symptoms (MELAS); Kearns-Sayre syndrome (KSS); chronic progressive external ophthalmoplegia (CPEO); diabetes mellitus and deafness (DAD); lactic acidosis; Leber's hereditary optic neuropathy (LHON); Wolff-Parkinson-White syndrome; Leigh syndrome; neuropathy, ataxia, retinitis pigmentosa, and ptosis (NARP); myoneurogenic gastrointestinal encephalopathy (MNGIE); or mitochondrial DNA depletion syndrome (MDS).

The methods, compositions, and systems described herein may be useful in the treatment of any neurodegenerative disease. In certain embodiments, the neurodegenerative disease is associated with a mitochondrial disorder, mitochondrial respiration, and/or a defective electron transport chain. In certain embodiments, the neurodegenerative disease is Parkinson's disease, Alzheimer's disease, amyotrophic lateral sclerosis (ALS), Huntington's disease, dementia, parkinsonism, neuropathy, or encephalopathy.

In an additional aspect, provided herein are methods, compositions, and systems for treating a proliferative disease comprising administering to a subject an agent that inhibits aspartate biosynthesis. In certain embodiments, mitochondrial respiration is impaired in proliferating cells (e.g., by hypoxia). In certain embodiments, the agent is an inhibitor or down-regulator of cytosolic aspartate aminotransferase (GOT1). In certain embodiments, the agent decreases the intracellular concentration of NAD$^+$ or the intracellular ratio of NAD$^+$ to NADH. In certain embodiments, the method further comprises administering an additional agent that impairs mitochondrial respiration in proliferating cells. Proliferative diseases include cancer, benign neoplasm, diseases associated with angiogenesis, inflammatory diseases, autoinflammatory diseases, and autoimmune diseases.

In another aspect, provided herein are pharmaceutical compositions comprising an agent useful for treating a mitochondrial disorder or neurodegenerative disease. The pharmaceutical composition may comprise aspartate, pyruvate, α-ketobutyrate, or an analog or prodrug thereof. The pharmaceutical composition may comprise an agent that increases intracellular levels of aspartate, or an electron acceptor agent such as pyruvate.

Also provided herein are methods of treating a disease by administering to a subject in need thereof a first substrate of an enzyme which converts the first substrate to a first product, wherein a concentration of a second product of the enzyme is modulated. The methods contemplate administration of an agent to cause consumption or formation of a product indirectly, such as a formation of a cofactor associated with the enzyme, but not directly incorporating the administered substrate. The first substrate may be a physiologically occurring substrate, or an analog thereof, or may not be a physiologically occurring substrate. As a non-limiting example, a mitochondrial disorder may be treated by administering α-ketobutyrate, an alternative substrate (to pyruvate) of lactate dehydrogenase (LDH). LDH converts α-ketobutyrate to α-hydroxybutyrate, and also converts NADH to NAD$^+$, thus increasing the concentration of NAD$^+$. The increase in the NAD$^+$/NADH ratio promotes aspartate biosynthesis. The reverse example, administering α-hydroxybutyrate, would decrease the NAD$^+$/NADH ratio, inhibiting aspartate biosynthesis which limits cell proliferation, and may be useful in the treatment of a proliferative disease (e.g., cancer).

In certain embodiments, the method, composition, or system modulates the redox state of a cell, or an organelle, by modulating levels of a cofactor. In some embodiments, the cofactor is NAD$^+$, NADH, NADP$^+$, NADPH, FAD, FADH$_2$, ADP, or ATP. In some embodiments, the enzyme is an oxidoreductase or dehydrogenase. The redox state of a cell in a particular tissue may be modulated by selecting an enzyme localized or expressed in the tissue (e.g., liver, central nervous system, pancreas, muscles). The redox state of particular organelles or regions of the cell may be modulated by selecting an enzyme localized or expressed in an organelle (e.g., mitochondria), the cytosol, the cell membrane, or the extracellular matrix.

In another aspect provided herein, are methods of treating a cancer associated with a defect in oxidative phosphorylation comprising administering to a subject in need thereof a therapeutically effective amount of a GOT1 inhibitor. In certain embodiments, the defect in oxidative phosphorylation comprises a mutation in mitochondrial DNA. In certain embodiments, the defect in oxidative phosphorylation comprises a mutation in a gene encoding succinate dehydrogenase, fumarate hydratase, or isocitrate dehydrogenase. In certain embodiments, the GOT1 inhibitor is 3-methylene-aspartate or aminooxyacetate, or a pharmaceutically acceptable salt thereof. In certain embodiments, the GOT1 inhibitor is an siRNA comprising an antisense sequence for GOT1 mRNA. In certain embodiments, the method further comprises administering to the subject in need thereof a therapeutically effective amount of one or more additional pharmaceutical agents. In some embodiments, the additional pharmaceutical agent is a biguanide (e.g., metformin or phenformin), or a pharmaceutically acceptable salt thereof. In certain embodiments, the cancer is brain cancer, breast cancer, colorectal cancer, leukemia, lymphoma, prostate cancer, stomach cancer, renal cancer, lung cancer, thyroid cancer, liver cancer, ovarian cancer, or a cancer of the endocrine system.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

The accompanying drawings, which constitute a part of this specification, illustrate several embodiments of the invention and together with the description, serve to explain the principles of the invention.

DETAILED DESCRIPTION OF CERTAIN EMBODIMENTS

Figure 1:
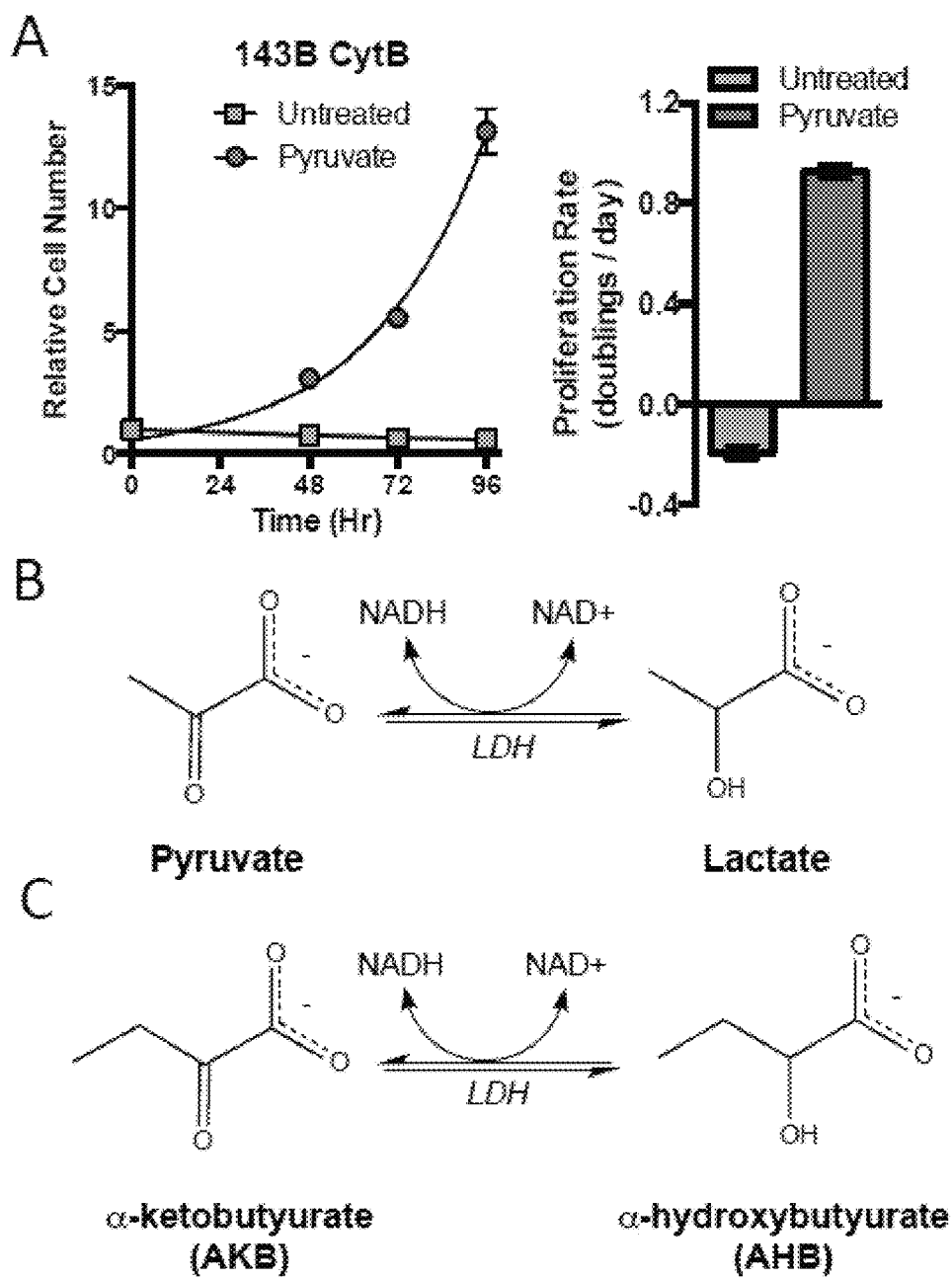
FIG. 1. Cytochrome B mutant 143B cybrid cells are auxotrophic for oxidized substrates that can regenerate $NAD^+$. (A) Proliferation rate of 143B CytB cells was determined in the presence or absence of pyruvate. (left) Cells were normalized to cell number at t=0 when media conditions were applied. (B) A major fate of pyruvate is as a substrate of lactate dehydrogenase (LDH) where it accepts electrons from NADH to produce $NAD^+$ and lactate. (C) α-Ketobutyrate (AKB) can act as an alternative electron acceptor substrate for LDH, yielding $NAD^+$ α-hydroxybutyrate (AHB). (D) Proliferation rate for 143B CytB cells in the presence or absence of AKB was determined as in (A). (E) Intracellular ratio of $NAD^+$/NADH was determined in 143B CytB cells in untreated media or in the presence of pyruvate (Pyr) or AKB. (F) The concentration of AKB and AHB in the media was determined by GC-MS analysis for each day of a proliferation assay of 143B CytB cells in the presence of AKB as in (D). Values in all figures denote mean±standard error of the mean (SEM), n=3.
Figure 1:
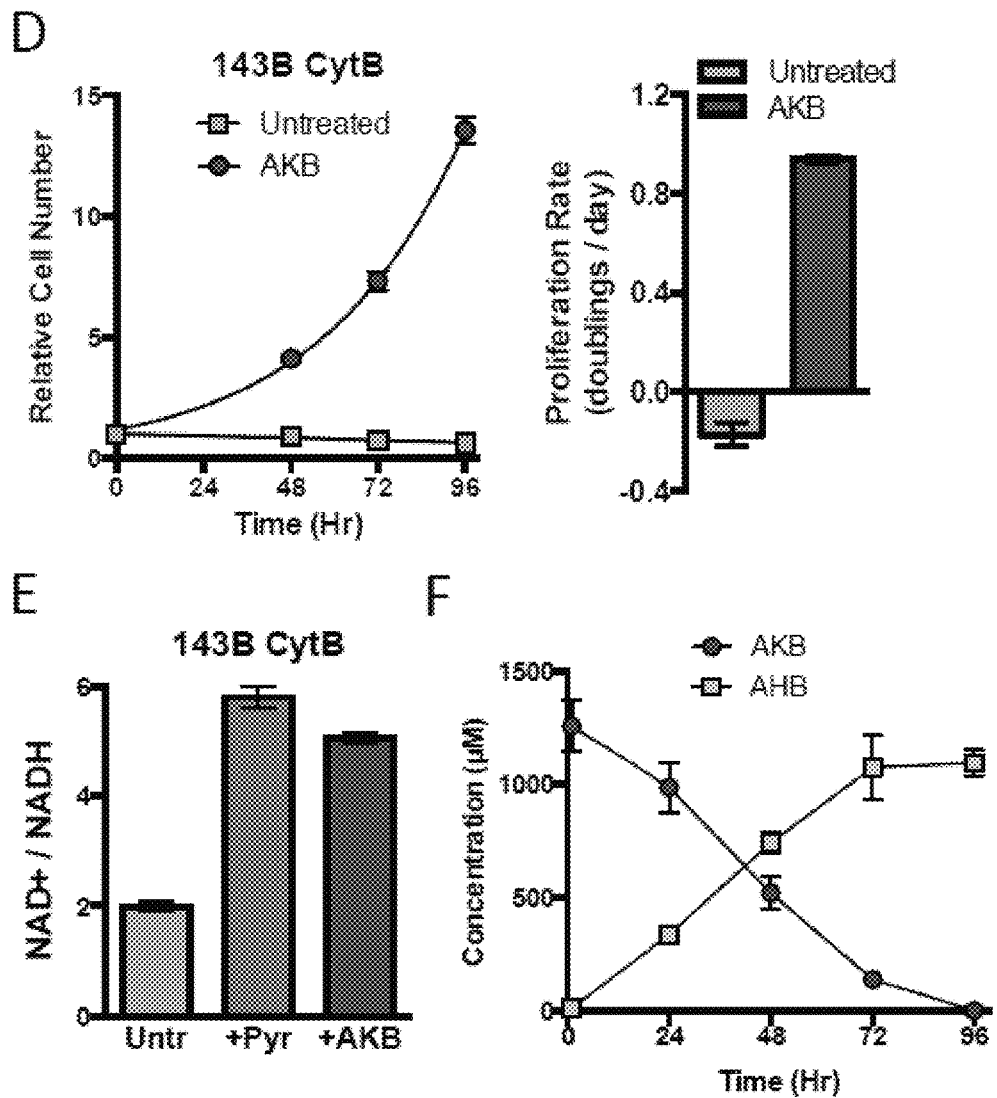

Methods for Treating Mitochondrial Disorders and Neurodegenerative Diseases

Provided herein are methods, compositions, and systems for treating mitochondrial disorders. Also contemplated are methods, compositions, and systems for treating neurodegenerative disorders. Certain embodiments of the methods involve the administration of an agent that modulates the metabolism of aspartate, preferably increasing intracellular levels of aspartate. Aspartate is the carboxylate anion of the proteinogenic amino acid aspartic acid, and is of formula:

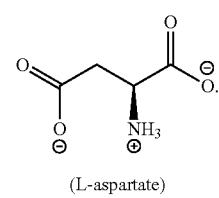

(L-aspartate)

In one aspect, provided herein are methods, compositions, and systems for treating mitochondrial disorders comprising administering to a subject in need thereof, aspartate, or an analog thereof, a prodrug of aspartate, a prodrug of an aspartate analog, a peptide or protein comprising aspartate, or a precursor to aspartate. In one aspect, provided herein are methods, compositions, and systems for treating neurodegenerative diseases comprising administering to a subject in need thereof, aspartate, or an analog thereof, a prodrug of aspartate, a prodrug of an aspartate analog, a polypeptide or protein comprising aspartate, or a precursor to aspartate. In certain embodiments, the method comprises administering aspartate, or an analog of aspartate, or a pharmaceutically acceptable salt, stereoisomer, tautomer, solvate, hydrate, polymorph, or prodrug thereof. In some embodiments, the method comprises administering aspartate, or a pharmaceutically acceptable salt, stereoisomer, tautomer, solvate, hydrate, polymorph, or prodrug thereof. In some embodiments, the method comprises administering aspartate, or a pharmaceutically acceptable salt, stereoisomer, or tautomer thereof. In some embodiments, the method comprises administering aspartate. In certain embodiments, the method comprises administering a prodrug of aspartate, or a prodrug of an aspartate analog. In certain embodiments, the aspartate analog or aspartate prodrug has a bioavailability greater than that of aspartate. In certain embodiments, the agent administered is not aspartate. In certain embodiments, the agent administered is not α-ketoglutarate. In certain embodiments, the agent administered is not an aspartate analog or aspartate prodrug.

Aspartate analogs include, but are not limited to, aspartate esters, anhydrides, alkylated aspartates, hydroxylated aspartates, halogenated aspartates, aminated aspartates, or protected aspartates. Analogs include aspartates with oxygen protecting groups at one or both carboxylate groups, and/or one or more nitrogen protecting groups at the amine. In certain embodiments, an analog or prodrug may be converted to aspartate in vivo after administration. In certain embodiments, an analog or prodrug may be converted to aspartate in vivo after entering the cytosol. In certain embodiments, the aspartate analog is N-methyl-aspartic acid, β-hydroxyaspartic acid, 2,2-azanediyldisuccinic acid, aspartic acid β-methyl ester, ethylenediamine-N,N-disuccinic acid, 2-aminobutyrylaspartic acid, 2-aminosuccinic acid 4-ethyl ester, 2-[(aminoacetyl)amino]butanedoic acid, aspartic acid 4-tert-butyl-1-methyl ester, N-acetyl-aspartic acid, cis-2,3-piperidinedicarboxylic acid, 4-allyloxy-4-oxobutanoic acid, aspartic acid di-tert-butyl ester, N-dodecanoyl aspartic acid, guanidinosuccinic acid, N-chloroacetyl-aspartic acid, 2-butyl-3-ureidosuccinic acid, 2-[(tert-butoxycarbonyl)amino]-4-methoxy-4-oxobutanoic acid, 2-[(tert-butoxycarbonyl)amino]-4-tert-butoxy-4-oxobutanoic acid, 2-[(tert-butoxycarbonyl)amino]-4-allyoxy-4-oxobutanoic acid, N-[(4,4-dimethyl-2,6-dioxocyclohexylidene)methyl]aspartic acid, arginosuccinic acid, N-benzyl-aspartic acid, β-benzylaspartic acid, N-benzoyl aspartic acid, aspartic acid β-benzyl ester, N-(2-hydroxybenzoyl) aspartic acid, aspartic acid bis-allyl ester, 2-[(benzyloxy) carbonylamino]-butanoic acid, aspartic acid dibenzyl ester, N-(anilinocarbonyl)aspartic acid, N-(tert-butoxycarbonyl)-valyl-aspartic acid, 2-[(benzyloxy)carbonylamino]-4-methoxy-oxobutanoic acid, 3-[(benzyloxy)carbonylamino]-4-methoxy-oxobutanoic acid, diethyl 2-[(4-aminobenzoyl) amino]succinate, carbobenzyloxyaspartic acid 1-tert-butyl ester, 3-(4-nitrophenyl)aspartic acid, or any salt, ester, or acid form thereof.

In certain embodiments, the method comprises administering a polypeptide comprising aspartate. In certain embodiments, the method comprises administering a polypeptide comprising an analog of aspartate. The polypeptide comprising aspartate, or an analog thereof, can be of any length (e.g., 2, 3, 4, 5, 6, 7, 8, 9, 10, 12, 14, 17, 21, 25, 30, 35, 50, 56, 67, 73, 85, 90, 100, 125, 250, 500, 1000, or more than 1000 residues). In some embodiments, all of the residues in the polypeptide are aspartate, or an analog thereof.

In some embodiments, at least 5% of the amino acids in the polypeptide are aspartate, or an analog thereof. In some embodiments, at least 10% of the amino acids in the polypeptide are aspartate, or an analog thereof. In some embodiments, at least 25% of the amino acids in the polypeptide are aspartate, or an analog thereof. In some embodiments, at least 50% of the amino acids in the polypeptide are aspartate, or an analog thereof. In some embodiments, at least 60% of the amino acids in the polypeptide are aspartate, or an analog thereof. In some embodiments, at least 70% of the amino acids in the polypeptide are aspartate, or an analog thereof. In some embodiments, at least 80% of the amino acids in the polypeptide are aspartate, or an analog thereof. In some embodiments, at least 90% of the amino acids in the polypeptide are aspartate, or an analog thereof.

In some embodiments, the polypeptide comprises at least 125 mg of aspartate, or an analog thereof, per gram of polypeptide. In some embodiments, the polypeptide comprises at least 130 mg, at least 140 mg, at least 150 mg, at least 160 mg, at least 170 mg, at least 200 mg, at least 225 mg, at least 250 mg of aspartate, or an analog thereof, per gram of polypeptide. In some embodiments, the polypeptide comprises at least 250 mg, at least 300 mg, at least 325 mg, at least 350 mg, least 375 mg, at least 400 mg, at least 500 mg, at least 600 mg, at least 700 mg, at least 800 mg, or up to at least 900 mg of aspartate, or an analog thereof, per gram of polypeptide. In some embodiments, the polypeptide comprises an aspartate-rich protein or a fragment thereof.

In certain embodiments, the polypeptide is enriched for aspartate, or an analog thereof. Those skilled in the art will appreciate that a variety of methods exist for obtaining polypeptides comprising and/or enriched for aspartate, including, for example, isolating aspartate-rich repeats or fragments from polypeptides enriched for aspartate, synthetic routes, and recombinant methods (e.g., in vitro transcription and/or translation of nucleic acids comprising aspartate codons GAU and GAC). Recombinant methods of producing a peptide through the introduction of a vector including nucleic acid encoding the peptide into a suitable host cell is well known in the art, such as is described in Sambrook et al, Molecular Cloning: A Laboratory Manual, 2d Ed., Vols. 1 to 8, Cold Spring Harbor, N.Y. (1989); M. W. Pennington and B. M. Dunn, Methods in Molecular Biology: Peptide Synthesis Protocols, Vol 35, Humana Press, Totawa, N.J. (1994), contents of both of which are herein incorporated by reference.

Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kirnrnerlin, T. and Seebach, D. J. Pept. Res. 65:229-260 (2005); Nilsson et al., Annu. Rev. Biophys. Biornol. Struct. (2005) 34:9 1-1 18; W. C. Chan and P. D. White (Eds.) Frnoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, 2nd Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

In some embodiments, the polypeptide comprising aspartate or enriched for aspartate is not a dietary source of aspartate. As used herein, "dietary source of aspartate" refers to a source of aspartate in which, prior to ingestion, chewing, or digestion, the aspartate is found in its natural state as part of an intact polypeptide within the source (e.g., meats (e.g., chicken, beef, etc.), legumes, grains, vegetables, dairy products (e.g., milk, cheese), eggs, nuts, seeds, seafood, etc.). In some embodiments, the polypeptide comprising aspartate or enriched for aspartate is not a whey protein isolate, casein, caseinate, or soy protein isolate.

In some embodiments, the polypeptide comprising aspartate or enriched for aspartate does not include any non-essential amino acids. In some embodiments, the polypeptide comprising aspartate or enriched for aspartate does not include any essential amino acids other than aspartate. In some embodiments, the polypeptide comprising aspartate or enriched for aspartate includes at least one non-native form of the amino acid aspartate.

The polypeptide comprising aspartate, or an analog thereof, may be incorporated in a food product, food composition, dietary supplement, nutritional composition, nutraceutical, powdered nutritional product to be reconstituted in water or milk before consumption, food additive, medicament, drink, or pet food, as described herein. In certain embodiments, the drink or food product is a fruit juice, fruit drink, artificially flavored drink, artificially sweetened drink, carbonated beverage, sports drink, liquid diary product, shake, food bar, snack bar, nutrition bar, cookie, brownie, muffin, cracker, ice cream bar, or frozen yogurt bar, as described herein.

In certain embodiments, the method comprises administering an aspartate precursor, or an analog thereof, or a pharmaceutically acceptable salt, stereoisomer, tautomer, solvate, hydrate, polymorph, or prodrug thereof. In some embodiments, the aspartate precursor is an intermediary in the tricarboxylic acid cycle, or an analog thereof, or a pharmaceutically acceptable salt, stereoisomer, tautomer, solvate, hydrate, polymorph, or prodrug thereof. In some embodiments, the aspartate precursor is oxaloacetate, or an analog thereof, or a pharmaceutically acceptable salt, stereoisomer, tautomer, solvate, hydrate, polymorph, or prodrug thereof. In some embodiments, the aspartate precursor is malate, or an analog thereof, or a pharmaceutically acceptable salt, stereoisomer, tautomer, solvate, hydrate, polymorph, or prodrug thereof. In some embodiments, the aspartate precursor is fumarate, or an analog thereof, or a pharmaceutically acceptable salt, stereoisomer, tautomer, solvate, hydrate, polymorph, or prodrug thereof. In some embodiments, the aspartate precursor is succinate, or an analog thereof, or a pharmaceutically acceptable salt, stereoisomer, tautomer, solvate, hydrate, polymorph, or prodrug thereof. In some embodiments, the aspartate precursor is α-ketoglutarate, glutamate, or glutamine, or an analog thereof, or a pharmaceutically acceptable salt, stereoisomer, tautomer, solvate, hydrate, polymorph, or prodrug thereof. In some embodiments, the aspartate precursor is isocitrate or citrate, or an analog thereof, or a pharmaceutically acceptable salt, stereoisomer, tautomer, solvate, hydrate, polymorph, or prodrug thereof. In some embodiments, the aspartate precursor is asparagine, or an analog thereof, or a pharmaceutically acceptable salt, stereoisomer, tautomer, solvate, hydrate, polymorph, or prodrug thereof.

In another aspect, provided herein are methods, compositions, and systems for treating a mitochondrial disorder comprising administering an agent that increases intracellular aspartate levels to a subject in need thereof. In another aspect, provided herein are methods, compositions, and systems for treating a neurodegenerative disease comprising administering an agent that increases intracellular aspartate levels to a subject in need thereof. The agent may increase intracellular levels of aspartate by increasing the activity of an enzyme associated with aspartate biosynthesis. In certain embodiments, the agent is a promoter of aspartate biosynthesis. In some embodiments, the agent is an activator of cytosolic aspartate aminotransferase (GOT1). In some embodiments, the agent is an activator of mitochondrial aspartate aminotransferase (GOT2). In some embodiments, the agent is an activator of malate dehydrogenase (MDH). In some embodiments, the agent is an activator of pyruvate carboxylase (PC). In some embodiments, the agent is an activator of isocitrate dehydrogenase (IDH). In some embodiments, the agent is a modulator of asparagine synthetase (ASNS). In some embodiments, the modulator of asparagine synthetase is an inverse activator, such that the rate of formation of aspartate from asparagine is enhanced. In some embodiments, the agent is an inhibitor of asparagine synthetase (ASNS).

The agent may increase intracellular levels of aspartate by up-regulating expression of a gene associated with aspartate biosynthesis. In certain embodiments, the agent up-regulates the expression of a gene associated with aspartate biosynthesis. In some embodiments, the agent up-regulates the expression of cytosolic aspartate aminotransferase (GOT1). In some embodiments, the agent up-regulates the expression of mitochondrial aspartate aminotransferase (GOT2). In some embodiments, the agent up-regulates the expression of malate dehydrogenase (MDH). In some embodiments, the agent up-regulates the expression of pyruvate carboxylase (PC). In some embodiments, the agent up-regulates the expression of isocitrate dehydrogenase (IDH). In some embodiments, the agent up-regulates the expression of asparagine synthetase (ASNS). In some embodiments, the agent down-regulates the expression of asparagine synthetase (ASNS).

The agent may increase intracellular levels of aspartate by increasing the activity of a protein capable of transporting aspartate, or an analog thereof, into a cell. In certain embodiments, the agent increases the uptake of aspartate, or an analog thereof, by a cell. In certain embodiments, the agent is an agonist of a transport protein capable of transporting aspartate, or an analog thereof, into a cell. In some embodiments, the agent is an agonist of an amino acid transport protein. In some embodiments, the agent is an agonist of solute carrier (SLC) family transport protein. In some embodiments, the agent is an agonist of a glutamate transport protein. In some embodiments, the agent is an agonist of an aspartate transport protein. In some embodiments, the agent is an agonist of solute carrier family 1, member 3 (SLC1A3). SLC1A3 is also known as glial high-affinity glutamate transporter, glutamate aspartate transporter (GLAST), and excitatory amino acid transporter 1 (EAAT1). In some embodiments, the agent is an agonist of an excitatory amino acid transporter (EAAT). In some embodiments, the EAAT is SLC1A1, SLC1A2, SLC1A4, SLC1A5, SLC1A5, SLC1A6, or SLC1A7. In some embodiments, the agent is an agonist of a vesicular glutamate transporter (VGLUT). In some embodiments, the VGLUT is SLC17A1, SLC17A2, SLC17A3, SLC17A4, SLC17A6, SLC17A7, SLC17A8, or SLC17A9. In some embodiments, the agent is an agonist of sialin (SLC17A5).

The agent may increase intracellular levels of aspartate by up-regulating the expression of a gene associated with enzymes capable of transporting aspartate, or an analog thereof, into a cell. In certain embodiments, the agent up-regulates the expression of a transport enzyme capable of transporting aspartate, or an analog thereof, into a cell. In some embodiments, the agent up-regulates the expression of an amino acid transport enzyme. In some embodiments, the agent up-regulates the expression of solute carrier (SLC) family transport protein. In some embodiments, the agent up-regulates the expression of a glutamate transport protein. In some embodiments, the agent up-regulates the expression of an aspartate transport protein. In some embodiments, the agent up-regulates the expression of solute carrier family 1, member 3 (SLC1A3). In some embodiments, the agent up-regulates the expression of an excitatory amino acid transporter (EAAT). In some embodiments, the EAAT is SLC1A1, SLC1A2, SLC1A4, SLC1A5, SLC1A5, SLC1A6, or SLC1A7. In some embodiments, the agent up-regulates the expression of a vesicular glutamate transporter (VGLUT). In some embodiments, the VGLUT is SLC17A1, SLC17A2, SLC17A3, SLC17A4, SLC17A6, SLC17A7, SLC17A8, or SLC17A9. In some embodiments, the agent up-regulates the expression of sialin (SLC17A5).

Administration of an agent described herein may increase intracellular aspartate levels in cells or tissue in need thereof relative to levels prior to administration of the agent. In some embodiments, the increase in intracellular levels of aspartate is at least about 1.1 fold, at least about 1.25 fold, at least about 1.5 fold, at least about 2 fold, at least about 2.5 fold, at least about 3 fold, at least about 5 fold, at least about 10 fold, at least about 15 fold, at least about 25 fold, at least about 50 fold, at least about 100 fold, at least about 200 fold, at least about 500 fold, or at least about 1000 fold, in cells or tissue in need thereof. In certain embodiments, the increase in intracellular levels of aspartate is between about 1.5 fold and about 50 fold, between about 1.5 fold and about 25 fold, between about 1.5 fold and 10 fold, or between about 1.5 fold and about 5 fold in cells or tissue in need thereof. In certain embodiments, the increase in intracellular levels of aspartate is between about 1.5 fold and about 100 fold, between about 2 fold and about 100 fold, between about 3 fold and about 100 fold, between about 5 fold and about 100 fold, between about 10 fold and 100 fold, between about 25 fold and about 100 fold, or between about 50 fold and about 100 fold, in cells or tissue in need thereof. In certain embodiments, administration of the agent causes an increase in intracellular levels of aspartate of between about 50 fold and about 1000 fold, between about 100 fold and about 1000 fold, between about 200 fold and about 1000 fold, or between about 500 fold and about 1000 fold, in cells or tissue in need thereof.

Administration of an agent described herein may restore the intracellular aspartate levels in cells or tissue in need thereof to normal levels. A normal level is defined as the homeostatic aspartate level in cells or tissue for a healthy subject, e.g., a subject with no mitochondrial disorder. In some embodiments, administration of the agent increases aspartate levels to normal levels for cells or tissue in need thereof. In some embodiments, administration of the agent increases aspartate levels to between about 90% and about 100% of normal levels, to between about 80% and about 90% of normal levels, to between about 70% and about 80% of normal levels, to between about 60% and about 70% of normal levels, or to between about 50% and about 60% of normal levels, for cells or tissue in need thereof. In some embodiments, administration of the agent increases aspartate levels to between about 30% and about 50% of normal levels, or to between about 10% and about 30% of normal levels, for cells or tissue in need thereof. In some embodiments, administration of the agent increases aspartate levels to between about 100% and about 125% of normal levels, between about 125% and about 150% of normal levels, or between about 150% and about 250% of normal levels, for cells or tissue in need thereof.

The increase in aspartate levels following administration of an agent described herein may occur in specific cells or specific tissue. In some embodiments, the increase occurs in cells with a mitochondrial disorder (e.g., cells with impaired mitochondrial respiration). In some embodiments, the increase occurs in nerve cells, muscle cells, cardiac muscle cells, or blood cells. In some embodiments, the increase occurs in nerve cells. In some embodiments, the increase occurs in tissue of the liver, central nervous system, pancreas, spleen, cardiovascular system, muscles, bone marrow, eye, or gastrointestinal system. In some embodiments, the increase occurs in tissue of the central nervous system. In some embodiments, the increase occurs in skeletal muscle tissue. In some embodiments, the increase occurs in cardiac muscle tissue.

The increase in aspartate levels relative to pre-administration levels or normal levels may be effective for a time duration following administration of the agent. For example, if in a particular embodiment the agent provides an increase of at least 2 fold, the intracellular levels will remain at or above a 2 fold increase for the length of the time duration. In some embodiments, the time duration is at least about 1 hour, at least about 2 hours, at least about 4 hours, at least about 8 hours, at least about 12 hours, at least about 24 hours, at least about 36 hours, or at least about 48 hours. In some embodiments, the time duration is at least about 3 days, at least about 7 days, at least about 14 days, or at least about 30 days. In some embodiments the time duration is between about 1 hour and 24 hours, between about 1 hour and 12 hours, between about 1 hour and 8 hours, or between about 1 hour and 4 hours. In some embodiments, the time duration is between about 4 hours and 48 hours, between about 8 hours and 48 hours, between about 12 hours and 48 hours, between about 24 hours and about 48 hours, or between about 36 hours and about 48 hours. In some embodiments, the time duration is between about 3 hours and 30 days, between about 3 days and about 14 days, or between about 3 days and about 7 days.

In order to increase the efficacy of administered aspartate, a method may combine both administration of aspartate and administration of an agent that increases the uptake of aspartate by a cell. In certain embodiments, the method comprises administering an agent that activates or up-regulates the expression of a transport protein, and administering aspartate, or an analog thereof, or a pharmaceutically acceptable salt, stereoisomer, tautomer, solvate, hydrate, polymorph, or prodrug thereof. In certain embodiments, the transport protein is an aspartate transport protein. In certain embodiments, the transport protein is an SLC protein (e.g., SLC1A3).

The biosynthesis of aspartate via the tricarboxylic acid cycle requires $NAD^+$, for example, in the oxidation of α-ketoglutarate to succinate, and the oxidation of malate to oxaloacetate. When mitochondrial respiration is defective, the TCA cycle may be blocked if NADH cannot transfer electrons (ultimately to $O_2$) to resupply $NAD^+$. An agent administered in a method described herein may increase intracellular levels of aspartate by acting as an electron acceptor in place of respiration (e.g., oxidizing NADH to NAD+). Thus, another type of agent capable of increasing intracellular aspartate levels are electron acceptor agents that promote oxidation of NADH to NAD+. In certain embodiments, provided herein are methods, compositions, and systems for treating a mitochondrial disorder comprising administering to a subject in need thereof an electron acceptor agent. In certain embodiments, provided herein are methods, compositions, and systems for treating a neurodegenerative disease comprising administering to a subject in need thereof an electron acceptor agent. In some embodiments, the electron acceptor agent is reduced by two electrons. In some embodiments, the electron acceptor agent is reduced by two electrons, and gains two protons. In some embodiments, the electron acceptor agent comprises a carbonyl. In some embodiments, the carbonyl is reduced to a secondary alcohol. In some embodiments, the electron acceptor agent is capable of oxidizing NADH. In some embodiments, the electron acceptor agent is a substrate of a dehydrogenase. In some embodiments, the electron acceptor agent is a substrate of lactate dehydrogenase (LDH). In some embodiments, the electron acceptor agent is a substrate of malate dehydrogenase or glutamate dehydrogenase.

In certain embodiments, the electron acceptor agent is pyruvate, or an analog thereof, or a pharmaceutically acceptable salt, stereoisomer, tautomer, solvate, hydrate, polymorph, or prodrug thereof. In some embodiments, the electron accepter agent is pyruvate, or an analog thereof. In some embodiments, the electron acceptor agent is pyruvate. In some embodiments, the electron acceptor agent is not pyruvate. In some embodiments, the electron acceptor agent is not aspartate, α-ketoglutarate, or α-ketobutyrate. In certain embodiments, the electron acceptor agent is α-ketobutyrate, or an analog thereof, or a pharmaceutically acceptable salt, stereoisomer, tautomer, solvate, hydrate, polymorph, or prodrug thereof. In some embodiments, the electron accepter agent is α-ketobutyrate, or an analog thereof. In some embodiments, the electron acceptor agent is α-ketobutyrate. Pyruvate and α-ketobutyrate are of the formula:

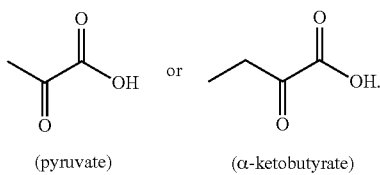

(pyruvate)     (α-ketobutyrate)

In some embodiments, the electron acceptor agent is an α-ketoacid. In some embodiments, the electron acceptor is an optionally substituted $C_3$-$C_6$ α-ketoacid.

In some embodiments, the electron acceptor agent is not metabolized the liver, or is metabolized to a lesser extent by the liver than pyruvate. In some embodiments, the electron acceptor is a pyruvate analog which is not metabolized the liver, or is metabolized to a lesser extent by the liver than pyruvate.

Pyruvate, formed biosynthetically (e.g., glycolysis) or administered exogenously, may be metabolized by the liver prior to uptake by cells elsewhere in the body. In certain embodiments, provided herein are methods, compositions, and systems for treating a mitochondrial disorder comprising administering to a subject an agent that reduces pyruvate consumption by the liver. In certain provided herein are methods, compositions, and systems for treating a neurodegenerative disease comprising administering to a subject an agent that reduces pyruvate consumption by the liver. In some embodiments, administering the agent increases the pyruvate concentration in the blood serum. In some embodiments, administering the agent increases intracellular levels of pyruvate in non-liver cells. In some embodiments, the agent is an inhibitor of the pyruvate dehydrogenase complex (PDC). In some embodiments, the agent is an inhibitor of pyruvate decarboxylase (PC). In some embodiments, the agent is an inhibitor of alanine transaminase (ALT). In some embodiments, the agent down-regulates the expression of one or more enzymes of the pyruvate dehydrogenase complex (PDC). In some embodiments, the agent down-regulates the expression of pyruvate decarboxylase (PC). In some embodiments, the agent down-regulates the expression of alanine transaminase (ALT).

The pyruvate dehydrogenase complex (PDC) converts pyruvate to acetyl-CoA. The PDC is regulated by pyruvate dehydrogenase kinase (PDK, deactivates PDC) and pyruvate dehydrogenase phosphatase (PDP, activates PDC). In some embodiments, the agent is an activator of pyruvate dehydrogenase kinase (PDK). In some embodiments, the agent is an inhibitor of pyruvate dehydrogenase phosphatase. In some embodiments, the agent up-regulates the expression of PDK. In some embodiments, the agent down-regulates the expression of PDP. In some embodiments, the agent is ATP, NADH, or acetyl-CoA.

In certain embodiments, the agent inhibits uptake of pyruvate by the liver. In certain embodiments, the agent inhibits uptake of pyruvate by mitochondria. In certain embodiments, the agent is an antagonist of a pyruvate transport protein. In certain embodiments, the agent is an antagonist of a lactate transport protein. In some embodiments, the agent is an antagonist of a monocarboxylate transporter (MCT). In some embodiments, the agent is an antagonist of pyruvate translocase. In some embodiments, the agent down-regulates the expression of pyruvate transport protein. In some embodiments, the agent down-regulates the expression of a lactate transport protein. In some embodiments, the agent down-regulates the expression of a monocarboxylate transporter. In some embodiments, the agent down-regulates the expression of pyruvate translocase.

Also contemplated as electron acceptor agents are substrates of lactate dehydrogenase (LDH) other than pyruvate and α-ketobutyrate. In certain embodiments, the substrate is a glyoxylic acid analog, or a pharmaceutically acceptable salt, stereoisomer, tautomer, solvate, hydrate, polymorph, or prodrug thereof. In certain embodiments, the substrate is 2-oxopentanoate, 3-methyl-2-oxopentanoate, 4-methyl-2-oxopentanoate, fluoropyruvate, or chloropyruvate, or an analog thereof, or a pharmaceutically acceptable salt, stereoisomer, tautomer, solvate, hydrate, polymorph, or prodrug thereof. In certain embodiments, the substrate is of formula:

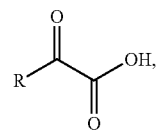

or a pharmaceutically acceptable salt, stereoisomer, tautomer, solvate, hydrate, polymorph, or prodrug thereof, wherein R is selected from the group consisting of hydrogen, methyl, ethyl, n-propyl, n-butyl, iso-propyl, cyclopropyl, benzyl, n-hexyl, indol-3-ylmethyl, 2-furyl, —CH$_2$F, —CH$_2$Cl, —CH$_2$Br, —CH$_2$OH, —CH$_2$SH, —CH$_2$CH$_2$OH, —CH$_2$CH$_2$OH, —CH$_2$(C=O)CH$_3$, and —CH$_2$CH$_2$SCH$_3$. In certain embodiments, the substrate is a lactate dehydrogenase (LDH) substrate disclosed in Kim et al., *J. Am. Chem. Soc.* (1988) 110, 2959-2964; or Chenault et al., *Bioorg. Chem.* (1989) 17, 400-409, each of which is incorporated herein by reference.

The electron acceptor agent may be a substrate of particular lactate dehydrogenase isozyme. The electron acceptor agent may be a substrate of particular lactate dehydrogenase subunit, including but not limited to: 'muscle subunit' LDH-M, encoded by the LDHA gene; 'heart subunit' LDH-H, encoded by the LDHB gene; LDHC, encoded by the LDHC gene; and LDHBx, a readthrough variant of the LDHB gene. In certain embodiments, the electron acceptor agent is a substrate of LDH-1, which has four heart subunits. In certain embodiments, the electron acceptor agent is a substrate of LDH-2, which has three heart and one muscle subunits. In certain embodiments, the electron acceptor agent is a substrate of LDH-3, which has two heart and two muscle subunits. In certain embodiments, the electron acceptor agent is a substrate of LDH-4, which has one hear and three muscle subunits. In certain embodiments, the electron acceptor agent is a substrate of LDH-5, which has four muscle subunits.

The electron acceptor agent may be a substrate of several LDH isozymes, but may, in some embodiments, be preferably metabolized by a particular isozyme compared to other LDH isozymes. The preference may be measured by comparing the $k_{cat}$ for consumption of the substrate by various isozymes. The isozyme with the largest $k_{cat}$ for the substrate is the isozyme that preferably metabolizes the substrate. In certain embodiments, the electron acceptor agent is preferably metabolized by LDH-1, which has four heart subunits. In certain embodiments, the electron acceptor agent is preferably metabolized by LDH-2, which has three heart and one muscle subunits. In certain embodiments, the electron acceptor agent is preferably metabolized by LDH-3, which has two heart and two muscle subunits. In certain embodiments, the electron acceptor agent is preferably metabolized by LDH-4, which has one hear and three muscle subunits. In certain embodiments, the electron acceptor agent is preferably metabolized by LDH-5, which has four muscle subunits.

The electron acceptor agent may be a substrate of LDH, and may be metabolized by LDH in a particular cell or tissue. In some embodiments, the electron acceptor is metabolized by LDH with a mitochondrial disorder (e.g., cells with impaired mitochondrial respiration). In some embodiments, the electron acceptor is metabolized by LDH in nerve cells, muscle cells, cardiac muscle cells, or blood cells. In some embodiments, the electron acceptor is metabolized by LDH in nerve cells. In some embodiments, the electron acceptor is metabolized by LDH in tissue of the liver, central nervous system, pancreas, spleen, cardiovascular system, muscles, bone marrow, eye, or gastrointestinal system. In some embodiments, the electron acceptor is metabolized by LDH in tissue of the central nervous system. In some embodiments, the electron acceptor is metabolized by LDH in skeletal muscle tissue. In some embodiments, the electron acceptor is metabolized by LDH in cardiac muscle tissue. In certain embodiments, the electron acceptor is metabolized by LDH in red blood cells. In certain embodiments, the electron acceptor is metabolized by LDH in cells or tissue of the mononuclear phagocyte system (e.g., phagocytes in reticular connective tissue, phagocytes in lymph nodes or the spleen, Kupffer cells, histiocytes).

In another aspect, provided herein are methods, compositions, and systems for treating a mitochondrial disorder comprising administering an agent that increases the ratio of NAD$^+$ to NADH. In another aspect, provided herein are methods, compositions, and systems for treating a neurodegenerative disease comprising administering an agent that increases the intracellular ratio of NAD$^+$ to NADH. In some embodiments, the agent is a substrate of a dehydrogenase. In some embodiments, the agent is a substrate of lactate dehydrogenase (LDH). In some embodiments, the agent is a substrate of malate dehydrogenase or glutamate dehydrogenase In certain embodiments, the agent is pyruvate, or an analog thereof, or a pharmaceutically acceptable salt, stereoisomer, tautomer, solvate, hydrate, polymorph, or prodrug thereof. In some embodiments, the agent is pyruvate, or an analog thereof. In some embodiments, the agent is pyruvate. In some embodiments, the agent is not pyruvate. In some embodiments, the agent is α-ketobutyrate, or an analog thereof. In some embodiments, the agent is α-ketobutyrate. In some embodiments, the agent is not α-ketobutyrate. In some embodiments, the agent is not aspartate. In some embodiments, the agent is not α-ketoglutarate. In certain embodiments, the agent is an antagonist of a pyruvate transport protein. In certain embodiments, the agent is an antagonist of a lactate transport protein. In some embodiments, the agent is an antagonist of a monocarboxylate transporter (MCT). In some embodiments, the agent is an antagonist of pyruvate translocase. In some embodiments, the agent down-regulates the expression of pyruvate transport protein. In some embodiments, the agent down-regulates the expression of a lactate transport protein. In some embodiments, the agent down-regulates the expression of a monocarboxylate transporter. In some embodiments, the agent down-regulates the expression of pyruvate translocase.

Administration of an agent (e.g., electron acceptor agent) described herein may increase the intracellular NAD$^+$/NADH ratio to a specific ratio or range. In some embodiments, administration of the agent provides an intracellular NAD$^+$/NADH ratio of at least about 1:1, at least about 1.5:1, at least about 2:1, at least about 3:1, at least about 4:1, at least about 5:1, at least about 6:1, at least about 7:1, at least about 8:1, at least about 9:1 or at least about 10:1, in cells or tissue in need thereof. In some embodiments, administration of the agent provides an intracellular NAD$^+$/NADH ratio of at least about 15:1, at least about 20:1, at least about 25:1, at least about 30:1, at least about 50:1, at least about 100:1, at least about 250:1, at least about 500:1, at least about 750:1, at least about 1000:1, at least about 1500:1, or at least about 2000:1, in cells or tissue in need thereof. In certain embodiments, administration of the agent provides an intracellular NAD$^+$/NADH ratio of between about 2:1 and about 100:1, between about 2:1 and about 50:1, between about 2:1 and about 20:1, or between about 2:1 and about 10:1, in cells or tissue in need thereof. In certain embodiments, administration of the agent provides an intracellular NAD$^+$/NADH ratio of between about 2:1 and about 8:1, between about 2:1 and about 6:1, between about 2:1 and about 4:1, or between about 2:1 and about 3:1, in cells or tissue in need thereof. In certain embodiments, administration of the agent provides an intracellular NAD$^+$/NADH ratio of between about 100:1 and about 2000:1, between about 200:1 and about 2000:1, between about 500:1 and about 2000:1, between about 750:1 and about 2000:1, or between about 1000:1 and about 2000:1, in cells or tissue in need thereof.

Administration of an agent (e.g., electron acceptor agent) described herein may increase the intracellular $NAD^+$/NADH ratio in cells or tissue in need thereof relative to the $NAD^+$/NADH ratio prior to administration of the agent. In certain embodiments, the increase in intracellular $NAD^+$/NADH ratio in cells or tissue in need thereof is at least about at least about 1.1 fold, at least about 1.25 fold, 1.5 fold, at least about 2 fold, at least about 3 fold, at least about 4 fold, at least about 5 fold, at least about 10 fold, at least about 20 fold, at least about 50 fold, at least about 100 fold, at least about 200 fold, at least about 500 fold, or at least about 1000 fold. In certain embodiments, the increase in intracellular $NAD^+$/NADH ratio in cells or tissue in need thereof is between about 1.25 fold and about 10 fold, between about 1.5 fold and about 10 fold, between about 2 fold and about 10 fold, between about 3 fold and about 10 fold, between about 4 fold and about 10 fold, or between about 5 fold and about 10 fold. In certain embodiments, the increase in intracellular $NAD^+$/NADH ratio in cells or tissue in need thereof is between about 2 fold and about 100 fold, between about 2 fold and about 50 fold, between about 2 fold and about 20 fold, between about 2 fold and about 10 fold, or between about 2 fold and about 5 fold. In certain embodiments, the increase in intracellular $NAD^+$/NADH ratio in cells or tissue in need thereof is between about 2 fold and about 1000 fold, between about 20 fold and about 1000 fold, between about 100 fold and about 1000 fold, between about 200 fold and about 1000 fold, or between about 500 fold and about 1000 fold.

The increase in $NAD^+$/NADH ratio following administration of an agent described herein may occur in specific cells or specific tissue. In some embodiments, the increase occurs in cells with a mitochondrial disorder (e.g., cells with impaired mitochondrial respiration). In some embodiments, the increase occurs in nerve cells, muscle cells, cardiac muscle cells, or blood cells. In some embodiments, the increase occurs in nerve cells. In some embodiments, the increase occurs in tissue of the liver, central nervous system, pancreas, spleen, cardiovascular system, muscles, bone marrow, eye, or gastrointestinal system. In some embodiments, the increase occurs in tissue of the central nervous system. In some embodiments, the increase occurs in skeletal muscle tissue. In some embodiments, the increase occurs in cardiac muscle tissue.

The increase in $NAD^+$/NADH ratio relative to pre-administration levels or normal levels may be effective for a time duration following administration of the agent. For example, if in a particular embodiment the agent provides an $NAD^+$/NADH ratio of at least 4:1, the ratio will remain at or above a 4:1 for the length of the time duration. In some embodiments, the time duration is at least about 1 hour, at least about 2 hours, at least about 4 hours, at least about 8 hours, at least about 12 hours, at least about 24 hours, at least about 36 hours, or at least about 48 hours. In some embodiments, the time duration is at least about 3 days, at least about 7 days, at least about 14 days, or at least about 30 days. In some embodiments the time duration is between about 1 hour and 24 hours, between about 1 hour and 12 hours, between about 1 hour and 8 hours, or between about 1 hour and 4 hours. In some embodiments, the time duration is between about 4 hours and 48 hours, between about 8 hours and 48 hours, between about 12 hours and 48 hours, between about 24 hours and about 48 hours, or between about 36 hours and about 48 hours. In some embodiments, the time duration is between about 3 hours and 30 days, between about 3 days and about 14 days, or between about 3 days and about 7 days.

Administration of an agent (e.g., electron acceptor agent) described herein may increase the intracellular $NAD^+$ levels in cells or tissue in need thereof relative to $NAD^+$ levels prior to administration of the agent. In certain embodiments, the increase in intracellular $NAD^+$ levels in cells or tissue in need thereof is at least about 1.1 fold, at least about 1.25 fold, at least about 1.5 fold, at least about 2 fold, at least about 5 fold, at least about 10 fold, at least about 20 fold, at least about 50 fold, at least about 100 fold, at least about 200 fold, at least about 500 fold, or at least about 1000 fold. In certain embodiments, the increase in intracellular $NAD^+$ levels in cells or tissue in need thereof is between about 2 fold and about 100 fold, between about 2 fold and about 50 fold, between about 2 fold and about 20 fold, between about 2 fold and about 10 fold, or between about 2 fold and about 5 fold. In certain embodiments, the increase in intracellular $NAD^+$ levels in cells or tissue in need thereof is between about 2 fold and about 1000 fold, between about 20 fold and about 1000 fold, between about 100 fold and about 1000 fold, between about 200 fold and about 1000 fold, or between about 500 fold and about 1000 fold.

Administration of an agent (e.g., electron acceptor agent) described herein may restore the intracellular $NAD^+$ levels in cells or tissue in need thereof to normal levels. A normal level is defined as the homeostatic $NAD^+$ level in cells or tissue for a healthy subject, e.g., a subject with no mitochondrial disorder. In some embodiments, administration of the agent increases NAD levels to normal levels for cells or tissue in need thereof. In some embodiments, administration of the agent increases $NAD^+$ levels to between about 90% and about 100% of normal levels, to between about 80% and about 90% of normal levels, to between about 70% and about 80% of normal levels, to between about 60% and about 70% of normal levels, or to between about 50% and about 60% of normal levels for cells or tissue in need thereof. In some embodiments, administration of the agent increases $NAD^+$ levels to between about 30% and about 50% of normal levels, or to between about 10% and about 30% of normal levels for cells or tissue in need thereof. In some embodiments, administration of the agent increases $NAD^+$ levels to between about 100% and about 125% of normal levels, between about 125% and about 150% of normal levels, or between about 150% and about 250% of normal levels for cells or tissue in need thereof.

The increase in $NAD^+$ levels following administration of an agent described herein may occur in specific cells or specific tissue. In some embodiments, the increase occurs in cells with a mitochondrial disorder (e.g., cells with impaired mitochondrial respiration). In some embodiments, the increase occurs in nerve cells, muscle cells, cardiac muscle cells, or blood cells. In some embodiments, the increase occurs in nerve cells. In some embodiments, the increase occurs in tissue of the liver, central nervous system, pancreas, spleen, cardiovascular system, muscles, bone marrow, eye, or gastrointestinal system. In some embodiments, the increase occurs in tissue of the central nervous system. In some embodiments, the increase occurs in skeletal muscle tissue. In some embodiments, the increase occurs in cardiac muscle tissue.

The increase in $NAD^+$ levels relative to pre-administration levels or normal levels may be effective for a time duration following administration of the agent. For example, if in a particular embodiment the agent provides an increase of at least 5 fold, the intracellular levels will remain at or above a 5 fold increase for the length of the time duration. In some embodiments, the time duration is at least about 1 hour, at least about 2 hours, at least about 4 hours, at least about 8 hours, at least about 12 hours, at least about 24 hours, at least about 36 hours, or at least about 48 hours. In some embodiments, the time duration is at least about 3 days, at least about 7 days, at least about 14 days, or at least about 30 days. In some embodiments the time duration is between about 1 hour and 24 hours, between about 1 hour and 12 hours, between about 1 hour and 8 hours, or between about 1 hour and 4 hours. In some embodiments, the time duration is between about 4 hours and 48 hours, between about 8 hours and 48 hours, between about 12 hours and 48 hours, between about 24 hours and about 48 hours, or between about 36 hours and about 48 hours. In some embodiments, the time duration is between about 3 hours and 30 days, between about 3 days and about 14 days, or between about 3 days and about 7 days.

In certain embodiments, the agent is nicotinamide, or an analog thereof, or a pharmaceutically acceptable salt, stereoisomer, tautomer, solvate, hydrate, polymorph, or prodrug thereof. In certain embodiments, the agent is nicotinamide riboside, or an analog thereof, or a pharmaceutically acceptable salt, stereoisomer, tautomer, solvate, hydrate, polymorph, or prodrug thereof. In certain embodiments, the agent is nicotinamide mononucleotide, or an analog thereof, or a pharmaceutically acceptable salt, stereoisomer, tautomer, solvate, hydrate, polymorph, or prodrug thereof. In certain embodiments, the agent is niacin, or an analog thereof, or a pharmaceutically acceptable salt, stereoisomer, tautomer, solvate, hydrate, polymorph, or prodrug thereof.

In certain embodiments, the agent is an inhibitor of a poly (ADP-ribose) polymerase (PARP). In some embodiments, the agent is an inhibitor of PARP1, PARP2, PARP3, VPARP, Tankyrase-1, Tankyrase-2, PARP6, TIPARP, PARP8, PARP9, PARP10, PARP11, PARP12, PARP14, PARP15, or PARP16. In some embodiments, the agent is iniparib, talazoparib, olaparib, rucaparib, veliparib, CEP 9722, MK 4827, BGB-290, 3-aminobenzamide, or an analog thereof, or a pharmaceutically acceptable salt, stereoisomer, tautomer, solvate, hydrate, polymorph, or prodrug thereof. In certain embodiments, the agent is an inhibitor of CD38. In certain embodiments, the agent is an inhibitor of a sirtuin. In some embodiments, the agent is an inhibitor of SIRT1, SIRT2, SIRT3, SIRT4, SIRT5, SIRT6, or SIRT7.

In certain embodiments, the agent is a compound disclosed in U.S. patent application Ser. No. 13/351,411, filed Jan. 17, 2012, which is incorporated herein by reference. In certain embodiments, the agent is not a compound disclosed in U.S. patent application Ser. No. 13/351,411. In certain embodiments, the agent is of formula:

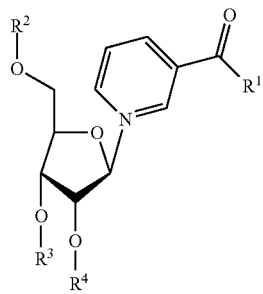

or

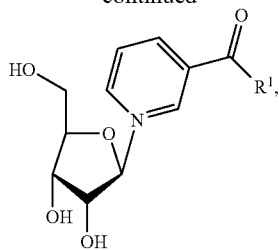

or a pharmaceutically acceptable salt, stereoisomer, or tautomer thereof, wherein:

$R^1$ is substituted or unsubstituted alkoxy, substituted or unsubstituted aryloxy, substituted or unsubstituted arylthio, substituted or unsubstituted aminooxy, substituted or unsubstituted N-alkylaminooxy, substituted or unsubstituted alkylamino, substituted or unsubstituted dialkylamino, substituted or unsubstituted hydrazine, substituted or unsubstituted N-alkylaminohydrazino, substituted or unsubstituted hydroxylamino, or substituted or unsubstituted O-alkoxyamino; and and each of $R^2$, $R^3$, and $R^4$ is independently substituted or unsubstituted carbonyl.

In certain embodiments, the agent is a compound disclosed in U.S. patent application Ser. No. 11/396,359, filed Mar. 30, 2006, which is incorporated herein by reference. In certain embodiments, the agent is not a compound disclosed in U.S. patent application Ser. No. 11/396,359. In certain embodiments, the agent is of formula:

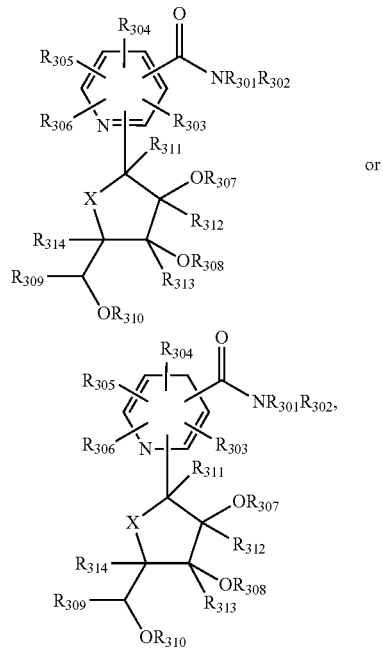

or a pharmaceutically acceptable salt, stereoisomer, or tautomer thereof, wherein:

each of $R_{301}$ and $R_{302}$ is independently hydrogen, substituted or unsubstituted alkyl, substituted or unsubstituted alkenyl, substituted or unsubstituted alkynyl, substituted or unsubstituted non-aromatic heterocyclyl, or substituted or unsubstituted aryl, or $R_{301}$ and $R_{302}$ taken together with the atom to which they are attached form a substituted or unsubstituted non-aromatic heterocyclic ring;

each of $R_{303}$, $R_{304}$, $R_{305}$ and $R_{306}$ is independently hydrogen, substituted or unsubstituted alkyl, substituted or unsubstituted aryl, substituted or unsubstituted non-aromatic heterocyclyl, halogen, —OR, —CN, —CO$_2$R, —OCOR, —OCO$_2$R, —C(O)NRR', —OC(O)NRR', —C(O)R, —COR, —SR, —OSO$_3$H, —S(O)$_n$R, —S(O)$_n$OR, —S(O)$_n$NRR', —NRR', —NRC(O)OR', —NO$_2$, or —NRC(O)R';

each of $R_{307}$, $R_{308}$ and $R_{310}$ is independently hydrogen, substituted or unsubstituted alkyl, substituted or unsubstituted aryl, —C(O)R, —C(O)OR, —C(O)NHR, —C(S)R, —C(S)OR, or —C(O)SR;

$R_{309}$ is hydrogen, substituted or unsubstituted alkyl, substituted or unsubstituted aryl, substituted or unsubstituted non-aromatic heterocyclyl, halogen, —OR, —CN, —CO$_2$R, —OCOR, —OCO$_2$R, —C(O)NRR', —OC(O)NRR', —C(O)R, —COR, —SR, —OSO$_3$H, —S(O)$_n$R, —S(O)$_n$OR, S(O)$_n$NRR', —NRR', —NRC(O)OR', or —NRC(O)R';

each of $R_{311}$, $R_{312}$, $R_{313}$ and $R_{314}$ is independently hydrogen, substituted or unsubstituted alkyl, substituted or unsubstituted aryl, substituted or unsubstituted non-aromatic heterocyclyl, halogen, —CN, —CO$_2$R, —OCOR, —OCO$_2$R, —C(O)NRR', —OC(O)NRR', —C(O)R, —COR, —OSO$_3$H, —S(O)$_n$R, —S(O)$_n$OR, —S(O)$_n$NRR', —NRR', —NRC(O)OR', —NO$_2$ and —NRC(O)R';

each occurrence of R and R' is independently hydrogen, substituted or unsubstituted alkyl, substituted or unsubstituted aryl, or substituted or unsubstituted non-aromatic heterocyclyl;

X is O or S; and each occurrence of n is independently 1 or 2.

In certain embodiments, the agent is a modulator of a dehydrogenase. In certain embodiments, the agent is a modulator of an NADH dehydrogenase. In certain embodiments, the agent is a modulator of a NADH (quinone) dehydrogenase. In certain embodiments, the agent is an activator of NAD(P)H dehydrogenase (quinone) 1 or 2 (NQO1 or NQO2). In some embodiments, the modulator is an activator.

In some embodiments, the modulator is a physiologically occurring substrate of the NADH dehydrogenase (e.g., NQO1, NQO2). In some embodiments, the modulator is a native substrate of the NADH dehydrogenase. In some embodiments, the modulator is non-physiologically occurring substrate of the NADH dehydrogenase. In certain embodiments, the substrate is a quinone, or an analog thereof, or a pharmaceutically acceptable salt, stereoisomer, tautomer, solvate, hydrate, polymorph, or prodrug thereof. In some embodiments, the substrate is ubiquinone, 1,2-benzoquinone, 1,4-benzoquinone, duroquinone, or juglone, or an analog thereof, or a pharmaceutically acceptable salt, stereoisomer, tautomer, solvate, hydrate, polymorph, or prodrug thereof. In some embodiments, the substrate is plastoquinone, phylloquinone (Vitamin K$_1$), menaquinone (Vitamin K$_2$), menadione (Vitamin K$_3$), Vitamin K$_4$, Vitamin K$_5$, 1,4-napthoquinone, lawsone, or pyrroloquinoline quinone, or an analog thereof, or a pharmaceutically acceptable salt, stereoisomer, tautomer, solvate, hydrate, polymorph, or prodrug thereof. In some embodiments, the substrate is mitomycin C, RH1, E09, streptonigrin, 3-lapchone, idebenone, or deoxynyboquinone, or an analog thereof, or a pharmaceutically acceptable salt, stereoisomer, tautomer, solvate, hydrate, polymorph, or prodrug thereof. In certain embodiments, the substrate is a quinonimine, or an analog thereof, or a pharmaceutically acceptable salt, stereoisomer, tautomer, solvate, hydrate, polymorph, or prodrug thereof. In certain embodiments, the substrate is a Vitamin E (e.g., α-tocopherol, β-tocopherol, γ-tocopherol, δ-tocopherol, α-tocotrienol, β-tocotrienol, γ-tocotrienol, δ-tocotrienol), or an analog thereof, or a pharmaceutically acceptable salt, stereoisomer, tautomer, solvate, hydrate, polymorph, or prodrug thereof. In some embodiments, the substrate is a nitroaromatic compound. In some embodiments, the substrate is an organic dye (e.g., methylene blue). In some embodiments, the substrate is an azo compound.

The agent may increase intracellular levels of aspartate by attenuating aspartate flux through the urea cycle. In certain embodiments, the agent is an inhibitor of arginosuccinate synthetase. In certain embodiments, the agent is an inhibitor of arginosuccinate lyase, arginase 1, or ornithine transcarbamoylase. In certain embodiments, the agent down-regulates the expression of arginosuccinate synthetase. In certain embodiments, the agent down-regulates the expression of arginosuccinate lyase, arginase 1, or ornithine transcarbamoylase. In certain embodiments, the agent is arginosuccinate, or an analog thereof. In certain embodiments, the agent is fumarate, or analog thereof. In certain embodiments, the agent is arginine, or an analog thereof.

An agent described herein may have more than one effect. The agent may directly or indirectly cause more than one of the desired changes in cellular metabolism described herein. For example, and electron acceptor agent may increase the NAD$^+$/NADH ratio, and the increased ratio may promote aspartate biosynthesis leading to increased intracellular aspartate levels. In certain embodiments, the agent is an electron acceptor agent and is an agent that increases intracellular levels of aspartate in cells or tissue in need thereof. In certain embodiments, the agent is pyruvate or α-ketobutyrate, or an analog thereof, and is an agent that increases intracellular levels of aspartate in cells or tissue in need thereof.

In certain embodiments, administration of the agent (i) increases intracellular levels of aspartate by at least about 1.1 fold, at least about 1.25 fold, at least about 1.5 fold, at least about 2 fold, at least about 2.5 fold, at least about 3 fold, at least about 5 fold, at least about 10 fold, at least about 15 fold, at least about 25 fold, at least about 50 fold, at least about 100 fold, at least about 200 fold, at least about 500 fold, or at least about 1000 fold; and (ii) increases the NAD$^+$/NADH ratio at least about 1.1 fold, at least about 1.25 fold, 1.5 fold, at least about 2 fold, at least about 3 fold, at least about 4 fold, at least about 5 fold, at least about 10 fold, at least about 20 fold, at least about 50 fold, at least about 100 fold, at least about 200 fold, at least about 500 fold, or at least about 1000 fold, in cells or tissue in need thereof.

In certain embodiments, administration of the agent (i) increases intracellular levels of aspartate by between about 1.5 fold and about 50 fold, between about 1.5 fold and about 25 fold, between about 1.5 fold and 10 fold, or between about 1.5 fold and about 5 fold; and (ii) increases the NAD$^+$/NADH ratio between about 1.25 fold and about 10 fold, between about 1.5 fold and about 10 fold, between about 2 fold and about 10 fold, between about 3 fold and about 10 fold, between about 4 fold and about 10 fold, or between about 5 fold and about 10 fold.

In certain embodiments, administration of the agent (i) increases intracellular levels of aspartate by between about 1.5 fold and about 50 fold, between about 1.5 fold and about 25 fold, between about 1.5 fold and 10 fold, or between about 1.5 fold and about 5 fold; and (ii) increases the NAD$^+$/NADH ratio between about 1.25 fold and about 10 fold, between about 1.5 fold and about 10 fold, between about 2 fold and about 10 fold, between about 3 fold and about 10 fold, between about 4 fold and about 10 fold, or between about 5 fold and about 10 fold.

The increase in intracellular aspartate levels and NAD$^+$/NADH ratio following administration of an agent described herein may occur in specific cells or specific tissue. In some embodiments, the increase occurs in cells with a mitochondrial disorder (e.g., cells with impaired mitochondrial respiration). In some embodiments, the increase occurs in nerve cells, muscle cells, cardiac muscle cells, or blood cells. In some embodiments, the increase occurs in nerve cells. In some embodiments, the increase occurs in tissue of the liver, central nervous system, pancreas, spleen, cardiovascular system, muscles, bone marrow, eye, or gastrointestinal system. In some embodiments, the increase occurs in tissue of the central nervous system. In some embodiments, the increase occurs in skeletal muscle tissue. In some embodiments, the increase occurs in cardiac muscle tissue.

The increase in intracellular aspartate levels and NAD$^+$/NADH ratio relative to pre-administration levels or normal levels may be effective for a time duration following administration of the agent. In some embodiments, the time duration is at least about 1 hour, at least about 2 hours, at least about 4 hours, at least about 8 hours, at least about 12 hours, at least about 24 hours, at least about 36 hours, or at least about 48 hours. In some embodiments, the time duration is at least about 3 days, at least about 7 days, at least about 14 days, or at least about 30 days. In some embodiments the time duration is between about 1 hour and 24 hours, between about 1 hour and 12 hours, between about 1 hour and 8 hours, or between about 1 hour and 4 hours. In some embodiments, the time duration is between about 4 hours and 48 hours, between about 8 hours and 48 hours, between about 12 hours and 48 hours, between about 24 hours and about 48 hours, or between about 36 hours and about 48 hours. In some embodiments, the time duration is between about 3 hours and 30 days, between about 3 days and about 14 days, or between about 3 days and about 7 days.

In certain embodiments, the method of treatment comprises administering two or more agents described herein. Such combinations include combinations of agents of the same type (e.g., both aspartate analogs) or different type (e.g., an electron acceptor agent and an agent which increases intracellular aspartate levels). In certain embodiments, the combination of two or more agents will have an additive effect. In certain embodiments, the combination of two or more agents will have a synergistic effect.

In certain embodiments, the method comprises administering an agent that increases intracellular aspartate levels and an electron acceptor agent. In certain embodiments, the method comprises administering an agent that increases intracellular aspartate levels and an agent that increases the NAD$^+$/NADH ratio. In some embodiments, the agent that increases intracellular aspartate levels is: aspartate, or an analog thereof; an aspartate prodrug; an agent that activates or up-regulates GOT1; an agent activates or up-regulates GOT2, MDH, PC or IDH; an agonist or up-regulator of a glutamate or aspartate transport protein. In some embodiments, the electron acceptor agent is: pyruvate, or an analog thereof; β-ketobutyrate, or an analog thereof; a substrate of LDH, malate dehydrogenase, or glutamate dehydrogenase. In some embodiments, the agent that increases the NAD$^+$/NADH ratio is an electron acceptor agent. In some embodiments, the agent that increases the NAD$^+$/NADH ratio is: nicotinamide, niacin, nicotinamide riboside, nicotinamide mononucleotide, or an analog thereof; or a substrate of NQO1 or NQO2 (e.g., ubiquinone, benzoquinone, juglone, duroquinone, a Vitamin K, a Vitamin E, or analogs thereof).

In certain embodiments, the method comprises administering aspartate or an aspartate prodrug, or an analog thereof, and an agent that increases the NAD$^+$/NADH ratio. In some embodiments, the agent that increases the NAD$^+$/NADH ratio is an electron acceptor agent. In some embodiments, the agent that increases the NAD$^+$/NADH ratio is: nicotinamide, niacin, nicotinamide riboside, nicotinamide mononucleotide, or an analog thereof; or a substrate of NQO1 or NQO2 (e.g., ubiquinone, benzoquinone, juglone, duroquinone, a Vitamin K, a Vitamin E, or analogs thereof).

In certain embodiments, the method comprises administering aspartate or an aspartate prodrug, or an analog thereof, and an agent that increases transport of aspartate, or an analog thereof, into cells. In some embodiments, the agent that increases transport of aspartate is an agonist of a glutamate or aspartate transport protein, an agent that up-regulates the expression of a glutamate or aspartate protein. In the agent that increases transport of aspartate is an agonist of SLC1A3, an EAAT, or a VGLUT, or an agent that up-regulates the expression of SLC1A3, an EAAT, or a VGLUT.

In some embodiments, the method comprises administering pyruvate, or an analog thereof, and an agent that reduces pyruvate consumption by the liver. In some embodiments, the agent that reduces pyruvate consumption by the liver is an inhibitor of PDC, PC, ALT, or PDP, or an agent that down-regulates expression of PDC, PC, ALT, or PDP. In some embodiments, the agent that reduces pyruvate consumption by the liver is an antagonist of a monocarboxylate transporter (MCT) (e.g., pyruvate translocase), or an agent that down-regulates expression of a monocarboxylate transporter.

Certain methods described herein may comprise administering one or more additional pharmaceutical agent(s) in combination with an agent or pharmaceutical composition described herein. The additional pharmaceutical agent(s) may be administered at the same time as the agent or pharmaceutical composition or at different times than the agent or pharmaceutical composition. For example, the agent the agent and the additional pharmaceutical agent(s) may be administered on the same dosing schedule or different dosing schedules. All or some doses of the an agent or pharmaceutical composition may be administered before all or some doses of an additional pharmaceutical agent, after all or some does an additional pharmaceutical agent, within a dosing schedule of an additional pharmaceutical agent, or a combination thereof. The timing of administration of the agent or pharmaceutical composition and additional pharmaceutical agents may be different for different additional pharmaceutical agents.

An additional pharmaceutical agent may be an agent useful in the treatment of mitochondrial disorders or neurodegenerative diseases. In certain embodiments, the additional agent is another agent described herein. In certain embodiments, the additional agent is aspartate, or an aspartate analog, or a pharmaceutically acceptable salt, stereoisomer, tautomer, solvate, hydrate, polymorph, or prodrug thereof. In certain embodiments, the additional agent is a prodrug of aspartate or a prodrug of an aspartate analog. In certain embodiments, the additional agent is a metabolic precursor to aspartate. In certain embodiments, the additional agent is a polypeptide comprising aspartate (e.g., an aspartate rich polypeptide or protein).

In certain embodiments, the additional agent is an agent that increases intracellular aspartate levels. In some embodiments, the additional agent is an activator of GOT1, or up-regulates the expression of GOT1. In some embodiments, the additional agent is an activator of GOT2, MDH, PC, or IDH, or up-regulates the expression of GOT2, MDH, PC, or IDH. In certain embodiments, the additional agent is an agent that increases the transport of aspartate, or an analog thereof, into cells. In some embodiments, the additional agent is an agonist of a glutamate or aspartate transport protein, or up-regulates the expression of a glutamate or aspartate protein. In some embodiments, the additional agent is an agonist of SLC1A3, or up-regulates the expression of SLC1A3. In some embodiments, the additional agent is an agonist of an excitatory amino acid transporter (EAAT) or a vesicular glutamate transporter (VGLUT), or an up-regulator of the expression of an EAAT or VGLUT.

In certain embodiments, the additional agent is an electron acceptor agent. In some embodiments, the electron acceptor agent is capable of oxidizing NADH. In some embodiments, the electron acceptor agent is a substrate of a dehydrogenase. In some embodiments, the electron acceptor agent is a substrate of LDH. In some embodiments, the electron acceptor agent is a substrate of malate dehydrogenase or glutamate dehydrogenase. In some embodiments, the electron acceptor agent is pyruvate, or an analog thereof, or a pharmaceutically acceptable salt, stereoisomer, tautomer, solvate, hydrate, polymorph, or prodrug thereof. In some embodiments, the electron acceptor agent is α-ketobutyrate, or an analog thereof, or a pharmaceutically acceptable salt, stereoisomer, tautomer, solvate, hydrate, polymorph, or prodrug thereof.

In certain embodiments, the additional agent is an agent that reduces pyruvate consumption by the liver. In some embodiments, the additional agent is an agent that increases intracellular levels of pyruvate in non-liver cells. In some embodiments, the additional agent is an inhibitor of PDC, PC, or ALT, or down-regulates the expression of PC, ALT, or a PDC protein. In some embodiments, the additional agent is an activator of PDK, or up-regulates the expression of PDK. In some embodiments, the additional agent is an inhibitor of PDP, or down-regulates the expression of PDP. In some embodiments, the additional agent is an antagonist of a monocarboxylate transporter (MCT) (e.g., pyruvate translocase), or down-regulates the expression of an MCT (e.g., pyruvate translocase). In certain embodiments, the additional agent is an agent that increases the ratio of NAD$^+$ to NADH (e.g., nicotinamide riboside, activator of NQO1 or NQO2). In certain embodiments, the additional agent is an agent that attenuates aspartate flux through the urea cycle (e.g., an inhibitor of arginosuccinate synthetase).

Exemplary agents or therapies that may be useful in the treatment of a mitochondrial disorder include, but are not limited to, mitochondrial gene replacement therapy, maternal mtDNA, coenzyme Q10, L-arginine, oxygen radical scavengers, creatine, platelet infusion, thymidine phosphorylase, bone marrow transplantation, rosiglitazone, pioglitazone, troglitazone, resveratrol, and bezafibrate.

Exemplary agents or therapies that may be useful in the treatment of neurodegenerative diseases include, but are not limited to, anti-Alzheimer's agents, such as acetylcholinesterase inhibitors (e.g., tacrine, rivastigimine, galantamine, donepezil), NMDA receptor agonists (e.g., memantine), glutamate, and huperzine A, and anti-Parkinson's agents, such as levodopa, carbidopa, benserazide, tolcapone, entacapone, dopamine agonists (e.g., bromocriptine, pergolide, pramipexole, ropinirole, piribedil, cabergoline, apomorphine, lisuride), MAO-B inhibitors (e.g., selegiline, rasagiline), amantadine, anticholinergics, donepezil, and anti-psychotics (e.g., clozapine, quetiapine, ziprasidone, aripiprazole, paliperidone).

The present invention also provides uses of any of the agents, or pharmaceutical compositions described herein, in the manufacture of a medicament for the treatment of a mitochondrial disorder, neurodegenerative disease, or proliferative disease, in a subject in need thereof. In certain embodiments, the medicament comprises aspartate, or an aspartate analog, or a pharmaceutically acceptable salt, stereoisomer, tautomer, solvate, hydrate, polymorph, or prodrug thereof. In certain embodiments, the medicament comprises a prodrug of aspartate, a prodrug of an aspartate analog, a polypeptide or protein comprising aspartate, or a metabolic precursor to aspartate. In certain embodiments, the medicament comprises an agent that increases intracellular aspartate levels (e.g., an activator of GOT1, an agent that increases transport of aspartate into cells). In certain embodiments, the medicament comprises an electron acceptor agent capable of oxidizing NADH (e.g., a substrate of a dehydrogenase (e.g., LDH). In certain embodiments, the medicament comprises pyruvate, α-ketobutyrate, or an analog thereof, or a pharmaceutically acceptable salt, stereoisomer, tautomer, solvate, hydrate, polymorph or prodrug thereof. In certain embodiments, the medicament comprises an agent that reduces pyruvate consumption by the liver (e.g., an inhibitor of PDF, an agent that decreases transport of pyruvate into mitochondria). In certain embodiments, the medicament comprises an agent that increases the ratio of NAD$^+$ to NADH (e.g., nicotinamide riboside, activator of NQO1 or NQO2). In certain embodiments, the medicament comprises a substrate of a dehydrogenase in a target tissue. In certain embodiments, the medicament comprises an agent that attenuates aspartate flux through the urea cycle (e.g., an inhibitor of arginosuccinate synthetase).

For any of the agents described herein, the increase in intracellular aspartate levels or NAD$^+$/NADH ratio may be effective for a time duration following administration of the agent(s). In some embodiments, the time duration is at least about 1 hour, at least about 2 hours, at least about 4 hours, at least about 8 hours, at least about 12 hours, at least about 24 hours, at least about 36 hours, or at least about 48 hours. In some embodiments, the time duration is at least about 3 days, at least about 7 days, at least about 14 days, or at least about 30 days. In some embodiments the time duration is between about 1 hour and 24 hours, between about 1 hour and 12 hours, between about 1 hour and 8 hours, or between about 1 hour and 4 hours. In some embodiments, the time duration is between about 4 hours and 48 hours, between about 8 hours and 48 hours, between about 12 hours and 48 hours, between about 24 hours and about 48 hours, or between about 36 hours and about 48 hours. In some embodiments, the time duration is between about 3 hours and 30 days, between about 3 days and about 14 days, or between about 3 days and about 7 days.

In certain embodiments, the agent is administered regularly to maintain the desired effect (e.g., increased intracellular aspartate levels or NAD$^+$/NADH ratio). In some embodiments, the agent is administered in an effective amount once per day, twice per day, three times per day, four times per day, or six times per day. In some embodiments, the agent is administered in an effective amount eight times per day, ten times per day, twelve times per day, eighteen times per day, or twenty-four times per day. In some embodiments, the agent is administered in an effective amount once every two days, once every three days, once every four days, once every five days, once every six days, once every seven days, once every fourteen days, or once every thirty days. In some embodiments, the agent is administered in an effective amount at a rate between about once per day and about six times per day. In some embodiments, the agent is administered in an effective amount at a rate between about six times per day and about twenty-four times per day. In some embodiments, the agent is administered in an effective amount at a rate between once per day and once every seven days.

In certain embodiments, the agent is administered orally. In certain embodiments, the agent is not administered orally. Agents described herein may be administered in relatively small doses (e.g., for an enzyme inhibitor) or relatively large doses (e.g., for aspartate taken as part of a food product). In certain embodiments, the agent is administered at a dose of between about 0.1 mg and about 1 mg per day, between about 1 mg and about 10 mg per day, between about 10 mg and about 50 mg per day, between about 50 mg and about 100 mg per day, between about 100 mg and about 250 mg per day, or between about 250 mg and about 500 mg per day. In certain embodiments, the agent is administered at a dose of between about 500 mg and about 1 g per day, between about 1 g and about 10 g per day, between about 10 g and about 50 g per day, or between about 50 g and about 100 g per day. The dose may be administered single dose or divided into smaller doses taken during the dosing regimen.

Some agents described herein may be administered on a dosing regimen based on a patients weight. In certain embodiments, the agent is administered at a dose of between about 0.1 mg/kg and about 1 mg/kg per day, between about 1 mg/kg and about 10 mg/kg per day, between about 10 mg/kg and about 50 mg/kg per day, between about 50 mg/kg and about 100 mg/kg per day, between about 100 mg/kg and about 250 mg/kg per day, or between about 250 mg/kg and 500 mg/kg per day, between about 500 mg/kg and about 1 g/kg per day, or between about 1 g/kg and about 5 g/kg per day. In some embodiments, the agent is administered at a dose less than 500 mg/kg/day. In some embodiments, the agent is administered at a dose less than 1 g/kg/day. In some embodiments, the agent is administered at a dose greater than 500 mg/kg/day. In some embodiments, the agent is administered at a dose greater than 1 g/kg/day. In some embodiments, the electron acceptor agent (e.g., pyruvate, or an analog thereof) is administered at a dose less than 500 mg/kg/day. In some embodiments, the electron acceptor agent (e.g., pyruvate, or an analog thereof) is administered at a dose less than 1 g/kg/day. In some embodiments, the electron acceptor agent (e.g., pyruvate, or an analog thereof) is administered at a dose greater than 500 mg/kg/day. In some embodiments, the electron acceptor agent (e.g., pyruvate, or an analog thereof) is administered at a dose greater than 1 g/kg/day.

Mitochondrial disorders are diseases that affect the function of mitochondria in a subject in one or more cell type. Mitochondrial diseases may be both multi-systemic or tissue specific (e.g., effecting neurons). A mitochondrial disorders may be the primary disease a patient is suffering from, or may be a disorder caused by or associated with another disease. Mitochondrial diseases may be caused by mutations of mitochondrial DNA and/or nuclear DNA genes that encode mitochondrial proteins. In certain embodiments, the mitochondrial disorder is a neurodegenerative disease. In certain embodiments, the mitochondrial disorder is not a neurodegenerative disease. In certain embodiments, the neurodegenerative disorder (e.g., Alzheimer's disease, Parkinson's disease) is, or is associated with a mitochondrial disorder or mitochondrial impairment. In certain embodiments, the mitochondrial disorder is an infantile mitochondrial disorder. In certain embodiments, the mitochondrial disorder is an inherited disorder (e.g., genetic disease). In certain embodiments, the mitochondrial disorder is a maternally inherited disorder.

In certain embodiments, the mitochondrial disorder is a myopathy. In certain embodiments, the mitochondrial disorder is an encephalopathy. In certain embodiments, the mitochondrial disorder is a cardiopathy. In certain embodiments, the mitochondrial disorder an encephalomyopathy. In certain embodiments, the mitochondrial disorder is a cardiomyopathy. In certain embodiments, the mitochondrial disorder is an encephalocardiopathy. In certain embodiments, the mitochondrial disorder is an encephalocardiomyopathy. In certain embodiments, the mitochondrial disorder is a neuropathy. In certain embodiments, the mitochondrial disorder is an epilepsy. In certain embodiments, the mitochondrial disorder is associated with parkinsonism.

In certain embodiments, the mitochondrial disorder is, myoclonic epilepsy with red ragged fibers (MERRF); mitochondrial encephalomyopathy, lactic acidosis, and stroke like symptoms (MELAS); Kearns-Sayre syndrome (KSS); chronic progressive external ophthalmoplegia (CPEO); diabetes mellitus and deafness (DAD); lactic acidosis; Leber's hereditary optic neuropathy (LHON); Wolff-Parkinson-White syndrome; Leigh syndrome; neuropathy, ataxia, retinitis pigmentosa, and ptosis (NARP); myoneurogenic gastrointestinal encephalopathy (MNGIE); or mitochondrial DNA depletion syndrome (MDS). In some embodiments, the mitochondrial disorder is MERRF. In some embodiments, the mitochondrial disorder is MELAS. In some embodiments, the mitochondrial disorder is KSS. In some embodiments, the mitochondrial disorder is Leigh syndrome. In some embodiments, the mitochondrial disorder is a myopathic, encephalomyopathic, or hepatocerebral MDS.

In certain embodiments, the mitochondrial disorder is myoclonic epilepsy with red ragged fibers (MERRF); Kearns-Sayre syndrome (KSS); chronic progressive external ophthalmoplegia (CPEO); diabetes mellitus and deafness (DAD); lactic acidosis; Leber's hereditary optic neuropathy (LHON); or Wolff-Parkinson-White syndrome.

In certain embodiments, the mitochondrial disorder is not Leigh syndrome; neuropathy, ataxia, retinitis pigmentosa, and ptosis (NARP); non-specific encephalomyopathy associated with complex I and IV combined deficiency; or myopathic mitochondrial DNA depletion syndrome. In certain embodiments, the mitochondrial disorder is not encephalomyopathy or mitochondrial DNA depletion syndrome.

In certain embodiments, the mitochondrial disorder is, or is associated with, Alzheimer's disease (AD), Alzheimer's disease and Parkinson's disease (ADPD), ataxia, myoclonus and deafness (AMDF), autism spectrum disorder (ASD), chronic intestinal pseudo-obstruction with myopathy and ophthalmoplegia (CIPO), chronic progressive external ophthalmoplegia (CPEO), maternally inherited deafness or aminoglycoside-induced deafness (DEAF), dementia and chorea (DEMCHO), diabetes mellitus and deafness (DMDF), exercise intolerance, epilepsy, strokes, optic atrophy and cognitive decline (ESOC), familial bilateral striatal necrosis (FBSN), fatal infantile cardiomyopathy plus (a MELAS-associated cardiomyopathy) (FICP), Finnish lethal neonatal metabolic syndrome (FLNMS), gastrointestinal reflux (GER), growth retardation, aminoaciduria, cholestasis, iron overload, lactic acidosis, and early death (GRACILE), Huntington's disease, Kearns-Sayre syndrome (KSS), Leber's hereditary optic neuropathy and dystonia (LDYT), Leber's hereditary optic neuropathy (LHON), Leigh syndrome, lethal infantile mitochondrial myopathy (LIMM), myopathy and diabetes mellitus (MDM), mitochondrial encephalomyopathy, lactic acidosis, and stroke-like episodes (MELAS), myoclonic epilepsy and psychomotor regression (MEPR), MERRF/MELAS overlap disease (MERME), myoclonic epilepsy and ragged red muscle fibers (MERRF), maternally inherited hypertrophic cardiomyopathy (MHCM), maternally inherited cardiomyopathy (MICM), maternally inherited Leigh syndrome (MILS), mitochondrial encephalocardiomyopathy, mitochondrial encephalomyopathy, mitochondrial myopathy (MM), mitochondrial neurogastrointestinal encephalomyopathy, maternal myopathy and cardiomyopathy (MMC), multisystem mitochondrial disorder (myopathy, encephalopathy, blindness, hearing loss, peripheral neuropathy), neurogenic muscle weakness, ataxia, and retinitis pigmentosa (NARP), non-insulin dependent diabetes mellitus (NIDDM), progressive encephalopathy (PEM), Parkinson's disease, parkinsonism, progressive myoclonus epilepsy (PME), Rett syndrome (RTT), sudden infant death syndrome (SIDS), or sensorineural hearing loss (SNHL).

In certain embodiments, the neurodegenerative disease is a neurological disease as defined herein. In certain embodiments, the neurodegenerative disease is Parkinson's disease, Alzheimer's disease, amyotrophic lateral sclerosis, Huntington's disease, dementia, parkinsonism, neuropathy, or encephalopathy. In certain embodiments, the neurodegenerative disease is Alzheimer's disease. In certain embodiments, the neurodegenerative disease is Parkinson's disease. In certain embodiments, the neurodegenerative disease is parkinsonism. In certain embodiments, the neurodegenerative disease is encephalopathy, encephalomyopathy, encephalocardiopathy, or encephalocardiomyopathy. In certain embodiments, the neurodegenerative disease is dementia. In certain embodiments, the neurodegenerative disease is Huntington's disease. In certain embodiments, the neurodegenerative disease is amyotrophic lateral sclerosis.

In certain embodiments, the methods of the invention comprise administering to the subject an effective amount of the agent or pharmaceutical composition described herein. In certain embodiments, the effective amount is effective for increasing cell proliferation in cells with impaired mitochondrial respiration. In certain embodiments, the effective amount is effective for preventing cell death in cells with impaired mitochondrial respiration. In certain embodiments, the effective amount is effective for increasing intracellular levels of aspartate or an aspartate anabolite (e.g., asparagine, purines, pyrimidines). In certain embodiments, the effective amount is effective for increasing intracellular levels of asparagine. In some embodiments, the effective amount is a therapeutically effective amount. In some embodiments, the effective amount is a prophylactically effective amount.

In certain embodiments, the subject described herein is a human. In certain embodiments, the subject is an animal. The animal may be of either sex and may be at any stage of development. In certain embodiments, the human is an infant or child. In certain embodiments, the human is an adolescent or adult. In certain embodiments, the human is not an infant or child. In certain embodiments, the subject is a mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Methods for Identifying an Agent for the Treatment of Mitochondrial Disorders and Neurodegenerative Diseases In another aspect, provided herein are screening methods for identifying agents for the treatment of a disease for use in the methods of treatment described herein. The method may comprise determining the effect of a candidate compound on intracellular concentrations of aspartate, $NAD^+$, and/or the $NAD^+$/NADH ratio.

In certain embodiments, provided herein is a method for identifying an agent that increases intracellular aspartate concentration, the method comprising:
(i) contacting a cell with a candidate compound;
(ii) measuring the concentration of aspartate in the contacted cell after a time duration;
(iii) comparing the measured concentration with the concentration of aspartate in a reference cell; and
(iv) identifying the candidate compound as an agent that increases intracellular aspartate concentration if the measured concentration is increased relative to concentration in the reference cell.

In certain embodiments, the increase relative to the reference cell is by at least about 1.1 fold, at least about 1.25 fold, at least about 1.5 fold, at least about 2 fold, at least about 2.5 fold, at least about 3 fold, at least about 5 fold, or at least about 10 fold. In certain embodiments, the time duration is at least about at least about 1 hour, at least about 2 hours, at least about 4 hours, at least about 8 hours, at least about 12 hours, at least about 24 hours, at least about 36 hours, or at least about 48 hours.

In certain embodiments, provided herein is a method for identifying an agent that increases the intracellular $NAD^+$/NADH ratio, the method comprising:
(i) contacting a cell with a candidate compound;
(ii) measuring the $NAD^+$/NADH ratio in the contacted cell after a time duration;
(iii) comparing the measured ratio with the $NAD^+$/NADH ratio in a reference cell; and
(iv) identifying the candidate compound as an agent that increases the intracellular $NAD^+$/NADH ratio if the measured ratio is increased relative to the ratio in the reference cell.

In certain embodiments, the increase relative to the reference cell is by at least about 1.1 fold, at least about 1.25 fold, 1.5 fold, at least about 2 fold, at least about 3 fold, at least about 4 fold, at least about 5 fold, at least about 10 fold. In certain embodiments, the time duration is at least about at least about 1 hour, at least about 2 hours, at least about 4 hours, at least about 8 hours, at least about 12 hours, at least about 24 hours, at least about 36 hours, or at least about 48 hours.

In certain embodiments, provided herein is a method for identifying an agent that increases the intracellular $NAD^+$ concentration, the method comprising:
(i) contacting a cell with a candidate compound;
(ii) measuring the $NAD^+$ concentration in the contacted cell after a time duration;
(iii) comparing the measured concentration with the concentration of $NAD^+$ in a reference cell; and
(iv) identifying the candidate compound as an agent that increases the intracellular NAD concentration if the measured concentration is increased relative to the concentration in the reference cell.

In certain embodiments, the increase relative to the reference cell is by at least about 2 fold, at least about 5 fold, at least about 10 fold, at least about 20 fold, at least about 50 fold. In certain embodiments, the time duration is at least about at least about 1 hour, at least about 2 hours, at least about 4 hours, at least about 8 hours, at least about 12 hours, at least about 24 hours, at least about 36 hours, or at least about 48 hours.

In some embodiments, the cell is a healthy cell. In some embodiments, the cell has a mitochondrial defect. In some embodiments, the cell has impaired mitochondrial respiration. In some embodiments, the cell is genetically modified to have a mitochondrial defect or impaired mitochondrial respiration. In some embodiments, the cell is genetically modified to not express a gene (e.g., GOT1, MDH1, SLC1A3). In some embodiments, the cell is genetically modified to overexpress a gene (e.g., a gene associated with mitochondrial respiration (e.g., GOT1, MDH1, SLC1A3)). In some embodiments, the cell is a cytoplasmic hybrid cell (cybrid), wherein the mitochondrial DNA of the cybrid has a pathogenic mutation.

In some embodiments, the reference cell is a different cell than the contacted cell. In some embodiments, the reference cell is the same as the contacted cell, measured before treatment with the candidate agent. In some embodiments, the reference cell is an untreated cell (e.g., a cell of the same type, a cell with the same mutation(s), a cell of the same cell line, a cell from the same biological sample). In some embodiments, the reference cell is a healthy cell. In some embodiments, the reference cell has a mitochondrial defect. In some embodiments, the reference cell has impaired mitochondrial respiration.

In some embodiments, aspartate levels are determined by GC-MS or LC-MS analysis. In some embodiments, aspartate levels are determined as an average of multiple cells of the same type contacted with the candidate agent (e.g., a 400,000 cell well contacted with media comprising the candidate agent). In some embodiments, aspartate and other polar metabolites are extracted with an organic solvent (e.g., 80% methanol in water). In some embodiments, aspartate is derivatized by treating the organic solution or solids isolated therefrom. In some embodiments, aspartate, or a derivative thereof, is quantified by GC-MS. In some embodiments, aspartate, or a derivative thereof, is quantified by LC-MS.

$NAD^+$ and NADH can be measured in cell extracts by assays known in the art (e.g., NAD/NADH-GLO™ Assay, Promega, Madison, Wis.). In some embodiments, $NAD^+$ and NADH levels are determined as an average of multiple cells of the same type contacted with the candidate agent (e.g., a 400,000 cell well contacted with media comprising the candidate agent). In some embodiments, cells are extracted into a basic buffer (e.g., lysis buffer (1% Dodecyltrimethylammonium bromide (DTAB) in 0.2 N NaOH diluted 1:1 with PBS)) and incubated at elevated temperature to selectively degrade $NAD^+$. In some embodiments, cells are extracted into an acidic buffer (e.g., 1:1 lysis buffer and 0.4 N HCl) and incubated at elevated temperature to selectively degrade NADH. In some embodiments, the extracted samples are quenched with an acidic or basic Tris buffer following incubation. In some embodiments, for an $NAD^+$ sample, $NAD^+$ is converted to NADH with an enzyme. In some embodiments, a solution containing a reductase enzyme and a proluciferin reductase substrate is contacted with the NADH containing sample, converting a proportionally amount of the substrate to luciferin. In some embodiments, the luciferin is quantified by luminescence measurement in the presence of a luciferase (e.g., Ultra-Glo™ Recombinant Luciferase, Promega, Madison, Wis.).

In another aspect, provided herein are in vivo screening methods for identifying agents for the treatment of a disease for use in the methods of treatment described herein.

In certain embodiments, provided herein is a method for identifying an agent that increases intracellular aspartate concentration, the method comprising:
(i) administering candidate compound to a subject
(ii) collecting a biological sample from the subject after a time duration;
(ii) measuring an aspartate concentration in the biological sample;
(iii) comparing the measured concentration with a concentration of aspartate in a reference sample; and
(iv) identifying the candidate compound as an agent that increases intracellular aspartate concentration if the measured concentration is increased relative to the concentration in the reference sample.

In certain embodiments, the increase relative to the reference sample by at least about 1.1 fold, at least about 1.25 fold, at least about 1.5 fold, at least about 2 fold, at least about 2.5 fold, at least about 3 fold, at least about 5 fold, or at least about 10 fold. In certain embodiments, the time duration is at least about at least about 1 hour, at least about 2 hours, at least about 4 hours, at least about 8 hours, at least about 12 hours, at least about 24 hours, at least about 36 hours, or at least about 48 hours.

In certain embodiments, provided herein is a method for identifying an agent that increases the intracellular $NAD^+$/NADH ratio, the method comprising:
(i) administering candidate compound to a subject
(ii) collecting a biological sample from the subject after a time duration;
(ii) measuring the $NAD^+$/NADH ratio in the biological sample;
(iii) comparing the measured ratio of aspartate with an $NAD^+$/NADH ratio in a reference sample; and
(iv) identifying the candidate compound as an agent that increases the intracellular $NAD^+$/NADH ratio if the measured ratio is increased relative to the ratio in the reference sample.

In certain embodiments, the increase relative to the reference sample by at least about 1.1 fold, at least about 1.25 fold, at least about 1.5 fold, at least about 2 fold, at least about 3 fold, at least about 4 fold, at least about 5 fold, at least about 10 fold. In certain embodiments, the time duration is at least about at least about 1 hour, at least about 2 hours, at least about 4 hours, at least about 8 hours, at least about 12 hours, at least about 24 hours, at least about 36 hours, or at least about 48 hours.

In certain embodiments, provided herein is a method for identifying an agent that increases the intracellular $NAD^+$ concentration, the method comprising:
(i) administering candidate compound to a subject;
(ii) collecting a biological sample from the subject after a time duration;
(ii) measuring the $NAD^+$ concentration in the biological sample;
(iii) comparing the measured concentration with the concentration of $NAD^+$ in a reference sample; and
(iv) identifying the candidate compound as an agent that increases the intracellular NAD concentration if the measured concentration is increased relative to the concentration in the reference sample.

In certain embodiments, the increase relative to the reference sample is by at least about 2 fold, at least about 5 fold, at least about 10 fold, at least about 20 fold, at least about 50 fold. In certain embodiments, the time duration is at least about at least about 1 hour, at least about 2 hours, at least about 4 hours, at least about 8 hours, at least about 12 hours, at least about 24 hours, at least about 36 hours, or at least about 48 hours.

In some embodiments, the biological sample is blood. In some embodiments, the biological sample is one or more cells. In some embodiments, the biological sample is one or more cells of a specific type or from a specific tissue. In some embodiments, the biological sample comprises nerve cells, muscle cells, cardiac muscle cells, cells form liver, the central nervous system, pancreases, spleen, cardiovascular system, muscles, bone marrow, eye, or gastrointestinal system.

In some embodiments, the subject is an animal (e.g., mouse, rat, dog, pig, non-human primate). In some embodiments, the subject is a human. In some embodiments, the subject is a healthy subject. In some embodiments, the subject has a mitochondrial disorder or neurodegenerative disease. In some embodiments, the subject is a genetically engineered animal. In some embodiments, the subject is an animal model for a mitochondrial disorder or neurodegenerative disease.

In some embodiments, reference sample is from the same subject as the biological sample. In some embodiments, the reference sample is from a different subject as the biological sample. In some embodiments, the reference sample is from a healthy subject. In some embodiments, the reference sample is from a subject with a mitochondrial disorder or neurodegenerative disease.

The screening methods described herein may further comprise determining the duration and magnitude of the effect on a biomolecule concentration (e.g., aspartate, $NAD^+$) or concentration ratio (e.g., $NAD^+/NADH$) after contacting a cell or administering to a subject the candidate agent. In some embodiments, the step of deterring the concentration is repeated for several cells contacted with the candidate agent at various times after the cells were contacted. In some embodiments, the step of determining the concentration is repeated for several subjects at various times after the candidate agent was administered to the subjects.

In some embodiments, the duration of the effect is at least about 1 hour, at least about 2 hours, at least about 4 hours, at least about 8 hours, at least about 12 hours, at least about 24 hours, at least about 36 hours, or at least about 48 hours. In some embodiments, the duration of the effect is at least about 3 days, at least about 7 days, at least about 14 days, or at least about 30 days. In some embodiments the duration of the effect is between about 1 hour and 24 hours, between about 1 hour and 12 hours, between about 1 hour and 8 hours, or between about 1 hour and 4 hours. In some embodiments, the duration of the effect is between about 4 hours and 48 hours, between about 8 hours and 48 hours, between about 12 hours and 48 hours, between about 24 hours and about 48 hours, or between about 36 hours and about 48 hours. In some embodiments, the duration of the effect is between about 3 hours and 30 days, between about 3 days and about 14 days, or between about 3 days and about 7 days.

In some embodiments, the step of determining the duration comprises determining the length of time that the concentration of the biomolecule (e.g., aspartate, $NAD^+$ or concentration ratio (e.g., $NAD^+/NADH$) remains above a certain threshold. In certain embodiments, the threshold is an increase relative to a reference cell or reference sample of at least about 1.1 fold, at least about 1.25 fold, at least about 1.5 fold, at least about 2 fold, at least about 2.5 fold, at least about 3 fold, at least about 5 fold, at least about 10 fold, at least about 15 fold, at least about 25 fold, at least about 50 fold, at least about 100 fold, at least about 200 fold, at least about 500 fold, or at least about 1000 fold. In certain embodiments, the threshold is a concentration relative to normal levels of a reference cell or reference sample of at least about 10% of normal levels, at least about 25% of normal levels, at least about 50% of normal levels, at least about 60% of normal levels, at least about 70% of normal levels, at least about 80% of normal levels, at least about 90% of normal levels, at least about 100% of normal levels, or at least about 110% of normal levels, at least about 125% of normal levels, at least about 150% of normal levels, or at least about 200% of normal levels.

Methods for Treating Proliferative Diseases

In an additional aspect, provided herein are methods, compositions, and systems for treating proliferative diseases. Proliferating cells may depend on intracellular levels of aspartate and/or aspartate anabolites (e.g., asparagine, purines, pyrimidines). Impairing aspartate biosynthesis may be a useful strategy for preventing cell proliferation, reducing the rate of cell proliferation, or inducing cell death. In certain embodiments, the method for treating a proliferative disease comprises administering to a subject an agent that inhibits aspartate biosynthesis. In certain embodiments, the proliferative disease comprises cells with impaired mitochondrial respiration. In some embodiments, the mitochondrial respiration of the cells is impaired by hypoxia. In certain embodiments, the agent is an inhibitor of cytosolic aspartate aminotransferase (GOT1). In certain embodiments, the agent is an inhibitor of mitochondrial aspartate aminotransferase (GOT2). In certain embodiments, the agent is an inhibitor of malate dehydrogenase (MDH). In certain embodiments, the agent down-regulates the expression of GOT1. In certain embodiments, the agent down-regulates the expression of GOT2. In certain embodiments, the agent down-regulates the expression of MDH. In certain embodiments, the agent is a modulator of asparagine synthetase (ASNS). In certain embodiments, the agent is an activator of asparagine synthetase (ASNS). In some embodiments, the agent up-regulates the expression of asparagine synthetase (ASNS).

In certain embodiments, the proliferative disease is a cancer associated with defects in mitochondrial metabolism. In certain embodiments, the proliferative disease is a cancer associated with defects in oxidative phosphorylation. In some embodiments, the cancer associated with defects in oxidative phosphorylation is brain cancer (e.g., glioma, glioblastoma), breast cancer, colorectal cancer, leukemia (e.g., acute myeloid leukemia), lymphoma, prostate cancer, stomach cancer, renal cancer (e.g., renal cell carcinoma, renal oncocytoma), lung cancer (e.g., lung epidermoid carcinoma), thyroid cancer (e.g., thyroid oncocytoma), liver cancer (e.g., hepatocellular carcinoma, Yoshida sarcoma), ovarian cancer, or a cancer of the endocrine system (e.g., phaeochromocytoma). In some embodiments, the proliferative disease is associated with mutations in mitochondrial DNA. In some embodiments, the proliferative disease is associated with a mutation in a gene encoding a protein associated with replication of mtDNA (e.g., polymerase γ gene). In some embodiments, the proliferative disease is associated with a mutation in a gene encoding proteins that are components of ETC complexes (e.g., Complex I, Complex II, Complex III, Complex IV). In some embodiments, the proliferative disease is associated with a mutation in a gene encoding succinate dehydrogenase (SDH), fumarate hydratase (FH), or isocitrate dehydrogenase. In certain embodiments, the cancer is not breast cancer. In certain embodiments, the cancer is a cancer associated with overexpression of GOT1 or GOT2. In certain embodiments, the cancer is a cancer associated with overexpression of c-Myc. In certain embodiments, the cancer is not a cancer associated with overexpression of GOT1 or GOT2. In certain embodiments, the cancer is not a cancer associated with overexpression of c-Myc.

Mutations associated with defects in oxidative phosphorylation include, but are not limited to, mutation in RNR1, ND1, ND2, ND3, ND4, ND5, ND6, CYB, CO1, CO2, CO3, ATP6, ENO1, GAPDH, GPI, HK1, PKM, SLC1A1, SLC2A3, TPI1, ALDOA, PFKP, PGI1, CYC1, UQCRC1, UQCRC2, PKM, PLA2G1B, MFSD3, DPEP2, CHID1, SCNN1B, SLC28A2, ALDOA, PPA1, B3GNT9, PLA2G7, LASS6, ABCA3, NUDT12, ATP2A2, ABCC12, NAPRT1, SLC45A4, CACNA1G, INPP5F, ACADSB, SLC9A7, ATP6VOd1, PLCG1, PIK3C3, ACOT9, ATP5H, NDUFV1, NDUFV2, NDUFA5, NDUFA7, NDUFA11, NDUFS1, NDUFS2, NDUFS3, NDUFS7, NDUFS8, NDUFB1, NDUFB5, NDUFB7, NDUFB8, NDUFB9, NDUFB10, COX5A, COX5B, ATP5I, PISD, ACAD9, ATP5O, UQCRB, ATP5C1, DLST, COX4I1, SCN4B, SRD5A3, PLA2G2C, CYP2W1, AHCY, ATP5J, PPAP2A, SLC8A1, SLC2A1, and SULT1A2, particularly mutations in these genes in mitochondrial DNA. Additional gene mutation associated with defects in oxidative phosphorylation are described in U.S. Patent App. Pub. No. 2014/0348749 A1, filed Feb. 25, 2015, which is incorporated by reference herein. In certain embodiments, the cancer is associated with a mutation in RNR1, ND1, ND2, ND3, ND4, ND5, ND6, CYB, CO1, CO2, CO3, ATP6, ENO1, GAPDH, GPI, HK1, PKM, SLC1A1, SLC2A3, TPI1, ALDOA, PFKP, PGI1, CYC1, or UQCRC1. In certain embodiments, the cancer is associated with a mutation in RNR1, ND1, ND2, ND3, ND4, ND5, ND6, CYB, CO1, CO2, CO3, or ATP6.

A cancer suitable for treatment with an agent that inhibits aspartate biosynthesis may be identified by sequencing of mitochondrial DNA and observing a mutation in a gene identified herein. A cancer suitable for treatment with an agent that inhibits aspartate biosynthesis may be identified by sequencing of mitochondrial DNA and observing a mutation in a gene that encodes a protein associated with oxidative phosphorylation, e.g., a gene the encodes a component of an ETC complex. In another aspect, provided herein are methods for identifying a cancer susceptible to treatment with an agent that inhibits aspartate biosynthesis comprising identifying a cancer with a defect in oxidative phosphorylation. In some embodiments, identifying a cancer with a defect in oxidative phosphorylation comprises sequencing of mitochondrial DNA. In some embodiments, identifying a cancer with a defect in oxidative phosphorylation comprises observing a mutation in or aberrant expression of a gene encoding an ETC complex protein, e.g., a Complex I protein. In some embodiments, identifying a cancer with a defect in oxidative phosphorylation comprises observing a mutation in or aberrant expression of succinate dehydrogenase, fumarate hydratase, or isocitrate dehydrogenase. In yet another aspect, provided herein are methods for identifying a subject for treatment with an agent that inhibits aspartate biosynthesis, wherein the method comprises identifying in the subject a cancer with a defect in oxidative phosphorylation. In some embodiments, the method comprises sequencing of mitochondrial DNA from cancer cells in the subject. In some embodiments, the method comprises observing a mutation in or aberrant expression of a gene encoding an ETC complex protein, e.g., a Complex I protein. In some embodiments, the method comprises observing a mutation in or aberrant expression of succinate dehydrogenase, fumarate hydratase, or isocitrate dehydrogenase.

Proliferative diseases associated with defects in oxidative phosphorylation may be susceptible to treatment with agents that inhibit aspartate biosynthesis (e.g. GOT1 inhibitors) and/or agents that inhibit oxidative phosphorylation (e.g., biguanides (e.g., metformin, phenformin)). In certain embodiments, the combination of treatment with an agent that inhibits aspartate biosynthesis and an agent that inhibits oxidative phosphorylation is synergistic, such that the therapeutic and/or prophylactic effect is greater than for treatment with an agent that inhibits aspartate biosynthesis alone or an agent that inhibits oxidative phosphorylation alone. In some embodiments, the agent that inhibits aspartate biosynthesis is an inhibitor of aspartate aminotransferase (GOT1). In some embodiments, the agent that inhibits oxidative phosphorylation is a biguanide. In some embodiments, the agent that inhibits oxidative phosphorylation is metformin or phenformin. In some embodiments, the agent that inhibits aspartate biosynthesis is a GOT1 inhibitor and the agent that inhibits oxidative phosphorylation is a biguanide. In some embodiments, the agent that inhibits aspartate biosynthesis is a GOT1 inhibitor and the agent that inhibits oxidative phosphorylation is metformin or phenformin.

Inhibitors of aspartate biosynthesis include selective inhibitors of GOT1 or GOT2, and non-specific inhibitors of GOT1, GOT2, or other aminotransferases. In certain embodiments, the inhibitor of aspartate biosynthesis is a GOT1/GOT2 selective inhibitor, a GOT1 selective inhibitor, or a GOT2 selective inhibitor, with selectivity relative to other amino transferases. In some embodiments, the selectivity for inhibiting GOT1 and/or GOT2 over inhibition of other amino transferases is between about 1.5-fold and about 2-fold, between about 2-fold and about 5-fold, between about 5-fold and about 10-fold, between about 10-fold and about 50-fold, between about 50-fold and about 100-fold, between about 100-fold and about 1000-fold, or greater than about 1000-fold.

The agent that inhibits aspartate biosynthesis may be a GOT1 inhibitor, including a small molecule that modulates GOT1 or an agent that impairs GOT1 activity indirectly by modulating gene expression of GOT1. In certain embodiments, the GOT1 inhibitor is 3-methylene-aspartic acid, or a pharmaceutically acceptable salt thereof. In certain embodiments, the GOT1 inhibitor is racemic 3-methyelene-aspartic acid, (R)-3-methylene-aspartic acid, or (S)-3-methylene aspartic acid, or a pharmaceutically acceptable salt thereof. In certain embodiments, the GOT1 inhibitor is aminoxyacetic acid, or a pharmaceutically acceptable salt thereof. In certain embodiments, when the GOT1 inhibitor is 3-methylene-acetic acid the cancer is not brain cancer. In certain embodiments, when the GOT1 inhibitor is aminoxyacetic acid the cancer is not breast cancer. In certain embodiments, when the GOT1 inhibitor is aminoxyacetic acid the cancer is not a cancer associated with overexpression of GOT1, GOT2, or c-Myc.

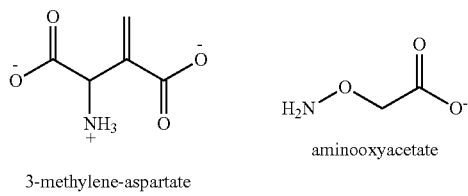

3-methylene-aspartate aminooxyacetate

GOT1 activity may also be impaired by interference in GOT1 expression. In certain embodiments, the GOT1 inhibitor is a down-regulator of GOT1. In certain embodiments, the GOT1 inhibitor is a small interfering RNA (siRNA) that interferes with GOT1 expression. In some embodiments, the siRNA comprises an antisense sequence of GOT1 messenger RNA (mRNA).

In certain embodiments, the agent decreases intracellular levels of $NAD^+$ or lowers the intracellular ratio of $NAD^+$ to NADH. In some embodiments, the agent is a substrate of a dehydrogenase. In some embodiments, the agent is a substrate of lactate dehydrogenase (LDH). In some embodiments, the agent is a substrate of malate dehydrogenase or glutamate dehydrogenase In certain embodiments, the agent is lactate, or an analog thereof, or a pharmaceutically acceptable salt, stereoisomer, tautomer, solvate, hydrate, polymorph, or prodrug thereof. In some embodiments, the agent is lactate, or an analog thereof. In some embodiments, the agent is lactate. In some embodiments, the agent is α-hydroxybutyrate, or an analog thereof. In some embodiments, the agent is α-hydroxybutyrate. In some embodiments, the agent is an α-hydroxy acid. In some embodiments, the agent is an optionally substituted $C_3$-$C_6$ α-hydroxy acid.

In certain embodiments, the method further comprises administering an additional pharmaceutical agent that impairs mitochondrial respiration. In certain embodiments, the additional pharmaceutical agent is an inhibitor of Complex I. In some embodiments, the additional pharmaceutical agent is rotenone, piericidin A, adenosine diphosphate ribose, an acetogenin (e.g., rolliniastatin-2), metformin, or phenformin. In certain embodiments, the additional pharmaceutical agent is an inhibitor of Complex II. In some embodiments, the additional pharmaceutical agent is carboxin, thenoyltrifluoroacetone, malonate, malate, or oxaloacetate. In certain embodiments, the additional pharmaceutical agent is an inhibitor of Complex III. In some embodiments, the additional pharmaceutical agent is antimycin A, myxothiazol, stigmatellin, or propylhexedrine. In certain embodiments, the additional pharmaceutical agent is Complex IV. In some embodiments, the additional pharmaceutical agent comprises is formic acid, adenosine triphosphate, or comprises a cyanide, sulfide, or azide counterion. In certain embodiments, the additional pharmaceutical agent is a down-regulator of gene expression of a gene associated with the electron transport chain (e.g., expression of Complex I, II, III, or IV).

In certain embodiments, the proliferative disease is cancer. In certain embodiments, the disease is a cancer selected from: acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple negative breast cancer (TNBC), ER positive breast cancer, ER negative breast cancer, PR positive breast cancer, PR negative breast cancer, ER/PR positive breast cancer, ER/PR negative breast cancer, HER2 positive breast cancer, HER2 negative breast cancer); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma, squamous cell carcinoma of the cervix); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

Pharmaceutical Compositions and Administration

Provided herein are pharmaceutical compositions comprising an agent useful for treating a disease. In some embodiments, the disease is a mitochondrial disorder or neurodegenerative disease. The agent may be any of the agents described for use in a method herein. In certain embodiments, the composition comprises aspartate, or an aspartate analog, or a pharmaceutically acceptable salt, stereoisomer, tautomer, solvate, hydrate, polymorph, or prodrug thereof. In certain embodiments, the composition comprises a prodrug of aspartate or a prodrug of an aspartate analog. In certain embodiments, the composition comprises a metabolic precursor to aspartate. In certain embodiments, the composition comprises a polypeptide comprising aspartate (e.g., an aspartate rich polypeptide).

In certain embodiments, the composition comprises an agent that increases intracellular aspartate levels. In some embodiments, the agent is an activator of GOT1, or up-regulates the expression of GOT1. In some embodiments, the agent is an activator of GOT2, MDH, PC, or IDH, or up-regulates the expression of GOT2, MDH, PC, or IDH. In certain embodiments, the composition comprises an agent that increases transport of aspartate, or an analog thereof, into cells. In some embodiments, the agent is an agonist of a glutamate or aspartate transport protein, or up-regulates the expression of a glutamate or aspartate protein. In some embodiments, the agent is an agonist of SLC1A3, or up-regulates the expression of SLC1A3. In some embodiments, the agent is an agonist of an excitatory amino acid transporter (EAAT) or a vesicular glutamate transporter (VGLUT), or an up-regulator of the expression of an EAAT or VGLUT.

In certain embodiments, the composition comprises an electron acceptor agent. In some embodiments, the electron acceptor agent is capable of oxidizing NADH. In some embodiments, electron acceptor agent is a substrate of a dehydrogenase. In some embodiments, the electron acceptor agent is a substrate of LDH. In some embodiments, the electron acceptor agent is a substrate of malate dehydrogenase or glutamate dehydrogenase. In some embodiments, the electron acceptor agent is pyruvate, or an analog thereof, or a pharmaceutically acceptable salt, stereoisomer, tautomer, solvate, hydrate, polymorph, or prodrug thereof. In some embodiments, the agent is not pyruvate. In some embodiments, the electron acceptor agent is α-ketobutyrate, or an analog thereof, or a pharmaceutically acceptable salt, stereoisomer, tautomer, solvate, hydrate, polymorph, or prodrug thereof.

In certain embodiments, the composition comprises an agent that reduces pyruvate consumption by the liver. In some embodiments, the composition comprises an agent that increases intracellular levels of pyruvate in non-liver cells. In some embodiments, the agent is an inhibitor of PDC, PC, or ALT, or down-regulates the expression of PC, ALT, or a PDC protein. In some embodiments, the agent is an activator of PDK, or up-regulates the expression of PDK. In some embodiments, the agent is an inhibitor of PDP, or down-regulates the expression of PDP. In some embodiments, the agent is an antagonist of a monocarboxylate transporter (MCT) (e.g., pyruvate translocase), or down-regulates the expression of an MCT (e.g., pyruvate translocase). In certain embodiments, the composition comprises an agent that increases the ratio of $NAD^+$ to NADH (e.g., nicotinamide riboside, activator of NQO1 or NQO2). In certain embodiments, the composition comprises an agent that attenuates aspartate flux through the urea cycle (e.g., an inhibitor of arginosuccinate synthetase).

In certain embodiments, the composition is for use in treating a mitochondrial disorder. In certain embodiments, the mitochondrial disorder is a myopathy. In certain embodiments, the mitochondrial disorder is an encephalopathy. In certain embodiments, the mitochondrial disorder is a cardiopathy. In certain embodiments, the mitochondrial disorder an encephalomyopathy. In certain embodiments, the mitochondrial disorder is a cardiomyopathy. In certain embodiments, the mitochondrial disorder is an encephalocardiopathy. In certain embodiments, the mitochondrial disorder is an encephalocardiomyopathy. In certain embodiments, the mitochondrial disorder is a neuropathy. In certain embodiments, the mitochondrial disorder is an epilepsy. In certain embodiments, the mitochondrial disorder is associated with parkinsonism.

In certain embodiments, the mitochondrial disorder is, myoclonic epilepsy with red ragged fibers (MERRF); mitochondrial encephalomyopathy, lactic acidosis, and stroke like symptoms (MELAS); Kearns-Sayre syndrome (KSS); chronic progressive external ophthalmoplegia (CPEO); diabetes mellitus and deafness (DAD); lactic acidosis; Leber's hereditary optic neuropathy (LHON); Wolff-Parkinson-White syndrome; Leigh syndrome; neuropathy, ataxia, retinitis pigmentosa, and ptosis (NARP); myoneurogenic gastrointestinal encephalopathy (MNGIE); or mitochondrial DNA depletion syndrome (MDS). In some embodiments, the mitochondrial disorder is MERRF. In some embodiments, the mitochondrial disorder is MELAS. In some embodiments, the mitochondrial disorder is KSS. In some embodiments, the mitochondrial disorder is Leigh syndrome. In some embodiments, the mitochondrial disorder is a myopathic, encephalomyopathic, or hepatocerebral MDS.

In certain embodiments, the composition is for use in treating a neurodegenerative disease. In some certain embodiments, the neurodegenerative disease is a neurological disease as defined herein. In certain embodiments, the neurodegenerative disease is Alzheimer's disease. In certain embodiments, the neurodegenerative disease is Parkinson's disease. In certain embodiments, the neurodegenerative disease is parkinsonism. In certain embodiments, the neurodegenerative disease is encephalopathy, encephalomyopathy, encephalocardiopathy, or encephalocardiomyopathy. In certain embodiments, the neurodegenerative disease is dementia. In certain embodiments, the neurodegenerative disease is Huntington's disease. In certain embodiments, the neurodegenerative disease is amyotrophic lateral sclerosis.

In certain embodiments, the agent is provided in an effective amount in the pharmaceutical composition. In certain embodiments, the effective amount is effective for increasing cell proliferation in cells with impaired mitochondrial respiration. In certain embodiments, the effective amount is effective for preventing cell death in cells with impaired mitochondrial respiration. In certain embodiments, the effective amount is effective for increasing intracellular levels of aspartate or an aspartate anabolite (e.g., asparagine, purines, pyrimidines). In certain embodiments, the effective amount is effective for increasing intracellular levels of asparagine. In some embodiments, the effective amount is a therapeutically effective amount. In some embodiments, the effective amount is a prophylactically effective amount.

It will also be appreciated that the compositions described herein can be employed in combination therapies, that is, the agents and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

In addition to the agent useful for treating mitochondrial disorders or neurodegenerative diseases, the pharmaceutical composition described herein may comprise one or more additional pharmaceutical agents. In certain embodiments, the additional pharmaceutical agent is an agent useful in the treatment a mitochondrial disorder. In certain embodiments, the additional pharmaceutical agent is an agent useful in the treatment of a neurodegenerative disease.

An additional pharmaceutical agent may be an agent useful for the treatment of mitochondrial disorders or neurodegenerative diseases. In certain embodiments, the additional agent is another agent described herein. In certain embodiments, the additional agent is aspartate, or an aspartate analog, or a pharmaceutically acceptable salt, stereoisomer, tautomer, solvate, hydrate, polymorph, or prodrug thereof. In certain embodiments, the additional agent is a prodrug of aspartate or a prodrug of an aspartate analog. In certain embodiments, the additional agent is a metabolic precursor to aspartate. In certain embodiments, the additional agent is a polypeptide comprising aspartate (e.g., an aspartate rich polypeptide).

In certain embodiments, the additional agent is an agent that increases intracellular aspartate levels. In some embodiments, the additional agent is an activator of GOT1, or up-regulates the expression of GOT1. In some embodiments, the additional agent is an activator of GOT2, MDH, PC, or IDH, or up-regulates the GOT2, MDH, PC, or IDH. In certain embodiments, the additional agent is an agent that increases transport of aspartate, or an analog thereof, into cells. In some embodiments, the additional agent is an agonist of a glutamate or aspartate transport protein, or up-regulates the expression of a glutamate or aspartate protein. In some embodiments, the additional agent is an agonist of SLC1A3, or up-regulates the expression of SLC1A3. In some embodiments, the additional agent is an agonist of an excitatory amino acid transporter (EAAT) or a vesicular glutamate transporter (VGLUT), or an up-regulator of the expression of an EAAT or VGLUT.

In certain embodiments, the additional agent is an electron acceptor agent. In some embodiments, the electron acceptor agent is capable of oxidizing NADH. In some embodiments, the electron acceptor agent is a substrate of a dehydrogenase. In some embodiments, the electron acceptor agent is a substrate of LDH. In some embodiments, the electron acceptor agent is a substrate of malate dehydrogenase or glutamate dehydrogenase. In some embodiments, the electron acceptor agent is pyruvate, or an analog thereof, or a pharmaceutically acceptable salt, stereoisomer, tautomer, solvate, hydrate, polymorph, or prodrug thereof. In some embodiments, the agent is not pyruvate. In some embodiments, electron acceptor agent is α-ketobutyrate, or an analog thereof, or a pharmaceutically acceptable salt, stereoisomer, tautomer, solvate, hydrate, polymorph, or prodrug thereof.

In certain embodiments, the additional agent is an agent that reduces pyruvate consumption by the liver. In some embodiments, the additional agent is an agent that increases intracellular levels of pyruvate in non-liver cells. In some embodiments, the additional agent is an inhibitor of PDC, PC, or ALT, or down-regulates the expression of PC, ALT, or a PDC protein. In some embodiments, the additional agent is an activator of PDK, or up-regulates the expression of PDK. In some embodiments, the additional agent is an inhibitor of PDP, or down-regulates the expression of PDP. In some embodiments, the additional agent is an antagonist of a monocarboxylate transporter (MCT) (e.g., pyruvate translocase), or down-regulates the expression of an MCT (e.g., pyruvate translocase). In certain embodiments, the additional agent is an agent that increases the ratio of $NAD^+$ to NADH (e.g., nicotinamide riboside, activator of NQO1 or NQO2). In certain embodiments, the additional agent attenuates aspartate flux through the urea cycle (e.g., an inhibitor of arginosuccinate synthetase).

Exemplary agents or therapies that may be useful in the treatment of a mitochondrial disorder include, but are not limited to, mitochondrial gene replacement therapy, maternal mtDNA, coenzyme Q10, L-arginine, oxygen radical scavengers, creatine, platelet infusion, thymidine phosphorylase, bone marrow transplantation, rosiglitazone, pioglitazone, troglitazone, resveratrol, and bezafibrate.

Exemplary agents or therapies that may be useful in the treatment of neurodegenerative diseases include, but are not limited to, anti-Alzheimer's agents, such as acetylcholinesterase inhibitors (e.g., tacrine, rivastigimine, galantamine, donepezil), NMDA receptor agonists (e.g., memantine), glutamate, and huperzine A, and anti-Parkinson's agents, such as levodopa, carbidopa, benserazide, tolcapone, entacapone, dopamine agonists (e.g., bromocriptine, pergolide, pramipexole, ropinirole, piribedil, cabergoline, apomorphine, lisuride), MAO-B inhibitors (e.g., selegiline, rasagiline), amantadine, anticholinergics, donepezil, and anti-psychotics (e.g., clozapine, quetiapine, ziprasidone, aripiprazole, paliperidone).

In another aspect, provided herein are pharmaceutical compositions comprising an agent useful for treating proliferative diseases. The an agent may be any of the agents described for use in a method herein. In certain embodiments, the agent is an inhibitor of GOT1. In certain embodiments, the agent down-regulates the expression of GOT1. In certain embodiments, the proliferative disease is cancer.

In addition to the agent useful for treating proliferative diseases, the pharmaceutical composition described herein may comprise one or more additional pharmaceutical agents. In certain embodiments, the additional pharmaceutical agent is an anti-cancer agent.

The compositions may be any kind of composition that is suitable for human and/or animal consumption. For example, the compositions may comprise food compositions, dietary supplements, nutritional compositions, nutraceuticals, powdered nutritional products to be reconstituted in water or milk before consumption, food additives (e.g., added to feed of a non-human animal or to human food), medicaments, drinks, and pet food. In some embodiments, the composition does not comprise milk or milk proteins. In some embodiments, the food compositions do not comprise natural foods. In some embodiments, the food compositions comprise synthetic foods. In some embodiments, the food compositions comprise processed foods.

The compositions disclosed herein may be incorporated into a food product. In some embodiments, the food product may be a drink for oral administration. Non-limiting examples of a suitable drink include fruit juice, a fruit drink, an artificially flavored drink, an artificially sweetened drink, a carbonated beverage, a sports drink, a liquid diary product, a shake, and so forth. Other suitable means for oral administration include aqueous and nonaqueous solutions, emulsions, suspensions and solutions and/or suspensions reconstituted from non-effervescent granules, containing suitable solvents, preservatives, emulsifying agents, suspending agents, diluents, sweeteners, coloring agents, and flavoring agents. The food product may also be a solid foodstuff. Suitable examples of a solid foodstuff include a food bar, a snack bar, a nutrition bar, a cookie, a brownie, a muffin, a cracker, an ice cream bar, a frozen yogurt bar, and the like.

In certain embodiments, the agent or pharmaceutical composition is a solid. In certain embodiments, the agent or pharmaceutical composition is a powder. In certain embodiments, the agent or pharmaceutical composition can be dissolved in a liquid to make a solution. In certain embodiments, the agent or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of this invention can be administered to humans and other animals orally, parenterally, intracisternally, intraperitoneally, topically, bucally, or the like, depending on the disease or condition being treated. In certain embodiments, the pharmaceutical composition is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the agents described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, each composition described herein is administered at a dose that is below the dose at which the agent causes non-specific effects.

In certain embodiments, the pharmaceutical composition is administered at a dose of about 0.001 mg to about 200 mg a day. In certain embodiments, the pharmaceutical composition is administered at a dose of about 0.01 mg to about 100 mg a day. In certain embodiments, pharmaceutical composition is administered at a dose of about 0.01 mg to about 50 mg a day. In certain embodiments, the pharmaceutical composition is administered at a dose of about 0.01 mg to about 10 mg a day. In certain embodiments, the pharmaceutical composition is administered at a dose of about 0.1 mg to about 10 mg a day.

Pharmaceutical compositions described herein can be prepared by any method known in the art of pharmacology. In general, such preparatory methods include the steps of bringing the composition into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™) polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present invention contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., quids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

In another aspect, provided are kits (e.g., pharmaceutical packs) for treating and/or preventing a pathological condition (e.g., mitochondrial disorder, neurodegenerative disease, proliferative disease) of a subject. The kit may comprises any pharmaceutical composition described herein, and any agent described for use in a method herein. The pharmaceutical compositions may comprise aspartate, or an aspartate analog, or a pharmaceutically acceptable salt, stereoisomer, tautomer, solvate, hydrate, polymorph, or prodrug thereof. The pharmaceutical composition may comprise a prodrug of aspartate, a prodrug of an aspartate analog, a polypeptide or protein comprising aspartate, or a metabolic precursor to aspartate. The pharmaceutical composition may comprise an agent that increases intracellular aspartate levels (e.g., an activator of GOT1, an agent that increases transport of aspartate into cells). The pharmaceutical composition may comprises an electron acceptor agent capable of oxidizing NADH (e.g., a substrate of LDH). The pharmaceutical composition may comprise pyruvate, α-ketobutyrate, or an analog thereof, or a pharmaceutically acceptable salt, stereoisomer, tautomer, solvate, hydrate, polymorph, or prodrug thereof. The pharmaceutical composition may comprise an agent that reduces pyruvate consumption by the liver (e.g., an inhibitor of PDF, an agent that decreases transport of pyruvate into mitochondria). The pharmaceutical composition may comprise an agent that attenuates aspartate flux through the urea cycle (e.g., an inhibitor of arginosuccinate synthetase).

In certain embodiments, the kit may comprise any of the agents or pharmaceutical compositions described herein, and a container (e.g., a vial, ampule, bottle, syringe, and/or dispenser package, or other suitable container). In certain embodiments, the kit includes a first container comprising any of the agents or pharmaceutical compositions described herein; and instructions for administering the agent or pharmaceutical composition to the subject to treat and/or prevent the pathological condition. In certain embodiments, the kits of the present invention include one or more additional approved pharmaceutical agent(s) (e.g., anti-mitochondrial disorder, anti-neurodegenerative). In certain embodiments, the instructions include a notice in the form prescribed by a governmental agency such as the U.S. Food and Drug Administration (FDA) regulating the manufacture, use, or sale of pharmaceutical products, which notice reflects approval by the agency of manufacture, use, or sale for human administration.

Methods of Regulating Redox State

The redox state of cells is affected by many metabolic pathways and enzymes. For example, the ratio of $NAD^+$ to NADH cofactors is one manifestation of the cellular redox state, and $NAD^+$ and NADH are interconverted by the activity of numerous enzymes. Most enzymes that interconvert $NAD^+$ and NADH, utilize those species as cofactors in the interconversion of other metabolic substrates. For example, many dehydrogenases oxidize a substrate and transfer protons and electrons to $NAD^+$, yielding the oxidized substrate and NADH as products. The reverse reaction also occurs for other enzymes or under different conditions (e.g., different substrate concentration, different $NAD^+$/NADH ratio).

Many diseases (e.g., metabolic disorders, mitochondrial disorders, neurological diseases) are associated with aberrant redox states of cells (e.g., insufficient $NAD^+$). Therapeutic approaches to increasing $NAD^+$ levels are limited, because $NAD^+$ typically cannot be directly administered as a pharmaceutical, and additionally, the de novo biosynthesis of $NAD^+$ involves many steps, and effective activators of the de novo pathway are not currently identified. The levels of $NAD^+$/NADH in cells are also low relative to rates of flux through enzymes that use these cofactors, limiting strategies that aim to modulate levels by inhibiting or activating enzymes involved in the synthesis or degradation of $NAD^+$ or NADH. However the conversion of NADH to $NAD^+$ by many dehydrogenases, and other enzymes, represents an indirect way of increasing $NAD^+$ or NADH levels in a cell or organelle, or of shifting the $NAD^+$/NADH ratio. The same approach may be exploited to increase levels of any cofactor by supplying a suitable substrate to the enzyme to drive the formation of a desired cofactor.

As a non-limiting example, the enzyme lactate dehydrogenase (LDH) converts the substrate pyruvate to lactate (e.g., under hypoxic conditions), and utilizes NADH as the reductant, thus forming $NAD^+$. Administering pyruvate to a subject or contacting a biological sample (e.g., cells) with pyruvate, at supra-physiological levels, thus increases the intracellular concentration of $NAD^+$ in a subject or biological sample. There may also be benefit in using an alternative substrate to the substrate typically consumed by the target enzyme. In the LDH example, lactate dehydrogenase also reduces α-ketobutyrate. The byproduct of LDH reduction of pyruvate is lactate, and the byproduct of α-ketobutyrate is α-hydroxybutyrate. Excess α-hydroxybutyrate is typically excreted and is not associated with toxic effects, while high lactic acid levels can lead to disease (e.g., lactic acidosis).

In the LDH example, α-ketobutyrate serves as an indirect therapeutic agent. α-ketobutyrate is not known to be administered for any therapeutic benefit. In addition the direct product of α-ketobutyrate, α-hydroxybutyrate does not provide a therapeutic benefit. However the conversion of α-ketobutyrate to α-hydroxybutyrate is coupled via LDH to the conversion of NADH to $NAD^+$. Thus, the indirect product ($NAD^+$) may provide a therapeutic benefit.

Provided herein are methods, compositions, and systems for treating a disease by administering to a subject in need thereof a first substrate, or a pharmaceutically acceptable salt, stereoisomer, tautomer, polymorph, or prodrug thereof, of an enzyme which converts the first substrate to a first product, wherein a concentration of a second product of the enzyme is increased. In another aspect, provided herein are methods, compositions, and systems for treating a disease by administering to a subject in need thereof a first substrate, or a pharmaceutically acceptable salt, stereoisomer, tautomer, polymorph, or prodrug thereof, of an enzyme which converts the first substrate to a first product, wherein a concentration of a second substrate of the enzyme is decreased.

In certain embodiments, the first substrate is a physiologically occurring substrate, and is a native substrate of the enzyme. In certain embodiments, the first substrate is a physiologically occurring substrate, and is not a native substrate of the enzyme. In certain embodiments, the first substrate is a physiologically occurring substrate wherein the substrate is administered in an amount sufficient to achieve supra-physiological extracellular or intracellular concentrations. In certain embodiments, the first substrate is not a physiologically occurring substrate. In certain embodiments, the first substrate is a synthetic analog of a physiologically occurring substrate. In certain embodiments, the first substrate is a synthetic analog of a native substrate. In certain embodiments, the first substrate is a synthetic analog of physiologically occurring non-native substrate. In certain embodiments, the first substrate is an alkylated, halogenated, hydroxylated, aminated, acylated, or hydrogenated analog of a physiologically occurring substrate. In certain embodiments, the first substrate is a dealkylated, dehalogenated, dehydroxylated, deaminated, deacylated, or dehydrogenated analog of a physiologically occurring substrate. In certain embodiments, the first substrate is an analog of a physiologically occuring substrate comprising a nitrogen, oxygen, or sulfur protecting group. In certain embodiments, the first substrate does not provide a therapeutic or prophylactic effect apart from the modulating the concentration of the second substrate or second product.

In certain embodiments, the first product of the enzyme is a physiologically occuring product. In certain embodiments, the first product of the enzyme is not a physiologically occurring product. In certain embodiments, the first product of the enzyme is non-toxic. In certain embodiments, the first product of the enzyme is excreted by the subject. In certain embodiments, the first product does not provide a therapeutic or prophylactic effect.

An increase in the concentration of the second product may alter the redox state of the cell, organelle, or extracellular matrix in which the second product is formed. In certain embodiments, the second product of the enzyme is a metabolite. In certain embodiments, the second product of the enzyme is a cofactor. In certain embodiments, the second product of the enzyme is a coenzyme. In certain embodiments, the second product is NADH or NAD$^+$. In certain embodiments, the second product is NADPH or NADP$^+$. In certain embodiments, the second product is FADH$_2$ or FAD. In certain embodiments, the second product is flavin mononucleotide (FMN) or FMNH$_2$. In certain embodiments, the second product is a flavoprotein comprising a flavin moiety (e.g., FAD, flavin mononucleotide). In some embodiments, the flavoprotein is α-ketoglutarate dehydrogenase or pyruvate dehydrogenase complex. In certain embodiments, the second product is a nucleotide monophosphate, nucleotide diphosphate, or nucleotide triphosphate. In certain embodiments, the second product is ATP or ADP. In certain embodiments, the second product is an ion transported by the enzyme across a membrane. In certain embodiments, redox state is altered by modulating a transmembrane potential.

A decrease in the concentration of the second substrate may alter the redox state of the cell, organelle, or extracellular matrix from which the second substrate is consumed. In certain embodiments, the second substrate of the enzyme is a metabolite. In certain embodiments, the second substrate of the enzyme is a cofactor. In certain embodiments, the second substrate of the enzyme is a coenzyme. In certain embodiments, the second product is NADH or NAD$^+$. In certain embodiments, the second substrate is NADPH or NADP$^+$. In certain embodiments, the second substrate is FADH$_2$ or FAD. In certain embodiments, the second product is FADH$_2$ or FAD. In certain embodiments, the second product is flavin mononucleotide (FMN) or FMNH$_2$. In certain embodiments, the second product is a flavoprotein comprising a flavin moiety (e.g., FAD, flavin mononucleotide). In some embodiments, the flavoprotein is α-ketoglutarate dehydrogenase or pyruvate dehydrogenase complex. In certain embodiments, the second substrate is a nucleotide monophosphate, nucleotide diphosphate, or nucleotide triphosphate. In certain embodiments, the second substrate is ATP or ADP. In certain embodiments, the second substrate is an ion transported by the enzyme across a membrane. In certain embodiments, redox state is altered by modulating a transmembrane potential.

The concentration of the second substrate or second product which is modulated may be a intracellular, extracellular, or intra-organelle concentration, or a combination thereof. In certain embodiments, the concentration is an intracellular concentration. In certain embodiments, the concentration is an extracellular concentration. In certain embodiments, the concentration is an intra-organelle concentration. In certain embodiments, the concentration is a mitochondrial concentration.

In certain embodiments, the enzyme is an oxidoreductase. In certain embodiments, the enzyme is an oxidase. In certain embodiments, the enzyme is an reductase. In certain embodiments, the enzyme is a dehydrogenase. In certain embodiments, the enzyme is a hydrogenase. In certain embodiments, the enzyme is an oxidoreductase. In certain embodiments, the enzyme is a transferase. In certain embodiments, the enzyme is a phosphatase. In certain embodiments, the enzyme is a kinase. In some embodiments, the enzyme is a hydrolase, lyase, isomerase, ligase, protease, lipase, polymerase, peptidase, synthetase, racemase, epimerase, anhydrase, or carboxylase. In certain embodiments, the enzyme modifies a cofactor. The cofactor may be the second substrate and/or may be modified to form the second product. In certain embodiments, the coenzyme is NADH or NAD$^+$. In certain embodiments, the coenzyme is NADPH or NADP$^+$. In certain embodiments, the coenzyme is FADH$_2$ or FAD. In certain embodiments, the second product is FADH$_2$ or FAD. In certain embodiments, the second product is flavin mononucleotide (FMN) or FMNH$_2$. In certain embodiments, the second product is a flavoprotein comprising a flavin moiety (e.g., FAD, flavin mononucleotide). In some embodiments, the flavoprotein is α-ketoglutarate dehydrogenase or pyruvate dehydrogenase complex. In certain embodiments, the coenzyme is a nucleotide monophosphate, nucleotide diphosphate, or nucleotide triphosphate. In certain embodiments, the coenzyme is ATP or ADP. In certain embodiments, the cofactor is thiamine pyrophosphate, pyridoxal phosphate, lipoamide, methylcobalamin, cobalamine, biotin, coenzyme A, tetrahydrofolic acid, menaquinone, ascorbic acid, flavin mononucleotide, S-adenosyl methionine, coenzyme Q, cytidine triphosphate, glutathione, heme, molybdopterin, a nucleotide sugar, 3'-phosphoadenosine-5'-phosphosulfate, and tetrahydrobiopterin.

In certain embodiments, the enzyme involved in the method is an enzyme typically localized or expressed in a particular tissue, type of cell, or organelle. In certain embodiments, the enzyme involved in the method is an enzyme expressed in a particular tissue, type of cell, or organelle. Targeting the substrate/cofactor system of such an enzyme may allow for treatment of defects in particular tissues (e.g., heart), cells (e.g., neurons), or organelles (e.g., mitochondria). In certain embodiments, the enzyme is localized or expressed in the liver, central nervous system, pancreas, spleen, cardiovascular system, muscles, bone marrow, eye, or gastrointestinal system. In certain embodiments, the enzyme is localized or expressed in nerve cells, muscle cells, cardiac muscle cells, or blood cells (e.g., lymphocyte). In certain embodiments, the enzyme is localized or expressed in the nucleus, cytosol, nuclear membrane, cell membrane, or extracellular matrix. In certain embodiments, the enzyme is localized or expressed in an organelle or organelle membrane. In certain embodiments, the enzyme is localized or expressed in mitochondria. In certain embodiments, the enzyme is located in Golgi apparatus, endoplasmic reticulum, ribosomes, proteasomes, or lysosomes.

In certain embodiments, the disease is a genetic disease, proliferative disease, hematological disease, neurological disease, painful condition, psychiatric disorder, or metabolic disorder, cardiovascular disease, infectious disease, or mitochondrial disorder. In certain embodiments, the disease is a proliferative disease. In certain embodiments, the disease is cancer, benign neoplasm, diseases associated with angiogenesis, an inflammatory disease, an autoinflammatory disease, or an autoimmune disease. In certain embodiments, the neurological disease is a neurodegenerative disease. In certain embodiments, the neurological disease is amyotrophic lateral sclerosis, Alzheimer's disease, Parkinson's disease, dementia, or Huntington's disease, muscular dystrophy, or multiple sclerosis. In certain embodiments, the disease is a mitochondrial disease. In some embodiments, the mitochondrial disease is myoclonic epilepsy with red ragged fibers (MERRF); mitochondrial encephalomyopathy, lactic acidosis, and stroke like symptoms (MELAS); Kearns-Sayre syndrome (KSS); chronic progressive external ophthalmoplegia (CPEO); diabetes mellitus and deafness (DAD); lactic acidosis; Leber's hereditary optic neuropathy (LHON); Wolff-Parkinson-White syndrome; Leigh syndrome; neuropathy, ataxia, retinitis pigmentosa, and ptosis (NARP); myoneurogenic gastrointestinal encephalopathy (MNGIE); or mitochondrial DNA depletion syndrome (MDS). In certain embodiments, the disease is a metabolic disorder. In certain embodiments the disease is diabetes (e.g., Type I diabetes, Type II diabetes, gestational diabetes), hyperglycemia, hyperinsulinemia, insulin resistance, and obesity.

In another aspect, provided herein are methods for identifying a substrate for the treatment of a disease by the methods described above. In certain embodiments, the method comprises (i) identifying a species (e.g., metabolite, cofactor, protein) associated with a disease; (ii) identifying an enzyme that regulates the concentration of the species; (iii) identifying a potential substrate of the enzyme; (iv) administering the potential substrate to a subject or contacting it to a biological sample; (v) measuring the concentration of the species after administration of the potential substrate; (vi) comparing the concentration of the species after administration of the potential substrate to the concentration of the species when the potential substrate is not administered to the subject or contacted to the biological sample.

The species may be a cofactor associated with the redox state of cells or organelles (e.g., $NAD^+$, NADH, ADP, ATP). In certain embodiments, the species is an agent, described herein. Species associated with various diseases are well known in the art. For many common metabolites, cofactors, and proteins, enzymes that regulate the concentration of said metabolites, cofactors, and proteins are well known in the art. In certain embodiments, the disease is a disease described herein. In certain embodiments, the enzyme is an enzyme described herein. In certain embodiments, the disease is associated with insufficient levels of the species. In certain embodiments, the disease is associated with levels of the species that are too high. In certain embodiments, the disease is associated with aberrant transport behavior of the species (e.g., excess or subcess of the species in a particular tissue, cell, or organelle).

Likewise, for many enzymes one or more physiologically occurring native or non-native substrates of the enzyme will be known in the art and may serve as potential substrates. The step of identifying a potential substrate may also involve identifying an analog or prodrug of a known physiologically occurring substrate. The step of identifying a potential substrate may involve synthesizing analogs of a known physiologically occurring substrate. The step of identifying a potential substrate may involve selecting a library of potential substrates. In certain embodiments, the potential substrate is an agent described herein.

The enzyme may regulate the concentration of the species by forming the species, or acting on another enzyme to form the species. Regulation refers to increasing the concentration or decreasing the concentration of the species, or transporting the species (e.g., across a membrane).

In certain embodiments, the subject is a healthy patient. In certain embodiments, the subject is a patient suffering from the disease of interest. In certain embodiments, the subject is a human. In certain embodiments, the subject is an animal. The animal may be of either sex and may be at any stage of development. In certain embodiments, the subject is a mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the biological sample comprises cells from a healthy subject, or cells not associated with the disease of interest. In certain embodiments, the biological sample comprises cells from a subject suffering from the disease of interest, or cells associated with the disease of interest (e.g., a cancer cell-line).

The step of measuring may comprise testing of a biological sample by any method known in the art. In certain embodiments, measuring comprises a spectroscopic assay. In certain embodiments, measuring comprises an immunologic assay. In certain embodiments, measuring comprises a mass spectrometric method.

DEFINITIONS

Chemical Terms

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, $5^{th}$ Edition, John Wiley & Sons, Inc., New York, 2001; Larock, Comprehensive Organic Transformations, VCH Publishers, Inc., New York, 1989; and Carruthers, Some Modern Methods of Organic Synthesis, $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

)

may be an (E)- or (Z)-double bond.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 πelectrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

The term "halo" or "halogen" refers to fluorine (fluoro, —F), chlorine (chloro, —Cl), bromine (bromo, —Br), or iodine (iodo, —I).

As used herein "alkylamino" or "dialkylamino" means one or two alkyl moiety attached through a nitrogen bridge (e.g., —NH-alkyl, —N(alkyl)$_2$), such as methylamino, ethylamino, dimethylamino, diethylamino, and the like.

As used herein "alkylthio" means an alkyl moiety attached through a sulfur bridge (i.e., —S-alkyl).

As used herein "alkoxy" means an alkyl moiety attached through an oxygen bridge (i.e., —O-alkyl) such as methoxy, ethoxy, and the like.

As used herein "aryloxy" means an aryl moiety attached through an oxygen bridge (i.e., —O-aryl).

As used herein "arylthio" means an alkyl moiety attached through a sulfur bridge (i.e., —S-aryl).

As used herein "aminooxy" means an amino moiety attached through an oxygen bridge (e.g., —O—NH$_2$).

As used herein "hydroxylamino" means hydroxyl moiety attached through an amine bridge (e.g., —NH—OH).

As used herein "O-alkoxyamino" means an alkoxy moiety attached through an amine bridge (e.g., —NH—O-alkyl).

As used herein "N-alkylaminooxy" means an alkylamino moiety attached through an oxygen bridge (e.g., —O—NH-alkyl).

As used herein "hydrazino" means an amino moiety attached through a nitrogen bridge (e.g., —NH—NH$_2$) depending on the context.

As used herein "alkylhydrazino" means an alkyl moiety attached through a hydrazine bridge (e.g., —NH—NH-alkyl).

As used herein "carbonyl" means —C(=O)alkyl or —C(=O)aryl.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.xH$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs, pp.* 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal "Disease," "disorder," and "condition" are used interchangeably herein.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing an agent described herein, or a composition thereof, in or on a subject.

The terms "condition," "disease," and "disorder" are used interchangeably.

As used herein, and unless otherwise specified, the terms "treat," "treating" and "treatment" contemplate an action that occurs while a subject is suffering from the specified disease or condition, which reduces the severity of the disease or condition, or retards or slows the progression of the disease or condition (i.e., "therapeutic treatment"), and also contemplates an action that occurs before a subject begins to suffer from the specified disease or condition (i.e., "prophylactic treatment").

An "effective amount" of an agent described herein refers to an amount sufficient to elicit the desired biological response. An effective amount of an agent described herein may vary depending on such factors as the desired biological endpoint, the pharmacokinetics of the agent, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of an agent described herein in a single dose. In certain embodiments, an effective amount is the combined amounts of an agent described herein in multiple doses.

A "therapeutically effective amount" of an agent described herein is an amount sufficient to provide a therapeutic benefit in the treatment of a condition or to delay or minimize one or more symptoms associated with the condition. A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of an agent described herein is an amount sufficient to prevent a condition, or one or more symptoms associated with the condition or prevent its recurrence. A prophylactically effective amount of an agent means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "neurodegenerative disease" refers to a type of neurological disease marked by the loss of nerve cells, including, but not limited to, Alzheimer's disease, Parkinson's disease, amyotrophic lateral sclerosis (ALS), tauopathies (including frontotemporal dementia), and Huntington's disease. Other examples include, but are not limited to, ataxia telangiectasia, autosomal dominant cerebellar ataxia, Batten disease, corticobasal degeneration, Creutzfeldt-Jakob disease, fatal familial insomnia, frontotemporal dementia and parkinsonism (FTDP), hereditary motor and sensory neuropathy (HMSN), infantile Refsum disease, locomotor ataxia, Lyme disease, Machado-Joseph disease, mental retardation and microcephaly with pontine and cerebellar hypoplasia (MICPCH), multiple system atrophy, motor neuron diseases, neuroacanthocytosis, Niemann-Pick disease, ponocerebellar hypoplasia, pyruvate dehydrogenase deficiency, prion disease, primary progressive aphasia, progressive supranuclear palsy, Refsum disease, Sandhoff disease, Shy-Drager syndrome, spinocerebellar ataxia, spinal muscular atrophy, subacute combined degeneration of spinal cord, subacute sclerosing panencephalitis, Tabes dorsalis, Tay-Sachs disease, toxic encephalopathy, and toxic leukoencephalopathy.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina *bifida*; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

The term "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, diseases associated with angiogenesis, inflammatory diseases, autoinflammatory diseases, and autoimmune diseases.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple negative breast cancer (TNBC), ER positive breast cancer, ER negative breast cancer, PR positive breast cancer, PR negative breast cancer, ER/PR positive breast cancer, ER/PR negative breast cancer, HER2 positive breast cancer, HER2 negative breast cancer); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma, squamous cell carcinoma of the cervix); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

As used herein the term "inhibit" or "inhibition" or "inhibitor" in the context of enzymes, for example, in the context of GOT1, refers to a reduction in the activity of the enzyme. In some embodiments, the term refers to a reduction of the level of enzyme activity, e.g., GOT1 activity, to a level that is statistically significantly lower than an initial level, which may, for example, be a baseline level of enzyme activity. In some embodiments, the term refers to a reduction of the level of enzyme activity, e.g., GOT1 activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

As used herein the term "activate" or "activation" or "activator" in the context of enzymes, for example, in the context of GOT1, refers to an increase in the activity of the enzyme. In some embodiments, the term refers to an increase of the level of enzyme activity, e.g., GOT1 activity, to a level that is statistically significantly higher than an initial level, which may, for example, be a baseline level of enzyme activity (e.g., a baseline for the subject or biological sample). In some embodiments, the term refers to a reduction of the level of enzyme activity, e.g., GOT1 activity, to a level that is more than 10%, more than 20%, more than 30%, more than 40%, more than 50%, more than 60%, more than 70%, more than 80%, more than 90%, more than 100%, more than 150%, more than 200%, more than 300%, more than 400%, more than 500%, more than 1000%, more than 2000%, more than 5000%, more than 10000%, more than 50000%, or more than 100000% higher than an initial level, which may, for example, be a baseline level of enzyme activity (e.g., a baseline for the subject or biological sample).

As used herein, the term "GOT1" refers to the protein cytosolic aspartate aminotransferase or the gene (GOT1) that encodes the protein, and is also known as aspartate transaminase (AST). GOT1 is a glutamic-oxaloacetic transaminase. GOT2 refers to the mitochondrial form. GOT1 catalyzes the interconversion of aspartate and oxaloacetate, as well as the interconversion of $\alpha$-ketoglutarate and glutamate, and relies on the interconversion of the cofactors pyridoxal phosphate (PLP) and pyridoxamine phosphate (PMP). GOT1 proteins and their respective encoding RNA and DNA sequences according to some aspects of this application include human GOT1 proteins and encoding sequences, as well as, in some embodiments, GOT1 proteins and encoding sequences from other species, for example, from other mammals (e.g., GOT1 proteins and encoding sequences from mouse, rat, cat, dog, cattle, goat, sheep, pig, or primate), from other vertebrates, and from insects. The term GOT1 further includes, in some embodiments, sequence variants and mutations (e.g., naturally occurring or synthetic GOT1 sequence variants or mutations), and different GOT1 isoforms. In some embodiments, the term GOT1 includes protein or encoding sequences that are homologous to a GOT1 protein or encoding sequence, for example, a protein or encoding sequence having at least 80%, at least 85%, at least 90%, at least 91%, at least 92%, at least 93%, at least 94%, at least 95%, at least 96%, at least 97%, at least 98%, at least 99%, or at least 99.5% sequence identity with a GOT1 sequence, for example, with a GOT1 sequence provided herein. In some embodiments, the term GOT1 refers to a protein exhibiting GOT1 activity, for example, a protein exhibiting aminotransferase activity on aspartate, or a nucleic acid sequence encoding such a protein. In some embodiments, the term GOT1 includes proteins that exhibit at least 50%, at least 60%, at least 70%, at least 80%, at least 90%, at least 95%, or at least 100% aminotransferase activity on aspartate as compared to a known GOT1 protein or encoding sequence, for example, as compared to a GOT1 sequence provided herein. GOT1 protein and encoding gene sequences are well known to those of skill in the art, and exemplary protein sequences include, but are not limited to, the following sequences. Additional GOT1 sequences, e.g., GOT1 homologues from other mammalian species, will be apparent to those of skill in the art, and the invention is not limited to the exemplary sequences provided herein.

>gi|4504067|ref|NP_002070.1| aspartate aminotransferase, cytoplasmic [*Homo sapiens*]

(SEQ ID NO: 1)
MAPPSVFAEVPQAQPVLVFKLTADFREDPDPRKVNLGVGAYRTDDCHPWV

LPVVKKVEQKIANDNSLNHEYLPILGLAEFRSCASRLALGDDSPALKEKR

VGGVQSLGGTGALRIGADFLARWYNGTNNKNTPVYVSSPTWENHNAVFSA

AGFKDIRSYRYWDAEKRGLDLQGFLNDLENAPEFSIVVLHACAHNPTGID

PTPEQWKQIASVMKHRFLFPFFDSAYQGFASGNLERDAWAIRYFVSEGFE

FFCAQSFSKNFGLYNERVGNLTVVGKEPESILQVLSQMEKIVRITWSNPP

AQGARIVASTLSNPELFEEWTGNVKTMADRILTMRSELRARLEALKTPGT

WNHITDQIGMFSFTGLNPKQVEYLVNEKHIYLLPSGRINVSGLTTKNLDY

VATSIHEAVTKIQ

EXAMPLES

In order that the invention described herein may be more fully understood, the following examples are set forth. The examples described in this application are offered to illustrate the methods, compositions, and systems provided herein and are not to be construed in any way as limiting their scope.

Metabolic Studies of Respiration Impaired Cells
Introduction

Among the first observations of the importance of oxygen for living organisms is Antoine Lavoisier's demonstration that organisms utilize oxygen to burn fuels for energy in a manner similar to combustion. Like combustion, respiration consists of a series of redox reactions, where free energy is released when the high-energy electrons of a reduced substrate are transferred to the electron acceptor oxygen. As a result of this process, the starting substrate is oxidized and loses electron pairs while the oxygen molecule acting as an electron acceptor gains electron pairs and forms water. A century after Lavoisier recognized that oxygen enables living organisms to "combust" fuel for energy, Pasteur found that in the presence of oxygen, yeast engage in less fermentation and grow significantly faster. Pasteur's finding provides some of the earliest evidence that oxygen plays an important role in supporting rapid proliferation.

Decades later, in apparent contrast to Pasteur's earlier findings, Warburg observed that unlike normal tissues, cancer cells consume increased amounts of glucose and metabolize much of this glucose to lactate even in the presence of ample oxygen. To reconcile this apparent difference, it was initially hypothesized that this fermentation of glucose in the presence of oxygen, termed aerobic glycolysis, was the result of a diminished mitochondrial function. However, Warburg and others have noted that, even in contexts where aerobic glycolysis is observed, tumors appear capable of oxidizing glucose and are dependent on oxygen for survival in certain contexts. Subsequent studies have confirmed that most cancer cells retain mitochondrial oxygen consumption. Furthermore, in some proliferative contexts where aerobic glycolysis is observed oxygen consumption has been noted to increase. Interestingly, in most cancer cell lines the primary substrate for oxidation is generally not glucose but rather glutamine, one of the most heavily consumed and essential nutrients under tissue culture conditions. Hence, it appears that aerobic glycolysis does not replace mitochondrial respiration, but rather, in rapidly proliferating cells these processes occur in parallel.

It is now well recognized that many cells that engage in aerobic glycolysis are not only capable of respiration but also require respiration for proliferation. Many cell culture studies have shown that exposing cancer cells to mitochondrial inhibitors blocks proliferation (Harris, 1980; Howell and Sager, 1979). With respect to in vivo conditions, maintenance of mitochondrial DNA (mtDNA) is required for autochthonous tumor formation (Weinberg et al., 2010), and inhibition of respiration in cancer cells suppresses tumor growth in xenografts (Wheaton et al., 2014a-b). These data highlight that mitochondrial respiration generally is essential for proliferation; however, the limiting metabolic functions supported by respiration in proliferating cells are poorly defined.

Despite the important role of mitochondrial respiration in supporting mammalian cell proliferation, under specific conditions cells can proliferate in the absence of respiration. Selective depletion of mitochondrial DNA (mtDNA) by low dose ethidium bromide treatment has been used to produce cells devoid of mtDNA (ρ0 cells) (King and Attardi, 1989, 1996). ρ0 cells lack a functional mitochondrial electron transport chain (ETC), and these respiration-incompetent cells fail to proliferate unless supra-physiological levels of two nutrients, uridine and pyruvate, are added to the culture media. The uridine auxotrophy is explained by the observation that the de novo pyrimidine biosynthesis enzyme, dihydroorotate dehydrogenase (DHODH), transfers electrons to the mitochondrial ETC, with $O_2$ as the final electron acceptor, to catalyze conversion of dihydroorotate to orotate. Loss of ability to transfer electrons to $O_2$ therefore prevents this reaction from proceeding and exogenous uridine is required (Gregoire et al., 1984). The requirement for pyruvate, however, was initially "unexpected" (King and Attardi, 1989) given that cells deficient in mtDNA are highly glycolytic and are capable of generating large amounts of pyruvate. The fact that supplementation of specific nutrients can substitute for respiration supports the hypothesis that respiration fulfills specific metabolic requirements for proliferating cells. While ATP synthesis via oxidative phosphorylation is widely assumed to be the critical output of respiration, the fact that neither exogenous uridine nor pyruvate can be oxidized to supply ATP in the absence of respiration suggests that respiration is likely important for metabolic requirements beyond the generation of ATP. However, what these specific metabolic requirements are remains poorly defined.

Here we elucidate the role of respiration in supporting proliferation by defining the specific metabolic requirements fulfilled by respiration. We show that cells lacking the ability to utilize oxygen as an oxidation source are functionally limited for electron acceptors. The lack of electron acceptors leads to a diminished capacity for de novo aspartate synthesis and subsequently inhibits proliferation. This proliferation block can be overcome by supplementing cells with exogenous electron acceptors, or by supra-physiological levels of aspartate. This requirement for respiration to support aspartate synthesis is present in a diverse array of proliferative cell types, including both transformed and non-transformed cells. Taken together our data argue that the most essential metabolic function provided by mitochondrial respiration is to provide access to electron acceptors to support aspartate biosynthesis.

Experimental Methods
Cell Culture

143B, A172, H1299, HeLa, U87 and MEF cells were cultured in Dulbecco's Modified Eagle's Medium (DMEM) (Gibco) supplemented with 10% fetal bovine serum (FBS) and penicillin-streptomycin. FL5.12 cells were cultured in the same medium and supplemented with 5 µg/mL recombinant mouse IL-3 (R&D Systems). 143B cybrid cell lines (WT Cybrid and CytB) were cultured in DMEM with 10% FBS, penicillin-streptomycin, and 0.1 mg/mL uridine. All cells incubated at 37° C. with 5% $CO_2$.

Proliferation Assays

Adherent cell lines growing in log phase were trypsinized, counted, and plated onto 6 well dishes (Corning) in 2 mL complete DMEM and incubated overnight. Initial seeding density was 2E4 cells per well for 143B, A172, H1299, HeLa, 143B WT Cybrid, and MEFs and 3E4 cells for 143B CytB and U87 cells. The following day, one plate of cells was counted to determine the initial cell count at the time of treatment. Cells were washed 2 times with 2 mL phosphate buffered saline (PBS) and 4 mL media premixed with the indicated treatments was added. FL5.12 cells, a suspension cell line, were washed 2 times in PBS and added directly to media containing the indicated treatments and 5 µg/mL recombinant mouse IL-3. Proliferation rate assay media was DMEM without pyruvate containing 10% dialyzed FBS, penicillin-streptomycin, and 0.1 mg/mL uridine, unless otherwise noted. For these cell lines at these seeding densities it was determined that for 4 days the cells maintained logarithmic proliferation (data not shown), therefore final cell counts were measured 4 days after treatment. Cells were counted using Cellometer Auto T4 Plus Cell Counter (Nexcelom Bioscience). Proliferation rate was determined using the following formula:

Proliferation Rate (Doublings per day)=($\log_2$(Final cell count (day 5)/Initial cell count (day 1))/4 (days)

Treatment concentrations for each cell line are included as a table in supplemental methods.

Measurement of Mitochondrial Oxygen Consumption

Oxygen consumption rates were determined on a Seahorse Bioscience Extracellular Flux Analyzer (XF24). Cells were plated in Seahorse Bioscience 24 well plates at 6E4 cells per well in 100 µL complete DMEM, allowed to attach for 1 hour, and 500 µl complete DMEM was added before overnight incubation. The following day cells were washed 2 times in assay media: DMEM without phenol red or pyruvate containing 0.5% dialyzed FBS and 0.1 mg/mL uridine at pH 7.4 and incubated in 500 µL of the same media for the assay. Oxygen consumption measurements were compared either, between basal measurements and following injection of the compound (AKB, rotenone, antimycin), or between wells cultured overnight in their treatment conditions (aspartate, oligomycin, FCCP). The latter conditions were used due to solubility constraints (aspartate) or kinetic constraints of the compound (oligomycin). These measurements were then subtracted from oxygen consumption measurements following addition of high dose rotenone and antimycin treatment (2 µM each) to determine the mitochondria specific oxygen consumption rate. Following measurements, the number of cells in the wells was counted, averaged for each treatment condition, and the mitochondrial oxygen consumption rates were normalized to 1E5 cells.

Lactate Dehydrogenase Assay

Immediately prior to the start of the assay 100 µL of a reaction buffer containing 50 mM HEPES-KOH pH 7.5, 20 mM KCl, 2 mM $MgCl_2$, 1 mM DTT, 180 µM NADH, 1 mM α-ketobutyrate (where applicable) was combined with LDH (where applicable) in 96-well plates. Lactate dehydrogenase activity was assayed by monitoring disappearance of NADH absorbance at 340 nm over time.

Purine Nucleotide Metabolite Extraction and LC-MS Analysis

143B CytB cells were seeded at 400,000 cells/well in 6 well dishes overnight. The following day, cells were washed 2 times in PBS and media was changed to proliferation assay media with or without the indicated treatments. After 15 hours polar metabolites were extracted from cells using 250 µL of ice cold 80% methanol. After scraping the cells, 250 µL of chloroform was added before vortexing for 10 min at 4° C. and centrifugation for 10 min at 4° C. at 16,000 g, 40 µL of the top, water-methanol, layer was transferred into a LC-MS tube and samples were analyzed. A Dionex UltiMate 3000 ultra-high performance liquid chromatography system connected to a Q Exactive benchtop Orbitrap mass spectrometer, equipped with an Ion Max source and a HESI II probe (Thermo Fisher Scientific) was used to quantify metabolites. Samples were separated by chromatography by injecting 10 µL of sample on a SeQuant ZIC-pHILIC Polymeric column (2.1×150 mm 5 µM, EMD Millipore). Flow rate was set to 150 µL/min, temperatures were set to 25° C. for column compartment and 4° C. for autosampler sample tray. Mobile Phase A consisted of 20 mM ammonium carbonate, 0.1% ammonium hydroxide. Mobile Phase B was 100% acetonitrile. The mobile phase gradient (% B) was set in the following protocol: 0-20 min.: linear gradient from 80% to 20% B; 20-20.5 min.: linear gradient from 20% to 80% B; 20.5-28 min.: hold at 80% B. Mobile phase was introduced into the ionization source set to the following parameters: sheath gas=40, auxiliary gas=15, sweep gas=1, spray voltage=−3.1 kV, capillary temperature=275° C., S-lens RF level=40, probe temperature=350° C. Metabolites were monitored using full scan in negative mode in the range of 285-700 m/z, with the resolution set at 140,000, the AGC target at 106, and the maximum injection time at 250 msec. Relative quantitation of metabolites was performed with XCalibur QuanBrowser 2.2 (Thermo Fisher Scientific) using a 5 ppm mass tolerance and referencing an in-house retention time library of chemical standards.

Amino Acid and TCA Cycle Metabolite Extraction and GC-MS Analysis 143B and 143B CytB cells were seeded at 400,000 cells/well in 6 well dishes overnight. The following day, cells were washed 2 times in PBS and media was changed to proliferation assay media with or without the indicated treatments. After 8 hours, polar metabolites were extracted using 80% methanol in water with 1 µg norvaline per sample. Soluble content was then dried under nitrogen gas. Polar samples were derivatized and measured as detailed in (Lewis). Relative metabolite abundances were determined by integrating ion peak area (Metran) and normalized to norvaline internal extraction standard.

Cell Cycle Distribution Measurements

143B CytB cells were incubated in untreated media or media containing AKB or 100 µM adenine for 78 hours before being washed with PBS, trypsinized, pelleted, and resuspended in 500 µL PBS. Cells were fixed by adding 4.5 mL 70% ethanol and incubated at 4° C. overnight. The following day cells were pelleted and resuspended in 1 mL PBS+0.1% (v/v) Triton X-100. RNase A and then propidium iodide (PI) were added to 0.2 mg/mL and 20 µg/mL, respectively. Samples were incubated at 37° C. for 15 minutes and filtered into a flow cytometry tube. DNA content was measured by flow cytometry (BD FACS Canto II) and analyzed (FACS Diva Software).

Measurement of $NAD^+$/NADH $NAD^+$/NADH measurements were done using a modified version of manufacturer instructions of NAD/NADH Glo Assay (Promega). Cells were plated and treated as for proliferation assays and cell extracts were taken 6 hours after treatment. For extraction, cells were quickly washed 3 times in ice cold PBS, extracted in 100 μL ice cold lysis buffer (1% Dodecyltrimethylammonium bromide (DTAB) in 0.2 N NaOH diluted 1:1 with PBS), and immediately frozen at −80° C. To measure NADH, 20 μL of sample was moved to PCR tubes and incubated at 75° C. for 30 min, where the basic conditions will selectively degrade $NAD^+$. To measure $NAD^+$, 20 μL of the samples was moved to PCR tubes containing 20 μL lysis buffer and 20 μL 0.4 N HCl and incubated at 60° C. for 15 min, where acidic conditions will degrade NADH. Following incubations, samples were allowed to equilibrate to room temperature and then quenched by neutralizing with 20 μL 0.25 M Tris in 0.2 N HCl (NADH) or 20 μL 0.5 M Tris base ($NAD^+$). Manufacturer instructions were followed thereafter to measure $NAD^+$/NADH.

Statistical Analysis

Data are presented as the mean±standard error of the mean (SEM). Sample size (n) indicates experimental replicates from a single representative experiment, where the results of the experiment were validated by independent repetitions. Statistical significance was determined using a two-tailed Welch's t test where significance is $p \leq 0.05$.

Results

α-Ketobutyrate can Substitute for Pyruvate to Support Proliferation in Respiration-Incompetent Cells.

Figure 7:
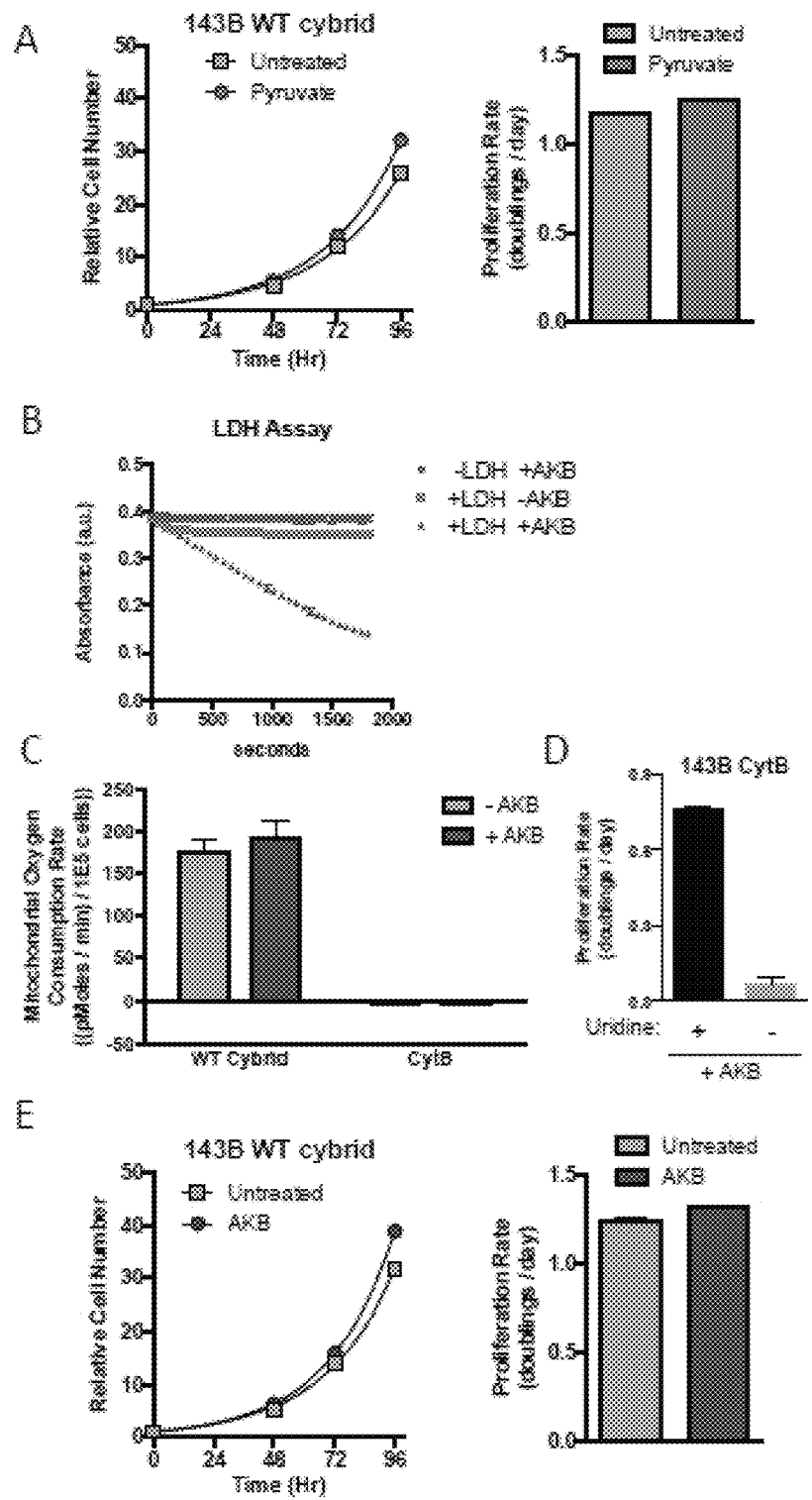
FIG. 7. (A) Proliferation rate of 143B wild-type (WT) cells was determined in the presence or absence of pyruvate. Cells were normalized to cell number at t=0 when media conditions were applied. (B) Assay to determine activity of lactate dehydrogenase (LDH) in the presence or absence of α-ketobutyrate (AKB). (C) Measurement of oxygen consumption rates in 14B WT cybrid and 143 CytB cells in the presence or absence of AKB. (D) Proliferation rate of 143B CytB cells exposed to AKB in the presence or absence of uridine. (E) Proliferation rate of 143B WT cells was determined in the presence or absence of α-ketobutyrate. Cells were normalized to cell number at t=0 when media conditions were applied.

Cells lacking functional respiratory chain, such as ρ0 cells, require pyruvate for proliferation suggesting that pyruvate substitutes for an essential metabolic function of respiration. We reasoned that better understanding the role of pyruvate in these cells would allow us to gain insight into how respiration supports the metabolic needs of proliferating cells. To eliminate respiration-independent effects of mtDNA depletion, we used 143B ρ0 cells that were repopulated with mtDNA harboring a frame shift deletion in cytochrome B (143B CytB), an essential component of complex III of the ETC (Rana et al., 2000). 143B CytB cells have otherwise wild-type mitochondria, but are respiration-incompetent due to lack of functional ETC. As a control we utilized 143B ρ0 cells repopulated with wild-type mtDNA (143B WT cybrid), which have functional ETC and are respiration-competent. 143B CytB cells are indeed auxotrophic for pyruvate as they failed to proliferate in the absence of pyruvate (FIG. 1A). 143B WT cybrid cells cultured with or without pyruvate, and 143B CytB cells with pyruvate divide at a similar rate confirming that pyruvate auxotrophy results from loss of mitochondrial respiration (FIG. 7A).

Several hypotheses have been proposed to explain pyruvate auxotrophy. Pyruvate carbon has many metabolic fates including conversion to oxaloacetate via pyruvate carboxylase, malate via malic enzyme, and acetyl-CoA via the pyruvate dehydrogenase complex. Thus, it has been proposed that pyruvate acts as a carbon substrate for synthesis of biosynthetic intermediates that are normally dependent on respiration. Another possible explanation for pyruvate auxotrophy is the hypothesis that, in the absence of a functional ETC, cells cannot adequately oxidize cellular NADH. Hence, pyruvate may be required to function as an exogenous electron acceptor to regenerate $NAD^+$ via the lactate dehydrogenase (LDH) reaction (FIG. 1B).

In order to decouple the different proposed roles of pyruvate in these cells we sought alternative substrates that could support 143B CytB cell proliferation in the absence of pyruvate. One candidate we identified is the four-carbon metabolite α-ketobutyrate (AKB), which, similar to pyruvate, can act as an substrate for LDH (FIG. 1C). Indeed, we show that in the presence of LDH, AKB is capable of regenerating $NAD^+$ from NADH (FIG. 7B). We then tested whether AKB was sufficient to support proliferation of 143B CytB cells in the absence of pyruvate. Indeed, AKB rescued proliferation rate of 143B CytB cells to levels similar to what was observed with pyruvate addition (FIG. 1D). Supplementation with AKB does not alter oxygen consumption (FIG. 7C), and AKB addition does not alleviate uridine auxotrophy of 143B CytB cells (FIG. 7D). Also, like pyruvate, AKB does not impact proliferation of 143B WT cybrids, demonstrating that the role for AKB in supporting proliferation is downstream of respiration deficiency (FIG. 7E).

As electron acceptors, AKB and pyruvate are both expected to regenerate $NAD^+$. To test whether AKB and pyruvate are sufficient to alter the $NAD^+$/NADH ratio in cells, we measured cellular $NAD^+$/NADH ratios in 143B CytB cells cultured in the absence or presence of either pyruvate or AKB. As expected, addition of either pyruvate or AKB is sufficient to increase the cellular $NAD^+$/NADH ratio, consistent with these molecules serving as exogenous electron acceptors (FIG. 1E).

Given the chemical structure differences between AKB and pyruvate, they cannot share direct carbon-fates, thus we reasoned that AKB is likely being used predominantly as an electron acceptor and not as a carbon substrate in metabolic pathways. To verify this we measured the consumption rate of AKB and the excretion rate of the reduced product, α-hydroxybutyrate (AHB), formed upon $NAD^+$ regeneration (FIG. 1C). Importantly, we found that the consumption rate of AKB matched the excretion rate of AHB (FIG. 1F). Since AKB and AHB are both four-carbon metabolites modified only by a oxidation state, this result strongly suggests that AKB does not provide net carbon for other metabolic pathways. Thus, since AKB is sufficient to replace pyruvate to support proliferation of 143B CytB cells, the pyruvate auxotrophy of these respiration incompetent cells is best explained as a requirement for exogenous electron acceptors. These data suggest that access to exogenous electron acceptors provided by respiration ($O_2$), pyruvate, or AKB are required to support proliferation.

Acute Inhibition of Respiration Causes Auxotrophy for Electron Acceptors.

Figure 2:
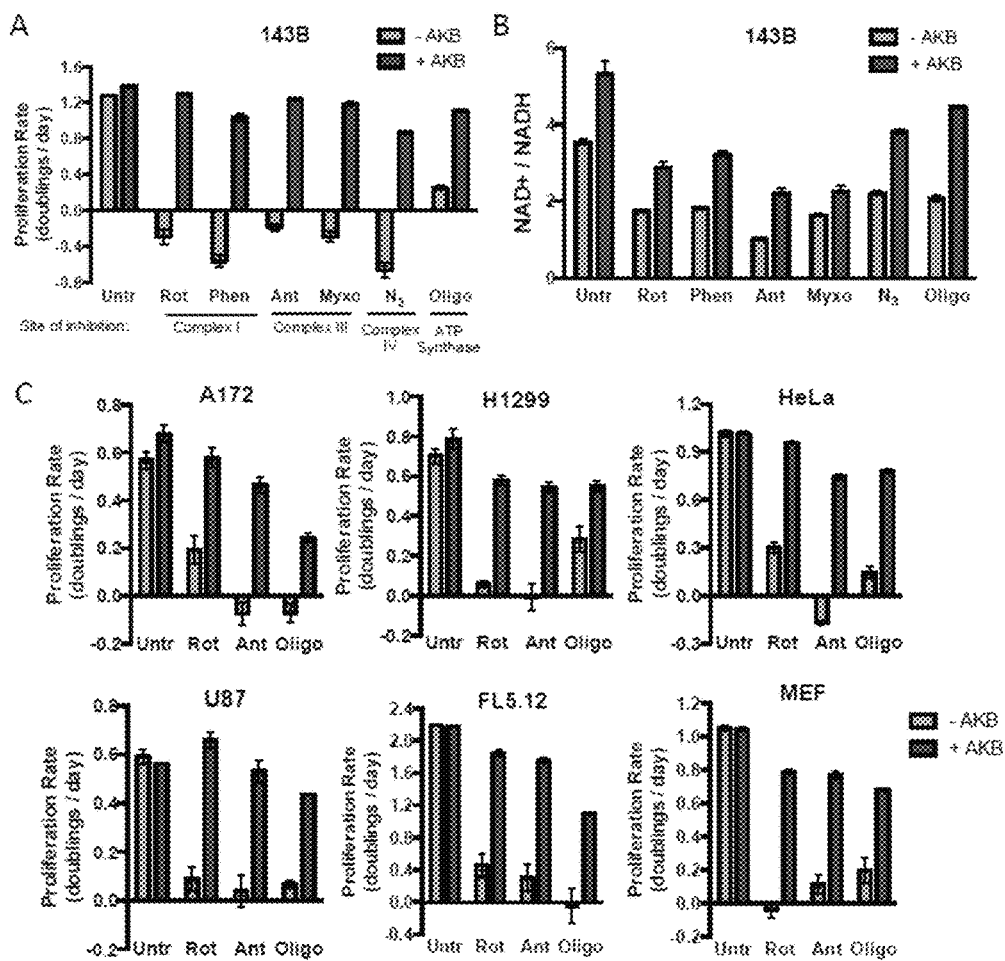
FIG. 2. The anti-proliferative activity of respiration inhibitors is blocked when exogenous electron acceptors are supplied. (A) The proliferation rate of 143B cells was determined in media with or without AKB supplementation in untreated media (untr) or in the presence of the mitochondrial respiration inhibitors rotenone (rot), phenformin (phen), antimycin (ant), myxothiazol (myxo), azide ($N_3$), or oligomycin (oligo). (B) The ratio of $NAD^+$/NADH was determined in 143B cells after 6 hours of treatment in media with or without AKB supplementation in untreated media or in the presence of respiration inhibitors as in (A). (C) The proliferation rate of A172, H1299, HeLa, U87, FL5.12, and MEF cell lines was determined with or without AKB supplementation in untreated media or in the presence of rotenone, antimycin, or oligomycin. Values in all figures denote mean±standard error of the mean (SEM), n=3.

Generation of 143B CytB cells requires a lengthy selection process which could select for uncharacterized adaptations that obscure the metabolic requirements provided by respiration for most proliferating cells. To test whether cells with a functional ETC have the same requirements for respiration, we treated wild-type 143B cells (143B), the unmodified parental cell line of the 143B CytB cells, with an array of respiration inhibitors in the presence of uridine. Inhibitors to mitochondrial complex I, complex III, complex IV, and ATP synthase were all sufficient to suppress proliferation and most resulted in some cell death (FIG. 2A). The doses of ETC inhibitors used decreased oxygen consumption (FIG. 8) and, thus, decreased access to electron acceptors.

Figure 8:
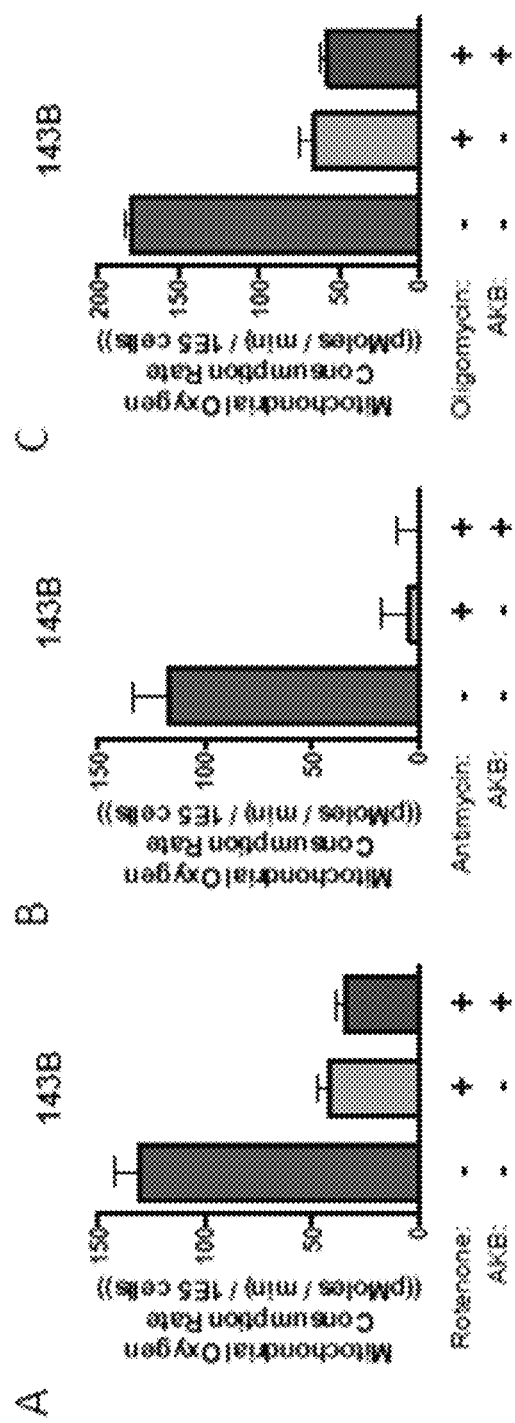
FIG. 8. (A)-(C) Measurement of oxygen consumption rate of 143B CytB cells in the presence or absence of α-ketobutyrate when treated with respiration inhibitors rotenone (A), antimycin (B), and oligomycin (C).

To test the hypothesis that respiration is necessary for proliferation because it provides access to electron acceptors, we tested if AKB supplementation could restore proliferation to respiration-inhibited cells. In all cases, AKB supplementation rescued proliferation, with proliferation rates comparable to that observed in untreated cells (FIG. 2A). To determine whether AKB acts similarly as an electron acceptor in this context, we measured the $NAD^+/NADH$ ratio in cells treated with ETC inhibitors in the absence or presence of AKB. ETC inhibitors all resulted in a decreased cellular $NAD^+/NADH$ ratio in the absence of AKB (FIG. 2B). Treatment with AKB restored $NAD^+/NADH$, while having no effect on $O_2$ consumption, confirming that AKB supplementation provides a source of electron acceptors and is sufficient to increase oxidized cofactor pools (FIG. 8, FIG. 2B). To determine whether a similar dependence on respiration exists in other cells, we treated a panel of genetically diverse cell lines, including both transformed and non-transformed cells, with three representative respiration inhibitors, rotenone (complex I inhibitor), antimycin (complex III inhibitor), and oligomycin (ATP synthase inhibitor). In all cell lines tested, treatment with these three inhibitors blocked proliferation, and addition of AKB was sufficient to restore proliferation in the presence of ETC inhibitors (FIG. 2C). Taken together, these data suggest that the ability to donate electrons to oxygen is a primary function of respiration in supporting proliferation.

Figure 3:
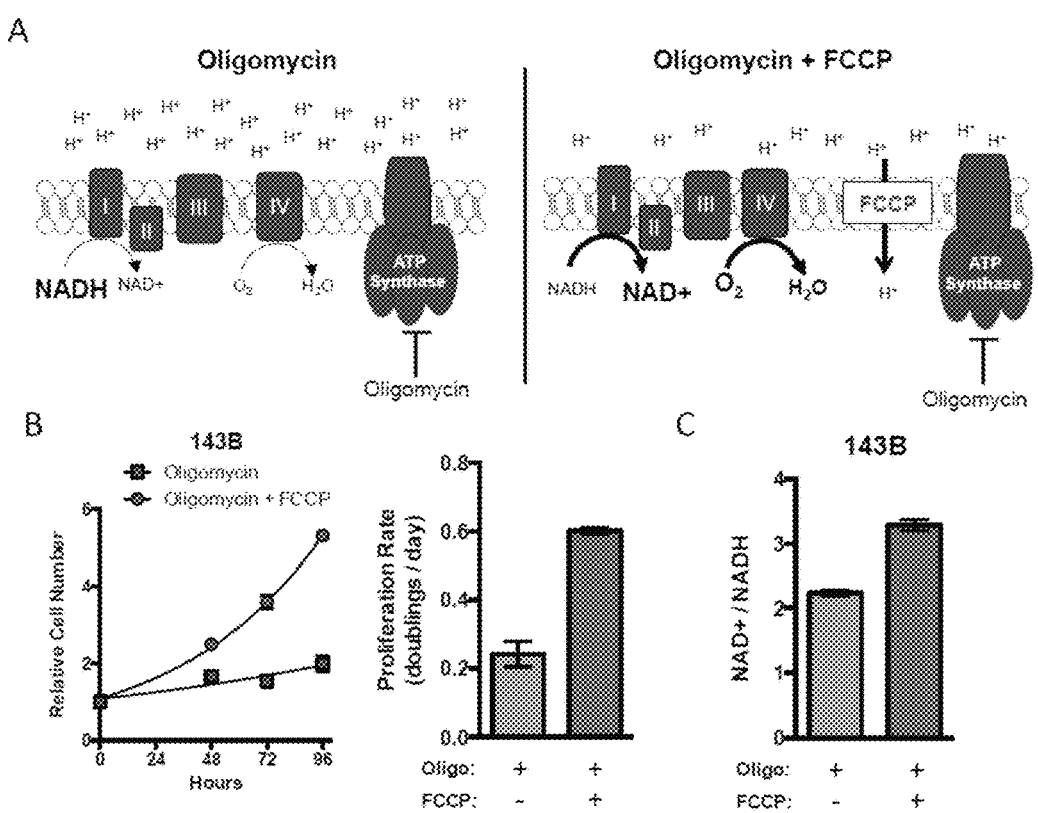
FIG. 3. Restoration of oxygen utilization in the absence of mitochondrial ATP production is sufficient to restore proliferation in oligomycin-treated cells. (A) Schematic illustrating the effects of oligomycin and FCCP on mitochondrial function. Oligomycin treatment inhibits ATP synthase, resulting in a hyperpolarized mitochondrial membrane. This hyperpolarization inhibits proton pumping and thereby inhibits the coupled electron transport activity resulting in decreased NADH oxidation and mitochondrial oxygen consumption (left). Treatment with FCCP in addition to oligomycin relieves the hyperpolarization of the mitochondrial membrane allowing restoration of NADH oxidation and mitochondrial oxygen consumption without restoring ATP production. (right). (B) Proliferation rate of 143B cells treated with oligomycin in the presence or absence of FCCP treatment. (C) Intracellular $NAD^+$/NADH was determined in oligomycin-treated 143B cells treated with oligomycin in the presence or absence of FCCP. Values in all figures denote mean±standard error of the mean (SEM), n=3.

The use of oxygen as a terminal electron acceptor by mitochondrial respiration is well described, however it is classically considered in the context of using NADH oxidation as a means of producing mitochondrial ATP. Notably, reduction of AKB allows regeneration of $NAD^+$ but does not support ATP production, arguing that mitochondrial ATP production is not required for proliferation. To directly test this idea, we utilized oligomycin, a specific ATP synthase inhibitor, and the ionophore carbonyl cyanide-4-(trifluoromethoxy)phenylhydrazone (FCCP), an uncoupler of the mitochondrial membrane potential. In normal respiration, high-energy electrons from NADH are passed through the ETC to pump protons across the mitochondrial inner membrane and generate a chemiosmotic membrane potential. ATP synthase then uses this membrane potential to drive ATP synthesis. As an ATP synthase inhibitor, oligomycin does not directly inhibit components of the ETC, however it does slow ETC activity by hyperpolarizing the membrane potential (FIG. 3A). When hyperpolarization becomes severe enough, the proton pumping components of the ETC become functionally blocked, resulting in decreased oxygen consumption (FIG. 3A). If providing access to electron acceptors were the essential function of respiration independent of ATP production, then restoring oxygen consumption by relieving membrane hyperpolarization with the uncoupling agent FCCP should restore proliferation of oligomycin treated cells (FIG. 3A).

Figure 9:
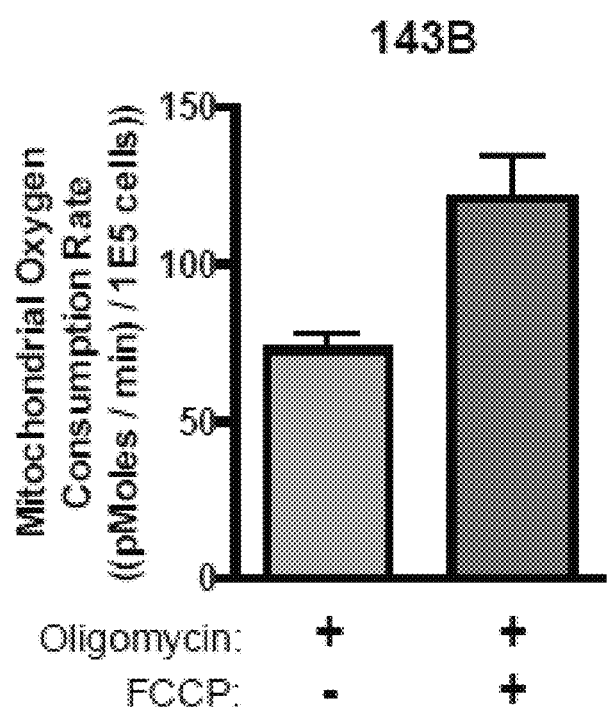
FIG. 9. Measurement of oxygen consumption rate of 143B CytB cells in the presence or absence of oligomycin and FCCP.

We compared the proliferation rate of 143B cells cultured in oligomycin treated with or without FCCP. Consistent with the hypothesis, FCCP addition increased proliferation of oligomycin treated cells (FIG. 3B). Also consistent with the hypothesis, FCCP increased both the $NAD^+/NADH$ ratio and oxygen consumption (FIG. 3C, FIG. 9). Since FCCP and oligomycin act independently, FCCP addition further inhibits mitochondrial ATP production since it decreases the mitochondrial membrane potential. However, since FCCP does restore proliferation, these data argue that providing access to electron acceptors, rather than supporting mitochondrial ATP production, is the most limiting function of mitochondrial respiration in supporting proliferation.

Electron Acceptor Insufficiency Causes Inhibition of Nucleotide Biosynthesis.

Figure 4:
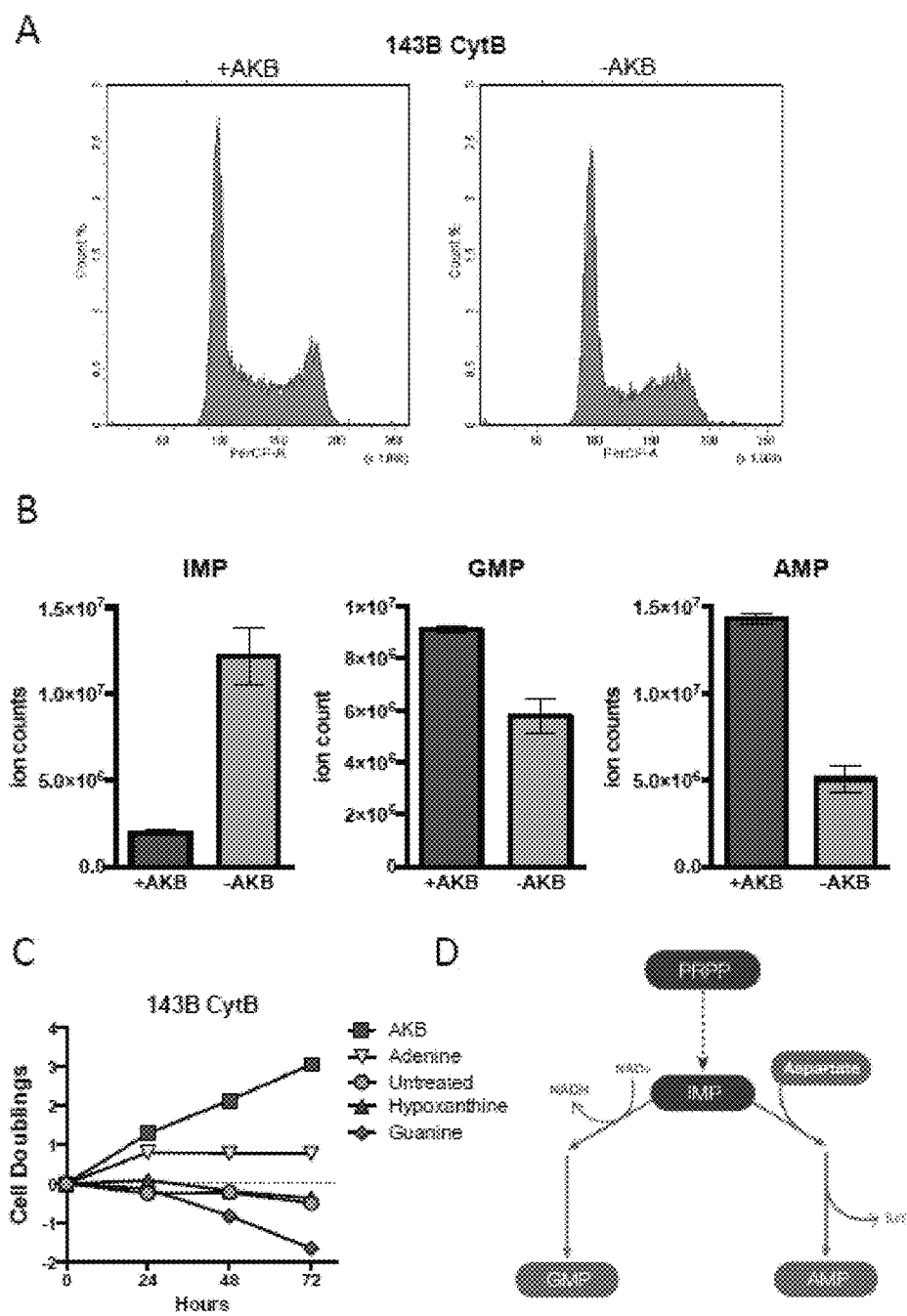
FIG. 4. Electron acceptor insufficiency dysregulates purine nucleotide biosynthesis. (A) Cell cycle distribution of 143B CytB cells was determined with our without AKB supplementation by propidium iodide staining of DNA content and measurement by flow cytometry. (B) LC-MS quantification of purine nucleotide levels in 143B CytB cells with or without AKB supplementation for 8 hours. (C) Cell doublings were measured over time for 143B Cytb cells in untreated media or media supplemented with AKB, adenine, hypoxanthine, or guanine. (D) Schematic illustrating the conversion of IMP into the downstream purine nucleotides GMP and AMP. Synthesis of GMP from IMP uses $NAD^+$, whereas synthesis of AMP requires aspartate. Values in (B) and (C) denote mean±standard error of the mean (SEM), n=3. Data in (A) is representative data from multiple experiments.

To gain mechanistic insight into why electron acceptors are required for proliferation, we further characterized the phenotype of respiration incompetent cells under conditions where access to electron acceptors is limiting. Analysis of DNA content in 143B CytB cells suggested that cells without AKB do not obviously arrest at a specific stage of the cell cycle (FIG. 4A). However, despite complete cessation of proliferation for 78 hours, a substantial fraction of the cells remained in S-phase and compared to cells proliferating with AKB, the non-proliferating population showed a slight accumulation of cells with a DNA content approaching 4N. Interestingly, the inability to generate sufficient nucleotides to support DNA synthesis can cause a similar inability to progress through S-phase (Lunt et al., 2015).

Figure 10:
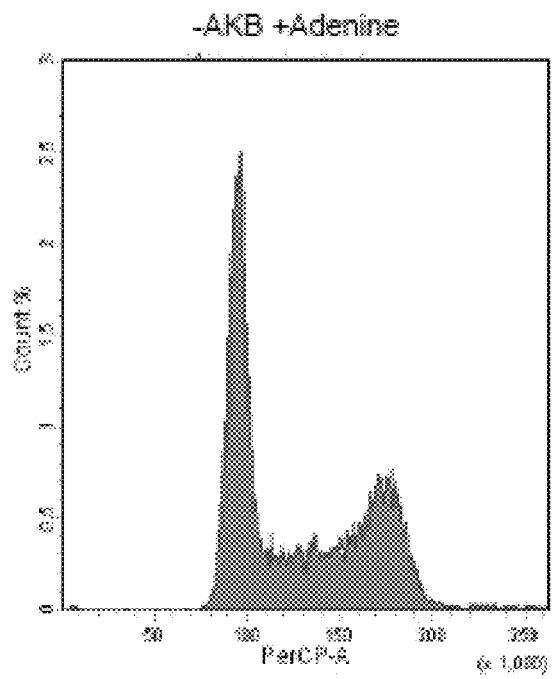
FIG. 10. (A) Cell cycle distribution of 143B CytB cells was determined with adenine supplementation by propidium iodide staining of DNA content and measurement by flow cytometry. (B) LC-MS quantification of purine nucleotide ratios in 143B CytB cells with or without AKB supplementation.
Figure 10:
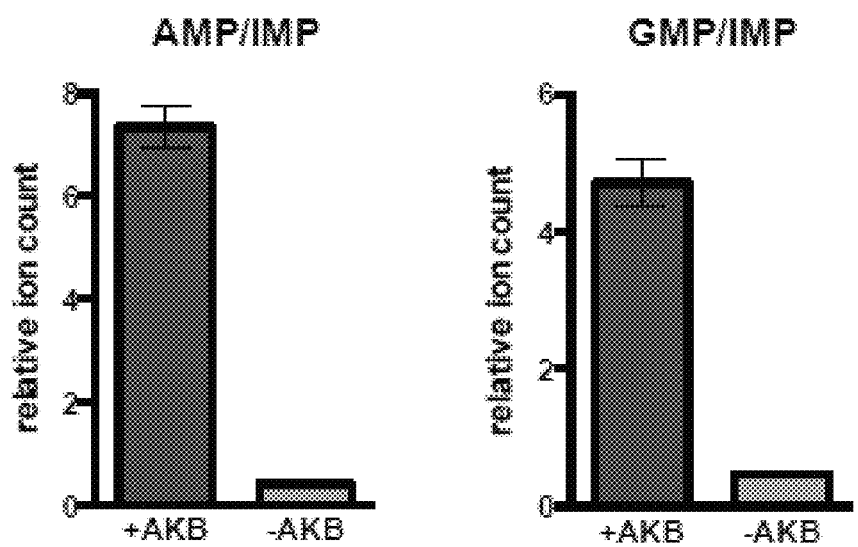

To determine if a deficiency in nucleotide synthesis contributes to the inability to proliferate in the absence of AKB, we quantified nucleotide pools in 143B CytB cells in the presence and absence of AKB using liquid chromatography mass spectrometry (LCMS). Because pyrimidine nucleotide pools are confounded by excess uridine supplemented in the media, we focused analysis on purine nucleotides. We found that compared to AKB replete cells, cells cultured without AKB showed increased levels of the purine nucleotide inosine-5'-monophosphate (IMP) (FIG. 4B). IMP is a precursor of both guanine-5'-monophosphate (GMP) and adenine-5'-monophosphate (AMP) synthesis, but despite an increase in IMP, both GMP and AMP levels were decreased in cells without AKB supplementation (FIG. 4B). To determine whether the deficiency of purine nucleotides is functionally significant, we supplemented 143B CytB cells with exogenous adenine, guanine, and hypoxanthine. Using nucleotide salvage pathways, these nucleobases are converted to AMP, GMP, and IMP, respectively. Surprisingly, whereas hypoxanthine had no effect on proliferation and guanine supplementation was somewhat toxic, supplementation with adenine restored proliferation for one doubling, and alleviated the slight accumulation of cells at the S/G2 transition (FIG. 4C, FIG. 10A). These data suggest that loss of respiration impairs adenine nucleotide synthesis, and the loss of adenine nucleotides appears functionally limiting for proliferation.

Both the AMP/IMP ratio and the GMP/IMP ratio dramatically decrease upon AKB withdrawal (FIG. 10B). This decrease in the AMP/IMP and GMP/IMP ratios suggests an inability to convert IMP to AMP and GMP. Conversion of IMP to GMP consumes an $NAD^+$ by inosine 5'monophosphate dehydrogenase (IMPDH), and, thus, this reaction may be inhibited by decreased $NAD^+$ availability (FIG. 4D). In contrast, conversion of IMP to AMP does not directly require oxidation, but instead consumes aspartate (FIG. 4D). This raises the possibility that aspartate deficiency may cause the lack of adenine nucleotides. Notably, an underlying aspartate deficiency could explain the transitory nature of adenine rescue, since adenine would only restore proliferation of transiently adenine limited cells and fail to meet other biosynthetic requirements for aspartate.

Aspartate Synthesis is Inhibited by Electron Acceptor Insufficiency.

Figure 5:
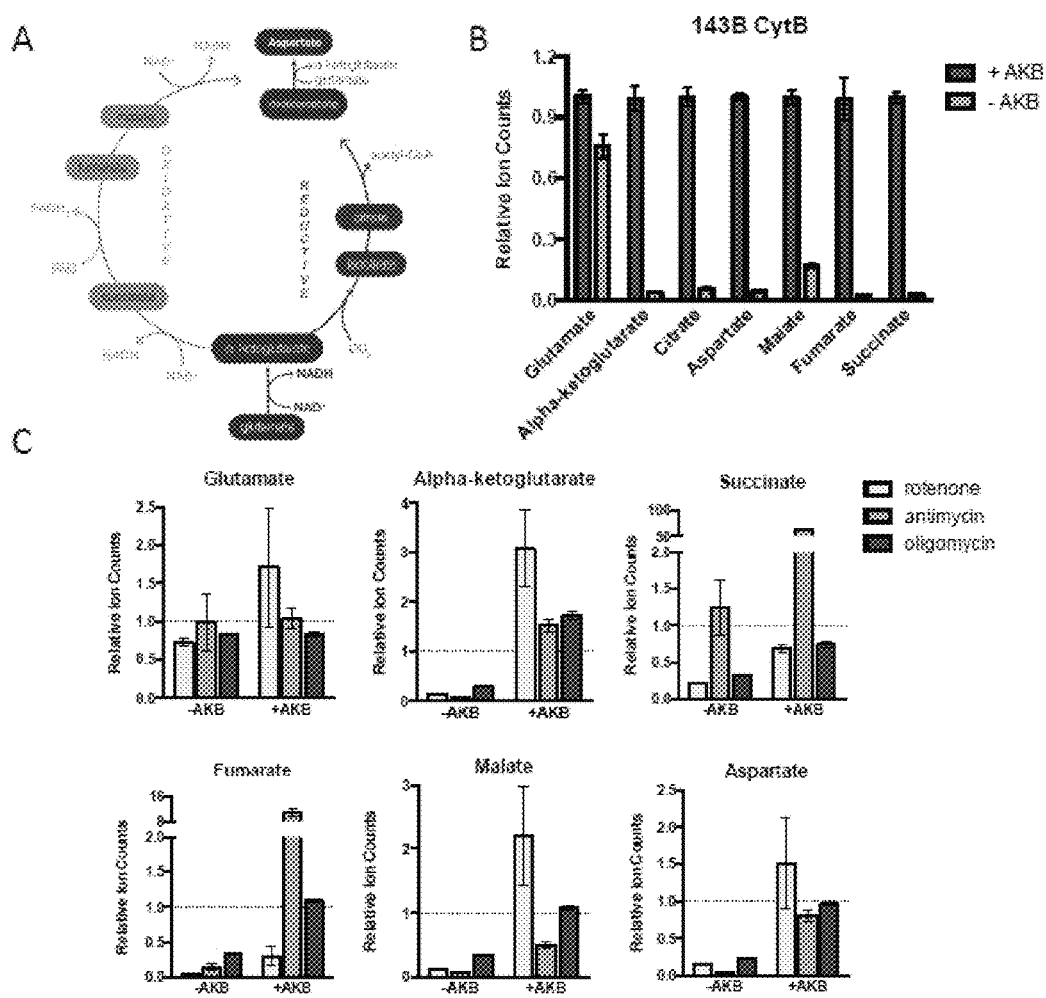
FIG. 5. Electron acceptor insufficiency suppresses TCA metabolite and aspartate pools. (A) Schematic detailing the primary intracellular reaction routes for the biosynthesis of aspartate from glutamine. (B) GC-MS quantification of TCA cycle metabolites, glutamate, and aspartate from 143B CytB cells supplemented with or without AKB for 6 hours. (C) GC-MS quantification of TCA metabolites, glutamate, and aspartate from 143B cells supplemented with or without AKB and mitochondrial inhibitors for 6 hours. Ion counts are relative to untreated 143B cells, which is denoted by the dashed grey line in each panel. Values in (B) and (C) denote mean±standard error of the mean (SEM), n=3.

In most tumor cells in culture, carbon for de novo aspartate synthesis is supplied by anaplerotic glutamine. Glutamine can generate glutamate, which can enter the TCA cycle upon conversion to α-ketoglutarate (FIG. 5A). α-Ketoglutarate is produced by glutamate dehydrogenase (GDH) or by transamination. While GDH uses $NAD^+$ as a co-substrate, the glutamate transaminases utilize α-ketoacids, such as pyruvate, as co-substrates. Regardless of which method is used, production of α-ketoglutarate from glutamate requires conversion of a carbon-nitrogen single bond to a carbon-oxygen double bond. Thus, an electron pair must be removed, and an electron acceptor is required. From α-ketoglutarate, oxidative synthesis of aspartate requires three additional oxidation reactions requiring removal of multiple net electron pairs (FIG. 5A). Aspartate can also be produced by reductive carboxylation of α-ketoglutarate, however this process requires high levels of α-ketoglutarate, which requires electron acceptors to generate from glutamate (Fendt et al., 2013b). Given that both of these aspartate synthesis pathways utilize electron acceptors, we hypothesized that electron acceptor deficiency in respiration-inhibited cells could be limited for aspartate production.

Figure 11:
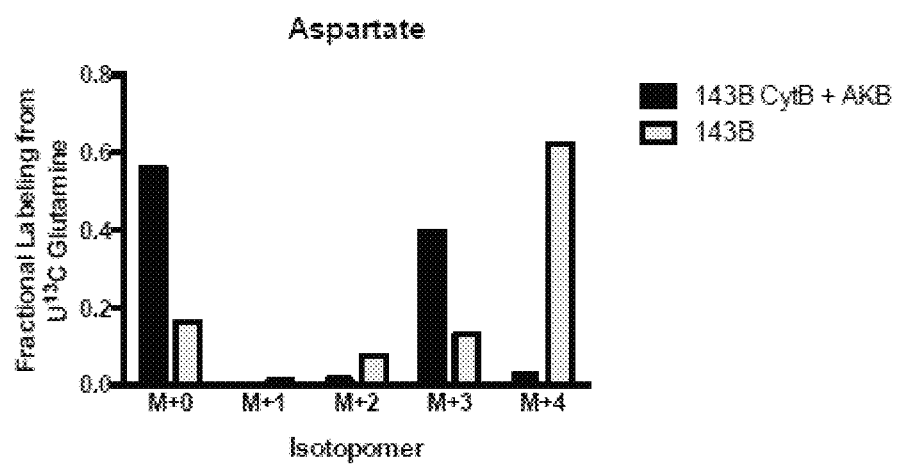
FIG. 11. (A) GCMS isotopomer quantification of aspartate in 143 CytB cells in the presence or absence of α-ketobutyrate and exposed to [U-$^{13}$C]-L-glutamine. (B) Schematic depicting oxidative and reductive glutamine metabolism pathways.
Figure 11:
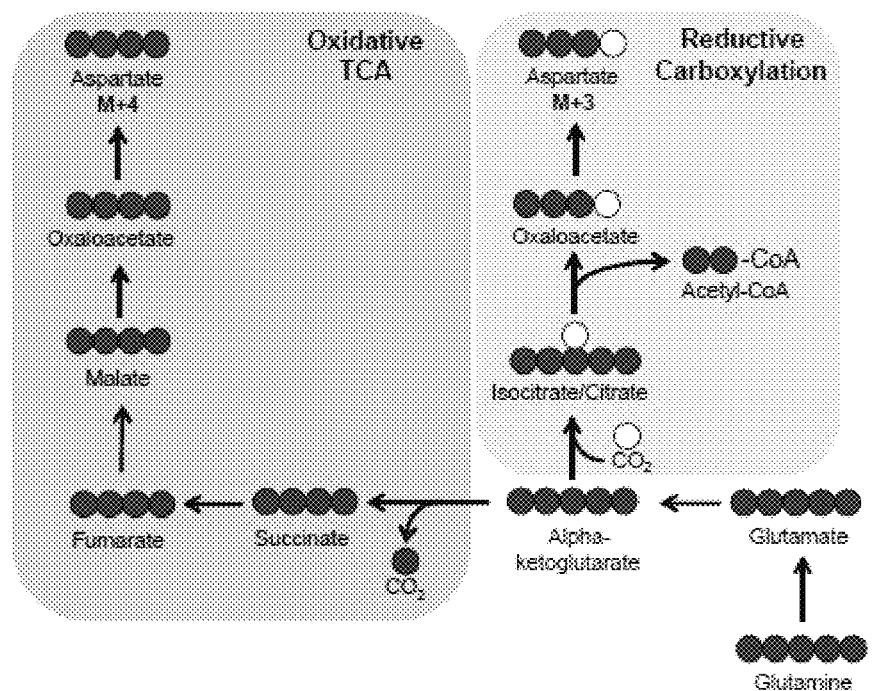

To test this possibility, we used gas chromatography mass spectrometry (GCMS) to measure the electron acceptor dependency of glutamate, aspartate, and TCA cycle metabolite intracellular pool sizes. In 143B CytB cells, which metabolize glutamine by reductive carboxylation (Mullen et al., 2012) (FIG. 11), while glutamate levels were only modestly decreased by AKB withdrawal, pool sizes of TCA cycle metabolites were drastically lowered (FIG. 5B). Importantly, aspartate was also decreased in these cells, supporting the hypothesis that aspartate limitation may explain the AMP/IMP imbalance in these cells. In wild-type 143B cells, which normally produce aspartate by oxidative TCA cycle activity (FIG. 11), treatment with the respiration inhibitors rotenone, antimycin, and oligomycin yielded similar results, with decreases in TCA metabolites and aspartate, but not glutamate (FIG. 5C). In all cases, treatment with AKB restored aspartate to levels comparable to, or higher than, untreated cells. These data demonstrate that lack of available electron acceptors restricts aspartate biosynthesis Aspartate Restores Proliferation in Cells with Electron Acceptor Insufficiency.

Figure 6:
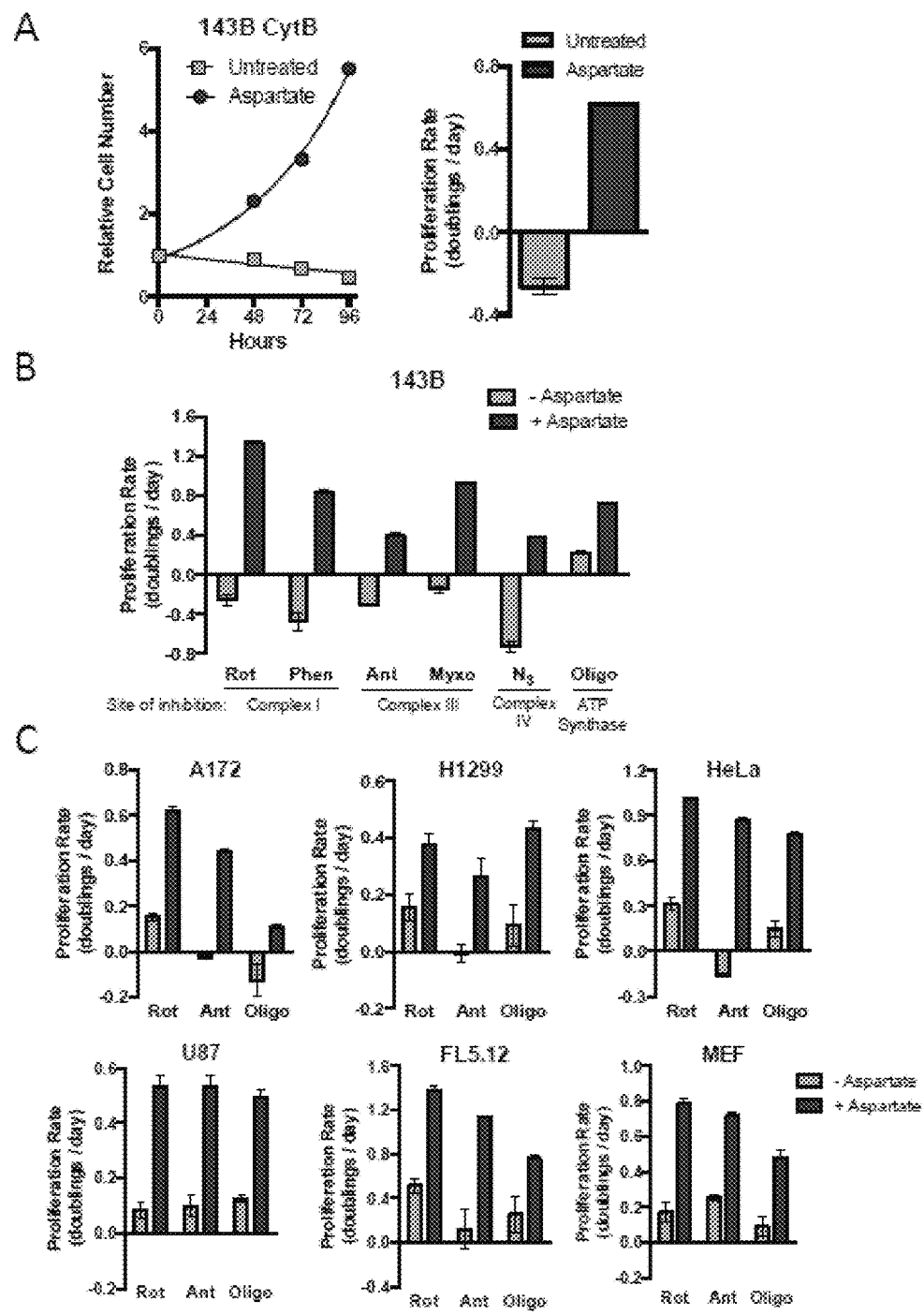
FIG. 6. Aspartate is the key biosynthetic precursor provided by respiration. (A) Proliferation rate of 143B CytB cells was determined in the presence or absence of aspartate. (B) The proliferation rate of 143B cells was determined in media with or without aspartate supplementation in the presence of the mitochondrial respiration inhibitors rotenone (rot), phenformin (phen), antimycin (ant), myxothiazol (myxo), azide ($N_3$), or oligomycin (oligo). (C) The proliferation rate of A172, H1299, HeLa, U87, FL5.12, and MEF cell lines was determined with or without aspartate supplementation in the presence of rotenone, antimycin, or oligomycin. (D) Schematic detailing the role of respiration and exogenous electron acceptors in aspartate biosynthesis. The conversion of glutamine into aspartate requires the removal of electrons and therefore necessitates access to terminal electron acceptors, which can be supplied by respiration, utilizing $O_2$, or other exogenous electron acceptors, such as AKB. Maintenance of aspartate pools supports biosynthesis by acting as a substrate for nucleotide biosynthesis of DNA and RNA as well as by acting as a substrate for protein synthesis. These factors combined indicate that a primary role of respiration is to provide electron acceptors to support aspartate production and thereby proliferation. Values in all figures denote mean±standard error of the mean (SEM), n=3.
Figure 6:
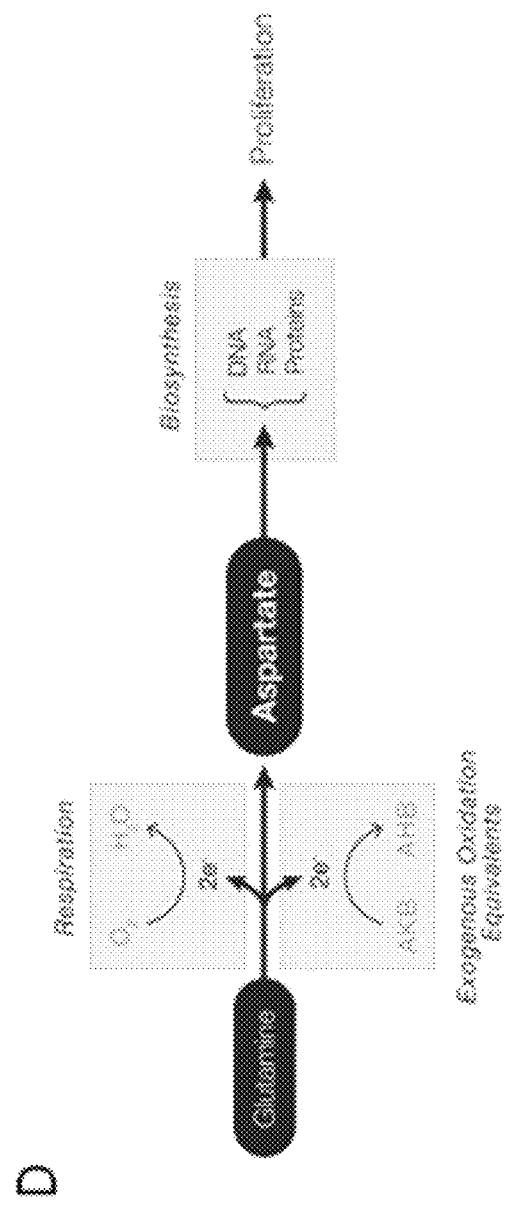
Figure 12:
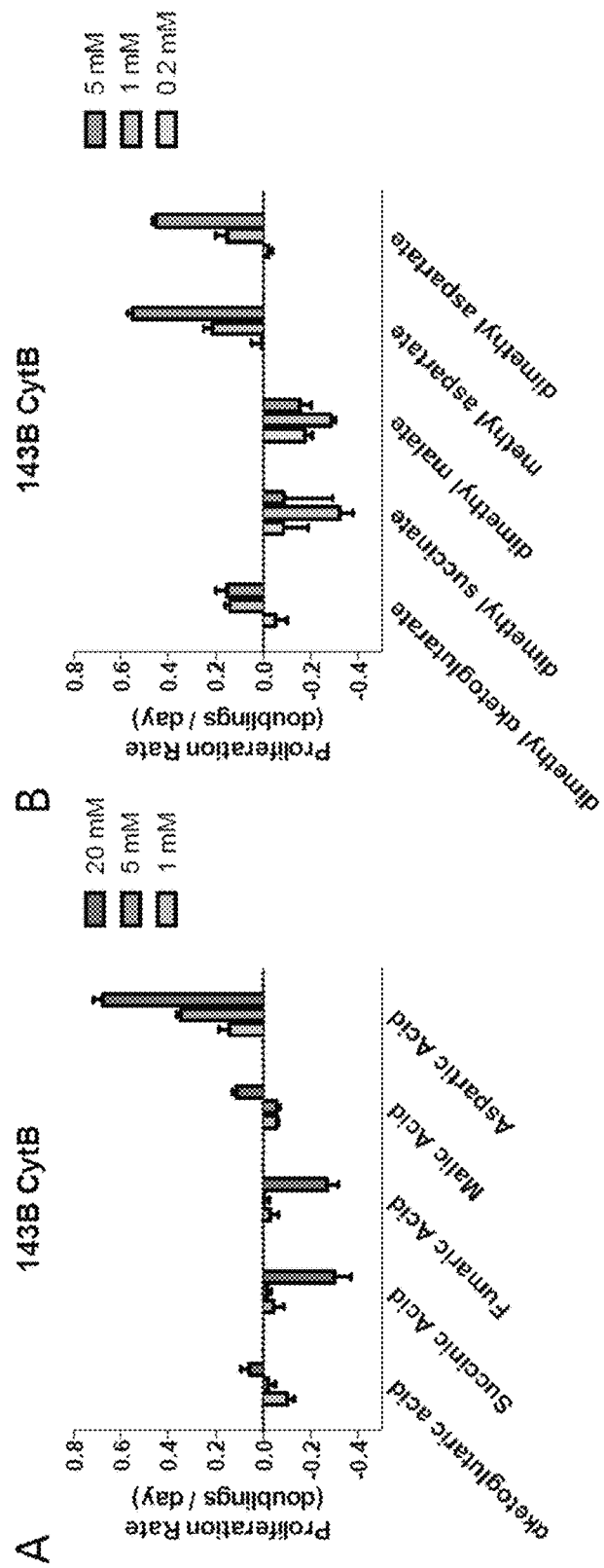
FIG. 12. (A) Proliferation rates of 143B CytB cells after supplementation with TCA cycle derivatives. (B) Proliferation rates of 143B CytB cells after supplementation with cell-permeable methylated derivatives of TCA cycle derivatives. (C) Proliferation rate of 143B WT cybrids was determined in the presence or absence of aspartate. Cells were normalized to cell number at t=0 when media conditions were applied. (D) Measurement of oxygen consumption rates in 143B WT cybrid and 143 CytB cells in the presence or absence of aspartate. (E) Measurement of NAD$^+$/NADH ratios of 143B CytB cells in the presence or absence of aspartate and α-ketobutyrate. (F) LC-MS quantification of purine nucleotide levels in 143B CytB cells with or without aspartate supplementation.
Figure 12:
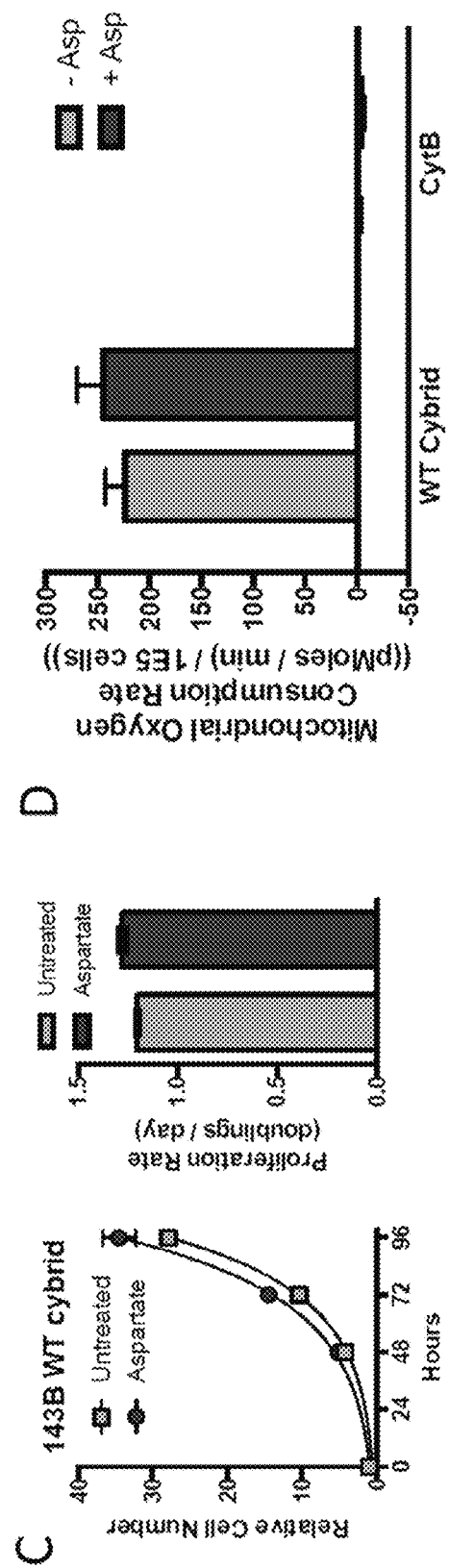
Figure 12:
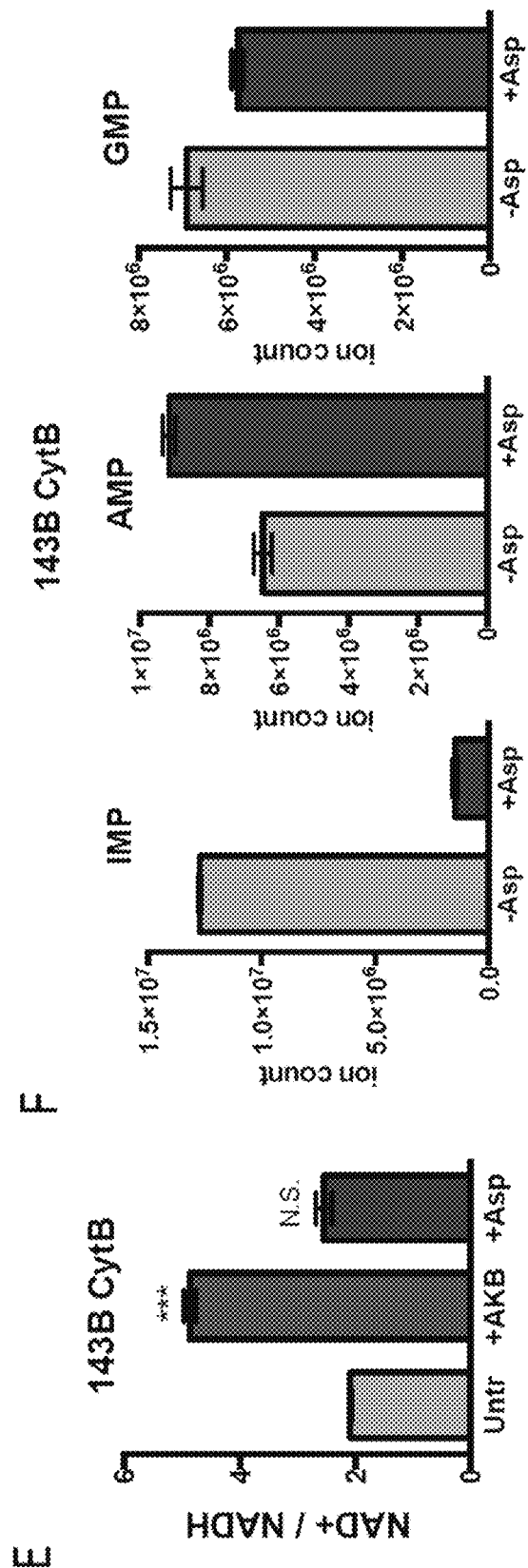

Our data show that in the absence of adequate access to exogenous electron acceptors, aspartate biosynthesis capacity becomes restricted. Because aspartate is required for both nucleotide and protein synthesis, we tested whether exogenous aspartate could replace the requirement for exogenous electron acceptors. Strikingly, in the absence of exogenous electron acceptors, supplementation with supra-physiological levels of aspartate was capable of supporting exponential growth of 143B CytB cells (FIG. 6A). Supplementation with other TCA cycle intermediates, or their cell-permeable derivatives, were unable to restore proliferation to a similar degree (FIG. 12A-B). Respiration-competent 143B WT cybrid cells did not have gross proliferation differences when supplemented with aspartate (FIG. 12C). Importantly, aspartate does not function as an exogenous electron acceptor as it neither increased mitochondrial oxygen consumption, nor did it affect the $NAD^+/NADH$ ratio (FIG. 12D-E). These data imply that aspartate is not an electron acceptor but rather is itself the biosynthetic demand required for proliferation in electron acceptor deficient cells.

Measurement of purine monophosphates shows that treatment of 143B CytB cells with aspartate relieves the accumulation of IMP and restores AMP pools (FIG. 12F). This is consistent with the observation that cells with insufficient electron acceptors, aspartate is limiting for adenine nucleotide synthesis. Interestingly, GMP levels are not restored by aspartate treatment, consistent with the conversion of IMP to GMP being dependent on $NAD^+$, which is not restored by aspartate (FIG. 12E). GMP levels were actually lower in aspartate treated cells, likely as a result of decreased IMP availability (FIG. 12F).

To determine whether aspartate is sufficient to restore proliferation in wild-type cells where respiration is inhibited, wild-type 143B cells were treated with a panel of respiration inhibitors with or without aspartate supplementation. Proliferation was restored in response to all ETC inhibitors when cells were supplemented with high levels of aspartate (FIG. 6B). Aspartate supplementation also rescued ETC inhibitor-induced proliferation decreases in all other cell lines tested (FIG. 6C). Taken together, these data support a model where the major metabolic requirement for proliferating cells fulfilled by respiration is providing access to electron acceptors in the form of oxygen. This access to electron acceptors is required to support de novo aspartate biosynthesis and in the absence of mitochondrial respiration, the demand for oxygen can be met through supplementation of other electron acceptors such as pyruvate or AKB. Alternatively, if the demand for aspartate can be met exogenously, electron acceptors become dispensable for proliferation. Surprisingly, this implies that the major function of respiration in proliferating cells is to support de novo aspartate biosynthesis (FIG. 6D).

In the above experiments metabolic roles of mitochondrial respiration were examined. Whereas in non-proliferating cells respiration is widely viewed primarily as an ATP producing catabolic process, we show that in proliferating cells respiration serves a crucial anabolic role in providing access to electron acceptors to support de novo aspartate biosynthesis. Furthermore, we find that in proliferating cells catabolic mitochondrial ATP production appears entirely dispensable. Proliferating cells have different metabolic requirements than non-proliferating cells; yet, the components of the metabolic network in both proliferating and non-proliferating cells are grossly the same. During cell proliferation these same network components must take on distinct roles to balance the contrasting anabolic and catabolic needs of the cell. Our findings regarding the specific role of respiration in proliferating cells highlight this difference.

All cells must overcome the fundamental thermodynamics problem of continuously performing processes that alone are thermodynamically unfavorable. One solution to this thermodynamics problem is to harness the free-energy of high-energy electrons to drive otherwise thermodynamically unfavorable reactions. The source of high-energy electrons can vary widely from inorganic material for chemolithotrophic bacteria to organic carbon for most heterotrophs. However, in all cases, to harness the free energy of these high-energy electrons, the electrons must be transferred to a terminal electron acceptor in a tightly controlled manner. Mammalian cells utilize high-energy electrons from carbohydrates, lipids, and amino acids. During respiration, these high-energy electrons are passed through the ETC where oxygen serves as the final electron acceptor. During this process, the free energy of the electrons is harnessed to produce cellular ATP. Evolutionarily, it is critical for this process to be tightly coupled to avoid "short-circuits" which burn potential energy. A consequence of this coupling is that in the absence of oxygen as an electron acceptor, the mammalian metabolic network is restricted for the net removal of electrons from consumed carbon substrates.

In physiological contexts where mammalian cells lack access to adequate amounts of molecular oxygen, cells become unable to regenerate oxidized cofactors. Typically, cells under these conditions adapt by engaging in lactic acid fermentation. However, because the production of pyruvate from glucose requires NADH generation, use of glucose-derived pyruvate for lactate fermentation cannot net produce $NAD^+$. For downstream fates of pyruvate other than lactate, cells will require regeneration of $NAD^+$ by the ETC or other oxidation source to maintain intracellular redox status. Thus, while fermentation of glucose can supply cells with net ATP, it cannot net oxidize carbon substrate. For proliferating cells with up-regulated glucose uptake and glycolytic machinery, the lactate fermentation is sufficient to meet the ATP demands for proliferation. However, interestingly, we find that proliferating cells exhibit a demand for net electron acceptors independent of ATP production. This finding suggests that net oxidation of carbon may therefore intrinsically serve an anabolic role. This conclusion is reasonable when considering that cells consume reduced material, with which they can meet the free-energy requirements to maintain homeostasis, but also have anabolic requirements to produce a daughter cell that contains components more oxidized than the nutrients consumed. In order to convert the nutrients taken up by the cell to relatively more oxidized molecules, such as nucleotides, the cell thus requires a source of electron acceptors.

This requirement for electron acceptors is likely not limited to the in vitro contexts investigated in this study. ρ0 cells have been shown to be unable to form xenografts, and reconstituting mtDNA in these cells restores tumorigenicity (Hayashi et al., 1992). This requirement for mtDNA is so strong that, in one study, injected ρ0 cells eventually formed tumors following a long latency, however the cells that grew out were shown to have acquired mtDNA from the host (Tan et al., 2015). While it is possible that ρ0 cells are limited for pyrimidines due to loss of DHODH activity, genetic loss of complex I, which blocks respiration but not DHODH, caused a similar inability to form tumors in vivo (Park et al., 2009). In addition, respiration inhibitors have been shown to inhibit tumor growth in several models of cancer (Wheaton et al., 2014). A consistent model to explain these data is that in vivo tumors with inhibited mitochondria may be limited for aspartate due to a loss of electron acceptors, as we observed in this study. While the serum does contain aspartate, its concentration is around 10 µM, amongst the lowest for circulating amino acids (Mayers and Vander Heiden, 2015). Interestingly, the liver is known to highly express the aspartate aminotransferase (AST) suggesting that the levels of circulating aspartate are highly regulated and maintained at low levels by the liver. Additionally aspartate is nearly impermeable to cells as shown by the supra-physiological doses required to restore growth in electron acceptor deficient cells. Given the low circulating levels and impermeability of aspartate, proliferating cells in vivo are likely required to de novo synthesize their own aspartate and, hence, are dependent on respiration to allow access to electron acceptors.

One intriguing possible method to circumvent the need for net electron acceptors is to fix carbon dioxide to produce a molecule with a fully oxidized carbon atom. This process has been observed primarily at two reactions in central carbon metabolism: pyruvate carboxylase (PC) and isocitrate dehydrogenase (IDH). Pyruvate carboxylation fixes carbon dioxide onto pyruvate to produce oxaloacetate, while reductive IDH activity fixes carbon dioxide onto αketoglutarate resulting in isocitrate. Interestingly, in both cases these reaction pathways can produce aspartate without the need for net removal of electrons. Thus, in contexts of limited electron acceptors these reaction paths would be expected to be important compensatory mechanisms. However, despite the apparent advantage of these paths, we show that in the absence of exogenous electron acceptors, cells do not have sufficient activity to support proliferation exclusively through these pathways and aspartate pools become severely depleted. We speculate that a likely reason for limited activity through these pathways is due to substrate level limitation. Both pathways use relatively oxidized α-ketoacids, pyruvate and α-ketoglutarate, as substrates. We have observed that pyruvate and α-ketoglutarate can themselves act as electron acceptors, and hence, the pool size of these molecules become extremely low when cells cannot access exogenous electron acceptors. To point, pyruvate pool sizes have been shown to be dependent on $NAD^+$/NADH ratio, and so PC activity is likely limited for pyruvate availability in cells without electron acceptors. In addition, reductive IDH activity has been shown to be dictated by the levels of α-ketoglutarate and citrate (Fendt et al., 2013b), thus low α-ketoglutarate levels are predicted to limit activity through this pathway. Interestingly, dimethyl α-ketoglutarate was able to restore some proliferation to 143B CytB cells, albeit at a much lower capacity than aspartate (FIG. 12B). Thus, while these carboxylation reactions may function as adaptive, oxidation equivalent efficient, pathways, they are still dependent on electron acceptors to maintain substrate pools to function at a capacity to restore proliferation.

Beyond reductive IDH and PC activity, because electron acceptor insufficiency suppresses various intermediary pools it is likely that there are other radiating effects that constrain metabolism that do not directly involve net oxidation of carbon. One example we identify in this study in the conversion of IMP to AMP in de novo purine biosynthesis. We show that this reaction appears functionally limited by aspartate depletion. However, in the conversion of IMP to AMP only the aspartate nitrogen is utilized while a fumarate is recycled. Notably, while the aspartate to fumarate conversion does not involve net oxidation or reduction of carbon, this reaction is inhibited because aspartate pools are depleted. In terms of other cascading effects of decreased access to electron acceptors, we find that when oxygen consumption is blocked, cellular $NAD^+$/NADH ratio can no longer be maintained. Beyond the metabolic implications of altered redox cofactor pools, given the emerging importance of the $NAD^+$ cofactor as a component of sirtuin and PARP signaling, we also speculate that electron acceptor insufficiency also likely perturbs various cellular signaling pathways.

Nevertheless, we find that when provided with an alternative source for aspartate, proliferating cells, surprisingly, appear to no longer require exogenous electron acceptors. Indeed, exogenous aspartate addition can restore proliferation in cells that have completely ceased proliferation due to respiration inhibition. Taken together with our finding that the major anabolic requirement filled by respiration is providing access to the electron acceptor oxygen, we conclude that a primary proliferative requirement for respiration is to maintain de novo aspartate biosynthesis.

Identification of Metabolic Genes Sensitive to Respiration Impairment and Metabolic Studies Introduction The mitochondrial electron transport chain (ETC) consists of four enzyme complexes that transfer electrons from donors like NADH to oxygen, the ultimate electron acceptor. During electron transfer, the ETC pumps protons into the intermembrane space, generating a gradient across the inner mitochondrial membrane that the FoF1 ATPase exploits to drive ATP synthesis (Mitchell, 1961; Nicholls and Budd, 2000; Wallace, 2013). Many metabolic pathways, including glycolysis, the TCA cycle, and beta-oxidation, produce the electron donors that fuel the ETC. In turn, ETC activity impacts a variety of processes beyond energy balance (Nunnari and Suomalainen, 2012; Pagliarini and Rutter, 2013), such as reactive oxygen species (ROS) production (Bell et al., 2007; Boveris et al., 1972), the redox state (Di Lisa and Ziegler, 2001; Stein and Imai, 2012), mitochondrial membrane potential (Chen et al., 2014), mitochondrial protein import (Geissler et al., 2000), apoptosis (Green and Reed, 1998; Newmeyer and Ferguson-Miller, 2003), and signaling (Chandel, 2014; Schieber and Chandel, 2014). Diseases caused by genetic defects in the ETC are characterized by diverse pathologies (Koopman et al., 2012), like neurodegeneration (Bender et al., 2006; Swerdlow et al., 1996), myopathy (DiMauro, 2010; Shoffner et al., 1990), and deafness (Kokotas et al., 2007; Raimundo et al., 2012), but in most cases it is unclear how ETC dysfunction leads to the specific symptom.

One consequence of ETC dysfunction is impaired cell proliferation, and human cells in culture arrest upon pharmacological or genetic inhibition of complex I (Fendt et al., 2013a; Wheaton et al., 2014a) or III (Han et al., 2008; Howell and Sager, 1979). Even though changes in ATP or ROS levels have been suggested to underlie the anti-proliferative effects of ETC inhibition (Wallace, 1999), the exact reason why proliferation requires the ETC is not understood. Interestingly, it has long been known that human cells lacking a functional ETC can proliferate if cultured in supra-physiological concentrations of pyruvate (King and Attardi, 1989). While pyruvate can serve as a biosynthetic substrate or affect the redox state of the cell by promoting the regeneration of $NAD^+$ (Harris, 1980; Howell and Sager, 1979), why it reverses the suppressive effects of ETC inhibition on cell proliferation is unknown.

Through a CRISPR (clustered regularly interspaced short palindromic repeat)-based genetic screen, we discovered that the key function of the ETC required for cell proliferation is to enable the synthesis of aspartate, a proteinogenic amino acid that is also a precursor in purine and pyrimidine synthesis (Lane and Fan, 2015). Aspartate becomes limiting upon ETC inhibition and its supplementation, like that of pyruvate, allows cells with defective ETC activity to proliferate. Finally, we find that pyruvate reverses the anti-proliferative effects of ETC inhibition by inducing aspartate synthesis.

Experimental Methods
Cell Lines, Constructs and Antibodies

Materials were obtained from the following sources: antibodies to GOT1 from Novus (NBP1-54778), to MDH1 from Proteintech (15904-1-AP), to PC from Novus (NBP1-49536), to Raptor, mTOR, and pan-Akt from Cell Signaling Technologies; HRP-conjugated anti-rabbit antibody from Santa Cruz; Cell-Tak from BD Biosciences; sodium pyruvate, aspartic acid, polybrene, puromycin from Sigma; and blasticidin from Invivogen.

The Jurkat and Raji cell lines were purchased from ATCC and KMS-26 cells from the JCRB Cell Bank. 143B ρ0, wild type, and CYTB cybrids were kindly provided by Navdeep Chandel (Northwestern University). MERRF cybrids were kindly provided by Giovanni Manfredi (Kwong et al., 2007; Wallace et al., 1988). All cell lines were grown in RPMI base medium containing 10% heat inactivated fetal bovine serum, 1 mM glutamine, penicillin, and streptomycin, unless otherwise indicated. For tracing experiments, RPMI without glucose and glutamine (US Biologicals-R9011), dialyzed fetal bovine serum (Sigma) and [U-$^{13}$C]-L-glutamine (CIL, CLM-1822-H-PK) were used. For cybrid and 143B ρ0 proliferation experiments, RPMI without amino acids (US Biologicals-R8999) was used. Mouse embryonic fibroblasts were cultured in DMEM with 10% heat inactivated fetal bovine serum. Individual amino acids were reconstituted to RPMI amino acid concentrations except for aspartate and asparagine for the experiment in FIG. 19D.

The lentiviral sgGOT1, sgMDH1 and sgPC vectors were generated via ligation of hybridized oligos (below) into lentiCRISPR-v1 vector linearized with BsmBI using Gibson assembly (NEB).

```
                            (SEQ ID NO: 2)
sgGOT1_10F,    caccgGATAGGCTGAGTCAAAGAAG (SEQ ID NO: 3)
sgGOT1_10R,    AAACCTTCTTTGACTCAGCCTATCC (SEQ ID NO: 4)
sgMDH1_1F,     caccgGACATCTGGATACTGAGTCG (SEQ ID NO: 5)
sgMDH1_1R,     aaacCGACTCAGTATCCAGATGTCc (SEQ ID NO: 6)
sgPC_1R,       caccgCAGGCCCGGAACACACGGA (SEQ ID NO: 7)
sgPC_1R,       aaacTCCGTGTGTTCCGGGCCTGc
```

The retroviral GOT1 and MDH1 vectors were generated by cloning sgGOT1_10 and sgMDH1_1 resistant GOT1 and MDH1 cDNAs synthesized by IDT (Geneblock) into the pMXS-ires-blast vector via Gibson Assembly. The retroviral SLC1A3 vector was generated by cloning an SLC1A3 PCR fragment into the pMXS-ires-blast vector A by Gibson Assembly. Primers for SLC1A3 PCR are below.

```
SLC1A3F,
                                        (SEQ ID NO: 8)
GCCGGATCTAGCTAGTTAATTAAGccaccATGACTAAAAGCAATGGAGA
AGAGCCC;

SLC1A3R,
                                        (SEQ ID NO: 9)
GGGCGGAATTTACGTAGCCTACATCTTGGTTTCACTGTCGATGGG
```

CRISPR-Based Screen

The metabolism-focused sgRNA library was designed as previously described (Wang et al., 2014). Oligonucleotides for sgRNAs were synthesized by CustomArray Inc. and amplified by PCR (Wang et al., 2014). Amplicons were inserted into lentiCRISPR-v1, linearized by BsmBI digestion, by Gibson Assembly (NEB). Gibson Assembly products were then transformed into E. coli 10G SUPREME electrocompetent cells (Lucigen). This plasmid pool was used to generate lentivirus-containing supernatants. The titer of lentiviral supernatants was determined by infecting targets cells at several amounts of virus in the presence of polybrene (4 μg/ml), counting the number of drug resistant infected cells after 3 days of selection. 40 million target cells were infected at an MOI of ~0.5 and selected with puromycin (4 μg/ml) 72 hours after infection. An initial pool of 40 million cells was harvested for genomic DNA extraction. The remaining cells were cultured for 14 doublings (with/without phenformin), after which cells were harvested for genomic DNA extraction. sgRNA inserts were PCR amplified, purified and sequenced on a HiSeq 2500 (Illumina) (primer sequences provided below). Sequencing reads were mapped and the abundance of each sgRNA was tallied. Gene score is defined as the median log 2 fold change in the abundance between the initial and final population of all sgRNAs targeting that gene. The differential gene score is the difference between the untreated and phenformin-treated gene scores.

PCR primers for library amplification:

```
                                           (SEQ ID NO: 10)
    F-GGCTTTATATATCTTGTGGAAAGGACGAAACACCG (SEQ ID NO: 11)
    R-CTAGCCTTATTTTAACTTGCTATTTCTAGCTCTAAAAC
```

Primer sequences for sgRNA quantification are:

```
                                           (SEQ ID NO: 12)
F-AATGATACGGCGACCACCGAGATCTAGAATACTGCCATTTGTCTCAAG (SEQ ID NO: 13)
R-CAAGCAGAAGACGGCATACGAGATCnnnnnnTTTCTTGGGTAGTTTGC

AGTTTT (nnnnn denotes the sample barcode).
```

Illumina sequencing primer is:

```
                                           (SEQ ID NO: 14)
CGGTGCCACTTTTTCAAGTTGATAACGGACTAGCCTTATTTTAACTTGCT

ATTTCTA GCTCTAAAAC.
```

Illumina indexing primer is:

```
                                           (SEQ ID NO: 15)
TTTCAAGTTACGGTAAGCATATGATAGTCCATTTTAAAACATAATTTTAA

AACTGCAA ACTACCCAAGAAA.
```

Proliferation Assays

Indicated cell lines were cultured in replicates of three in 96-well plates at 2-3,000 cells per well in 200 μL RPMI base media under the conditions described in each experiment, and a separate group of 3 wells was also plated for each cell line with no treatment for an initial time point. After 5 hours (untreated cells for initial time point) or after 5 days (with varying treatment conditions), 40 μL of Cell Titer Glo reagent (Promega) was added to each well, mixed briefly, and the luminescence read on a Luminometer (Molecular Devices). For each well, the fold change in luminescence relative to the initial luminescence was measured and reported in a log 2 scale.

Cell Counting Assays

Cybrids or 143B ρ0 cells were plated in triplicate in 12 well plates at 5,000-20,000 cells per well in 1.5 mL as described in each experiment. After six days, the entire contents of the well was trypsinized and counted using a Beckman Z2 Coulter Counter with a size selection setting of 8-30 um.

Seahorse Measurements

Oxygen consumption of intact cells was measured using an XF24 Extracellular Flux Analyzer (Seahorse Bioscience). For Jurkat cells, seahorse plates were coated with cell TAK (BD, 0.02 mg/ml in 0.1 μM NaHO3) for 20 minutes to increase adherence of suspension cells. 200,000 cells were then attached to the plate by centrifugation at 2,200 rpm without brakes for 5 min. RPMI 8226 (US biological #9011) assay media was used as previously described (Birsoy et al., 2014). For basal oxygen consumption measurements the cell number was used to normalize.

Generation of Knock-Out and cDNA Overexpression Cell Lines sgRNAs (oligonucleotide sequences are indicated above) were cloned into lentiCRISPR-v1 linearized with BsmBI by Gibson Assembly (NEB). sgRNA expressing vector along with lentiviral packaging vectors Delta-VPR and CMV VSVG were transfected into HEK-293T cells using the XTremeGene 9 transfection reagent (Roche). Similarly, for overexpression cell lines, cDNA vectors along with retroviral packaging vectors gag-pol and CMV VSV-G were transfected into HEK-293T cells. Media was changed 24 hours after transfection. The virus-containing supernatant was collected 48 and 72 hours after transfection and passed through a 0.45 μm filter to eliminate cells. Target cells in 6-well tissue culture plates were infected in media containing 8 μg/mL of polybrene and a spin infection was performed by centrifugation at 2,200 rpm for 1 hour. Post-infection, virus was removed and cells were selected with puromycin or blastocidin. For knock out cells, after selection, cells were single-cell sorted with a flow cytometer into the wells of a 96-well plate containing 200 μL of RPMI supplemented with 20% FBS. Cells were grown for two weeks, and the resultant colonies were trypsinized and expanded. Clones were validated for loss of the relevant protein via immunoblotting.

Immunoblotting 1.5 million Jurkat cells were rinsed twice in ice-cold PBS and harvested in a standard lysis buffer containing 50 mM Hepes, pH 7.4, 40 mM NaCl, 2 mM EDTA, 1.5 mM orthovanadate, 50 mM NaF, 10 mM pyrophosphate, 10 mM glycerophosphate, protease inhibitors (Roche) and 1% Triton-X-100. Proteins from total lysates were resolved by 8-12% SDS-PAGE, and analyzed by immunoblotting as described (Birsoy et al., 2014).

Gene Set Enrichment Analysis

To study the association of gene sets with sensitivity to phenformin, we used the GSEA tool developed by the Broad Institute (Subramanian et al., 2005). The enrichment scores (ES) were computed for the ranked genes from the phenformin CRISPR-based screen.

Metabolite Profiling and Isotope Tracing

LC/MS analyses were conducted on a QExactive benchtop orbitrap mass spectrometer equipped with an Ion Max source and a HESI II probe, which was coupled to a Dionex UltiMate 3000 UPLC system (Thermo Fisher Scientific, San Jose, Calif.). External mass calibration was performed using the standard calibration mixture every 7 days.

For metabolite profiling experiments, Jurkat cells (2 million per sample) were incubated with 10 μM phenformin for 24 hours. Similarly, for glutamine tracing experiments, Jurkat cells (2 million per sample) were incubated with 10 μM phenformin for 18 hours; the cells were spun down and media was replaced with RPMI supplemented with 1 mM [U-$^{13}$C]-L-glutamine for 7 hours. Polar metabolites were extracted using 1 ml of ice-cold 80% methanol with 10 ng/ml valine-$d_8$ as an internal standard. After a 10 min vortex and centrifugation for 10 min at 4° C. at 10,000 g, samples were dried under nitrogen gas. Dried samples were stored at −80° C. and then resuspended in 100 μL water; 1 μl of each sample was injected onto a ZIC-pHILIC 2.1×150 mm (5 μm particle size) column (EMD Millipore). Buffer A was 20 mM ammonium carbonate, 0.1% ammonium hydroxide; buffer B was acetonitrile. The chromatographic gradient was run at a flow rate of 0.150 ml/min as follows: 0-20 min.: linear gradient from 80% to 20% B; 20-20.5 min.:

linear gradient from 20% to 80% B; 20.5-28 min.: hold at 80% B. The mass spectrometer was operated in fullscan, polarity switching mode with the spray voltage set to 3.0 kV, the heated capillary held at 275° C., and the HESI probe held at 350° C. The sheath gas flow was set to 40 units, the auxiliary gas flow was set to 15 units, and the sweep gas flow was set to 1 unit. The MS data acquisition was performed in a range of 70-1000 m/z, with the resolution set at 70,000, the AGC target at 106, and the maximum injection time at 80 msec. Relative quantitation of polar metabolites was performed with XCalibur QuanBrowser 2.2 (Thermo Fisher Scientific) using a 5 ppm mass tolerance and referencing an in-house library of chemical standards.

NAD$^+$ and NADH Measurements:

Measurement of NAD$^+$/NADH was done by modification of manufacturer instructions for NAD$^+$/NADH Glo Assay (Promega). Jurkat cells were incubated in RPMI under the conditions listed for 8 hours before cell extracts were taken. To extract NAD$^+$/NADH, cells were centrifuged for 1 minute at 300×g, and washed 3 times by quickly resuspending in 15 mL PBS and centrifuging for 1 minute at 300×g. Pelleted samples were extracted in 100 µL ice cold lysis buffer (1% Dodecyltrimethylammonium bromide (DTAB) in 0.2 N NaOH diluted 1:1 with PBS) and frozen at −80° C. To measure NADH, 20 µL of extracts were heated to 75° C. for 30 min in the basic lysis buffer to degrade NAD$^+$. To measure NAD$^+$, samples were diluted 1:1 with 0.4 N HCl and incubated at 60° C. for 15 min where acidic conditions will degrade NADH. Following incubations, samples were quenched by adding 20 µL of 0.25 M Tris, 0.2 N HCl (NADH) or 20 µL of 0.5 M Tris base (NAD$^+$). Manufacturer instructions were then followed to measure NAD$^+$/NADH.

Results

Figure 13:
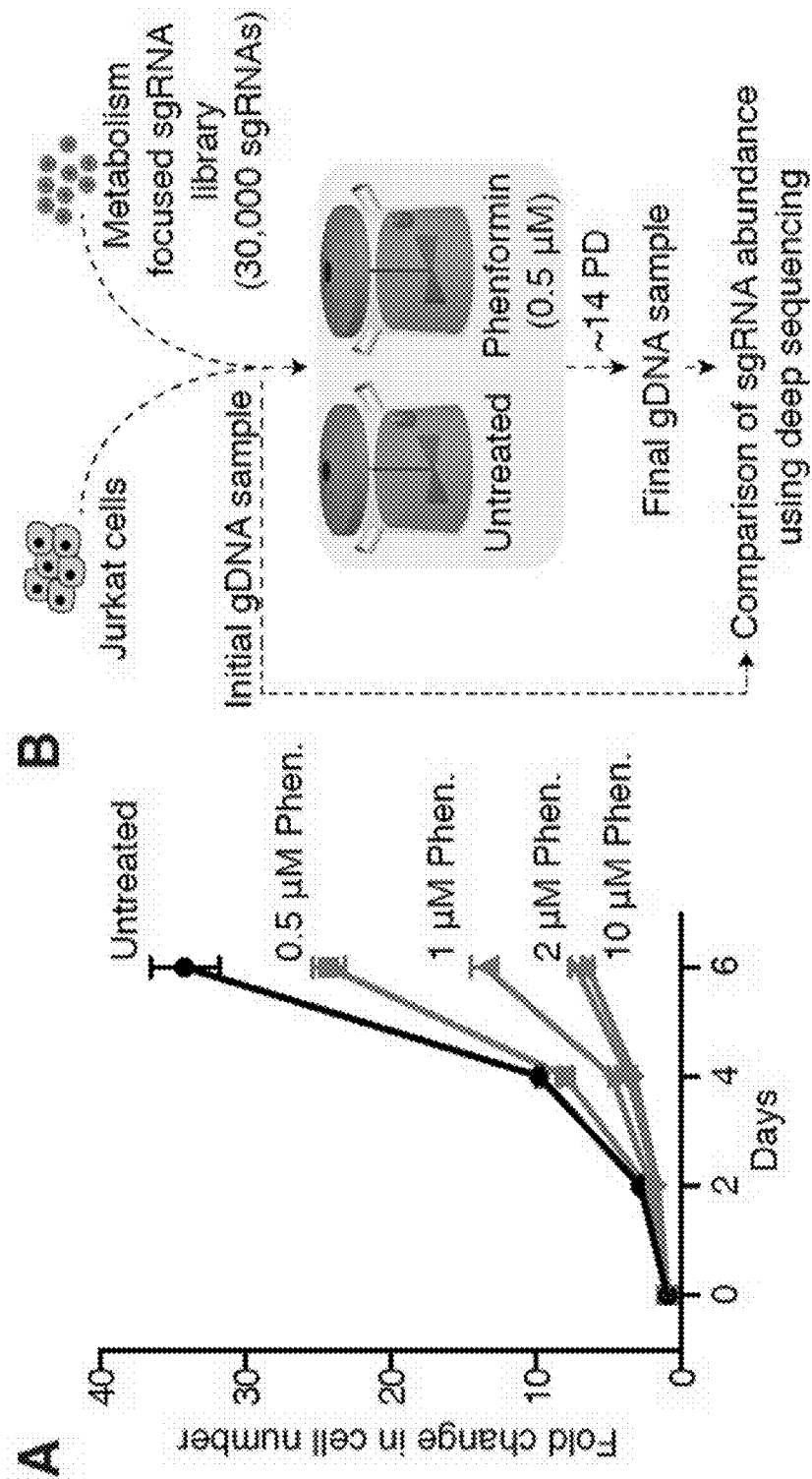
FIG. 13. A CRISPR-based genetic screen identifies metabolic genes whose loss sensitizes human cells to phenformin. (A) Dose-dependent effects of phenformin on Jurkat cell proliferation (mean±SD, n=3). (B) Schematic depicting the pooled CRISPR-based screen. (C) Gene scores in untreated versus phenformin-treated (0.5 μM)Jurkat cells. The gene score is the median log 2 fold change in the abundance of all sgRNAs targeting that gene during the culture period. Most genes, as well as non-targeting control sgRNAs, have similar scores in the presence or absence of phenformin. (D) Top 25 genes scoring as differentially required upon phenformin treatment (top). Genes linked to the GOT1-catalyzed transamination reaction are indicated in red, the ETC in blue, and to nucleotide biosynthesis in green. The top-scoring gene, GOT1, catalyzes the transamination of aspartate to α-ketoglutarate yielding L-glutamate and oxaloacetate (OAA) and requires PLP as a cofactor (bottom). (E) Changes in abundance in the primary screen of the individual GOT1 sgRNAs in the presence (gray) or absence (black) of phenformin. (F) GOT1-null cells die upon phenformin treatment. Immunoblot analysis for indicated proteins of wild type and GOT1-null Jurkat cells (top). Akt was used as a loading control. Fold change in cell number (log 2) of wild type (black) and GOT1-null (blue) Jurkat cells after treatment with indicated phenformin concentrations for 5 days (mean±SD, n=3) (bottom). Representative bright-field micrographs of indicated cells after a 5-day phenformin treatment (right). (G) Expression of an sgRNA-resistant GOT1 cDNA rescues phenformin sensitivity of the GOT1-null Jurkat cells. Immunoblot analysis of wild type, GOT1-null, and rescued null cells (top). Raptor was used as a loading control. Fold change in cell number (log 2) of wild type (black), GOT1-null (blue), and rescued GOT1-null (gray) cells after a 5-day treatment with indicated phenformin concentrations (mean±SD, for n=3) (bottom).
Figure 13:
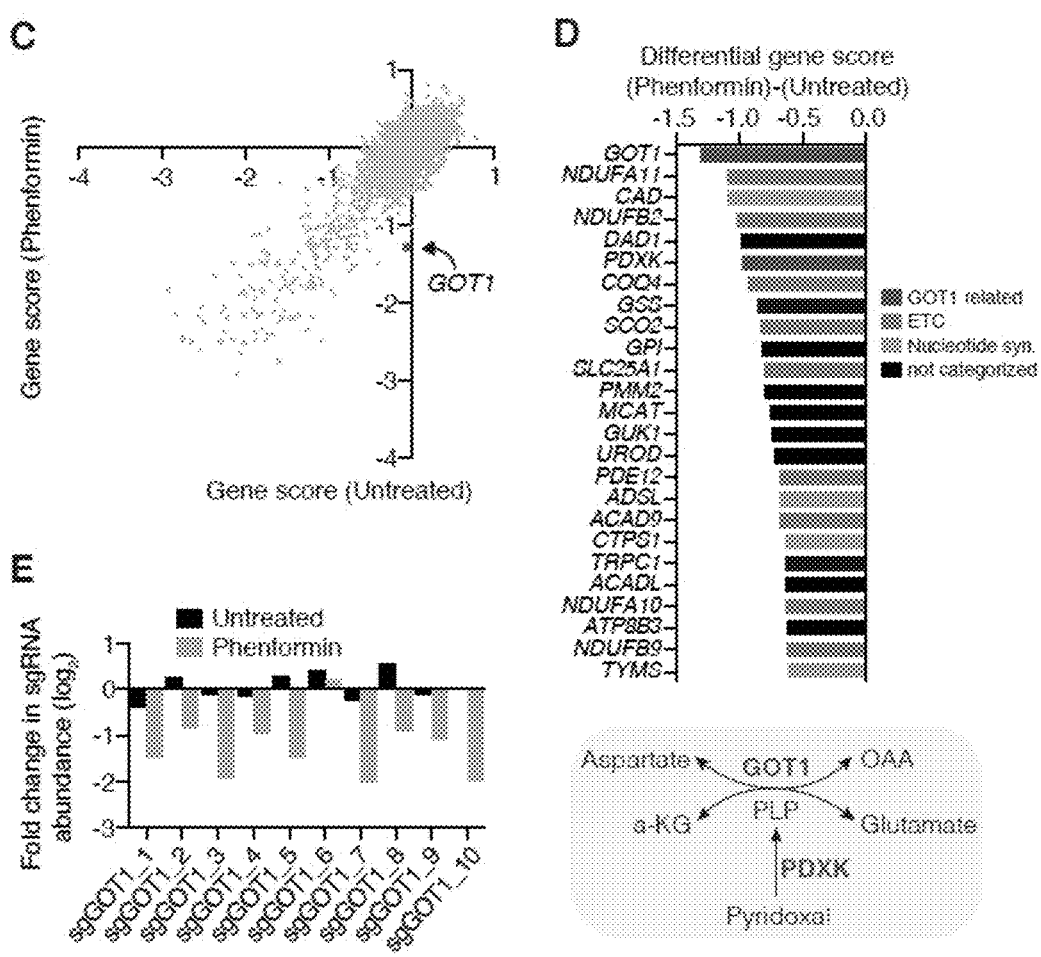
Figure 13:
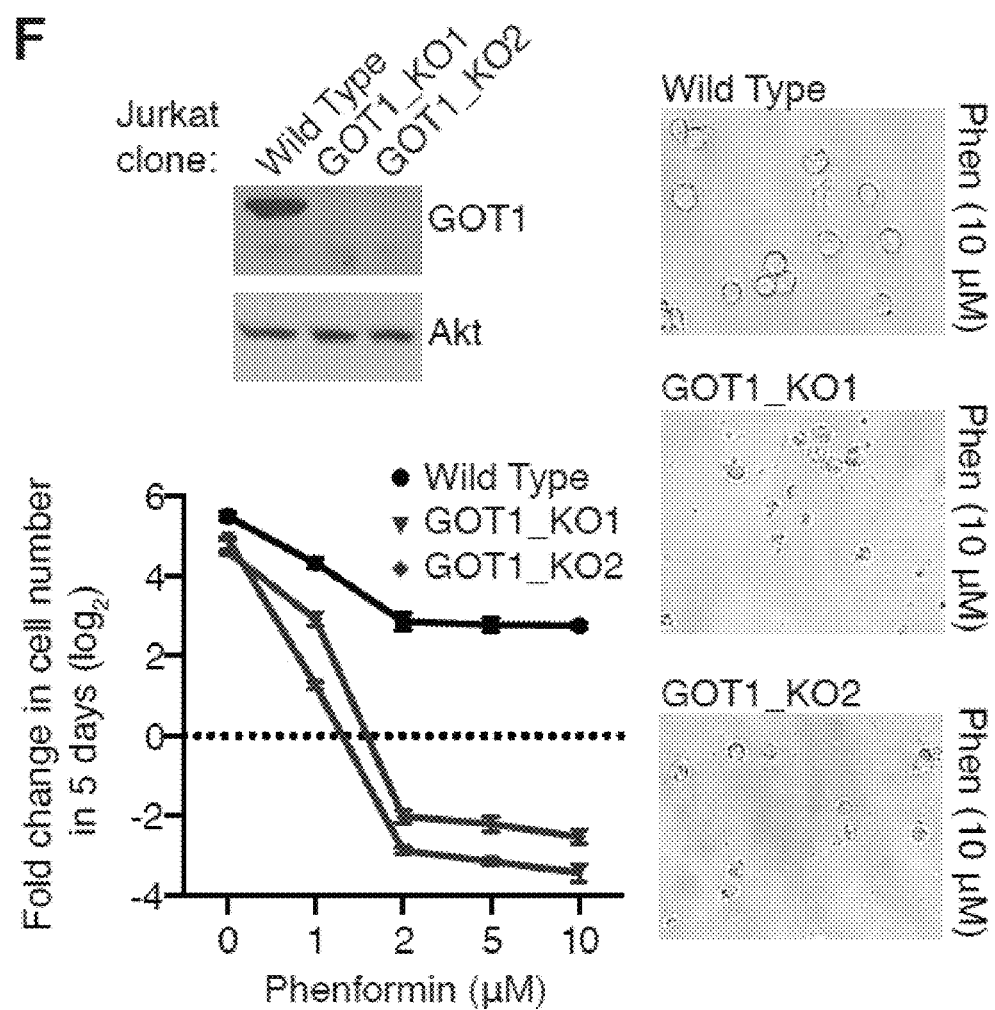
Figure 13:
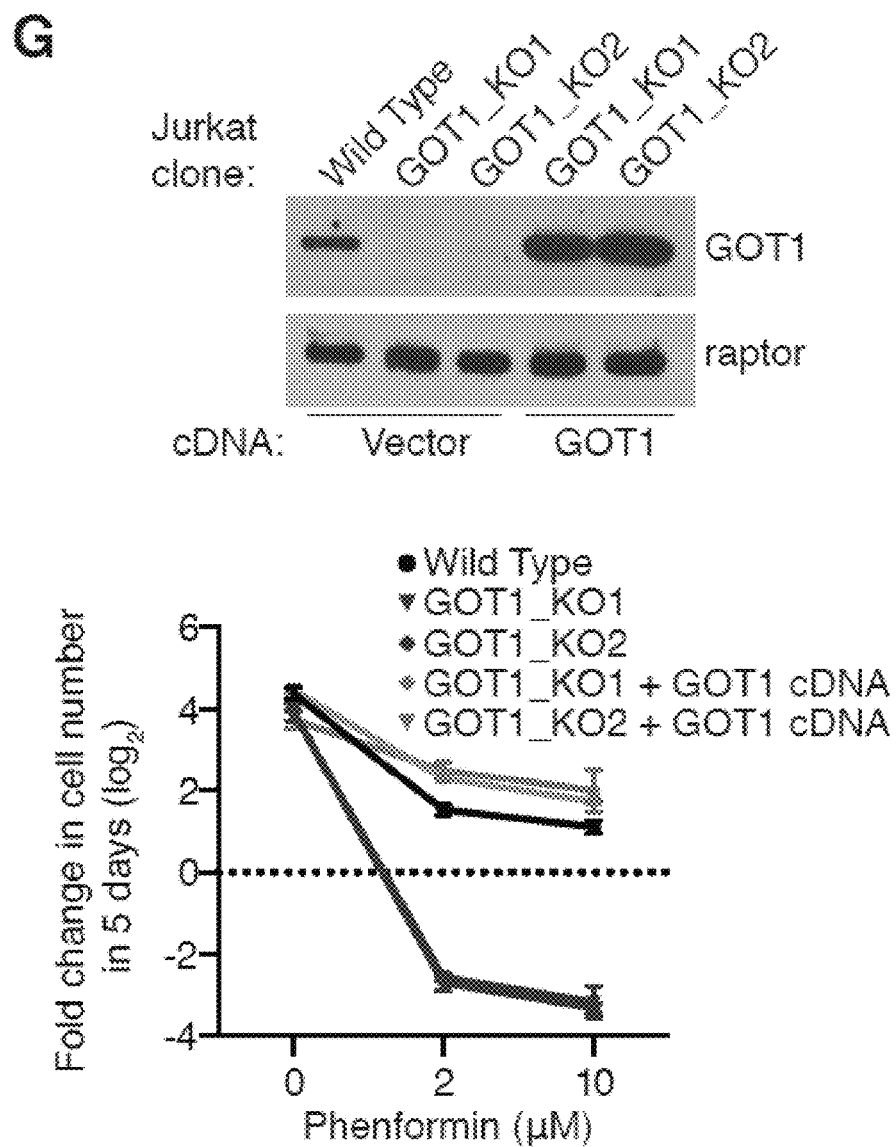

A CRISPR-Based Genetic Screen for Metabolic Genes that when Lost Sensitize Human Cells to Phenformin Pharmacological or genetic inhibition of the ETC greatly suppresses cell proliferation (Santidrian et al., 2013; Wheaton et al., 2014a) (FIG. 13A), but exactly why is unclear. To study this question, we performed a CRISPR-based negative selection screen for genes whose loss potentiates the anti-proliferative effects of mild ETC inhibition. Such genes should reveal processes that help cells adapt to ETC impairment and thus pinpoint key ETC functions in proliferating cells. Given the central role of mitochondria in metabolism, we generated a library consisting of ~30,000 sgRNAs targeting ~3,000 metabolic enzymes, small molecule transporters, and metabolism-related transcription factors (~10 sgRNA/gene) as well as 500 control sgRNAs in a Cas9-expressing lentiviral vector (FIG. 13B). We transduced human Jurkat leukemic T-cells with the sgRNA library, and passaged the pool of knockout cells in pyruvate-free RPMI media for 14 population doublings in the presence or absence of 0.5 µM phenformin. This lipophilic biguanide inhibits complex I of the ETC (Birsoy et al., 2014; Owen et al., 2000; Wheaton et al., 2014a) and only mildly slowed proliferation at the concentration used (FIG. 13A). As expected for an ETC inhibitor, phenformin suppressed respiration as measured by oxygen consumption (FIG. 20D).

Using massively parallel sequencing, we measured the abundances of all the sgRNAs in the vehicle- and phenformin-treated Jurkat cells at the beginning and at the end of the culture period. For each gene we calculated its score as the median log 2 fold change in the abundance of the 10 sgRNAs targeting the gene. As expected, most genes, as well as the control sgRNAs, scored similarly in the presence or absence of phenformin (FIG. 13C).

Figure 20:
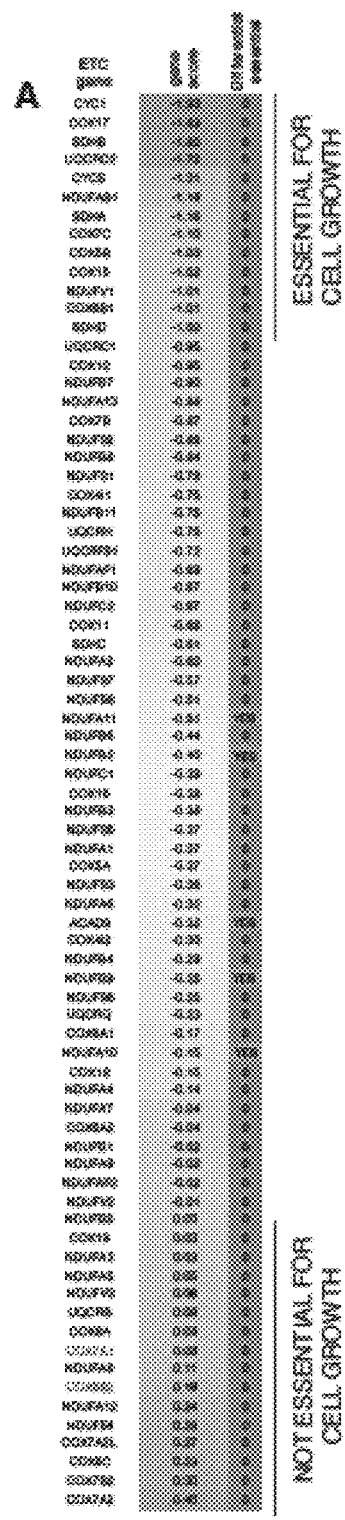
FIG. 20. (A) Gene scores for individual electron transport chain components in the absence of phenformin. ETC components with a gene score less than −1 indicates essentiality for cell growth in RPMI media. Right column indicates if ETC components also scored as differentially essential (highlighted in red) under phenformin treatment. (B) ETC components (top) and nucleotide biosynthesis (bottom) genes that are differentially essential for cell proliferation with phenformin treatment. Gene set enrichment analysis (GSEA) for the metabolic genes ranked based on their score in the CRISPR-based screen (right). (C) Changes in abundances in the primary screen for individual PDXK sgRNAs in the presence (gray) or absence (black) of phenformin. (D) Phenformin (10 µM) inhibits oxygen consumption of wild type and GOT1 null Jurkat cells. Oxygen consumption was measured using the XF-24 Seahorse Extracellular Flux Analyzer. The measurements were displayed as percent OCR before phenformin injection for each cell line. (E) Effect of phenformin (10 µM) on the proliferation of wild type and GOT1-null Jurkat cells (mean±SD, for n=3).
Figure 20:
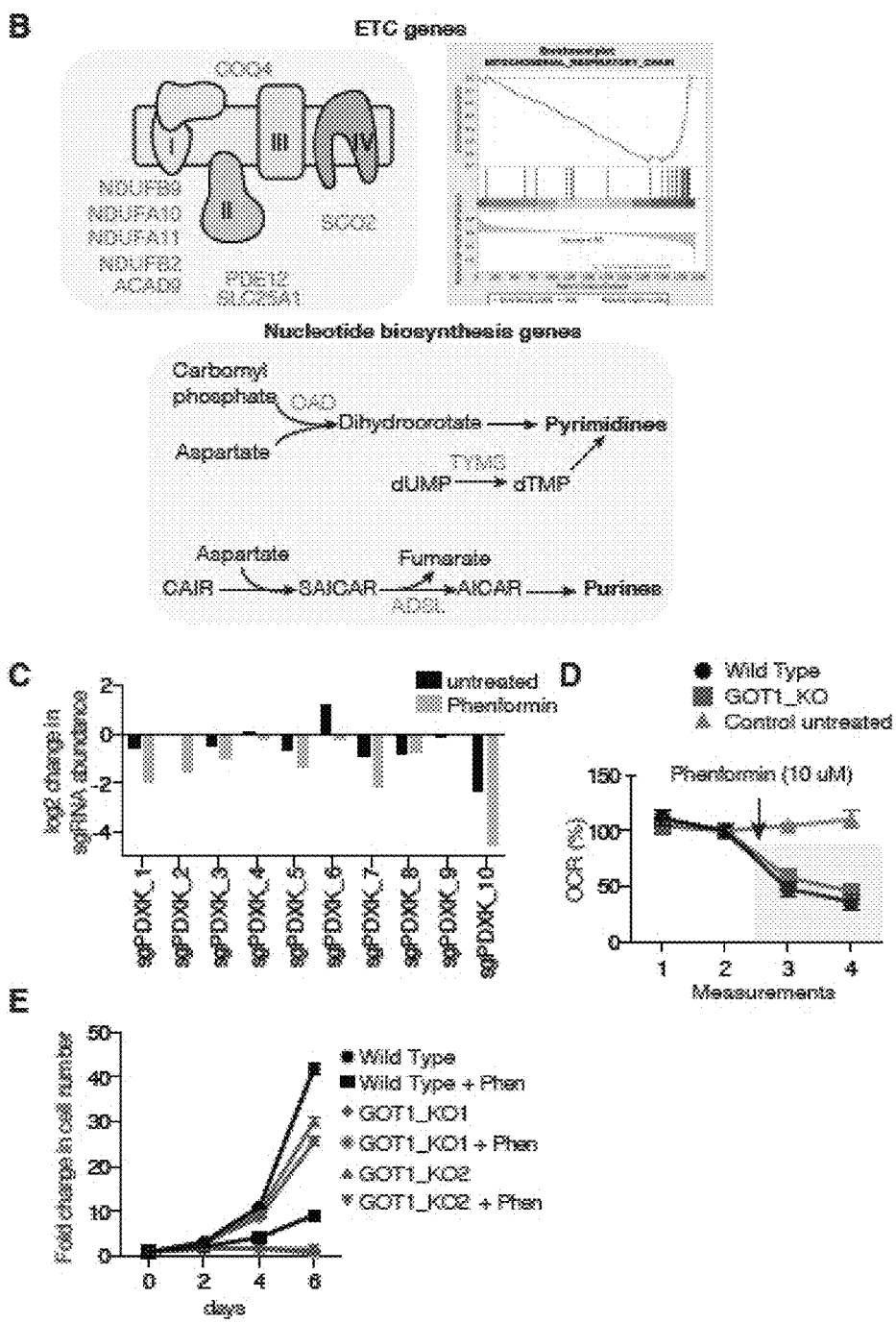

Among the genes selectively required in the presence of phenformin, were several encoding ETC-related proteins, including complex I subunits (NDUFA11, NDUFB2, NDUFA10, NDUFB9), mitochondrial RNA processing and ubiquinone synthesis enzymes (PDE12 and COQ4), and ETC assembly factors (ACAD9 and SCO2) (FIG. 13D, FIG. 20B). Unlike genes encoding core ETC components, these genes were not essential in the absence of phenformin (FIG. 20A). This suggests that they are not absolutely required for ETC function, explaining why their loss synergize with low-dose phenformin. These results are consistent with the previous finding that cells having heteroplasmic mitochondrial DNA mutations that partially impair the ETC are hypersensitive to phenformin (Birsoy et al., 2014).

The best scoring gene in the screen was GOT1, which encodes the cytosolic aspartate aminotransferase that is part of the malate-aspartate shuttle for transferring reducing equivalents to the mitochondrial matrix (FIG. 13E). GOT1 catalyzes the reversible transfer of an amino group between aspartate and glutamate, and like other transaminases, requires pyridoxal-5-phosphate (PLP) as a cofactor (Toney, 2014) (FIG. 13D). The fourth highest scoring gene, PDXK, encodes a pyridoxal kinase, which converts vitamin B6 to PLP (FIG. 20C). These data strongly suggest that a GOT1-catalyzed reaction is important for maintaining cellular fitness upon mild phenformin treatment. Given its high score and unexplored role during ETC inhibition, we focused our attention on GOT1.

ETC Inhibition Kills Cells Lacking GOT1

To begin to understand how GOT1 loss sensitizes cells to phenformin, we used the CRISPR/Cas9 system to generate two clonal Jurkat cell lines in which the GOT1 protein was undetectable (GOT1_KO1 and GOT1_KO2) (FIG. 13F). Under normal culture conditions, GOT1-null cells are viable and proliferate at slightly slower rates than wild type cells (FIG. 20E). Consistent with the results of the screen, low doses of phenformin inhibited the proliferation of GOT1-null cells to a much greater extent than that of wild type cells (FIG. 13F). Remarkably, at the higher concentrations of phenformin that strongly repress respiration (FIG. 20D), GOT1-null cells arrested and died, while the wild type counterparts did not (FIG. 13F, FIG. 20E). Importantly, expression of an sgGOT1-resistant human GOT1 cDNA in the null cells eliminated their hypersensitivity to phenformin (FIG. 13G). These findings validate the screening results and reveal that GOT1 loss and phenformin have a true synthetic lethal interaction in Jurkat cells.

Figure 14:
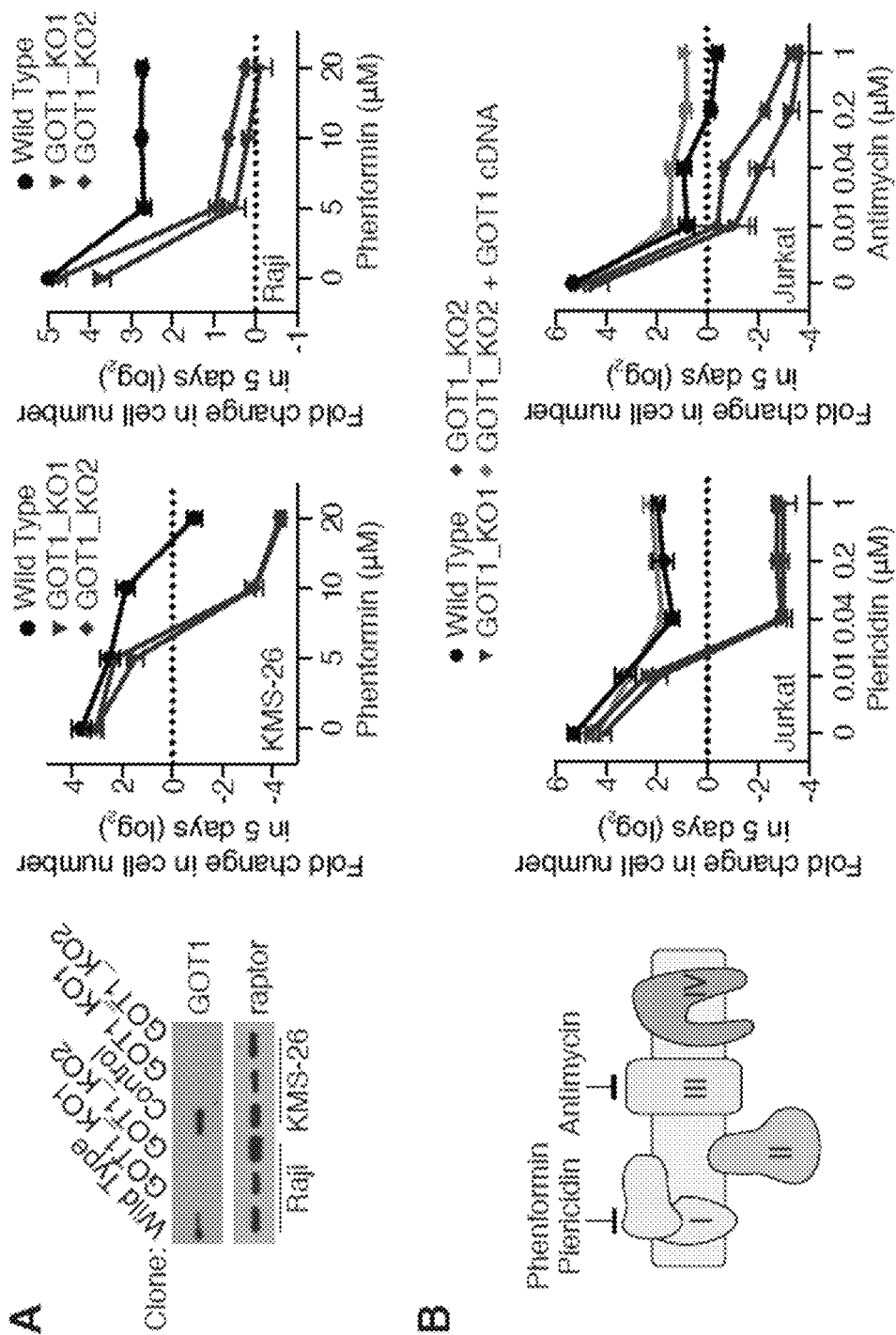
FIG. 14. ETC inhibition kills cells lacking GOT1. (A) GOT1 loss sensitizes various human cell types to phenformin treatment. Immunoblot analysis of wild type and GOT1-null Raji and KMS-26 cells (left). Raptor was used as a loading control. Fold change in cell number (log 2) of wild type (black) and GOT1-null (blue) KMS-26 and Raji cells after a 5-day treatment with indicated phenformin concentrations (mean±SD, n=3) (right). (B) GOT1-null cells die upon ETC dysfunction induced with various ETC inhibitors. Graphical scheme depicting effects of phenformin (complex I inhibitor), piericidin (complex I inhibitor), and antimycin (complex III inhibitor) (left). Fold change in cell number (log 2) of wild type (black), GOT1-null (blue), and rescued GOT1-null (gray) Jurkat cells after a 5-day treatment with indicated piericidin and antimycin concentrations (mean±SD, n=3) (right).
Figure 21:
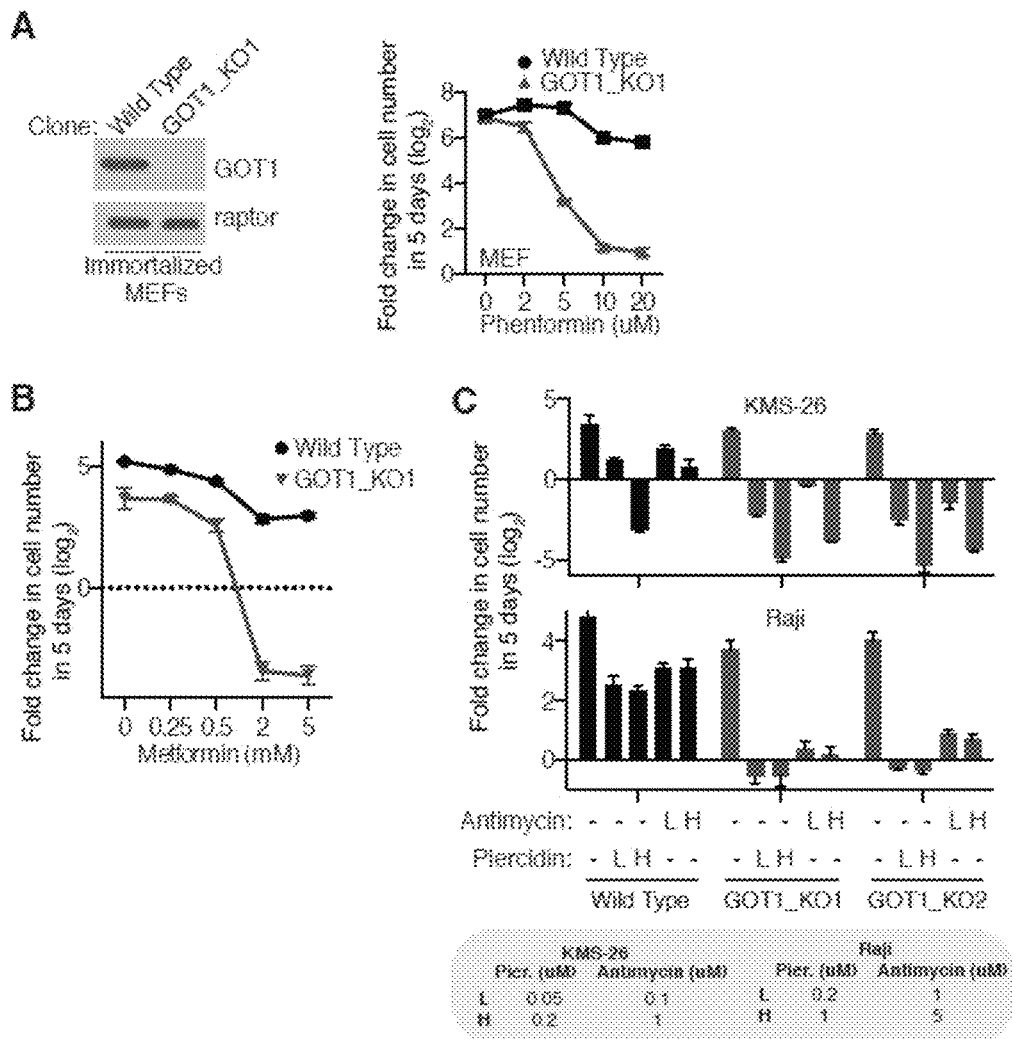
FIG. 21. (A) GOT1 loss sensitizes immortalized mouse embryonic fibroblasts (MEF) to phenformin. Immunoblot analysis of wild type and GOT1-null MEFs (left). Raptor was used as a loading control. Fold change in cell number (log 2) of wild type (black) and GOT1-null (blue) MEFs after a 5-day treatment with indicated phenformin concentrations in DMEM with pyruvate (mean±SD, n=3) (right). (B) GOT1-null cells die upon ETC inhibition with metformin. Fold change in cell number (log 2) of wild type (black) and GOT1-null (blue) Jurkat cells after a 5-day treatment with indicated metformin concentrations (mean±SD, n=3) (right). (C) GOT1-null KMS-26 and Raji cells die upon ETC inhibition with other mitochondrial toxins besides phenformin. Fold change in cell number (log 2) of wild type (black) and GOT1-null (blue) KMS-26 (top) and Raji (bottom) cells after a 5-day treatment with indicated antimycin or piericidin concentrations (mean±SD, n=3) (right).

To ask if GOT1 loss sensitizes other cell types to ETC inhibition, we knocked out GOT1 in human Raji lymphoma and KMS-26 multiple myeloma cells, as well as immortalized mouse embryonic fibroblasts (MEFs) (FIG. 14A, FIG. 21A). Indeed, all the GOT1-null cells were far more sensitive to phenformin than their wild type counterparts, indicating a generalizable role for GOT1 in cells treated with phenformin (FIG. 14A, FIG. 21A).

Finally, inhibition of different complexes of the ETC can have pleiotropic effects on metabolism (Bell et al., 2007; Frezza et al., 2011). This raised the possibility that the sensitizing effect of GOT1 loss might be specific to complex I inhibition or even just phenformin treatment. However, this is not the case because compared to wild-type cells, those lacking GOT1 were substantially more sensitive to other complex I inhibitors (metformin and piericidin) as well as the complex III inhibitor antimycin (FIG. 14B, FIG. 21B-C). These data indicate that GOT1 loss has a synthetic lethal interaction with ETC dysfunction, independently of which complex is inhibited.

Upon ETC Inhibition GOT1 Reverses Flux and Generates Aspartate

Figure 22:
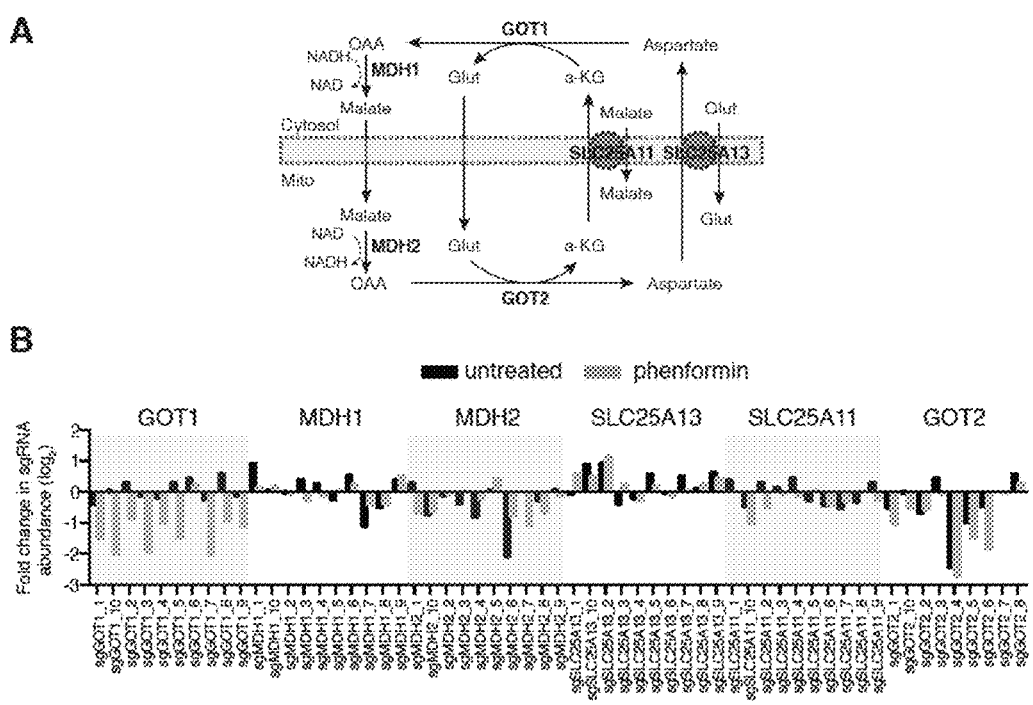
FIG. 22. (A) Detailed depiction of the malate-aspartate shuttle components and direction of the shuttle under normal conditions. (B) Changes in abundance in the primary screen for individual sgRNAs (10 sgRNAs for each gene) targeting malate-aspartate shuttle components in the presence (gray) or absence (black) of phenformin. (C) Metabolic pathways that lead to oxaloacetic acid (OAA) and aspartate production. In human cells, the primary carbon source for aspartate is oxaloacetate (OAA). OAA can be generated by multiple metabolic reactions. One source of OAA is through the malate dehydrogenases present in cytosol (MDH1) and mitochondria (MDH2). Secondly, pyruvate carboxylase can yield OAA from pyruvate in mitochondria. Finally, another source for OAA is through ATP-citrate lyase, which catalyzes the conversion of citrate and CoA into acetyl-CoA and OAA in cytoplasm. Citrate and malate can be derived from glutamine through reductive and oxidative pathways, respectively. (D) Changes in in during the primary screen for individual PC and ACLY sgRNAs in the presence (gray) or absence (black) of phenformin.
Figure 22:
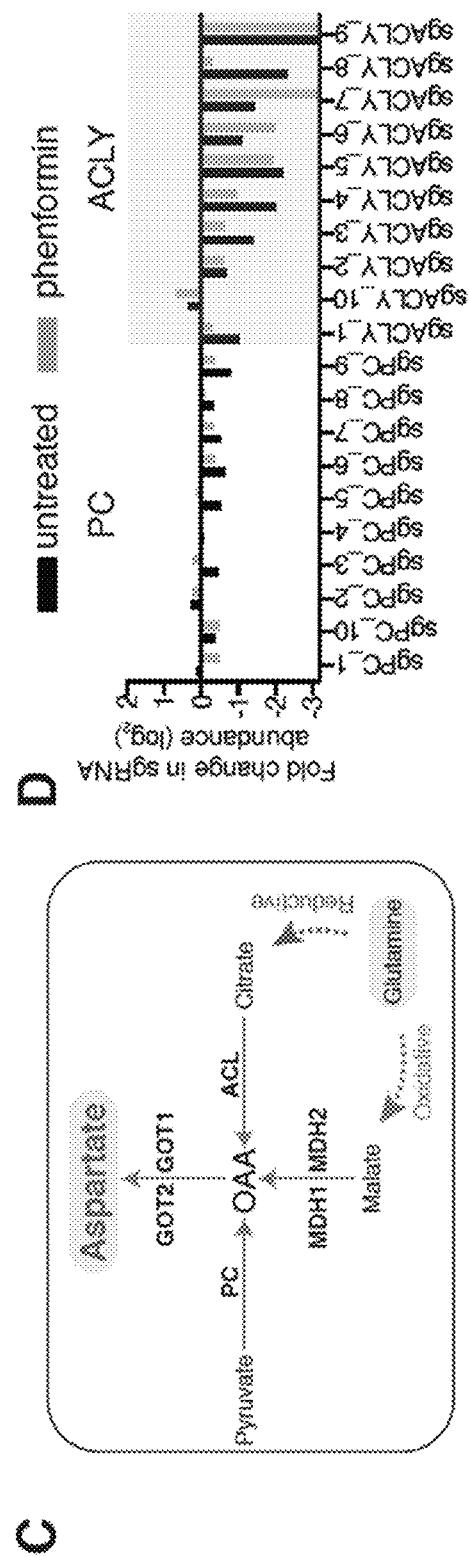

GOT1 is part of the malate-aspartate shuttle (FIG. 15A, FIG. 22A), but no other component of the shuttle (MDH1, MDH2, SLC25A13, GOT2) scored in the screen (FIG. 22B). Given these results, we focused on the reaction mediated by GOT1 itself rather than the overall function of the shuttle in transferring reducing equivalents into the mitochondrial matrix.

Figure 15:
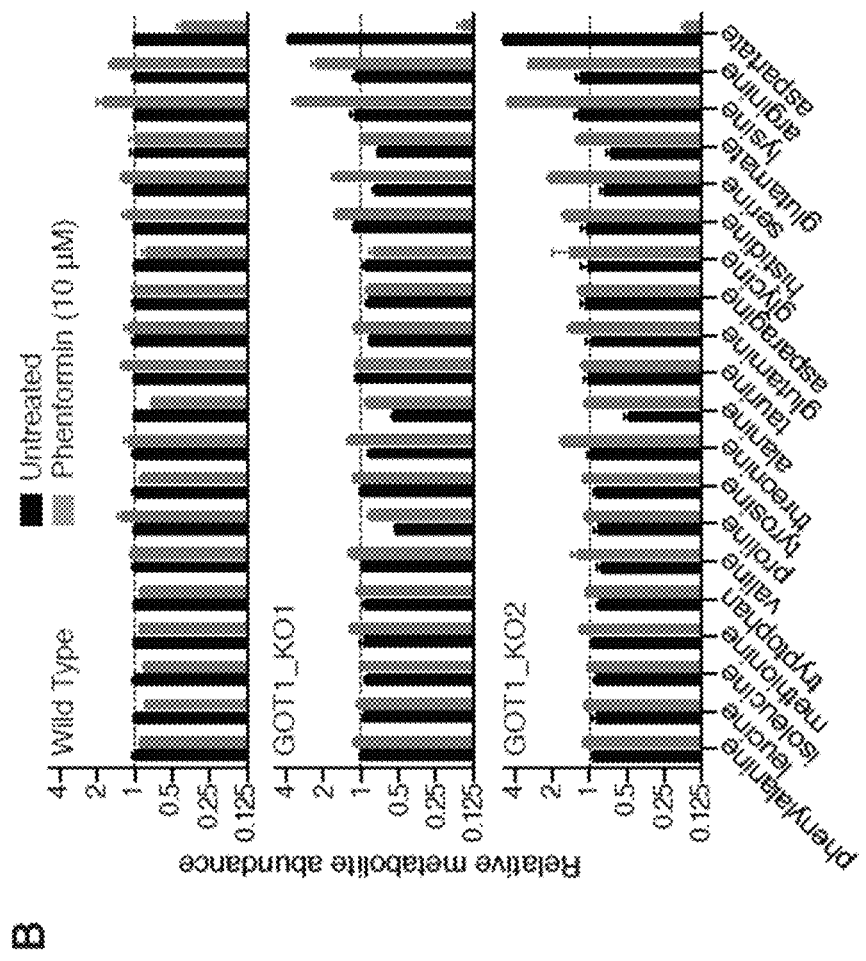
FIG. 15. Upon ETC inhibition, GOT1 reverses and generates aspartate, which is limiting for cell proliferation. (A) Schematic depicting the malate-aspartate shuttle. Normally, the malate-aspartate shuttle runs in the forward direction to transfer reducing equivalents across the mitochondrial membrane. GOT1 is part of the malate-aspartate shuttle and consumes aspartate to generate oxaloacetate (OAA). Aspartate produced by mitochondria is a precursor for protein and nucleotide biosynthesis. (B) Upon ETC inhibition, GOT1 reverses and consumes aspartate. Relative abundance of indicated amino acids in wild type and GOT1-null Jurkat cells after a 24-hour treatment with (gray) or without (black) phenformin (mean±SD, n=3, p<0.05). All measurements are relative to untreated wild type Jurkat cells. (C) Aspartate supplementation rescues death of GOT1-null cells upon ETC inhibition. Fold change in cell number (log 2) of wild type (black), GOT1-null (blue) and rescued GOT1-null (gray) Jurkat cells in the absence and presence (10 mM) of aspartate after treatment with the indicated phenformin concentrations for 5 days (mean±SD, n=3) (top). Representative bright-field micrographs of indicated cells after a 5-day phenformin treatment in the absence or presence of aspartate (bottom). (D) Expression of a glutamate-aspartate transporter (SLC1A3) rescues the phenformin-induced death of GOT1-null cells cultured in standard RPMI media, which contains only 150 μM aspartate. Fold change in cell number (log 2) of GOT1-null (blue) and SLC1A3-overexpressing GOT1-null (gray) Jurkat cells in RPMI (150 μM aspartate) after a 5-day treatment with 10 μM phenformin (mean±SD, n=3, p<0.05).
Figure 15:
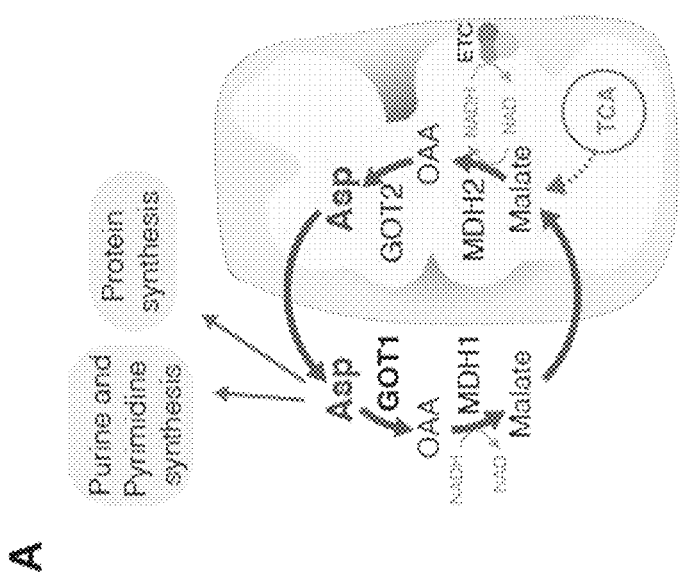
Figure 15:
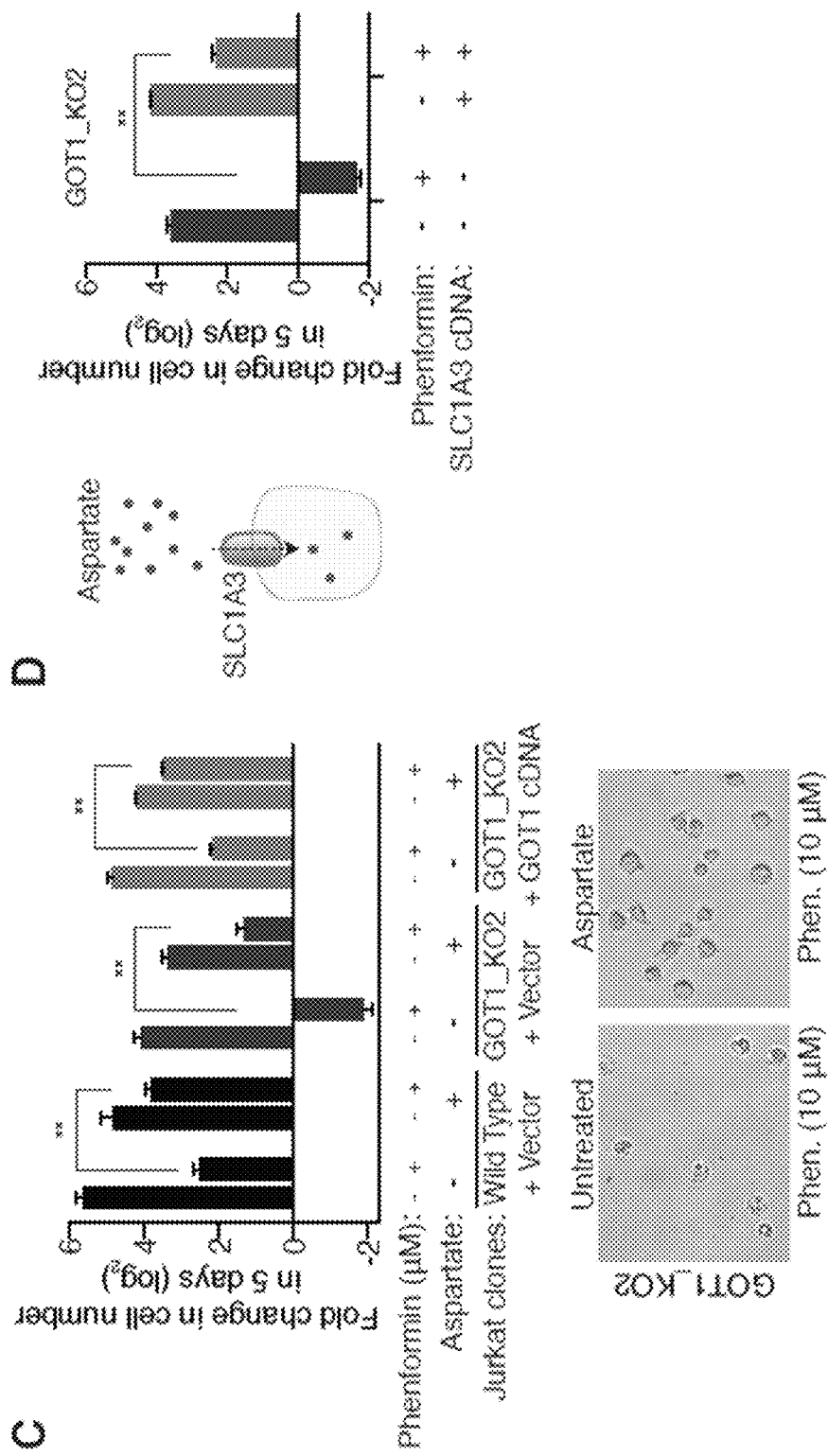

In normal cells GOT1 is thought to use aspartate and α-ketoglutarate to make oxaloacetate and glutamate (Safer, 1975). Consistent with GOT1 consuming aspartate, its levels are 4-5 fold higher in GOT1-null than wild-type Jurkat cells (FIG. 15B). Aspartate is normally synthesized in the mitochondrial matrix through the sequential actions of MDH2 and GOT2 and then transported to the cytosol for use by GOT1 and other enzymes (FIG. 15A). Because MDH2 is an oxidoreductase, the drop in the $NAD^+$/NADH ratio that occurs upon ETC dysfunction should inhibit MDH2 and thus mitochondrial aspartate synthesis. Indeed, in wild type Jurkat cells, phenformin caused aspartate levels to fall by ~3-fold (FIG. 15B).

As GOT1 is bidirectional, the drop in aspartate levels might allow GOT1 to reverse flux so that in cells with ETC dysfunction GOT1 generates rather than consumes aspartate. If this were the case, ETC inhibition should cause aspartate to drop to a greater extent in GOT1-null than wild-type cells. Indeed, in GOT1-null cells phenformin treatment lead to an almost complete loss of cellular aspartate (~30-fold reduction) without much effect on other amino acids (FIG. 15B). Thus, upon ETC inhibition, cells use a GOT1-dependent pathway to generate aspartate. It is important to note, however, that this pathway does not fully compensate for loss of mitochondrial aspartate synthesis as aspartate is three-fold lower in cells without a functional ETC (FIG. 15B).

Aspartate Supplementation Enables Cells to Proliferate Under Pharmacological ETC Inhibition Because aspartate is required for the synthesis of proteins as well as purines and pyrimidines (Lane and Fan, 2015), we reasoned that the drop in aspartate levels caused by ETC inhibition might lead to the concomitant suppression of cell proliferation. Consistent with this notion, supplementation of RPMI media with aspartate (10 mM) partially reversed the anti-proliferative effects of phenformin on wild-type cells (FIG. 15C). Aspartate addition also prevented the phenformin induced death of GOT1-null cells and even enabled these cells to proliferate in the presence of the drug (FIG. 15C). Given these findings, we re-examined our screen hits and noted that several enzymes scored that use aspartate for purine and pyrimidine synthesis (FIG. 7D, FIG. 20B).

Figure 23:
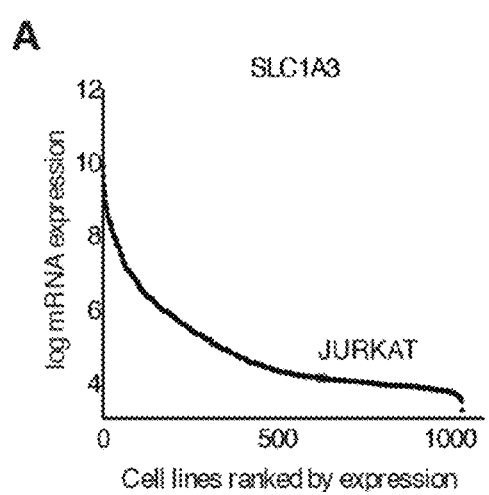
FIG. 23. (A) SLC1A3 mRNA expression in cancer cell lines (obtained from Cancer Cell line Encyclopedia (CCLE)). (B) SLC1A3 mRNA expression in human tissues (obtained from GTEX). (C) Expression of a glutamate-aspartate transporter (SLC1A3) rescues the phenformin-induced death of GOT1-null cells at different aspartate concentrations. Fold change in cell number (log 2) of GOT1-null (blue) and SLC1A3-overexpressing GOT1-null (gray) Jurkat cells in RPMI (150 µM aspartate) after a 5-day treatment with 10 µM phenformin and increasing concentrations of aspartate (mean±SD, n=3). (D) Expression of an sgRNA-resistant GOT1 cDNA rescues ETC inhibitor sensitivity of GOT1-null Jurkat cells. Fold change in cell number (log 2) of wild type (black), GOT1-null (blue), and rescued GOT1-null (gray) cells after a 5-day treatment with antimycin (1 µM) or piericidin (0.5 µM) (mean±SD, for n=3).
Figure 23:
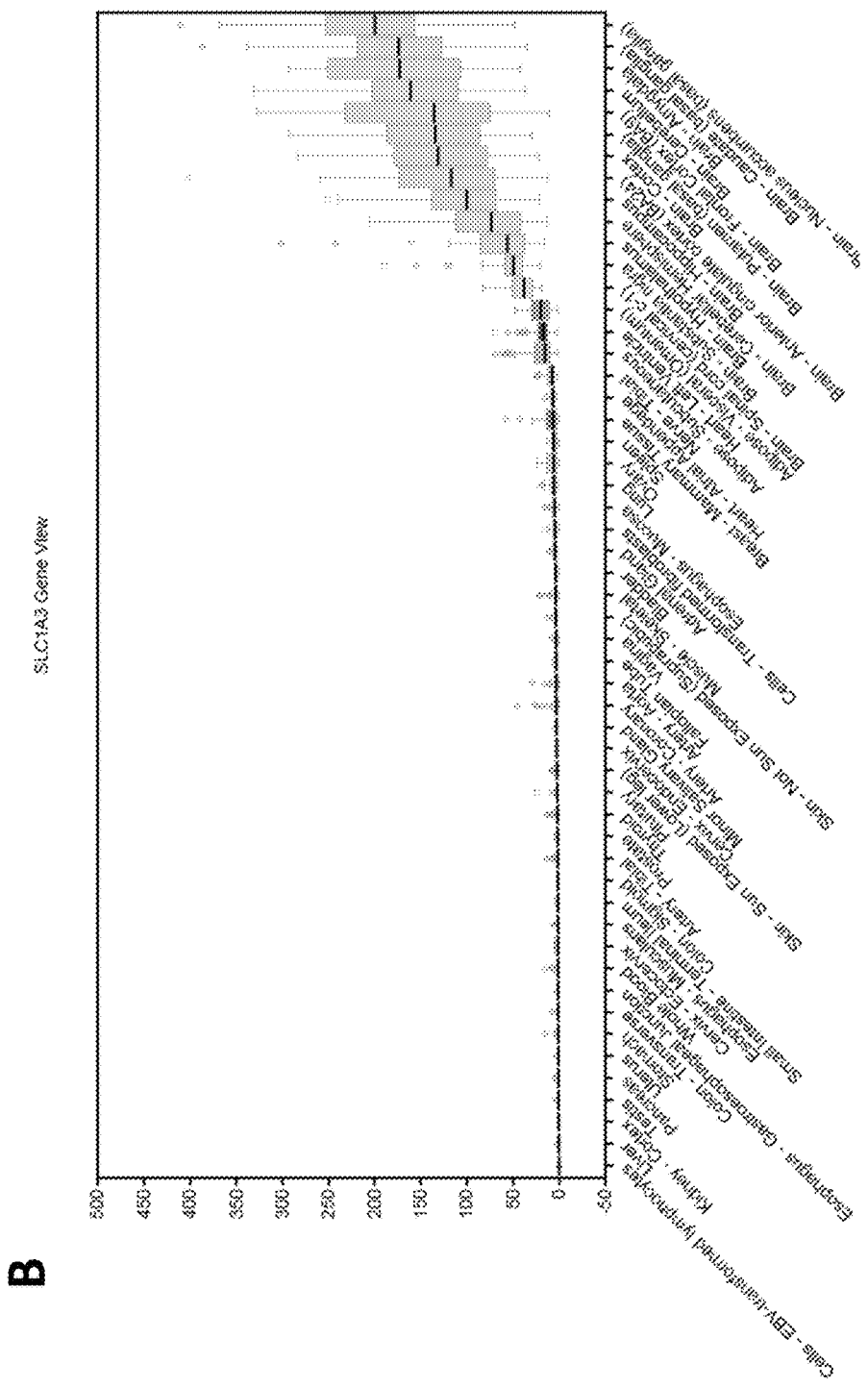
Figure 23:
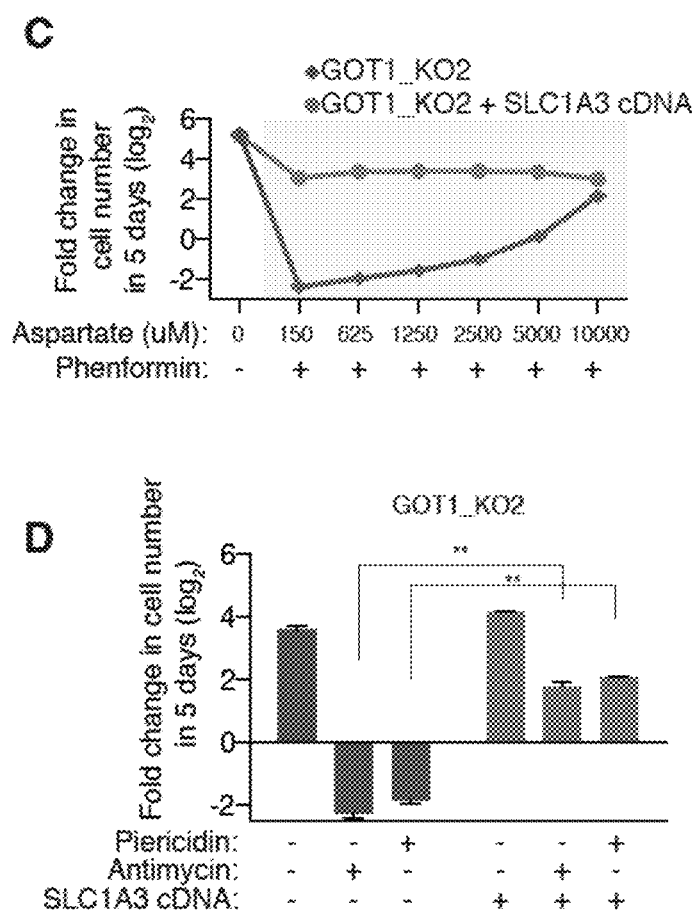

The aspartate rescue experiments required supplementation of the media with concentrations of aspartate (10 mM) that are higher than those found in standard media (FIG. 15C), which is likely a consequence of Jurkat cells having poor aspartate transport. To test this possibility, we cultured GOT1-null cells stably expressing the SLC1A3 glutamate-aspartate transporter in standard RPMI, which only has 150 μM aspartate. SLC1A3 imports aspartate (Storck et al., 1992) and is highly expressed in neuronal tissues but not in Jurkat cells (FIG. 23A-B). SLC1A3 overexpression prevented the death of the GOT1-null cells caused by phenformin (FIG. 15D, FIG. 23C) and other ETC inhibitors (FIG. 23D), and, like high dose aspartate, enabled the proliferation of these cells (FIG. 15D, FIG. 23C-D). Thus, we conclude that upon ETC inhibition, aspartate becomes limiting for maintaining the viability and proliferation of cells.

Metabolic Route for Aspartate Synthesis in Cells with ETC Inhibition

To generate aspartate in cells with ETC inhibition, GOT1 must have a source of oxaloacetate (FIG. 22C), which can be made from (i) malate by the cytosolic (MDH1) or mitochondrial (MDH2) malate dehydrogenases; (ii) pyruvate by pyruvate carboxylase (PC) in mitochondria; or (iii) citrate by ATP-citrate lyase (ACL) in the cytosol. MDH1, MDH2 or PC did not score in our screen as differentially essential upon mild phenformin treatment (Figure S3B, FIG. 22C-D), so we focused on the possible generation of oxaloacetate from citrate upon ETC inhibition. In cells with ETC dysfunction, glutamine is a major source of citrate through the "reductive carboxylation" pathway (Metallo et al., 2012; Mullen et al., 2012). In reductive carboxylation, the mitochondrial citrate carrier (SLC25A1) transports glutamine derived citrate to the cytosol, where ACL cleaves it into oxaloacetate. Consistent with oxaloacetate being generated from citrate in cells with ETC inhibition, SLC25A1 scored as differentially required in our phenformin screen (FIG. 13D). The differential requirement of ACL could not be assessed because it scored as essential under all conditions (FIG. 22D), likely because it is required for fatty acid synthesis.

Figure 16:
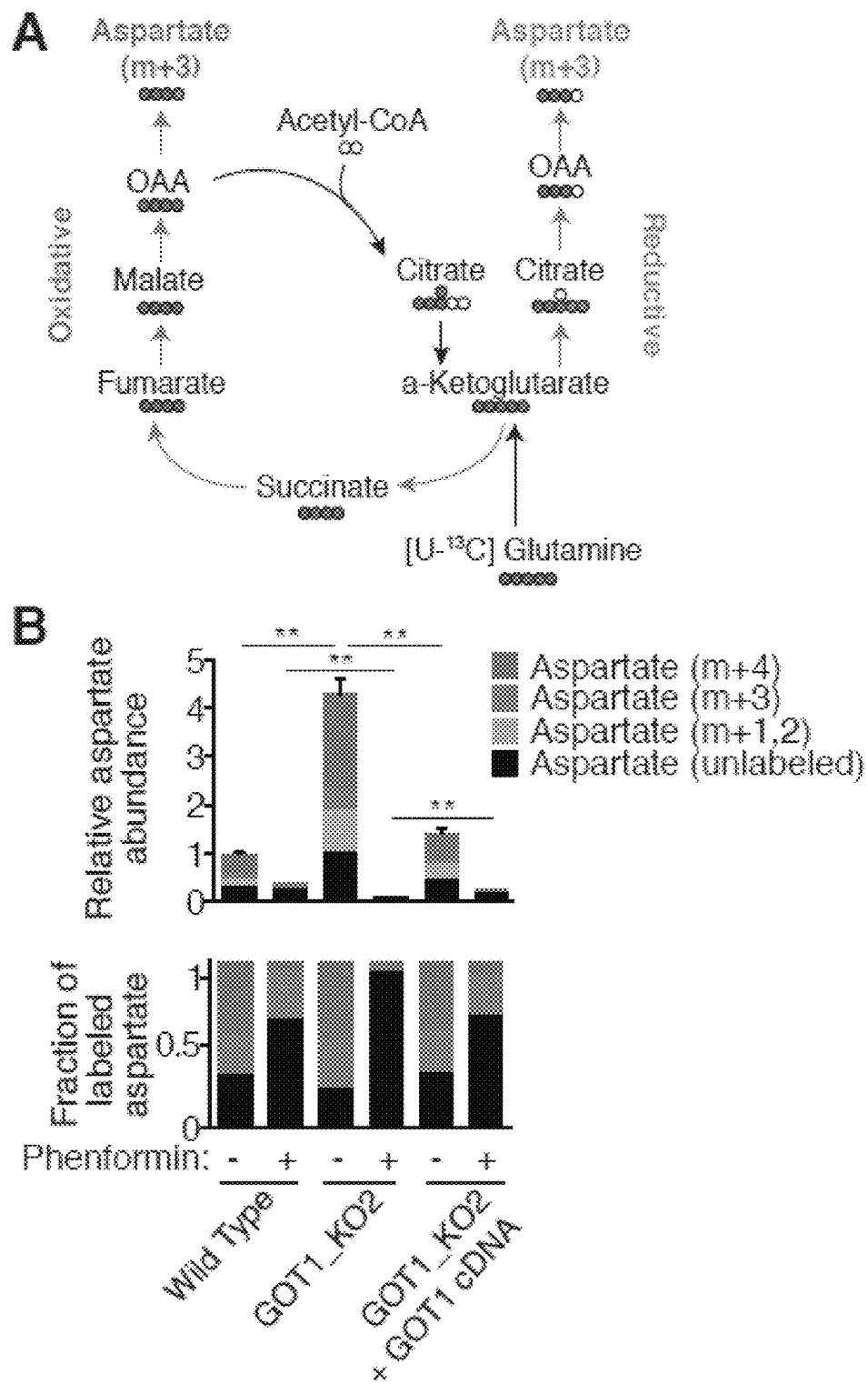
FIG. 16. Metabolic routes of aspartate synthesis in cells with ETC inhibition. (A) Schematic depicting oxidative and reductive glutamine metabolism pathways (top). Green and blue arrows indicate oxidative and reductive arms of the TCA cycle, respectively. Filled circles represent $^{13}$C atoms derived from [U-$^{13}$C]-L-glutamine. (B) Upon ETC inhibition, aspartate is mainly synthesized by reductive metabolism of glutamine in a GOT1-dependent manner. Mass isotopomer analysis of aspartate in wild type and GOT1-null Jurkat cells cultured for 7 hours with [U-$^{13}$C]-L-glutamine in the presence or absence of phenformin (10 μM). Aspartate pool sizes (middle) and fraction of labeled aspartate derived from labeled glutamine (bottom) for each sample are indicated in separate graphs (mean±SD, for n=3, **p<0.05). OAA, oxaloacetate.

To directly determine how aspartate is made, we measured its generation from [U-$^{13}$C]-L-glutamine in wild type and GOT1-null Jurkat cells treated with or without phenformin. Oxidative metabolism of the labeled glutamine will generate aspartate with four $^{13}$C atoms (m+4), while aspartate made by reductive carboxylation will have three $^{13}$C atoms (m+3) (FIG. 16A). Under normal conditions, we found that oxidative glutamine metabolism was the predominant source of aspartate (~50% of total aspartate pool) in both wild type and GOT1-null Jurkat cells (FIG. 16B). Upon ETC inhibition, aspartate synthesis dropped, and what remained came primarily from reductive glutamine metabolism with almost no contribution from the oxidative pathway (FIG. 16B). Reductive formation of aspartate completely depends on GOT1 activity, as in phenformin-treated GOT1-null cells there was almost no generation of aspartate from labeled glutamine (FIG. 16B). These results indicate that upon ETC inhibition cells use the reductive carboxylation of glutamine to fuel compensatory aspartate synthesis via a GOT1-requiring pathway.

Pyruvate Stimulates Aspartate Synthesis in a GOT1-Dependent Fashion

Human cells with ETC dysfunction can proliferate when cultured in media containing supra-physiological concentrations of pyruvate (Harris, 1980). Pyruvate even enables the proliferation of cells that have deleterious mutations in their mitochondrial DNA or lack it altogether (143B ρ0 cells) (King and Attardi, 1989). Pyruvate has been hypothesized to act as a biosynthetic substrate or to maintain the cellular redox state in cells with ETC dysfunction via reduction by lactate dehydrogenase, which helps regenerate the $NAD^+$ that is lost upon ETC inhibition (Harris, 1980; Wilkins et al., 2014). The $NAD^+$ made through pyruvate reduction should facilitate glycolytic flux and thus ATP production in cells lacking ETC function, but the key metabolic consequence of pyruvate addition that allows such cells to proliferate is unclear.

Figure 17:
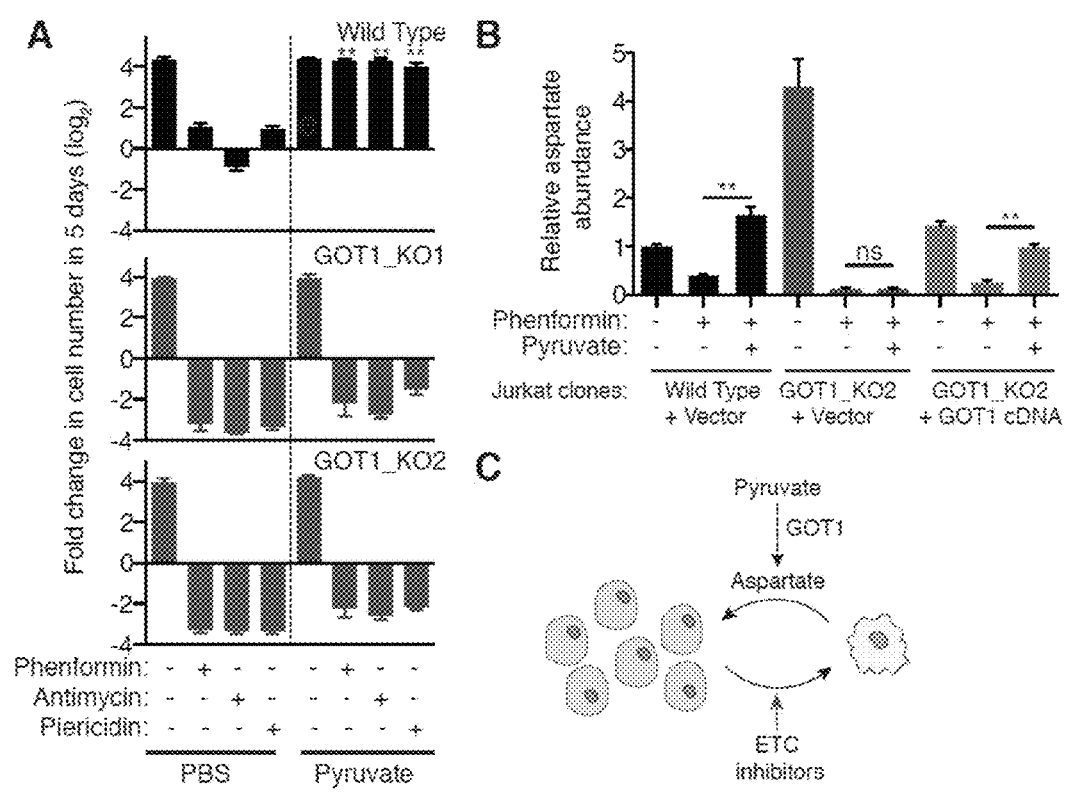
FIG. 17. In cells with ETC inhibition pyruvate stimulates aspartate synthesis in a GOT1-dependent fashion. (A) Pyruvate cannot rescue death of GOT1-null cells induced by ETC inhibitors. Fold change in cell number (log 2) of wild type (black) and GOT1-null (blue) Jurkat cells in the presence or absence of pyruvate (1 mM) after treatment with the indicated phenformin, antimycin and piericidin concentrations for 5 days (mean±SD, n=3, p<0.05). (B) In cells with ETC inhibition pyruvate addition increases cellular aspartate levels in a GOT1-dependent manner. Relative aspartate levels were measured in wild type (black), GOT1-null (blue), and rescued GOT1-null (gray) Jurkat cells in the presence (1 mM) or absence of pyruvate after a 24-hour phenformin (10 µM) treatment using LC-MS/MS (mean±SD, for n=3, p<0.05). All measurements are relative to untreated wild type Jurkat cells. (C) Proposed mechanism of pyruvate-mediated rescue of cell proliferation upon ETC inhibition.

As both pyruvate and aspartate supplementation enables the proliferation of cells with ETC dysfunction, we explored a possible link between the two by culturing wild type and GOT1-null cells in the presence or absence of pyruvate and treating them with ETC inhibitors. Consistent with previous reports (Harris, 1980), pyruvate almost completely blocked the anti-proliferative effects of several ETC inhibitors (phenformin, piericidin, and antimycin) on wild type Jurkat cells (FIG. 17A). In contrast, pyruvate had no beneficial effect on the GOT1-null cells (FIG. 17A), suggesting that the pyruvate-mediated rescue requires aspartate synthesis via GOT1. Indeed, pyruvate restored aspartate levels to normal in phenformin-treated wild type cells, but had no effect on aspartate in phenformin-treated GOT1-null cells (FIG. 17B). Collectively, these data indicate that a key mechanism through which pyruvates restores the proliferation of cells with ETC inhibition is to promote GOT1-catalyzed aspartate synthesis.

Metabolic Path of Pyruvate-Induced Aspartate Synthesis

Figure 18:
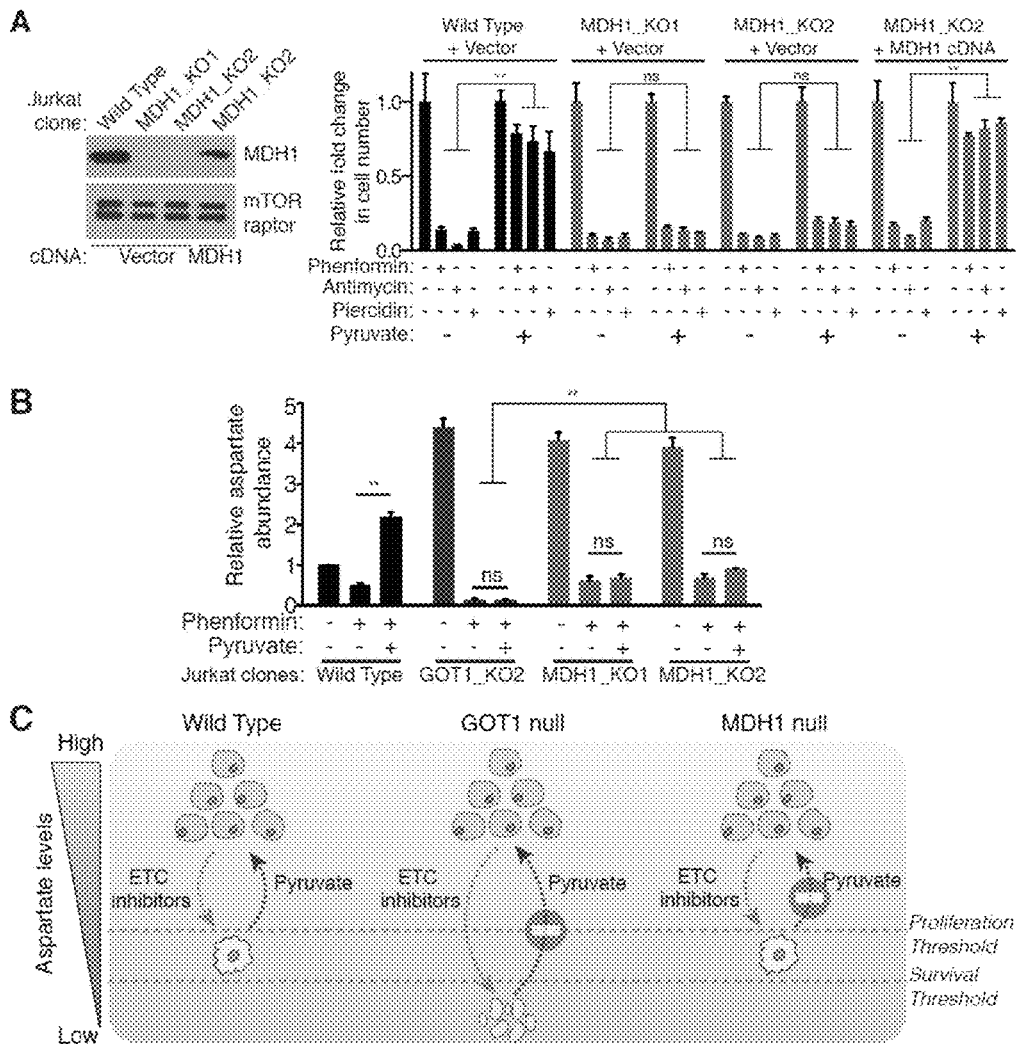
FIG. 18. Cells with ETC inhibition require MDH1 for pyruvate to stimulate aspartate synthesis and enable proliferation. (A) Pyruvate does not rescue the proliferation of phenformin-treated MDH1 null cells. Immunoblot analysis of wild type and MDH1-null Jurkat cells along with counterparts expressing an sgRNA-resistant MDH1 cDNA (left). mTOR and Raptor were used as loading controls. Fold change in cell number (log 2) of wild type (black), MDH1-null (light blue), and rescued MDH1-null (gray) Jurkat cells after a 5-day treatment with the indicated phenformin, piericidin, and antimycin concentrations in the presence or absence of pyruvate (1 mM) (mean±SD, n=3) (right). (B) The pyruvate-induced increase in aspartate synthesis depends on MDH1. Relative aspartate levels were determined in wild type (black), GOT1-null (blue), and MDH1-null (light blue) Jurkat cells in the presence or absence of pyruvate (1 mM) after a 24-hour phenformin (10 µM) treatment (mean±SD, for n=3). All measurements are relative to untreated wild type Jurkat cells. (C) Aspartate levels correlate with cellular health upon ETC inhibition. ETC inhibition leads to a decrease in aspartate levels and inhibits cell proliferation in wild type cells. The residual aspartate generated by GOT1 is sufficient to maintain viability, as GOT1 loss results in cell death and corresponds to an almost complete depletion of aspartate. Pyruvate addition rescues aspartate levels and proliferation under ETC inhibition in a GOT1- and MDH1-dependent fashion.
Figure 24:
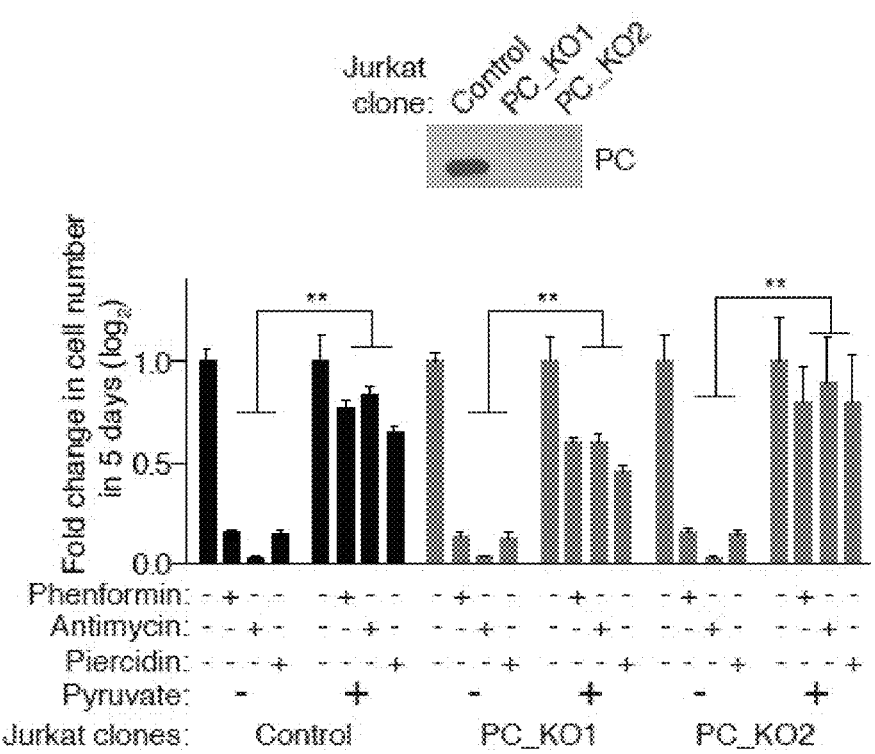
FIG. 24. (A) Pyruvate can rescue the death of PC-null cells induced by ETC inhibition. Immunoblot analysis of wild type and GOT1-null Jurkat cells (top). Fold change in cell number (log 2) of wild type (black) and PC-null (blue) Jurkat cells in the presence or absence of pyruvate (1 mM) after a 5-day treatment with phenformin (10 µM), antimycin (1 µM), or piericidin (0.5 µM) (mean±SD, n=3). (B) Unlike pyruvate, aspartate does not increase the $NAD^+/NADH$ ratio in cells with ETC inhibition. $NAD^+/NADH$ ratio was determined for wild type Jurkat cells after 24 hours phenformin treatment (10 µM) in the presence or absence of pyruvate (1 mM) or aspartate (10 mM) (mean±SD, for n=3). (C) Metabolic routes for pyruvate-induced aspartate synthesis under ETC inhibition. Pyruvate addition, through lactate dehydrogenases, regenerates $NAD^+$ in the cytoplasm. This $NAD^+$ can activate the cytoplasmic malate dehydrogenase to provide OAA, which is then used by GOT1 to make aspartate. Alternatively, another source for OAA is through ATP-citrate lyase, which catalyzes the conversion of citrate and CoA into acetyl-CoA and OAA in the cytosol. Under ETC inhibition, the latter reaction is likely less dependent on $NAD^+$ and can work even in the absence of pyruvate supplementation. Note that both pathways are dependent on GOT1.
Figure 24:
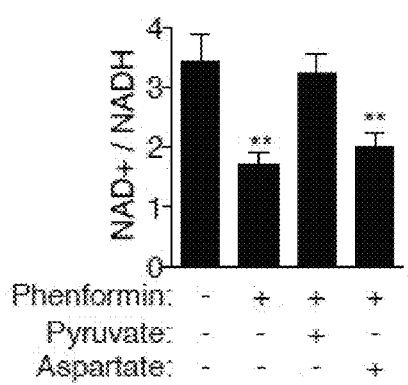
Figure 24:
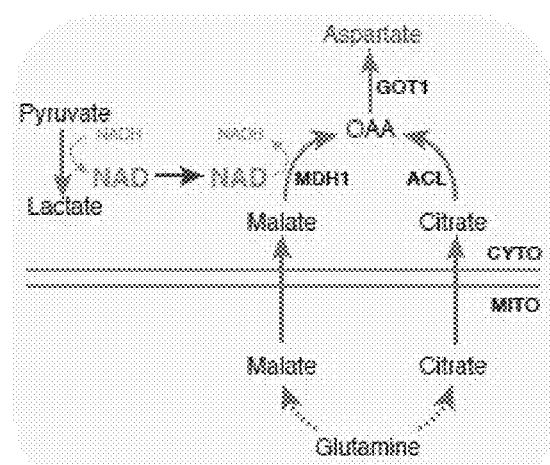
Figure 25:
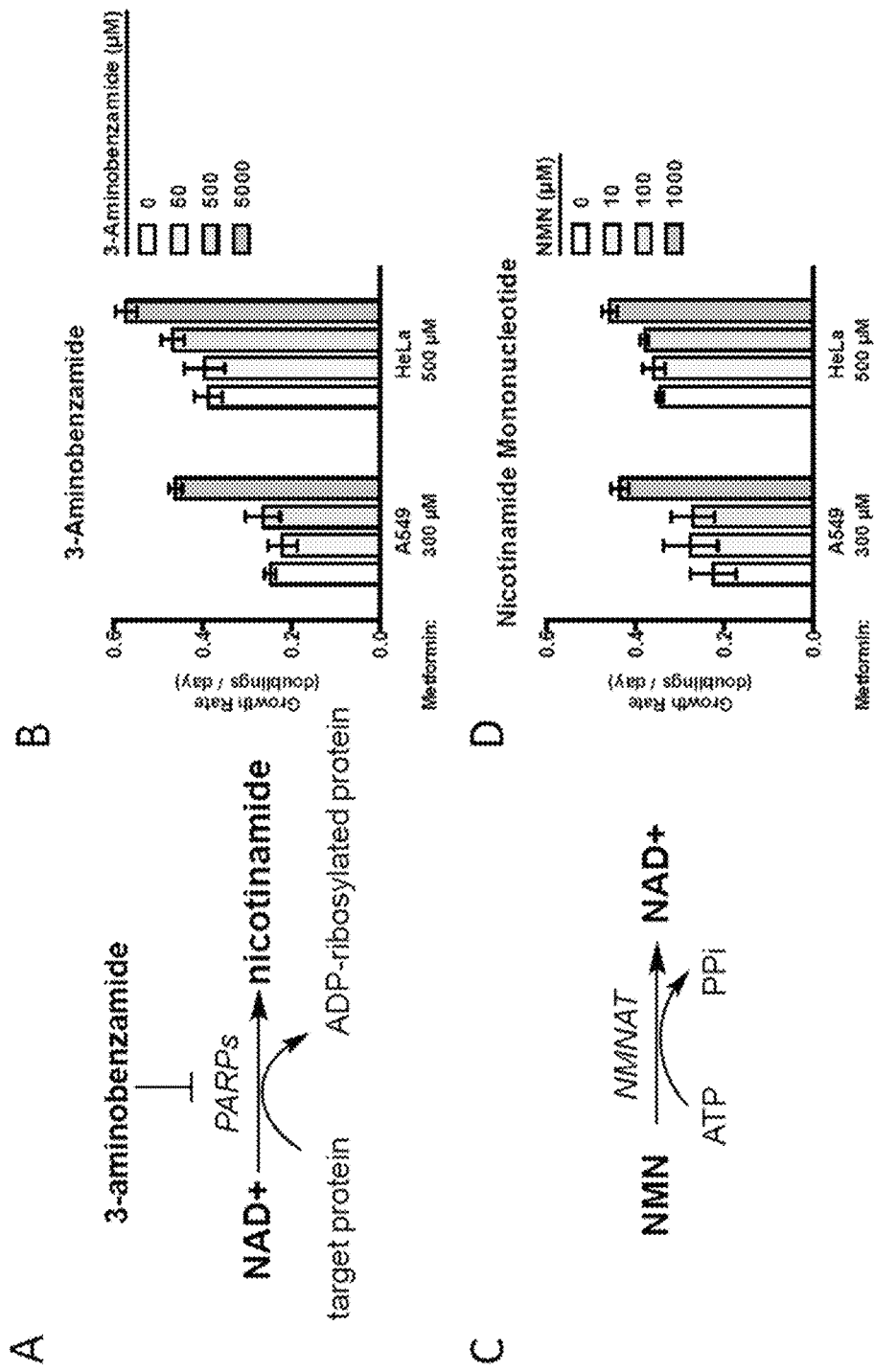
FIG. 25. Orthogonal elevation of $NAD^+/NADH$ restores growth in metformin treated cells. (A) Schematic model illustrating how PARPs consume $NAD^+$ to ADP-ribosylate proteins, yielding nicotinamide. (B) Growth rate calculated for A549 and HeLa cells in DMEM without pyruvate treated with the indicated amounts of metformin and 3-aminobenzamide. (C) Schematic model illustrating how nicotinamide mononucleotide increases the intracellular synthesis of $NAD^+$. (D) Growth rate calculated for A549 and HeLa cells in DMEM without pyruvate treated with the indicated amounts of metformin and NMN (E) Schematic model illustrating how duroquinone is converted to dihydroduroquinone by intracellular dehydrogenases, resulting in NADH conversion to $NAD^+$. (F) Growth rate calculated for A549 and HeLa cells in DMEM without pyruvate treated with the indicated amounts of metformin and duroquinone (H)-(G) $NAD^+/NADH$ was measured 24 hours after the indicated treatments in A549 and HeLa.
Figure 25:
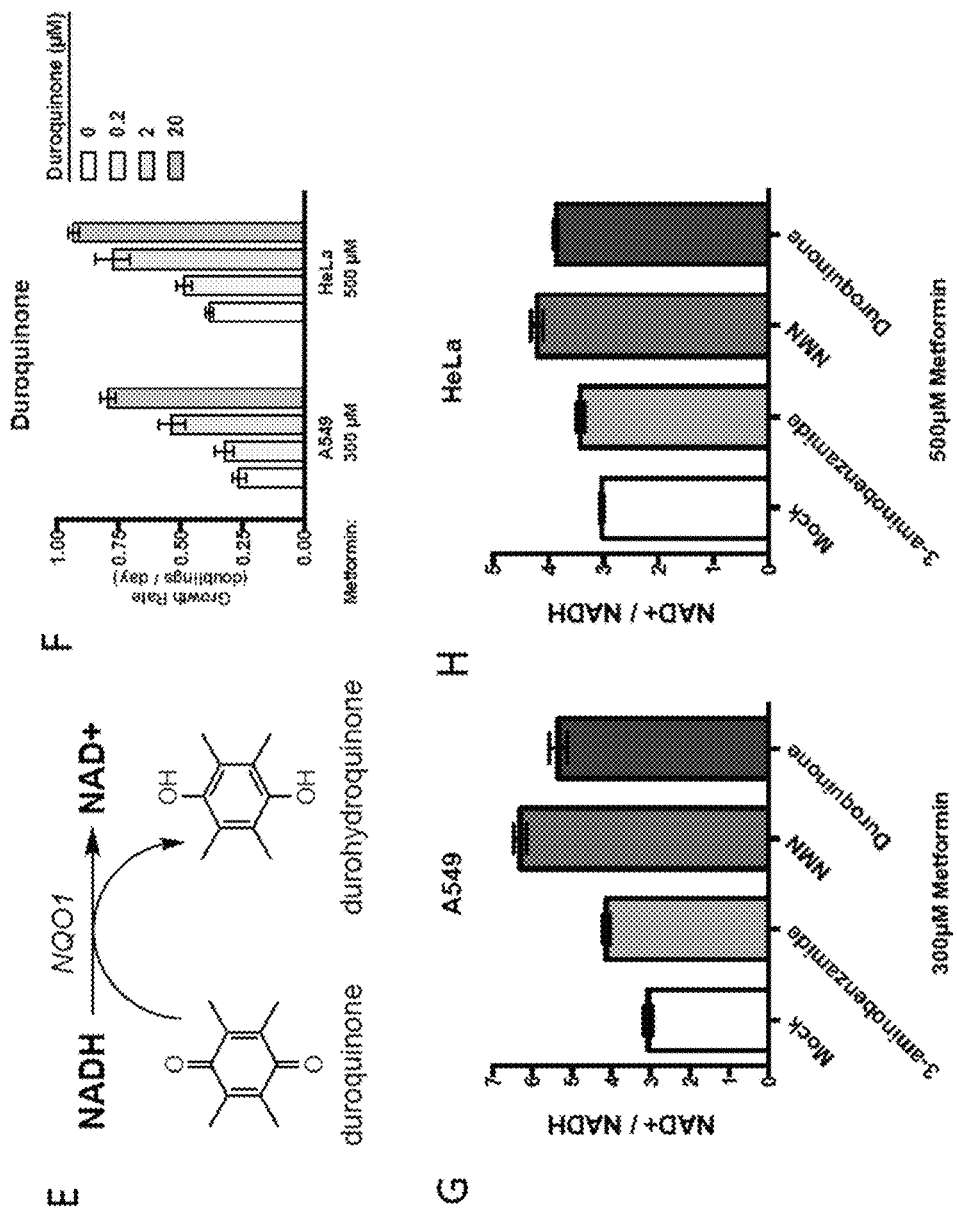

To understand how pyruvate stimulates aspartate synthesis in cells with ETC inhibition, we considered two pathways through which pyruvate might contribute to the aspartate pool. (i) One possibility is that pyruvate carboxylase (PC) directly carboxylates pyruvate into oxaloacetate, which GOT1 then uses to generate aspartate. However, we quickly ruled out this pathway as in PC-null Jurkat cell lines pyruvate still prevented the anti-proliferative effects of ETC inhibitors (FIG. 22D, FIG. 24A). (ii) As described earlier, pyruvate can also promote aspartate synthesis through the regeneration of $NAD^+$ in the cytosol. Given this, we hypothesized that $NAD^+$ might activate the cytosolic malate dehydrogenase (MDH1) to generate oxaloacetate that then drives aspartate synthesis by GOT1 (FIG. 24B). To investigate this possibility, we generated MDH1-null Jurkat cells (MDH1_KO1 and MDH1_KO2) (FIG. 18A). In the absence of ETC inhibitors, these cells had similar levels of aspartate as GOT1-null cells, consistent with MDH1 normally consuming the oxaloacetate generated by GOT1 from aspartate (FIG. 18B). Upon phenformin treatment, aspartate in the MDH1-null cells dropped to the same level as it did in wild type cells (FIG. 18B). Pyruvate, however, had no effect on the MDH1-null cells: in cells treated with ETC inhibitors it did not stimulate aspartate synthesis or rescue proliferation (FIG. 18A-B). Importantly, expression in the null cells of an sgRNA-resistant human MDH1 cDNA reversed these defects (FIG. 18A-B). Our findings suggest a model in which pyruvate-induced $NAD^+$ activates MDH1 to produce oxaloacetate and drive aspartate synthesis via GOT1 (FIG. 24C). Supporting the idea that redox balance is upstream of aspartate synthesis, aspartate addition, unlike that of pyruvate, did not restore the NAD/NADH ratio in cells with ETC inhibition (FIG. 24C). A similar role for $NAD^+$ regeneration in the production of aspartate was identified as a key function of electron transport in a complementary study (Sullivan, Gui et al., unpublished).

Although under normal conditions both GOT1- and MDH1-null cells have high aspartate levels, they behave strikingly differently upon ETC inhibition: aspartate levels become almost undetectable in GOT1-null cells and the cells die, while in MDH1-null cells aspartate and proliferation drop to the same extent as in wild-type cells (FIG. 18C). This difference in aspartate levels upon ETC inhibition is a consequence of the MDH1-null (and also wild type) cells being able to generate some aspartate even in the absence of pyruvate through the reductive carboxylation pathway described earlier while the GOT1-null cells cannot (FIG. 15C). In other words, in the absence of ETC function, the loss of GOT1 eliminates all routes to aspartate synthesis while the reductive carboxylation path is still available in the MDH1-null and wild type cells.

This conclusion also provides a rationale for why MDH1 did not score like GOT1 in our screen, which was performed in RPMI, a pyruvate-free medium (FIG. 13B). In the absence of pyruvate and when treated with ETC inhibitors, MDH1-null and wild type cells have comparable aspartate levels and proliferate equally poorly (FIG. 18A-C). Interestingly, aspartate levels in wild type, GOT1-null, and MDH1-null cells treated with ETC inhibitors is a good predictor of whether the cells proliferate, arrest, or die (FIG. 18C).

Aspartate Supplementation Enables the Proliferation of Cybrids with Patient Derived mtDNA Mutations Even in the Absence of Pyruvate Transmitochondrial cytoplasmic hybrid cells (cybrids) are commonly used to study the mechanisms through which mutations in mitochondrial DNA (mtDNA) impair cellular function (Schon et al., 2012). These cells harbor patient-derived mitochondrial genomes with pathogenic mutations, and, like cells treated with ETC inhibitors, require pyruvate to proliferate in culture (King and Attardi, 1989, 1996). To expand upon our work with pharmacological inhibition of the ETC, we asked if aspartate supplementation rescues the proliferation of cells with genetic ETC defects. We used two patient-derived cybrid cells, the first with a homoplasmic microdeletion in the cytochrome b subunit of complex III (CYTB) associated with a form of parkinsonism and encephalopathy (De Coo et al., 1999; Rana et al., 2000), and the second with a homoplasmic point mutation in the mitochondrially encoded tRNA lysine (MT-TK) associated with myoclonic epilepsy with ragged red fibers (MERRF) (Wallace et al., 1988). To characterize the metabolic needs of these cybrids, as well as cells lacking mtDNA (143B ρ0), we cultured them in media with or without pyruvate or aspartate. In agreement with previous reports, the ETC-deficient cybrids and ρ0 cells proliferated in media supplemented with pyruvate (FIG. 19A).

Figure 19:
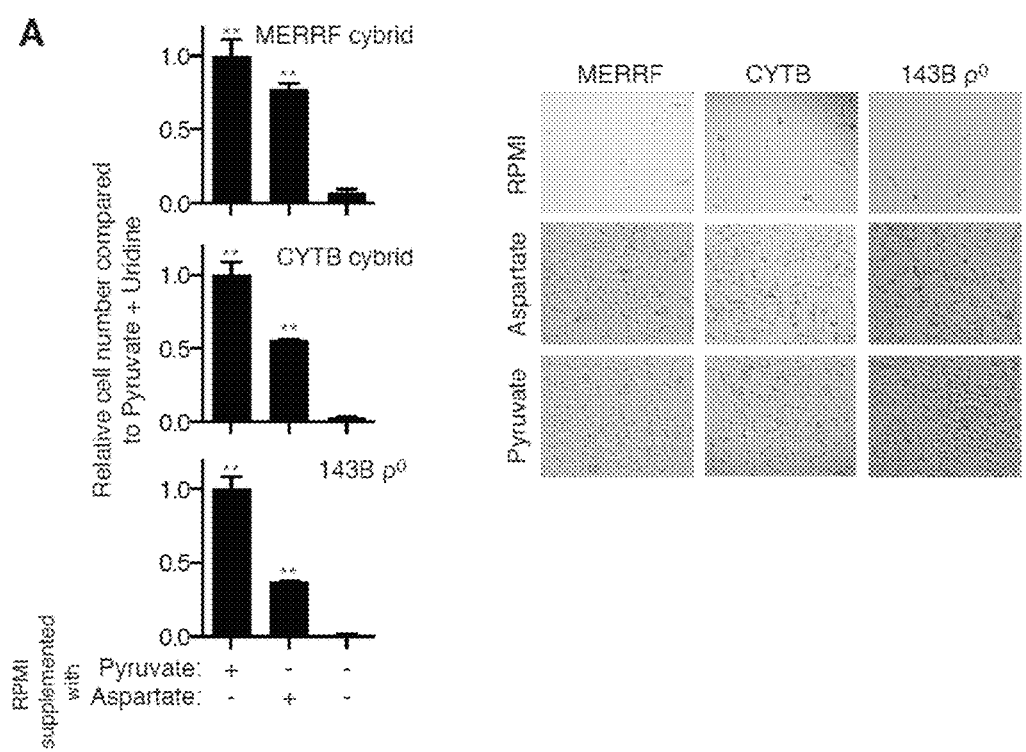
FIG. 19. Aspartate supplementation enables the proliferation of patient-derived cybrids with mtDNA mutations and replaces the need for pyruvate (A) Aspartate can replace pyruvate in enabling the proliferation of patient-derived mtDNA mutant cybrids and 143B ρ0 cells devoid of mtDNA. Cell line models of ETC dysfunction were cultured in RPMI (supplemented with uridine) with pyruvate (1 mM) or aspartate (10 mM) for 6 days. Relative cell number was determined by normalizing to the pyruvate-supplemented condition. Representative bright-field micrographs of MERRF, CYTB, and 143B ρ0 cells after 6 days in indicated conditions (right) (mean±SD, n=3, p<0.05). (B) Pyruvate stimulates aspartate biosynthesis in cybrid cells with ETC dysfunction. Mass isotopomer analysis of aspartate in wild type, phenformin-treated wild type, and ETC-defective cybrid cells cultured for 7 hours with [U-$^{13}$C]-L-glutamine (middle) in the presence or absence of pyruvate (1 mM) (top). The fraction of labeled aspartate from [U-$^{13}$C]-L-glutamine is indicated (mean±SD, for n=3, p<0.05) (bottom). OAA, oxaloacetate. (C) Pyruvate supplementation enables the proliferation of patient-derived cybrid cells in a GOT1-dependent fashion that can be bypassed by aspartate. Immunoblot analysis of wild type, MERRF, and CYTB cybrid cells expressing sgControl and sgGOT1 (top). Raptor was used as a loading control. Cell line models of ETC dysfunction expressing sgControl or sgGOT1 were cultured in RPMI (supplemented with uridine (50 µg/ml) and pyruvate (1 mM)) with or without aspartate (10 mM) for 6 days (bottom). Relative cell number was determined by normalizing to sgControl expressing cell line (mean±SD, for n=3, p<0.05). (D) SLC1A3 overexpression enables CYTB cells to proliferate in standard RPMI media without pyruvate addition. Fold changes in cell number over time of 143B wild type, CYTB cybrid cells, and their SLC1A3-expressing counterparts when cultured in RPMI media lacking aspartate and pyruvate (blue), or supplemented with aspartate (150 µM) (black) or pyruvate (1 mM) (gray) (mean±SD, n=3, p<0.05).
Figure 19:
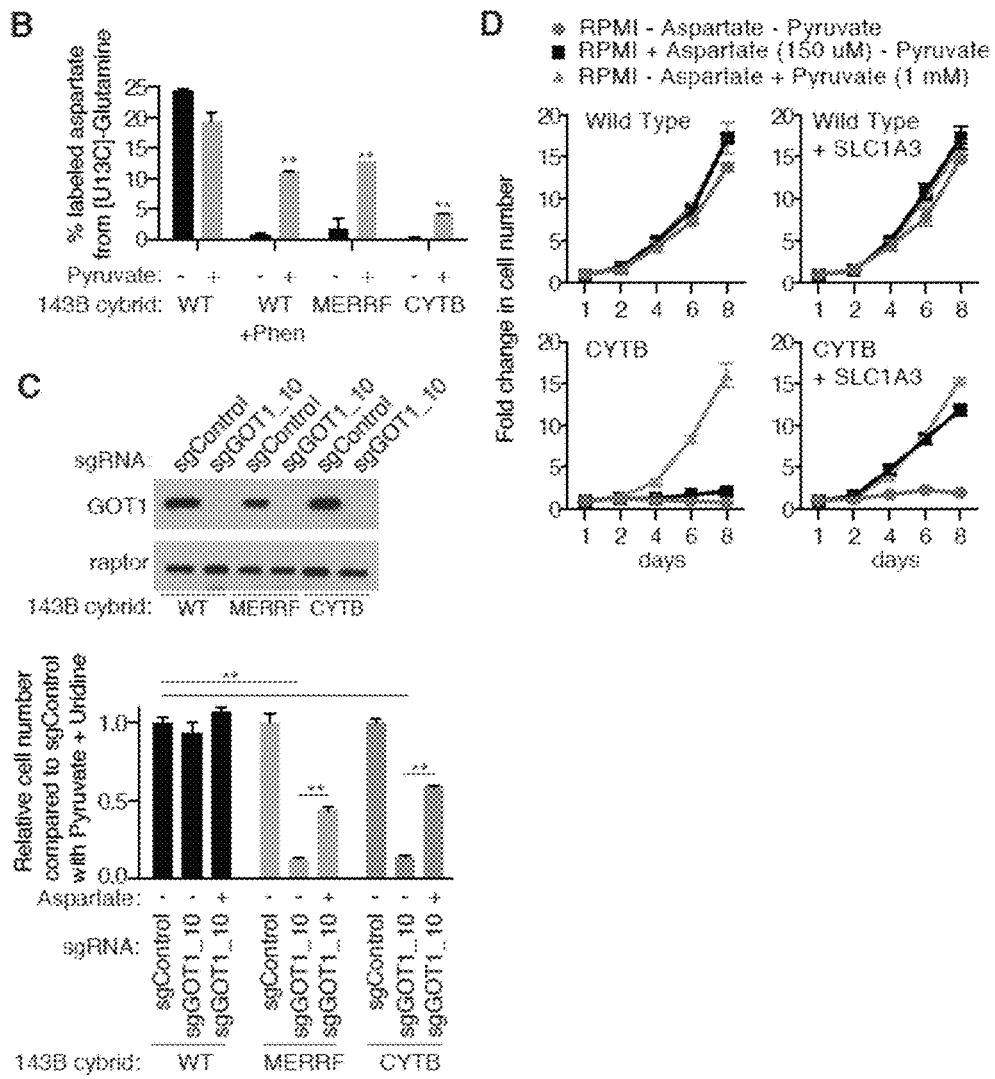

Consistent with the data obtained with pharmacological inhibitors, pyruvate stimulated aspartate synthesis in the ETC-defective cells (FIG. 19B) and aspartate on its own enabled their proliferation (FIG. 19A). The pyruvate-mediated rescue requires GOT1 as knocking it out in the ETC-defective cybrids severely impaired their proliferation (FIG. 19C). Importantly, aspartate supplementation bypassed the need for GOT1 (FIG. 19C).

To definitely test the sufficiency of aspartate in enabling the proliferation of cells with genetic ETC defects, we stably expressed the glutamate-aspartate SLC1A3 transporter in the CYTB cybrids (FIG. 19D). Strikingly, SLC1A3 expression was sufficient to enable the cybrids to proliferate in standard RPMI media, which has a low aspartate concentration (150 μM) and no pyruvate (FIG. 19D). To rule out the possibility that SLC1A3 enables proliferation by transporting a molecule other than aspartate, we cultured the cells in aspartate-free RPMI. Now, the SLC1A3-expressing CYTB cybrids failed to proliferate in the absence of pyruvate. Thus, we conclude that aspartate is sufficient to enable the proliferation of cells with a genetic ETC defect.

The above experiments suggests that the essential role of the electron transport chain (ETC) in cell proliferation is to enable the biosynthesis of aspartate. Even though ETC inhibition impacts many processes, the supplementation of media with just aspartate or the expression in cells of an aspartate transporter, is sufficient to allow ETC-defective cells to proliferate in culture. We also provide an explanation for the classic finding of King and Attardi (King and Attardi, 1989, 1996) that respiration defective mammalian cells require supra-physiological levels of pyruvate to proliferate. We find that pyruvate, likely by normalizing redox levels (Sullivan, Gui et. al., unpublished), promotes aspartate synthesis, which is then required for pyruvate to rescue the proliferation of cells with ETC defects. As blood aspartate concentrations in children and adults are very low (0-15 μM (Newgard et al., 2009; Wuu et al., 1988), it is unlikely that in vivo cells with ETC inhibition can take up sufficient aspartate to compensate for the decrease in its synthesis.

Figure 26:
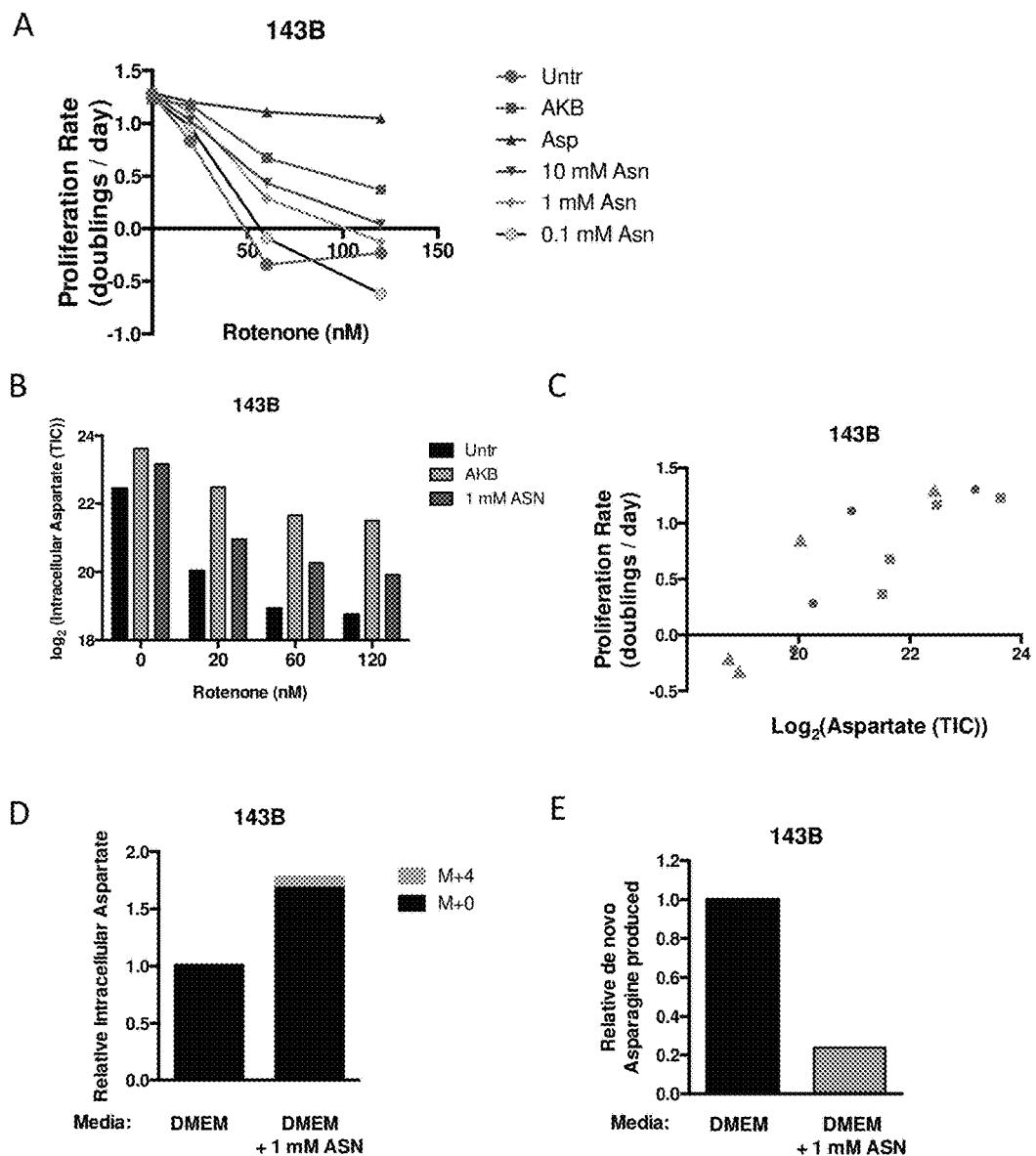
FIG. 26. Asparagine treatment restores intracellular aspartate levels and proliferation in rotenone treated cells by decreasing intracellular aspartate consumption. (A) Proliferation rate was measured after 4 days in DMEM without pyruvate and the indicated media conditions. Untr; Untreated. AKB; 1 mM alpha-ketobutyrate. Asp; 20 mM aspartate. Asn; asparagine, with the indicated concentrations. (B) GCMS measurement of intracellular levels of aspartate after 24 hours from the indicated treatment conditions. Aspartate levels are shown as the $\log_2$ of the measured total ion count (TIC). (C) The proliferation rate from FIG. 26A and the aspartate levels from FIG. 26B were graphed against one another to show a correlation between aspartate levels and proliferation rate. Grey triangles are the untreated conditions, blue squares are the AKB conditions, and green dots are the 1 mM ASN conditions. (D) GCMS measurement of intracellular aspartate levels after a 24-hour incubation in untreated media or media treated with 1 mM $^{13}C$ asparagine. The bars are split to show the fraction of aspartate that is unlabeled (M+0) and the fraction of aspartate that is labeled with 4 $^{13}C$ carbons (M+4). (E) GCMS measurement of unlabeled (M+0) asparagine released into the media (de novo produced asparagine) after a 24-hour incubation in untreated media or media treated with 1 mM $^{13}C$ asparagine.

Effect of Asparagine Treatment on Aspartate Levels in Proliferation Inhibited Cells 143B cells were treated with extracellular asparagine in the media to determine if the excess asparagine would cause resistance to the antiproliferative effects of the mitochondrial inhibitor rotenone. Consistent with results described elsewhere herein, α-ketobutyrate (AKB) and aspartate (Asp) treatment restore proliferation in 143B cells over a wide range of rotenone doses (FIG. 26A). At low doses of rotenone, treatment with asparagine (ASN) is also sufficient to restore proliferation; however, at high doses of rotenone, asparagine treatment is not able to restore proliferation (FIG. 26A). The hypothesis that asparagine treatment causes resistance to rotenone by increasing intracellular aspartate, which as described herein is rate limiting for proliferation in mitochondrial inhibited cells, was tested. Indeed, both AKB and 1 mM asparagine increased intracellular aspartate (FIG. 26B). Importantly, asparagine mediated restoration of intracellular aspartate was incomplete compared to AKB, consistent with only a partial restoration of proliferation. A comparison of the proliferation rate for all 143B conditions under which intracellular aspartate levels were determined (untreated, AKB treated, or 1 mM Asn treated) demonstrated that regardless of treatment group intracellular aspartate levels correlate with proliferation rate (FIG. 26C). The data indicate that asparagine is an agent that can increase intracellular aspartate levels at low to moderate levels of mitochondrial inhibition, such as those frequently observed in mitochondrial diseases.

The mechanism by which extracellular asparagine treatment can restore intracellular aspartate levels was also investigated. First, we treated 143B cells with 1 mM asparagine containing four $^{13}C$ carbon atoms. If the cells had asparaginase activity, which has not been described in humans, it would be predicted that the increased intracellular aspartate would also have four $^{13}C$ carbon atoms (M+4). However, while treatment with $^{13}C$ asparagine did increase intracellular aspartate levels, nearly all of the intracellular aspartate pool was unlabeled (M+0), indicating that is was not derived from the added extracellular asparagine (FIG. 26D). The small fraction containing labeled aspartate was likely from $^{13}C$ aspartate contamination in the $^{13}C$ asparagine added to the media. Since the increased aspartate pool was not primarily a result of increased aspartate production from asparagine, it was hypothesized that the increased intracellular aspartate was instead a result of decreased intracellular aspartate consumption. One plausible mechanism by which providing the cells with extracellular asparagine would decrease intracellular aspartate consumption is through product inhibition of asparagine synthetase (ASNS) activity. Decreased ASNS activity would decrease aspartate consumption and therefore increased aspartate levels. To test this, we measured the release of unlabeled asparagine in the media of untreated cells or cells treated with 1 mM $^{13}C$ asparagine. Indeed, it was observed that asparagine treated cells produce less asparagine, indicating decreased aspartate consumption is likely the mechanism of increased intracellular aspartate levels in asparagine treated cells (FIG. 26E). Thus, decreasing aspartate consumption, such as through inhibition of asparagine synthetase, is a potential mechanism to increase aspartate levels and promote resistance to mitochondrial inhibition.

Xenograft Study Showing Correlation Between Aspartate Levels and Tumor Growth

Figure 27:
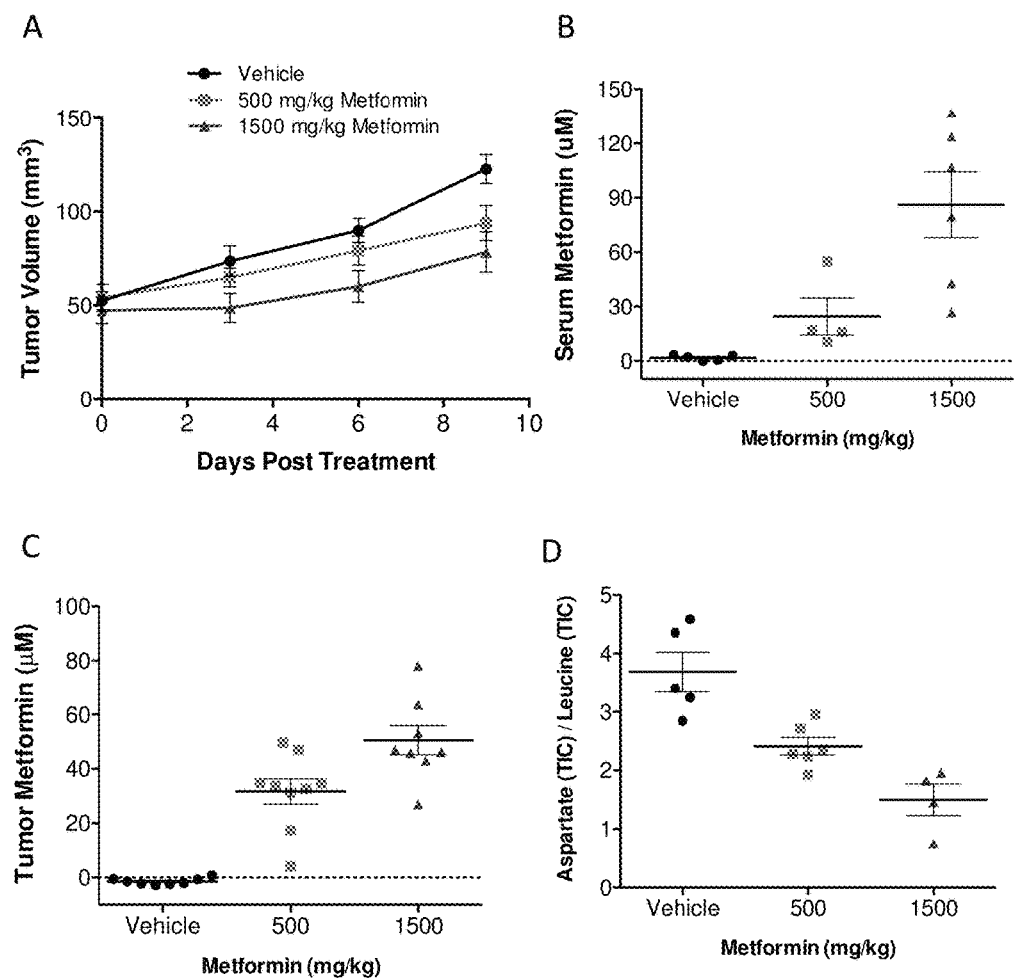
FIG. 27. In vivo mitochondrial inhibition inhibits cellular proliferation and decreases intracellular growth rate. (A) A549 xenografts in nude mice were treated with varying doses of the mitochondrial inhibitor, metformin, once a day by oral gavage at the indicated concentrations. LCMS measurement of (B) serum and (C) tumor metformin concentration for the indicated metformin treatment conditions. (D) GCMS measurement of intracellular aspartate levels in the tumors following 10 days of the indicated treatment. Aspartate levels are shown as aspartate total ion count (TIC) normalized to leucine TIC.

An in vivo correlation between mitochondrial inhibition and growth inhibition, and further, a correlation between the degree of growth inhibition and intracellular aspartate levels were shown in a xenograft study. A549 lung carcinoma cells were xenografted into nude mice, and the cells were allowed to grow until they formed a tumor 50 $mm^3$ in volume. When the tumors reached 50 $mm^3$, the mice were randomly sorted into three groups and treated once a day by oral gavage with vehicle or the mitochondrial inhibitor metformin (500 mg/kg or 1500 mg/kg). Increasing dosages of mitochondrial inhibitor dose dependently inhibited tumor growth (FIG. 27A). The serum concentrations of metformin were measured at the doses of metformin administered and confirmed to be at concentrations that would be therapeutically relevant and tolerable in humans (FIG. 27B). Further, the escalating doses of metformin resulted in increased tumor concentration of metformin (FIG. 27C). Finally, measurement of aspartate levels shows that the normalized intracellular aspartate levels decrease in a dose-dependent manner with increased doses of mitochondrial inhibitor, and importantly, the aspartate level directly correlates with tumor growth rate (FIG. 27D).

REFERENCES

1. Bell, E. L., Klimova, T. A., Eisenbart, J., Moraes, C. T., Murphy, M. P., Budinger, G. R., and Chandel, N. S. (2007). The Qo site of the mitochondrial complex III is required for the transduction of hypoxic signaling via reactive oxygen species production. The Journal of cell biology 177, 1029-1036.
2. Bender, A., Krishnan, K. J., Morris, C. M., Taylor, G. A., Reeve, A. K., Perry, R. H., Jaros, E., Hersheson, J. S., Betts, J., Klopstock, T., et al. (2006). High levels of mitochondrial DNA deletions in substantia nigra neurons in aging and Parkinson disease. Nature genetics 38, 515-517.
3. Birsoy, K., Possemato, R., Lorbeer, F. K., Bayraktar, E. C., Thiru, P., Yucel, B., Wang, T., Chen, W. W., Clish, C. B., and Sabatini, D. M. (2014). Metabolic determinants of cancer cell sensitivity to glucose limitation and biguanides. Nature 508, 108-112.
4. Boveris, A., Oshino, N., and Chance, B. (1972). The cellular production of hydrogen peroxide. The Biochemical journal 128, 617-630.
5. Chandel, N. S. (2014). Mitochondria as signaling organelles. BMC biology 12, 34.
6. Chen, W. W., Birsoy, K., Mihaylova, M. M., Snitkin, H., Stasinski, I., Yucel, B., Bayraktar, E. C., Carette, J. E., Clish, C. B., Brummelkamp, T. R., et al. (2014). Inhibition of ATPIF1 ameliorates severe mitochondrial respiratory chain dysfunction in mammalian cells. Cell reports 7, 27-34.
7. De Coo, I. F., Renier, W. O., Ruitenbeek, W., Ter Laak, H. J., Bakker, M., Schagger, H., Van Oost, B. A., and Smeets, H. J. (1999). A 4-base pair deletion in the mitochondrial cytochrome b gene associated with parkinsonism/MELAS overlap syndrome. Annals of neurology 45, 130-133.
8. Di Lisa, F., and Ziegler, M. (2001). Pathophysiological relevance of mitochondria in NAD metabolism. FEBS letters 492, 4-8.

9. DiMauro, S. (2010). Pathogenesis and treatment of mitochondrial myopathies: recent advances. Acta myologica: myopathies and cardiomyopathies: official journal of the Mediterranean Society of Myology/edited by the Gaetano Conte Academy for the study of striated muscle diseases 29, 333-338.
10. Fendt, S. M., Bell, E. L., Keibler, M. A., Davidson, S. M., Wirth, G. J., Fiske, B., Mayers, J. R., Schwab, M., Bellinger, G., Csibi, A., et al. (2013a). Metformin decreases glucose oxidation and increases the dependency of prostate cancer cells on reductive glutamine metabolism. Cancer research 73, 4429-4438.
11. Fendt, S. M., Bell, E. L., Keibler, M. A., Olenchock, B. A., Mayers, J. R., Wasylenko, T. M., Vokes, N. I., Guarente, L., Vander Heiden, M. G., and Stephanopoulos, G. (2013b). Reductive glutamine metabolism is a function of the α-ketoglutarate to citrate ratio in cells. Nature communications 4, 2236.
12. Frezza, C., Zheng, L., Folger, O., Rajagopalan, K. N., MacKenzie, E. D., Jerby, L., Micaroni, M., Chaneton, B., Adam, J., Hedley, A., et al. (2011). Haem oxygenase is synthetically lethal with the tumour suppressor fumarate hydratase. Nature 477, 225-228.
13. Fujii, T., Nozaki, F., Saito, K., Hayashi, A., Nishigaki, Y., Murayama, K., Tanaka, M., Koga, Y., Hiejima, I., and Kumada, T. (2014). Efficacy of pyruvate therapy in patients with mitochondrial disease: a semi-quantitative clinical evaluation study. Molecular genetics and metabolism 112, 133-138.
14. Geissler, A., Krimmer, T., Bomer, U., Guiard, B., Rassow, J., and Pfanner, N. (2000). Membrane potential-driven protein import into mitochondria. The sorting sequence of cytochrome b(2) modulates the deltapsi-dependence of translocation of the matrixtargeting sequence. Molecular biology of the cell 11, 3977-3991.
15. Green, D. R., and Reed, J. C. (1998). Mitochondria and apoptosis. Science 281, 1309-1312.
16. Gregoire, M., Morais, R., Quilliam, M. A., and Gravel, D. (1984). On auxotrophy for pyrimidines of respiration-deficient chick embryo cells. European journal of biochemistry/FEBS 142, 49-55.
17. Han, Y. H., Kim, S. H., Kim, S. Z., and Park, W. H. (2008). Antimycin A as a mitochondrial electron transport inhibitor prevents the growth of human lung cancer A549 cells. Oncology reports 20, 689-693.
18. Harris, M. (1980). Pyruvate blocks expression of sensitivity to antimycin A and chloramphenicol. Somatic cell genetics 6, 699-708.
19. Hayashi, J., Takemitsu, M., and Nonaka, I. (1992). Recovery of the missing tumorigenicity in mitochondrial DNA-less HeLa cells by introduction of mitochondrial DNA from normal human cells. Somatic cell and molecular genetics 18, 123-129.
20. Howell, N., and Sager, R. (1979). Cytoplasmic genetics of mammalian cells: conditional sensitivity to mitochondrial inhibitors and isolation of new mutant phenotypes. Somatic cell genetics 5, 833-845.
21. King, M. P., and Attardi, G. (1989). Human cells lacking mtDNA: repopulation with exogenous mitochondria by complementation. Science 246, 500-503.
22. King, M. P., and Attardi, G. (1996). Isolation of human cell lines lacking mitochondrial DNA. Methods in enzymology 264, 304-313.
23. Kokotas, H., Petersen, M. B., and Willems, P. J. (2007). Mitochondrial deafness. Clinical genetics 71, 379-391.
24. Koopman, W. J., Willems, P. H., and Smeitink, J. A. (2012). Monogenic mitochondrial disorders. The New England journal of medicine 366, 1132-1141.
25. Kwong, J. Q., Henning, M. S., Starkov, A. A., and Manfredi, G. (2007). The mitochondrial respiratory chain is a modulator of apoptosis. The Journal of cell biology 179, 1163-1177.
26. Lane, A. N., and Fan, T. W. (2015). Regulation of mammalian nucleotide metabolism and biosynthesis. Nucleic acids research 43, 2466-2485.
27. Lunt, S. Y., Muralidhar, V., Hosios, A. M., Israelsen, W. J., Gui, D. Y., Newhouse, L., Ogrodzinski, M., Hecht, V., Xu, K., Acevedo, P. N., et al. (2015). Pyruvate kinase isoform expression alters nucleotide synthesis to impact cell proliferation. Molecular cell 57, 95-107.
28. Mayers, J. R., and Vander Heiden, M. G. (2015). Famine versus feast: understanding the metabolism of tumors in vivo. Trends in biochemical sciences 40, 130-140.
29. Metallo, C. M., Gameiro, P. A., Bell, E. L., Mattaini, K. R., Yang, J., Hiller, K., Jewell, C. M., Johnson, Z. R., Irvine, D. J., Guarente, L., et al. (2012). Reductive glutamine metabolism by IDH1 mediates lipogenesis under hypoxia. Nature 481, 380-384.
30. Mitchell, P. (1961). Coupling of phosphorylation to electron and hydrogen transfer by a chemi-osmotic type of mechanism. Nature 191, 144-148.
31. Mullen, A. R., Wheaton, W. W., Jin, E. S., Chen, P. H., Sullivan, L. B., Cheng, T., Yang, Y., Linehan, W. M., Chandel, N. S., and DeBerardinis, R. J. (2012). Reductive carboxylation supports growth in tumour cells with defective mitochondria. Nature 481, 385-388.
32. Newgard, C. B., An, J., Bain, J. R., Muehlbauer, M. J., Stevens, R. D., Lien, L. F., Haqq, A. M., Shah, S. H., Arlotto, M., Slentz, C. A., et al. (2009). A branched-chain amino acid-related metabolic signature that differentiates obese and lean humans and contributes to insulin resistance. Cell metabolism 9, 311-326.
33. Newmeyer, D. D., and Ferguson-Miller, S. (2003). Mitochondria: releasing power for life and unleashing the machineries of death. Cell 112, 481-490.
34. Nicholls, D. G., and Budd, S. L. (2000). Mitochondria and neuronal survival. Physiological reviews 80, 315-360.
35. Nunnari, J., and Suomalainen, A. (2012). Mitochondria: in sickness and in health. Cell 148, 1145-1159.
36. Owen, M. R., Doran, E., and Halestrap, A. P. (2000). Evidence that metformin exerts its anti-diabetic effects through inhibition of complex 1 of the mitochondrial respiratory chain. The Biochemical journal 348 Pt 3, 607-614.
37. Pagliarini, D. J., and Rutter, J. (2013). Hallmarks of a new era in mitochondrial biochemistry. Genes & development 27, 2615-2627.
38. Park, J. S., Sharma, L. K., Li, H., Xiang, R., Holstein, D., Wu, J., Lechleiter, J., Naylor, S. L., Deng, J. J., Lu, J., et al. (2009). A heteroplasmic, not homoplasmic, mitochondrial DNA mutation promotes tumorigenesis via alteration in reactive oxygen species generation and apoptosis. Human molecular genetics 18, 1578-1589.
39. Pfeffer, G., Majamaa, K., Turnbull, D. M., Thorburn, D., and Chinnery, P. F. (2012). Treatment for mitochondrial disorders. The Cochrane database of systematic reviews 4, CD004426.
40. Raimundo, N., Song, L., Shutt, T. E., McKay, S. E., Cotney, J., Guan, M. X., Gilliland, T. C., Hohuan, D., Santos-Sacchi, J., and Shadel, G. S. (2012). Mitochondrial stress engages E2F1 apoptotic signaling to cause deafness. Cell 148, 716-726.

41. Rana, M., de Coo, I., Diaz, F., Smeets, H., and Moraes, C. T. (2000). An out-of-frame cytochrome b gene deletion from a patient with parkinsonism is associated with impaired complex III assembly and an increase in free radical production. Annals of neurology 48, 774-781.
42. Safer, B. (1975). The Metabolic Significance of the Malate-Aspartate Cycle in Heart. Circulation research 37, 527-533.
43. Saito, K., Kimura, N., Oda, N., Shimomura, H., Kumada, T., Miyajima, T., Murayama, K., Tanaka, M., and Fujii, T. (2012). Pyruvate therapy for mitochondrial DNA depletion syndrome. Biochimica et biophysica acta 1820, 632-636.
44. Santidrian, A. F., Matsuno-Yagi, A., Ritland, M., Seo, B. B., LeBoeuf, S. E., Gay, L. J., Yagi, T., and Felding-Habermann, B. (2013). Mitochondrial complex I activity and $NAD^+/NADH$ balance regulate breast cancer progression. The Journal of clinical investigation 123, 1068-1081.
45. Schieber, M., and Chandel, N. S. (2014). ROS function in redox signaling and oxidative stress. Current biology: CB 24, R453-462.
46. Schon, E. A., DiMauro, S., and Hirano, M. (2012). Human mitochondrial DNA: roles of inherited and somatic mutations. Nature reviews Genetics 13, 878-890.
47. Shoffner, J. M., Lott, M. T., Lezza, A. M., Seibel, P., Ballinger, S. W., and Wallace, D. C. (1990). Myoclonic epilepsy and ragged-red fiber disease (MERRF) is associated with a mitochondrial DNA tRNA(Lys) mutation. Cell 61, 931-937.
48. Stein, L. R., and Imai, S. (2012). The dynamic regulation of NAD metabolism in mitochondria. Trends in endocrinology and metabolism: TEM 23, 420-428.
49. Storck, T., Schulte, S., Hofmann, K., and Stoffel, W. (1992). Structure, expression, and functional analysis of a Natdependent glutamate/aspartate transporter from rat brain. Proceedings of the National Academy of Sciences of the United States of America 89, 10955-10959.
50. Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.
51. Swerdlow, R. H., Parks, J. K., Miller, S. W., Tuttle, J. B., Trimmer, P. A., Sheehan, J. P., Bennett, J. P., Jr., Davis, R. E., and Parker, W. D., Jr. (1996). Origin and functional consequences of the complex I defect in Parkinson's disease. Annals of neurology 40, 663-671.
52. Tan, A. S., Baty, J. W., Dong, L. F., Bezawork-Geleta, A., Endaya, B., Goodwin, J., Bajzikova, M., Kovarova, J., Peterka, M., Yan, B., et al. (2015). Mitochondrial genome acquisition restores respiratory function and tumorigenic potential of cancer cells without mitochondrial DNA. Cell metabolism 21, 81-94.
53. Toney, M. D. (2014). Aspartate aminotransferase: an old dog teaches new tricks. Archives of biochemistry and biophysics 544, 119-127.
54. Wallace, D. C. (1999). Mitochondrial diseases in man and mouse. Science 283, 1482-1488.
55. Wallace, D. C. (2013). A mitochondrial bioenergetic etiology of disease. The Journal of clinical investigation 123, 1405-1412.
56. Wallace, D. C., Zheng, X. X., Lott, M. T., Shoffner, J. M., Hodge, J. A., Kelley, R. I., Epstein, C. M., and Hopkins, L. C. (1988). Familial mitochondrial encephalomyopathy (MERRF): genetic, pathophysiological, and biochemical characterization of a mitochondrial DNA disease. Cell 55, 601-610.
57. Wang, T., Wei, J. J., Sabatini, D. M., and Lander, E. S. (2014). Genetic screens in human cells using the CRISPR-Cas9 system. Science 343, 80-84.
58. Weinberg, F., Hamanaka, R., Wheaton, W. W., Weinberg, S., Joseph, J., Lopez, M., Kalyanaraman, B., Mutlu, G. M., Budinger, G. R., and Chandel, N. S. (2010). Mitochondrial metabolism and ROS generation are essential for Kras-mediated tumorigenicity. Proceedings of the National Academy of Sciences of the United States of America 107, 8788-8793.
59. Wheaton, W. W., Weinberg, S. E., Hamanaka, R. B., Soberanes, S., Sullivan, L. B., Anso, E., Glasauer, A., Dufour, E., Mutlu, G. M., Budigner, G. S., et al. (2014a). Metformin inhibits mitochondrial complex I of cancer cells to reduce tumorigenesis. eLife 3, e02242.
60. Wheaton, W. W., Weinberg, S. E., Hamanaka, R. B., Soberanes, S., Sullivan, L. B., Anso, E., Glasauer, A., Dufour, E., Mutlu, G. M., Budinger, G. R., et al. (2014b). Metformin inhibits mitochondrial complex I of cancer cells to reduce tumorigenesis. eLife 3.
61. Wilkins, H. M., Carl, S. M., and Swerdlow, R. H. (2014). Cytoplasmic hybrid (cybrid) cell lines as a practical model for mitochondriopathies. Redox biology 2C, 619-631.
62. Wuu, J. A., Wen, L. Y., Chuang, T. Y., and Chang, G. G. (1988). Amino acid concentrations in serum and aqueous humor from subjects with extreme myopia or senile cataract. Clinical chemistry 34, 1610-1613.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a disease by administering to a subject in need thereof alpha-ketobutyrate, or a pharmaceutically acceptable salt thereof,
   wherein the disease is selected from the group consisting of myoclonic epilepsy with red ragged fibers (MERRF); mitochondrial encephalomyopathy, lactic acidosis, and stroke like symptoms (MELAS); Kearns-Sayre syndrome (KSS); chronic progressive external ophthalmoplegia (CPEO); lactic acidosis; Leber's hereditary optic neuropathy (LHON); Wolff-Parkinson-White syndrome; Leigh syndrome; neurogenic muscle weakness, ataxia, and retinitis pigmentosa (NARP); myoneurogenic gastrointestinal encephalopathy (MNGIE); and mitochondrial DNA depletion syndrome (MDS).

2. The method of claim 1, wherein the disease is myoclonic epilepsy with red ragged fibers (MERRF).

3. The method of claim 1, wherein the disease is mitochondrial encephalomyopathy, lactic acidosis, and stroke like symptoms (MELAS).

4. The method of claim 1, wherein the disease is Kearns-Sayre syndrome (KSS).

5. The method of claim 1, wherein the disease is chronic progressive external ophthalmoplegia (CPEO).

6. The method of claim 1, wherein the disease is lactic acidosis.

7. The method of claim 1, wherein the disease is Leber's hereditary optic neuropathy (LHON).

8. The method of claim 1, wherein the disease is Wolff-Parkinson-White syndrome.

9. The method of claim 1, wherein the disease is Leigh syndrome.

10. The method of claim 1, wherein the disease is neurogenic muscle weakness, ataxia, and retinitis pigmentosa (NARP).

11. The method of claim 1, wherein the disease is myoneurogenic gastrointestinal encephalopathy (MNGIE).

12. The method of claim 1, wherein the disease is mitochondrial DNA depletion syndrome (MDS).

13. The method of claim 1, wherein the subject is a human.

* * * * *

UNITED STATES PATENT AND TRADEMARK OFFICE
CERTIFICATE OF CORRECTION

PATENT NO. : 10,123,985 B2
APPLICATION NO. : 15/177243
DATED : November 13, 2018
INVENTOR(S) : David M. Sabatini et al.

Page 1 of 1

It is certified that error appears in the above-identified patent and that said Letters Patent is hereby corrected as shown below:

On the Title Page

Item (73):
"(73) Assignees: Whitehead Institute for Biomedical Research, Cambridge, MA (US); Massachusetts Institute of Technology, Cambridge, MA (US); Howard Hughes Medical Institute, Chevy Chase, MD (US)"

Should be replaced with the following amended section:
-- (73) Assignees: Whitehead Institute for Biomedical Research, Cambridge, MA (US); Massachusetts Institute of Technology, Cambridge, MA (US) --

Signed and Sealed this
Tenth Day of September, 2019

Andrei Iancu
*Director of the United States Patent and Trademark Office*